(12) United States Patent
Abdou

(10) Patent No.: US 11,918,486 B2
(45) Date of Patent: *Mar. 5, 2024

(54) DEVICES AND METHODS FOR MINIMALLY INVASIVE SPINAL STABILIZATION AND INSTRUMENTATION

(71) Applicant: Samy Abdou, San Diego, CA (US)

(72) Inventor: Samy Abdou, San Diego, CA (US)

(*) Notice: Subject to any disclaimer, the term of this patent is extended or adjusted under 35 U.S.C. 154(b) by 263 days.

This patent is subject to a terminal disclaimer.

(21) Appl. No.: 17/114,358

(22) Filed: Dec. 7, 2020

(65) Prior Publication Data
US 2021/0228379 A1    Jul. 29, 2021

Related U.S. Application Data

(60) Continuation of application No. 15/887,854, filed on Feb. 2, 2018, now Pat. No. 10,857,004, which is a
(Continued)

(51) Int. Cl.
*A61F 2/46* (2006.01)
*A61B 17/02* (2006.01)
(Continued)

(52) U.S. Cl.
CPC ........ *A61F 2/4611* (2013.01); *A61B 17/0206* (2013.01); *A61B 17/0218* (2013.01);
(Continued)

(58) Field of Classification Search
CPC .............. A61B 17/025; A61B 17/0206; A61B 17/0218; A61B 2017/0256; A61F 2/4611
See application file for complete search history.

(56) References Cited

U.S. PATENT DOCUMENTS

| 167,625 A | 9/1875 | Charles |
|---|---|---|
| 203,512 A | 5/1878 | Nicholas |

(Continued)

FOREIGN PATENT DOCUMENTS

| AU | 2006214001 B2 | 5/2011 |
|---|---|---|
| AU | 2011213872 A1 | 9/2011 |

(Continued)

OTHER PUBLICATIONS

Abstract for French Patent Publication FR2781359, Published Jan. 28, 2000, entitled: "Osteosynthesis Frame for Spinal Surgery has Rod with Clamps to Hold Cross Bars with Anchor Screws". Accession No. 9867555 (Derwent Information Ltd.).
(Continued)

*Primary Examiner* — Eduardo C Robert
*Assistant Examiner* — Michelle C Eckman
(74) *Attorney, Agent, or Firm* — Patent Beach PC

(57) ABSTRACT

Described herein are devices and methods for fusion of adjacent vertebral bones using distractor platforms for exposure and resection of at least a portion of a facet joint, such as in performance of a TLiF procedure. In one embodiment, the distractor platform contains at least a first receptacle and/or extension adapted to couple to the implanted screw/bone marker, and the method includes advancing a threaded segment of a bone fastener assembly into the identified first pedicle of the first vertebral bone, the bone fastener assembly further comprises a second segment adapted to couple with a distraction platform, which is adapted to concurrently attach onto at least one tissue retention blade, and retain the tissue retention blade in the displaced position. Stabilization of a spinal segment is also provided by advancing a substantially concave orthopedic implant through an opening made in a posterior aspect of a disc space.

25 Claims, 63 Drawing Sheets

Related U.S. Application Data continuation of application No. 15/620,633, filed on Jun. 12, 2017, now Pat. No. 10,543,107, which is a continuation of application No. 15/162,468, filed on May 23, 2016, now Pat. No. 9,675,389, which is a continuation of application No. 14/616,439, filed on Feb. 6, 2015, now Pat. No. 9,345,464, which is a division of application No. 14/320,349, filed on Jun. 30, 2014, now abandoned, which is a continuation of application No. 13/875,228, filed on May 1, 2013, now Pat. No. 8,764,806, which is a continuation of application No. 12/962,534, filed on Dec. 7, 2010, now abandoned.

(60) Provisional application No. 61/283,745, filed on Dec. 7, 2009.

(51) Int. Cl.
  *A61B 17/16* (2006.01)
  *A61B 17/17* (2006.01)
  *A61B 17/70* (2006.01)
  *A61B 17/88* (2006.01)
  *A61F 2/44* (2006.01)
  *A61B 17/00* (2006.01)
  *A61B 17/56* (2006.01)
  *A61B 17/68* (2006.01)
  *A61F 2/30* (2006.01)

(52) U.S. Cl.
  CPC ........ *A61B 17/025* (2013.01); *A61B 17/1611* (2013.01); *A61B 17/1757* (2013.01); *A61B 17/7032* (2013.01); *A61B 17/7037* (2013.01); *A61B 17/7077* (2013.01); *A61B 17/7079* (2013.01); *A61B 17/708* (2013.01); *A61B 17/7082* (2013.01); *A61B 17/88* (2013.01); *A61F 2/442* (2013.01); *A61F 2/4455* (2013.01); *A61B 2017/00473* (2013.01); *A61B 2017/0256* (2013.01); *A61B 2017/564* (2013.01); *A61B 2017/681* (2013.01); *A61B 17/7083* (2013.01); *A61F 2002/30131* (2013.01); *A61F 2002/30772* (2013.01); *A61F 2002/4435* (2013.01); *A61F 2002/4485* (2013.01); *A61F 2002/4635* (2013.01); *A61F 2310/00359* (2013.01)

(56) References Cited

U.S. PATENT DOCUMENTS

| | | |
|---|---|---|
| 203,624 A | 5/1878 | Josias |
| 229,347 A | 6/1880 | Shepherd |
| 267,269 A | 11/1882 | John |
| 824,983 A | 7/1906 | Charles |
| 944,725 A | 12/1909 | Ferguson, Jr. |
| 1,015,890 A | 1/1912 | Hyde |
| 1,156,440 A | 10/1915 | Smith |
| 1,213,599 A | 1/1917 | Dow |
| 1,785,709 A | 12/1930 | Harry et al. |
| 2,248,054 A | 7/1941 | Becker |
| 2,329,398 A | 9/1943 | Duffy |
| 2,370,407 A | 2/1945 | McCartney |
| 2,574,352 A | 11/1951 | Senter |
| 2,677,369 A | 5/1954 | Knowles |
| 2,774,350 A | 12/1956 | Cleveland, Jr. et al. |
| 3,025,853 A | 3/1962 | Mason |
| 3,037,596 A | 6/1962 | Fordyce |
| 3,072,423 A | 1/1963 | Charlton |
| 3,073,584 A | 1/1963 | Henry et al. |
| 3,090,386 A | 5/1963 | William et al. |
| 3,236,141 A | 2/1966 | Smith |
| 3,242,922 A | 3/1966 | Thomas |
| 3,260,412 A | 7/1966 | Larkin |
| 3,277,555 A | 10/1966 | Kutash |
| 3,374,786 A | 3/1968 | Callender, Jr. et al. |
| 3,383,769 A | 5/1968 | Davis |
| 3,384,077 A | 5/1968 | Gauthier |
| 3,426,364 A | 2/1969 | Lumb et al. |
| 3,604,487 A | 9/1971 | Gilbert |
| 3,648,691 A | 3/1972 | Lumb et al. |
| 3,659,595 A | 5/1972 | Haboush |
| 3,695,259 A | 10/1972 | Yost et al. |
| 3,708,883 A | 1/1973 | Flander et al. |
| 3,741,205 A | 6/1973 | Markolf et al. |
| 3,749,088 A | 7/1973 | Kohlmann et al. |
| 3,791,380 A | 2/1974 | Dawidowski et al. |
| 3,795,981 A | 3/1974 | Franklin et al. |
| 3,805,219 A | 4/1974 | Bright et al. |
| 3,825,992 A | 7/1974 | Troeger et al. |
| 3,858,578 A | 1/1975 | Milo |
| 3,865,105 A | 2/1975 | Lode |
| 3,867,728 A | 2/1975 | Stubstad et al. |
| 3,892,232 A | 7/1975 | Neufeld |
| 3,965,890 A | 6/1976 | Gauthier |
| 4,009,712 A | 3/1977 | Burstein et al. |
| 4,037,592 A | 7/1977 | Kronner |
| 4,047,524 A | 9/1977 | Hall |
| 4,074,542 A | 2/1978 | Hankosky et al. |
| 4,135,506 A | 1/1979 | Ulrich |
| 4,143,883 A | 3/1979 | Paynter |
| 4,165,746 A | 8/1979 | Burgin |
| 4,175,555 A | 11/1979 | Herbert |
| 4,237,875 A | 12/1980 | Termanini |
| 4,254,763 A | 3/1981 | McCready et al. |
| 4,289,123 A | 9/1981 | Dunn |
| 4,309,777 A | 1/1982 | Patil |
| 4,349,921 A | 9/1982 | Kuntz et al. |
| 4,399,813 A | 8/1983 | Barber |
| 4,409,974 A | 10/1983 | Freedland |
| 4,432,358 A | 2/1984 | Fixel |
| 4,448,181 A | 5/1984 | Ishikawa et al. |
| 4,448,191 A | 5/1984 | Rodnyansky et al. |
| 4,488,543 A | 12/1984 | Tornier |
| 4,493,317 A | 1/1985 | Klaue |
| 4,494,535 A | 1/1985 | Haig |
| 4,503,848 A | 3/1985 | Caspar et al. |
| 4,545,374 A | 10/1985 | Jacobson et al. |
| 4,554,914 A | 11/1985 | Kapp et al. |
| 4,561,432 A | 12/1985 | Mazor |
| 4,569,662 A | 2/1986 | Dragan |
| 4,570,618 A | 2/1986 | Wu |
| 4,580,563 A | 4/1986 | Gross |
| 4,604,995 A | 8/1986 | Stephens et al. |
| 4,611,581 A | 9/1986 | Steffee |
| 4,611,582 A | 9/1986 | Duff |
| 4,612,920 A | 9/1986 | Lower |
| 4,632,101 A | 12/1986 | Freedland |
| 4,636,217 A | 1/1987 | Ogilvie et al. |
| 4,653,481 A | 3/1987 | Howland et al. |
| 4,655,462 A | 4/1987 | Balsells |
| 4,655,629 A | 4/1987 | Flaherty |
| 4,655,778 A | 4/1987 | Koeneman |
| 4,664,305 A | 5/1987 | Blake, III et al. |
| 4,697,582 A | 10/1987 | William |
| 4,699,076 A | 10/1987 | Curtis et al. |
| 4,702,230 A | 10/1987 | Pelta |
| 4,711,232 A | 12/1987 | Fischer et al. |
| 4,714,469 A | 12/1987 | Kenna |
| 4,722,331 A | 2/1988 | Fox |
| 4,747,394 A | 5/1988 | Watanabe |
| 4,747,395 A | 5/1988 | Brief |
| 4,756,711 A | 7/1988 | Mai et al. |
| 4,759,766 A | 7/1988 | Buettner-Janz et al. |
| 4,759,769 A | 7/1988 | Hedman et al. |
| 4,773,402 A | 9/1988 | Asher et al. |
| 4,787,908 A | 11/1988 | Wyss et al. |
| 4,790,303 A | 12/1988 | Steffee |
| 4,791,918 A | 12/1988 | Von Hasselbach |
| 4,794,918 A | 1/1989 | Wolter |
| 4,820,305 A | 4/1989 | Harms et al. |
| 4,834,757 A | 5/1989 | Brantigan |

(56) References Cited

U.S. PATENT DOCUMENTS

| | | |
|---|---|---|
| 4,867,404 A | 9/1989 | Harrington et al. |
| 4,874,389 A | 10/1989 | Downey |
| 4,877,020 A | 10/1989 | Vich |
| 4,881,525 A | 11/1989 | Williams |
| 4,887,595 A | 12/1989 | Heinig et al. |
| 4,898,156 A | 2/1990 | Gatturna et al. |
| 4,899,761 A | 2/1990 | Brown et al. |
| 4,903,692 A | 2/1990 | Reese |
| 4,904,110 A | 2/1990 | Klein |
| 4,907,577 A | 3/1990 | Wu |
| 4,911,718 A | 3/1990 | Lee et al. |
| 4,913,134 A | 4/1990 | Luque |
| 4,932,975 A | 6/1990 | Main et al. |
| 4,934,352 A | 6/1990 | Sullivan, Jr. |
| 4,938,769 A | 7/1990 | Shaw |
| 4,944,757 A | 7/1990 | Martinez et al. |
| 4,946,378 A | 8/1990 | Hirayama et al. |
| 4,946,468 A | 8/1990 | Li |
| 4,949,707 A | 8/1990 | LeVahn et al. |
| 4,955,908 A | 9/1990 | Frey et al. |
| 4,957,495 A | 9/1990 | Kluger |
| 4,957,497 A | 9/1990 | Hoogland et al. |
| 4,961,740 A | 10/1990 | Ray et al. |
| 4,963,152 A | 10/1990 | Hofmann et al. |
| 4,964,403 A | 10/1990 | Karas et al. |
| 4,969,886 A | 11/1990 | Cziffer et al. |
| 4,969,887 A | 11/1990 | Sodhi |
| 4,973,332 A | 11/1990 | Kummer |
| 4,997,123 A | 3/1991 | Backus et al. |
| 4,997,432 A | 3/1991 | Keller |
| 5,002,550 A | 3/1991 | Li |
| 5,002,576 A | 3/1991 | Fuhrmann et al. |
| 5,007,880 A | 4/1991 | Walker |
| 5,007,910 A | 4/1991 | Anapliotis et al. |
| 5,011,484 A | 4/1991 | Breard |
| 5,015,247 A | 5/1991 | Michelson |
| 5,026,373 A | 6/1991 | Ray et al. |
| 5,052,711 A | 10/1991 | Pirkey et al. |
| 5,055,104 A | 10/1991 | Ray |
| 5,061,271 A | 10/1991 | Van Zile |
| 5,071,437 A | 12/1991 | Steffee |
| 5,084,049 A | 1/1992 | Asher et al. |
| 5,087,266 A | 2/1992 | Connell et al. |
| 5,092,866 A | 3/1992 | Breard et al. |
| 5,092,893 A | 3/1992 | Smith |
| 5,098,435 A | 3/1992 | Stednitz et al. |
| 5,116,336 A | 5/1992 | Frigg |
| 5,122,130 A | 6/1992 | Keller |
| 5,122,131 A | 6/1992 | Tsou |
| 5,127,914 A | 7/1992 | Calderale et al. |
| 5,129,899 A | 7/1992 | Small et al. |
| 5,131,904 A | 7/1992 | Markoll |
| 5,133,717 A | 7/1992 | Chopin |
| 5,147,360 A | 9/1992 | Dubousset |
| 5,147,361 A | 9/1992 | Ojima et al. |
| 5,152,303 A | 10/1992 | Allen |
| 5,167,662 A | 12/1992 | Hayes et al. |
| 5,176,680 A | 1/1993 | Vignaud et al. |
| 5,180,381 A | 1/1993 | Aust et al. |
| 5,180,393 A | 1/1993 | Commarmond |
| 5,192,327 A | 3/1993 | Brantigan |
| 5,207,679 A | 5/1993 | Li |
| 5,222,954 A | 6/1993 | Baker et al. |
| 5,226,766 A | 7/1993 | Lasner |
| 5,234,431 A | 8/1993 | Keller |
| 5,234,432 A | 8/1993 | Brown |
| 5,234,447 A | 8/1993 | Kaster et al. |
| 5,236,460 A | 8/1993 | Barber |
| 5,242,444 A | 9/1993 | MacMillan |
| 5,242,445 A | 9/1993 | Ashman |
| 5,246,442 A | 9/1993 | Ashman et al. |
| 5,246,458 A | 9/1993 | Graham |
| 5,250,055 A | 10/1993 | Moore et al. |
| 5,252,016 A | 10/1993 | Schmid et al. |
| 5,254,118 A | 10/1993 | Mirkovic |
| 5,258,031 A | 11/1993 | Salib et al. |
| 5,261,907 A | 11/1993 | Vignaud et al. |
| 5,261,909 A | 11/1993 | Sutterlin et al. |
| 5,261,910 A | 11/1993 | Warden et al. |
| 5,261,911 A | 11/1993 | Carl |
| 5,261,914 A | 11/1993 | Warren |
| 5,275,600 A | 1/1994 | Allard et al. |
| 5,275,601 A | 1/1994 | Gogolewski et al. |
| 5,281,222 A | 1/1994 | Allard et al. |
| 5,282,801 A | 2/1994 | Sherman |
| 5,282,862 A | 2/1994 | Baker et al. |
| 5,290,312 A | 3/1994 | Kojimoto et al. |
| 5,300,074 A | 4/1994 | Frigg |
| 5,304,178 A | 4/1994 | Stahurski |
| 5,306,307 A | 4/1994 | Senter et al. |
| 5,312,405 A | 5/1994 | Korotko et al. |
| 5,324,290 A | 6/1994 | Zdeblick et al. |
| 5,324,292 A | 6/1994 | Meyers |
| 5,330,468 A | 7/1994 | Burkhart |
| 5,330,473 A | 7/1994 | Howland |
| 5,334,205 A | 8/1994 | Cain |
| 5,335,418 A | 8/1994 | Krivec |
| 5,336,225 A | 8/1994 | Zang |
| 5,336,226 A | 8/1994 | McDaniel et al. |
| 5,342,394 A | 8/1994 | Matsuno et al. |
| 5,344,421 A | 9/1994 | Crook |
| 5,344,422 A | 9/1994 | Frigg |
| 5,346,493 A | 9/1994 | Stahurski et al. |
| 5,350,380 A | 9/1994 | Goble et al. |
| 5,352,226 A | 10/1994 | Lin |
| 5,352,231 A | 10/1994 | Brumfield et al. |
| 5,354,292 A | 10/1994 | Braeuer et al. |
| 5,356,410 A | 10/1994 | Pennig |
| 5,358,289 A | 10/1994 | Banker et al. |
| 5,360,429 A | 11/1994 | Jeanson et al. |
| 5,360,431 A | 11/1994 | Puno et al. |
| 5,361,766 A | 11/1994 | Nichols et al. |
| 5,364,399 A | 11/1994 | Lowery et al. |
| 5,366,455 A | 11/1994 | Dove et al. |
| 5,370,697 A | 12/1994 | Baumgartner |
| 5,372,599 A | 12/1994 | Martins |
| 5,374,267 A | 12/1994 | Siegal |
| 5,375,823 A | 12/1994 | Navas |
| 5,380,324 A | 1/1995 | Mueller et al. |
| 5,385,583 A | 1/1995 | Cotrel |
| 5,387,176 A | 2/1995 | Markoll |
| 5,387,213 A | 2/1995 | Breard et al. |
| 5,395,371 A | 3/1995 | Miller et al. |
| 5,397,363 A | 3/1995 | Gelbard |
| 5,397,364 A | 3/1995 | Kozak et al. |
| 5,403,316 A | 4/1995 | Ashman |
| 5,413,576 A | 5/1995 | Rivard |
| 5,415,661 A | 5/1995 | Holmes |
| 5,417,712 A | 5/1995 | Whittaker et al. |
| 5,423,816 A | 6/1995 | Lin |
| 5,423,818 A | 6/1995 | Van Hoeck et al. |
| 5,423,819 A | 6/1995 | Small et al. |
| 5,423,826 A | 6/1995 | Coates et al. |
| 5,425,772 A | 6/1995 | Brantigan |
| 5,425,773 A | 6/1995 | Boyd et al. |
| 5,427,418 A | 6/1995 | Watts |
| 5,429,639 A | 7/1995 | Judet |
| 5,431,658 A | 7/1995 | Moskovich |
| 5,437,669 A | 8/1995 | Yuan et al. |
| 5,437,670 A | 8/1995 | Sherman et al. |
| 5,437,672 A | 8/1995 | Alleyne |
| 5,437,674 A | 8/1995 | Worcel et al. |
| 5,439,339 A | 8/1995 | Batchelor |
| 5,439,463 A | 8/1995 | Lin |
| 5,443,467 A | 8/1995 | Biedermann et al. |
| 5,443,514 A | 8/1995 | Steffee |
| 5,449,257 A | 9/1995 | Giannuzzi |
| 5,453,073 A | 9/1995 | Markoll |
| 5,456,714 A | 10/1995 | Owen |
| 5,458,638 A | 10/1995 | Kuslich et al. |
| 5,466,237 A | 11/1995 | Byrd, III et al. |
| 5,468,241 A | 11/1995 | Metz-Stavenhagen et al. |
| 5,472,452 A | 12/1995 | Trott |
| 5,474,551 A | 12/1995 | Finn et al. |

(56) References Cited

U.S. PATENT DOCUMENTS

| | | |
|---|---|---|
| 5,474,555 A | 12/1995 | Puno et al. |
| 5,476,462 A | 12/1995 | Allard et al. |
| 5,476,464 A | 12/1995 | Metz-Stavenhagen et al. |
| 5,478,342 A | 12/1995 | Kohrs |
| 5,480,401 A | 1/1996 | Navas |
| 5,484,437 A | 1/1996 | Michelson |
| 5,484,440 A | 1/1996 | Allard |
| 5,486,174 A | 1/1996 | Fournet-Fayard et al. |
| 5,486,176 A | 1/1996 | Hildebrand et al. |
| 5,487,742 A | 1/1996 | Cotrel |
| 5,489,307 A | 2/1996 | Kuslich et al. |
| 5,489,308 A | 2/1996 | Kuslich et al. |
| 5,490,750 A | 2/1996 | Gundy |
| 5,496,318 A | 3/1996 | Howland et al. |
| 5,496,321 A | 3/1996 | Puno et al. |
| 5,499,892 A | 3/1996 | Reed |
| 5,505,731 A | 4/1996 | Tornier |
| 5,507,745 A | 4/1996 | Logroscino et al. |
| 5,507,754 A | 4/1996 | Green et al. |
| 5,507,816 A | 4/1996 | Bullivant |
| 5,512,038 A | 4/1996 | O'Neal et al. |
| 5,514,180 A | 5/1996 | Heggeness et al. |
| 5,520,690 A | 5/1996 | Errico et al. |
| 5,522,899 A | 6/1996 | Michelson |
| 5,527,314 A | 6/1996 | Brumfield et al. |
| 5,531,747 A | 7/1996 | Ray |
| 5,531,751 A | 7/1996 | Schultheiss et al. |
| 5,534,001 A | 7/1996 | Schlapfer et al. |
| 5,534,002 A | 7/1996 | Brumfield et al. |
| 5,534,027 A | 7/1996 | Hodorek |
| 5,540,688 A | 7/1996 | Navas |
| 5,545,163 A | 8/1996 | Miller et al. |
| 5,545,164 A | 8/1996 | Howland |
| 5,545,165 A | 8/1996 | Harms et al. |
| 5,545,179 A | 8/1996 | Williamson, IV |
| 5,549,607 A | 8/1996 | Olson et al. |
| 5,549,612 A | 8/1996 | Yapp et al. |
| 5,554,157 A | 9/1996 | Errico et al. |
| 5,556,431 A | 9/1996 | Buettner-Janz |
| 5,558,674 A | 9/1996 | Heggeness et al. |
| 5,562,660 A | 10/1996 | Grob |
| 5,562,661 A | 10/1996 | Yoshimi et al. |
| 5,562,662 A | 10/1996 | Brumfield et al. |
| 5,562,663 A | 10/1996 | Wisnewski et al. |
| 5,562,737 A | 10/1996 | Graf |
| 5,562,738 A | 10/1996 | Boyd et al. |
| 5,569,247 A | 10/1996 | Morrison |
| 5,569,248 A | 10/1996 | Mathews |
| 5,569,250 A | 10/1996 | Sarver et al. |
| 5,569,251 A | 10/1996 | Baker et al. |
| 5,569,252 A | 10/1996 | Justin et al. |
| 5,575,792 A | 11/1996 | Errico et al. |
| 5,578,033 A | 11/1996 | Errico et al. |
| 5,578,034 A | 11/1996 | Estes |
| 5,582,612 A | 12/1996 | Lin |
| 5,584,833 A | 12/1996 | Fournet-Fayard et al. |
| 5,584,834 A | 12/1996 | Errico et al. |
| 5,586,984 A | 12/1996 | Errico et al. |
| 5,591,166 A | 1/1997 | Bernhardt et al. |
| 5,599,279 A | 2/1997 | Slotman et al. |
| 5,601,553 A | 2/1997 | Trebing et al. |
| 5,603,714 A | 2/1997 | Kaneda et al. |
| 5,607,304 A | 3/1997 | Bailey et al. |
| 5,607,425 A | 3/1997 | Rogozinski |
| 5,607,426 A | 3/1997 | Ralph et al. |
| 5,607,428 A | 3/1997 | Lin |
| 5,609,593 A | 3/1997 | Errico et al. |
| 5,609,594 A | 3/1997 | Errico et al. |
| 5,609,634 A | 3/1997 | Voydeville |
| 5,609,635 A | 3/1997 | Michelson |
| 5,609,636 A | 3/1997 | Kohrs et al. |
| 5,609,637 A | 3/1997 | Biedermann et al. |
| 5,611,800 A | 3/1997 | Davis et al. |
| 5,616,142 A | 4/1997 | Yuan et al. |
| 5,620,169 A | 4/1997 | Payne |
| 5,620,443 A | 4/1997 | Gertzbein et al. |
| 5,628,740 A | 5/1997 | Mullane |
| 5,630,817 A | 5/1997 | Rokegem et al. |
| 5,641,256 A | 6/1997 | Gundy |
| 5,643,260 A | 7/1997 | Doherty |
| 5,643,261 A | 7/1997 | Schaefer et al. |
| 5,643,262 A | 7/1997 | Metz-Stavenhagen et al. |
| 5,643,321 A | 7/1997 | McDevitt |
| 5,645,544 A | 7/1997 | Tai et al. |
| 5,645,599 A | 7/1997 | Samani |
| 5,647,873 A | 7/1997 | Errico et al. |
| 5,649,931 A | 7/1997 | Bryant et al. |
| 5,653,763 A | 8/1997 | Errico et al. |
| 5,662,652 A | 9/1997 | Schaefer et al. |
| 5,662,653 A | 9/1997 | Songer et al. |
| 5,665,049 A | 9/1997 | Markoll |
| 5,667,513 A | 9/1997 | Torrie et al. |
| 5,669,868 A | 9/1997 | Markoll |
| 5,669,909 A | 9/1997 | Zdeblick et al. |
| 5,669,911 A | 9/1997 | Errico et al. |
| 5,669,912 A | 9/1997 | Spetzler |
| 5,672,175 A | 9/1997 | Martin |
| 5,672,176 A | 9/1997 | Biedermann et al. |
| 5,674,294 A | 10/1997 | Bainville et al. |
| 5,674,296 A | 10/1997 | Bryan et al. |
| 5,676,666 A | 10/1997 | Oxland et al. |
| 5,676,697 A | 10/1997 | McDonald |
| 5,676,701 A | 10/1997 | Yuan et al. |
| 5,676,703 A | 10/1997 | Gelbard |
| 5,681,311 A | 10/1997 | Foley et al. |
| 5,681,312 A | 10/1997 | Yuan et al. |
| 5,681,313 A | 10/1997 | Diez |
| 5,681,319 A | 10/1997 | Biedermann et al. |
| 5,683,390 A | 11/1997 | Metz-Stavenhagen et al. |
| 5,683,391 A | 11/1997 | Boyd |
| 5,683,392 A | 11/1997 | Richelsoph et al. |
| 5,683,394 A | 11/1997 | Rinner |
| 5,683,464 A | 11/1997 | Wagner et al. |
| 5,688,275 A | 11/1997 | Koros et al. |
| 5,690,630 A | 11/1997 | Errico et al. |
| 5,697,929 A | 12/1997 | Mellinger |
| 5,702,451 A | 12/1997 | Biedermann et al. |
| 5,704,936 A | 1/1998 | Mazel |
| 5,707,372 A | 1/1998 | Errico et al. |
| 5,709,686 A | 1/1998 | Talos et al. |
| 5,711,709 A | 1/1998 | McCoy |
| 5,713,672 A | 2/1998 | Lu |
| 5,713,898 A | 2/1998 | Stuecker et al. |
| 5,713,899 A | 2/1998 | Marnay et al. |
| 5,713,900 A | 2/1998 | Benzel et al. |
| 5,713,904 A | 2/1998 | Errico et al. |
| 5,716,356 A | 2/1998 | Biedermann et al. |
| 5,716,357 A | 2/1998 | Rogozinski |
| 5,720,751 A | 2/1998 | Jackson |
| 5,722,976 A | 3/1998 | Brown |
| 5,722,977 A | 3/1998 | Wilhelmy |
| 5,723,013 A | 3/1998 | Jeanson et al. |
| 5,725,527 A | 3/1998 | Biedermann et al. |
| 5,725,528 A | 3/1998 | Errico et al. |
| 5,725,582 A | 3/1998 | Bevan et al. |
| 5,728,046 A | 3/1998 | Mayer et al. |
| 5,728,098 A | 3/1998 | Sherman et al. |
| 5,733,284 A | 3/1998 | Martin |
| 5,733,285 A | 3/1998 | Errico et al. |
| 5,733,286 A | 3/1998 | Errico et al. |
| 5,733,290 A | 3/1998 | McCue et al. |
| 5,735,853 A | 4/1998 | Olerud |
| 5,738,685 A | 4/1998 | Halm et al. |
| 5,741,254 A | 4/1998 | Henry et al. |
| 5,741,261 A | 4/1998 | Moskovitz et al. |
| 5,746,743 A | 5/1998 | Greenberg |
| 5,749,916 A | 5/1998 | Richelsoph |
| 5,749,968 A | 5/1998 | Melanson et al. |
| 5,752,957 A | 5/1998 | Ralph et al. |
| 5,755,660 A | 5/1998 | Tyagi |
| 5,755,732 A | 5/1998 | Green et al. |
| 5,766,252 A | 6/1998 | Henry et al. |
| 5,772,583 A | 6/1998 | Wright et al. |
| 5,776,135 A | 7/1998 | Errico et al. |

(56) References Cited

U.S. PATENT DOCUMENTS

| | | |
|---|---|---|
| 5,776,199 A | 7/1998 | Michelson |
| 5,782,830 A | 7/1998 | Farris |
| 5,782,832 A | 7/1998 | Larsen et al. |
| 5,782,833 A | 7/1998 | Haider |
| 5,782,919 A | 7/1998 | Zdeblick et al. |
| 5,792,044 A | 8/1998 | Foley et al. |
| 5,795,289 A | 8/1998 | Wyttenbach |
| 5,795,291 A | 8/1998 | Koros et al. |
| 5,795,584 A | 8/1998 | Totakura et al. |
| 5,797,911 A | 8/1998 | Sherman et al. |
| 5,800,433 A | 9/1998 | Benzel et al. |
| 5,800,435 A | 9/1998 | Errico et al. |
| 5,800,547 A | 9/1998 | Schaefer et al. |
| 5,807,403 A | 9/1998 | Beyar et al. |
| 5,810,818 A | 9/1998 | Errico et al. |
| 5,810,819 A | 9/1998 | Errico et al. |
| 5,817,094 A | 10/1998 | Errico et al. |
| 5,833,418 A | 11/1998 | Shoji |
| 5,836,948 A | 11/1998 | Zucherman et al. |
| 5,842,966 A | 12/1998 | Markoll |
| 5,846,192 A | 12/1998 | Teixido |
| 5,860,977 A | 1/1999 | Zucherman et al. |
| 5,863,293 A | 1/1999 | Richelsoph |
| 5,865,848 A | 2/1999 | Baker |
| 5,873,878 A | 2/1999 | Harms et al. |
| 5,876,402 A | 3/1999 | Errico et al. |
| 5,876,404 A | 3/1999 | Zucherman et al. |
| 5,879,350 A | 3/1999 | Sherman et al. |
| 5,879,351 A | 3/1999 | Viart |
| 5,882,298 A | 3/1999 | Sharratt |
| 5,882,350 A | 3/1999 | Ralph et al. |
| 5,882,351 A | 3/1999 | Fox |
| 5,884,702 A | 3/1999 | Yokley et al. |
| 5,885,286 A | 3/1999 | Sherman et al. |
| 5,888,197 A | 3/1999 | Mulac et al. |
| 5,888,222 A | 3/1999 | Coates et al. |
| 5,888,224 A | 3/1999 | Beckers et al. |
| 5,888,226 A | 3/1999 | Rogozinski |
| 5,890,271 A | 4/1999 | Bromley et al. |
| 5,891,145 A | 4/1999 | Morrison et al. |
| 5,893,831 A | 4/1999 | Koros et al. |
| 5,899,425 A | 5/1999 | Corey, Jr. et al. |
| 5,899,904 A | 5/1999 | Errico et al. |
| 5,899,905 A | 5/1999 | Errico et al. |
| 5,902,231 A | 5/1999 | Foley et al. |
| 5,902,233 A | 5/1999 | Farley et al. |
| 5,902,304 A | 5/1999 | Walker et al. |
| 5,904,683 A | 5/1999 | Pohndorf et al. |
| RE36,221 E | 6/1999 | Breard et al. |
| 5,908,382 A | 6/1999 | Koros et al. |
| 5,910,141 A | 6/1999 | Morrison et al. |
| 5,928,139 A | 7/1999 | Koros et al. |
| 5,928,231 A | 7/1999 | Klein et al. |
| 5,928,233 A | 7/1999 | Apfelbaum et al. |
| 5,931,777 A | 8/1999 | Sava |
| 5,938,663 A | 8/1999 | Petreto |
| 5,941,885 A | 8/1999 | Jackson |
| 5,944,465 A | 8/1999 | Janitzki |
| 5,944,658 A | 8/1999 | Koros et al. |
| 5,947,967 A | 9/1999 | Barker |
| 5,947,970 A | 9/1999 | Schmelzeisen et al. |
| 5,951,553 A | 9/1999 | Betz et al. |
| 5,951,558 A | 9/1999 | Fiz |
| 5,954,722 A | 9/1999 | Bono |
| 5,954,725 A | 9/1999 | Sherman et al. |
| 5,961,516 A | 10/1999 | Graf |
| 5,961,517 A | 10/1999 | Biedermann et al. |
| 5,961,518 A | 10/1999 | Errico et al. |
| 5,964,760 A | 10/1999 | Richelsoph |
| 5,964,762 A | 10/1999 | Biedermann et al. |
| 5,964,763 A | 10/1999 | Incavo et al. |
| 5,967,970 A | 10/1999 | Cowan et al. |
| 5,967,972 A | 10/1999 | Santilli et al. |
| 5,971,987 A | 10/1999 | Huxel et al. |
| 5,976,135 A | 11/1999 | Sherman et al. |
| 5,976,140 A | 11/1999 | Haas |
| 5,976,146 A | 11/1999 | Ogawa et al. |
| 5,976,186 A | 11/1999 | Bao et al. |
| 5,980,522 A | 11/1999 | Koros et al. |
| 5,984,865 A | 11/1999 | Farley et al. |
| 5,984,923 A | 11/1999 | Breard |
| 5,984,967 A | 11/1999 | Zdeblick et al. |
| 5,993,385 A | 11/1999 | Johnston et al. |
| 5,993,449 A | 11/1999 | Schlaepfer et al. |
| 5,997,539 A | 12/1999 | Errico et al. |
| 6,001,098 A | 12/1999 | Metz-Stavenhagen et al. |
| 6,001,130 A | 12/1999 | Bryan et al. |
| 6,004,326 A | 12/1999 | Castro et al. |
| 6,004,349 A | 12/1999 | Jackson |
| 6,010,503 A | 1/2000 | Richelsoph et al. |
| 6,010,692 A | 1/2000 | Goldberg et al. |
| 6,016,727 A | 1/2000 | Morgan |
| 6,017,342 A | 1/2000 | Rinner |
| 6,017,344 A | 1/2000 | Errico et al. |
| 6,019,759 A | 2/2000 | Rogozinski |
| 6,019,792 A | 2/2000 | Cauthen |
| 6,022,350 A | 2/2000 | Ganem |
| 6,022,376 A | 2/2000 | Assell et al. |
| 6,030,388 A | 2/2000 | Yoshimi et al. |
| 6,033,170 A | 3/2000 | Gold |
| 6,033,406 A | 3/2000 | Mathews |
| 6,033,436 A | 3/2000 | Steinke et al. |
| 6,039,740 A | 3/2000 | Olerud |
| 6,039,761 A | 3/2000 | Li et al. |
| D422,705 S | 4/2000 | Koros et al. |
| 6,045,555 A | 4/2000 | Smith et al. |
| 6,045,579 A | 4/2000 | Hochshuler et al. |
| 6,048,302 A | 4/2000 | Markoll |
| 6,048,342 A | 4/2000 | Zucherman et al. |
| 6,048,343 A | 4/2000 | Mathis et al. |
| 6,050,997 A | 4/2000 | Mullane |
| 6,053,917 A | 4/2000 | Sherman et al. |
| 6,059,785 A | 5/2000 | Schavan et al. |
| 6,059,786 A | 5/2000 | Jackson |
| 6,063,089 A | 5/2000 | Errico et al. |
| 6,063,090 A | 5/2000 | Schlaepfer |
| 6,066,174 A | 5/2000 | Farris |
| 6,066,175 A | 5/2000 | Henderson et al. |
| 6,068,630 A | 5/2000 | Zucherman et al. |
| 6,071,310 A | 6/2000 | Picha et al. |
| 6,074,343 A * | 6/2000 | Nathanson ......... A61B 17/0206 600/224 |
| 6,074,390 A | 6/2000 | Zucherman et al. |
| 6,074,391 A | 6/2000 | Metz-Stavenhagen et al. |
| 6,077,262 A | 6/2000 | Schlaepfer et al. |
| 6,080,193 A | 6/2000 | Hochshuler et al. |
| 6,083,224 A | 7/2000 | Gertzbein et al. |
| 6,083,225 A | 7/2000 | Winslow et al. |
| 6,083,624 A | 7/2000 | Hiura |
| 6,086,588 A | 7/2000 | Ameil et al. |
| 6,086,589 A | 7/2000 | Kuslich et al. |
| 6,086,613 A | 7/2000 | Camino et al. |
| 6,090,110 A | 7/2000 | Metz-Stavenhagen |
| 6,090,111 A | 7/2000 | Nichols |
| 6,090,113 A | 7/2000 | Le Couedic et al. |
| 6,093,205 A | 7/2000 | McLeod et al. |
| 6,096,060 A | 8/2000 | Fitts et al. |
| 6,099,528 A | 8/2000 | Saurat |
| 6,099,531 A | 8/2000 | Bonutti |
| 6,102,912 A | 8/2000 | Cazin et al. |
| 6,102,913 A | 8/2000 | Jackson |
| 6,110,172 A | 8/2000 | Jackson |
| 6,110,173 A | 8/2000 | Thomas, Jr. |
| 6,111,164 A | 8/2000 | Rainey et al. |
| 6,113,599 A | 9/2000 | Landsberger |
| 6,113,601 A | 9/2000 | Tatar |
| 6,113,638 A | 9/2000 | Williams et al. |
| 6,117,135 A | 9/2000 | Schlaepfer |
| 6,117,137 A | 9/2000 | Halm et al. |
| 6,119,631 A | 9/2000 | Markoll |
| 6,120,502 A | 9/2000 | Michelson |
| 6,123,706 A | 9/2000 | Lange |
| 6,123,707 A | 9/2000 | Wagner |
| 6,126,689 A | 10/2000 | Brett |

(56) References Cited

U.S. PATENT DOCUMENTS

| | | | |
|---|---|---|---|
| 6,132,370 A | 10/2000 | Furnish et al. | |
| 6,132,430 A | 10/2000 | Wagner | |
| 6,132,431 A | 10/2000 | Nilsson et al. | |
| 6,132,432 A | 10/2000 | Richelsoph | |
| 6,132,434 A | 10/2000 | Sherman et al. | |
| 6,132,464 A | 10/2000 | Martin | |
| 6,136,000 A | 10/2000 | Louis et al. | |
| 6,136,002 A | 10/2000 | Shih et al. | |
| 6,139,316 A | 10/2000 | Sachdeva et al. | |
| 6,139,493 A | 10/2000 | Koros et al. | |
| 6,139,549 A | 10/2000 | Keller | |
| 6,143,032 A | 11/2000 | Schafer et al. | |
| 6,143,033 A * | 11/2000 | Paul | A61F 2/447 623/17.11 |
| 6,146,044 A | 11/2000 | Calvet | |
| 6,146,383 A | 11/2000 | Studer et al. | |
| 6,146,422 A | 11/2000 | Lawson | |
| 6,149,650 A | 11/2000 | Michelson | |
| 6,152,927 A | 11/2000 | Farris et al. | |
| 6,156,037 A | 12/2000 | Lehuec et al. | |
| 6,159,210 A | 12/2000 | Voor | |
| 6,159,211 A | 12/2000 | Boriani et al. | |
| 6,159,215 A | 12/2000 | Urbahns et al. | |
| 6,159,244 A | 12/2000 | Suddaby | |
| 6,162,252 A | 12/2000 | Kuras et al. | |
| 6,174,311 B1 | 1/2001 | Branch et al. | |
| 6,176,882 B1 | 1/2001 | Biedermann et al. | |
| 6,179,838 B1 | 1/2001 | Fiz | |
| 6,179,873 B1 | 1/2001 | Zientek | |
| 6,179,874 B1 | 1/2001 | Cauthen | |
| 6,183,472 B1 | 2/2001 | Lutz | |
| 6,183,473 B1 | 2/2001 | Ashman | |
| 6,186,005 B1 | 2/2001 | Leidl | |
| 6,186,718 B1 | 2/2001 | Fogard | |
| 6,187,005 B1 | 2/2001 | Brace et al. | |
| 6,193,720 B1 | 2/2001 | Yuan et al. | |
| 6,193,721 B1 | 2/2001 | Michelson | |
| 6,193,757 B1 | 2/2001 | Foley et al. | |
| 6,197,033 B1 | 3/2001 | Haid, Jr. et al. | |
| 6,200,322 B1 | 3/2001 | Branch et al. | |
| 6,206,826 B1 | 3/2001 | Mathews et al. | |
| 6,206,879 B1 | 3/2001 | Marnay et al. | |
| 6,206,922 B1 | 3/2001 | Zdeblick et al. | |
| 6,206,923 B1 | 3/2001 | Boyd et al. | |
| D440,311 S | 4/2001 | Michelson | |
| 6,210,376 B1 | 4/2001 | Grayson | |
| 6,210,412 B1 | 4/2001 | Michelson | |
| 6,210,413 B1 | 4/2001 | Justis et al. | |
| 6,214,005 B1 | 4/2001 | Benzel et al. | |
| 6,214,012 B1 | 4/2001 | Karpman et al. | |
| 6,221,077 B1 | 4/2001 | Rinner et al. | |
| RE37,161 E | 5/2001 | Michelson et al. | |
| 6,224,545 B1 | 5/2001 | Cocchia et al. | |
| 6,224,595 B1 | 5/2001 | Michelson | |
| 6,224,596 B1 | 5/2001 | Jackson | |
| 6,224,598 B1 | 5/2001 | Jackson | |
| 6,224,602 B1 | 5/2001 | Hayes | |
| 6,224,607 B1 | 5/2001 | Michelson | |
| 6,226,548 B1 | 5/2001 | Foley et al. | |
| 6,228,022 B1 | 5/2001 | Friesem et al. | |
| 6,228,085 B1 | 5/2001 | Theken et al. | |
| 6,231,575 B1 | 5/2001 | Krag | |
| 6,234,705 B1 | 5/2001 | Troxell | |
| 6,235,028 B1 | 5/2001 | Brumfield et al. | |
| 6,235,034 B1 | 5/2001 | Bray | |
| 6,235,726 B1 | 5/2001 | Burns et al. | |
| 6,238,396 B1 | 5/2001 | Lombardo | |
| 6,241,729 B1 | 6/2001 | Estes et al. | |
| 6,241,730 B1 | 6/2001 | Alby | |
| 6,241,769 B1 | 6/2001 | Nicholson et al. | |
| 6,241,770 B1 | 6/2001 | Michelson | |
| 6,245,072 B1 | 6/2001 | Zdeblick et al. | |
| 6,245,108 B1 | 6/2001 | Biscup | |
| 6,248,104 B1 | 6/2001 | Chopin et al. | |
| 6,248,105 B1 | 6/2001 | Schlaepfer et al. | |
| 6,248,106 B1 | 6/2001 | Ferree | |
| 6,248,107 B1 | 6/2001 | Foley et al. | |
| 6,248,110 B1 | 6/2001 | Reiley et al. | |
| 6,250,984 B1 | 6/2001 | Jin et al. | |
| 6,251,112 B1 | 6/2001 | Jackson | |
| 6,251,140 B1 | 6/2001 | Marino et al. | |
| 6,254,146 B1 | 7/2001 | Church | |
| 6,254,602 B1 | 7/2001 | Justis | |
| 6,254,603 B1 | 7/2001 | Gertzbein et al. | |
| 6,258,089 B1 | 7/2001 | Campbell et al. | |
| 6,258,125 B1 | 7/2001 | Paul et al. | |
| 6,261,287 B1 | 7/2001 | Metz-Stavenhagen | |
| 6,261,291 B1 | 7/2001 | Talaber et al. | |
| 6,264,656 B1 | 7/2001 | Michelson | |
| 6,267,764 B1 | 7/2001 | Elberg | |
| 6,267,765 B1 | 7/2001 | Taylor et al. | |
| 6,270,498 B1 | 8/2001 | Michelson | |
| 6,273,888 B1 | 8/2001 | Justis | |
| 6,273,889 B1 | 8/2001 | Richelsoph | |
| 6,277,122 B1 | 8/2001 | McGahan et al. | |
| 6,277,149 B1 | 8/2001 | Boyle et al. | |
| 6,280,442 B1 | 8/2001 | Barker et al. | |
| 6,280,445 B1 | 8/2001 | Morrison et al. | |
| D448,081 S | 9/2001 | Koros et al. | |
| 6,283,967 B1 | 9/2001 | Troxell et al. | |
| 6,287,308 B1 | 9/2001 | Betz et al. | |
| 6,287,309 B1 | 9/2001 | Baccelli et al. | |
| 6,287,311 B1 | 9/2001 | Sherman et al. | |
| 6,290,703 B1 | 9/2001 | Ganem | |
| 6,293,949 B1 | 9/2001 | Justis et al. | |
| 6,294,202 B1 | 9/2001 | Burns et al. | |
| D449,692 S | 10/2001 | Michelson | |
| 6,296,642 B1 | 10/2001 | Morrison et al. | |
| 6,296,643 B1 | 10/2001 | Hopf et al. | |
| 6,296,664 B1 | 10/2001 | Middleton | |
| 6,299,613 B1 | 10/2001 | Ogilvie et al. | |
| 6,302,843 B1 | 10/2001 | Lees et al. | |
| 6,302,888 B1 | 10/2001 | Mellinger et al. | |
| 6,302,914 B1 | 10/2001 | Michelson | |
| 6,304,178 B1 | 10/2001 | Hayashida | |
| 6,306,136 B1 | 10/2001 | Baccelli | |
| 6,306,137 B2 | 10/2001 | Troxell | |
| 6,306,170 B2 | 10/2001 | Ray | |
| 6,309,391 B1 | 10/2001 | Crandall et al. | |
| 6,312,431 B1 | 11/2001 | Asfora | |
| 6,315,564 B1 | 11/2001 | Levisman | |
| 6,315,779 B1 | 11/2001 | Morrison et al. | |
| 6,317,957 B1 | 11/2001 | Gregor et al. | |
| 6,319,002 B1 | 11/2001 | Pond | |
| 6,319,257 B1 | 11/2001 | Carignan et al. | |
| 6,322,500 B1 | 11/2001 | Sikora et al. | |
| RE37,479 E | 12/2001 | Kuslich | |
| 6,331,179 B1 | 12/2001 | Freid et al. | |
| 6,332,882 B1 | 12/2001 | Zucherman et al. | |
| 6,340,345 B1 | 1/2002 | Lees et al. | |
| 6,342,074 B1 | 1/2002 | Simpson | |
| 6,344,057 B1 | 2/2002 | Rabbe et al. | |
| 6,348,058 B1 | 2/2002 | Melkent et al. | |
| 6,348,071 B1 | 2/2002 | Steffee et al. | |
| 6,350,283 B1 | 2/2002 | Michelson | |
| 6,355,038 B1 | 3/2002 | Pisharodi | |
| 6,355,039 B1 | 3/2002 | Troussel et al. | |
| 6,355,040 B1 | 3/2002 | Richelsoph et al. | |
| 6,360,750 B1 | 3/2002 | Gerber et al. | |
| 6,361,258 B1 | 3/2002 | Heesch | |
| RE37,665 E | 4/2002 | Ralph | |
| 6,364,880 B1 | 4/2002 | Michelson | |
| 6,364,881 B1 | 4/2002 | Apgar et al. | |
| 6,364,883 B1 | 4/2002 | Santilli | |
| 6,368,320 B1 | 4/2002 | Le Couedic et al. | |
| 6,368,321 B1 | 4/2002 | Jackson | |
| 6,368,350 B1 | 4/2002 | Erickson et al. | |
| 6,371,957 B1 | 4/2002 | Amrein et al. | |
| 6,371,987 B1 | 4/2002 | Weiland et al. | |
| 6,371,988 B1 | 4/2002 | Pafford et al. | |
| 6,375,655 B1 | 4/2002 | Zdeblick et al. | |
| 6,375,681 B1 | 4/2002 | Truscott | |
| 6,379,355 B1 | 4/2002 | Zucherman et al. | |
| 6,379,357 B1 | 4/2002 | Bernstein et al. | |

(56) References Cited

U.S. PATENT DOCUMENTS

| | | |
|---|---|---|
| 6,387,130 B1 | 5/2002 | Stone et al. |
| 6,389,391 B1 | 5/2002 | Terauchi |
| 6,395,031 B1 | 5/2002 | Foley et al. |
| 6,395,035 B2 | 5/2002 | Bresina et al. |
| 6,398,783 B1 | 6/2002 | Michelson |
| 6,402,749 B1 | 6/2002 | Ashman |
| 6,402,750 B1 | 6/2002 | Atkinson et al. |
| 6,402,751 B1 | 6/2002 | Hoeck et al. |
| 6,402,752 B2 | 6/2002 | Schaffler-Wachter et al. |
| 6,402,756 B1 | 6/2002 | Ralph et al. |
| 6,402,757 B1 | 6/2002 | Moore, III et al. |
| 6,402,785 B1 | 6/2002 | Zdeblick et al. |
| 6,406,478 B1 | 6/2002 | Kuo |
| 6,409,765 B1 | 6/2002 | Bianchi et al. |
| 6,412,999 B1 | 7/2002 | Pierpont |
| 6,413,258 B1 | 7/2002 | Bernhardt, Jr. |
| 6,413,259 B1 | 7/2002 | Lyons et al. |
| 6,413,278 B1 | 7/2002 | Marchosky |
| 6,416,465 B2 | 7/2002 | Brau |
| 6,416,515 B1 | 7/2002 | Wagner |
| 6,419,676 B1 | 7/2002 | Zucherman et al. |
| 6,419,677 B2 | 7/2002 | Zucherman et al. |
| 6,419,703 B1 | 7/2002 | Fallin et al. |
| 6,419,704 B1 | 7/2002 | Ferree |
| 6,419,706 B1 | 7/2002 | Graf |
| 6,423,063 B1 | 7/2002 | Bonutti |
| 6,423,095 B1 | 7/2002 | Hoeck et al. |
| 6,428,542 B1 | 8/2002 | Michelson |
| 6,428,576 B1 | 8/2002 | Haldimann |
| 6,432,108 B1 | 8/2002 | Burgess et al. |
| 6,432,140 B1 | 8/2002 | Lin |
| 6,440,133 B1 | 8/2002 | Beale et al. |
| 6,440,137 B1 | 8/2002 | Horvath et al. |
| 6,440,139 B2 | 8/2002 | Michelson |
| 6,440,168 B1 | 8/2002 | Cauthen |
| 6,440,169 B1 | 8/2002 | Elberg et al. |
| 6,440,170 B1 | 8/2002 | Jackson |
| 6,443,956 B1 | 9/2002 | Ray |
| 6,443,989 B1 | 9/2002 | Jackson |
| 6,447,440 B1 | 9/2002 | Markoll |
| 6,447,443 B1 | 9/2002 | Keogh et al. |
| 6,447,547 B1 | 9/2002 | Michelson |
| 6,447,548 B1 | 9/2002 | Ralph et al. |
| 6,451,019 B1 | 9/2002 | Zucherman et al. |
| 6,451,020 B1 | 9/2002 | Zucherman et al. |
| 6,451,021 B1 | 9/2002 | Ralph et al. |
| 6,454,769 B2 | 9/2002 | Wagner et al. |
| 6,454,771 B1 | 9/2002 | Michelson |
| 6,454,773 B1 | 9/2002 | Sherman et al. |
| 6,458,159 B1 | 10/2002 | Thalgott |
| 6,461,358 B1 | 10/2002 | Faccioli et al. |
| 6,461,359 B1 | 10/2002 | Tribus et al. |
| 6,468,310 B1 | 10/2002 | Ralph et al. |
| 6,471,703 B1 | 10/2002 | Ashman |
| 6,471,704 B2 | 10/2002 | Gertzbein et al. |
| 6,471,705 B1 | 10/2002 | Biedermann et al. |
| 6,471,724 B2 | 10/2002 | Zdeblick et al. |
| 6,475,218 B2 | 11/2002 | Gournay et al. |
| 6,478,796 B2 | 11/2002 | Zucherman et al. |
| 6,478,798 B1 | 11/2002 | Howland |
| 6,478,800 B1 | 11/2002 | Fraser et al. |
| 6,478,801 B1 | 11/2002 | Ralph et al. |
| 6,482,234 B1 | 11/2002 | Weber et al. |
| 6,485,491 B1 | 11/2002 | Farris et al. |
| 6,485,492 B1 | 11/2002 | Halm et al. |
| 6,485,494 B1 | 11/2002 | Haider |
| 6,485,517 B1 | 11/2002 | Michelson |
| 6,485,518 B1 | 11/2002 | Cornwall et al. |
| 6,488,681 B2 | 12/2002 | Martin et al. |
| 6,497,726 B1 | 12/2002 | Carter et al. |
| 6,500,205 B1 | 12/2002 | Michelson |
| 6,503,250 B2 | 1/2003 | Paul |
| 6,508,818 B2 | 1/2003 | Steiner et al. |
| 6,508,839 B1 | 1/2003 | Lambrecht et al. |
| 6,511,484 B2 | 1/2003 | Torode et al. |
| 6,514,256 B2 | 2/2003 | Zucherman et al. |
| 6,514,260 B1 | 2/2003 | Zdeblick et al. |
| 6,517,580 B1 | 2/2003 | Ramadan et al. |
| 6,520,962 B1 | 2/2003 | Taylor et al. |
| 6,520,967 B1 | 2/2003 | Cauthen |
| 6,520,996 B1 | 2/2003 | Manasas et al. |
| 6,521,223 B1 | 2/2003 | Calias et al. |
| 6,524,233 B2 | 2/2003 | Markoll |
| 6,524,238 B2 | 2/2003 | Velikaris et al. |
| 6,524,312 B2 | 2/2003 | Landry et al. |
| 6,524,315 B1 | 2/2003 | Selvitelli et al. |
| 6,527,773 B1 | 3/2003 | Lin et al. |
| 6,527,803 B1 | 3/2003 | Crozet et al. |
| 6,527,804 B1 | 3/2003 | Gauchet et al. |
| 6,527,806 B2 | 3/2003 | Ralph et al. |
| 6,530,929 B1 | 3/2003 | Justis et al. |
| 6,531,146 B2 | 3/2003 | Calhoun et al. |
| 6,533,786 B1 | 3/2003 | Needham et al. |
| 6,537,276 B2 | 3/2003 | Metz-Stavenhagen |
| 6,537,279 B1 | 3/2003 | Michelson |
| 6,538,262 B1 | 3/2003 | Crespi et al. |
| 6,539,826 B2 | 4/2003 | Oesterle et al. |
| 6,540,749 B2 | 4/2003 | Schaefer et al. |
| 6,540,785 B1 | 4/2003 | Gill et al. |
| 6,547,790 B2 | 4/2003 | Harkey, III et al. |
| 6,547,795 B2 | 4/2003 | Schneiderman |
| 6,551,242 B1 | 4/2003 | Furnish et al. |
| 6,551,320 B2 | 4/2003 | Lieberman |
| 6,551,322 B1 | 4/2003 | Lieberman |
| 6,551,323 B2 | 4/2003 | Doubler et al. |
| 6,554,831 B1 | 4/2003 | Rivard et al. |
| 6,554,832 B2 | 4/2003 | Shluzas |
| 6,554,834 B1 | 4/2003 | Crozet et al. |
| 6,554,863 B2 | 4/2003 | Paul et al. |
| 6,558,386 B1 | 5/2003 | Cragg |
| 6,558,387 B2 | 5/2003 | Errico et al. |
| 6,558,390 B2 | 5/2003 | Cragg |
| 6,558,423 B1 | 5/2003 | Michelson |
| 6,558,424 B2 | 5/2003 | Thalgott |
| 6,562,038 B1 | 5/2003 | Morrison |
| 6,562,040 B1 | 5/2003 | Wagner |
| 6,562,046 B2 | 5/2003 | Sasso |
| 6,562,074 B2 | 5/2003 | Gerbec et al. |
| 6,565,565 B1 | 5/2003 | Yuan et al. |
| 6,565,567 B1 | 5/2003 | Haider |
| 6,565,571 B1 | 5/2003 | Jackowski et al. |
| 6,565,605 B2 | 5/2003 | Goble et al. |
| 6,569,168 B2 | 5/2003 | Lin |
| 6,572,618 B1 | 6/2003 | Morrison |
| 6,575,899 B1 | 6/2003 | Foley et al. |
| 6,575,981 B1 | 6/2003 | Boyd et al. |
| 6,576,016 B1 | 6/2003 | Hochshuler et al. |
| 6,579,291 B1 | 6/2003 | Keith et al. |
| 6,579,319 B2 | 6/2003 | Goble et al. |
| 6,582,431 B1 | 6/2003 | Ray |
| 6,582,433 B2 | 6/2003 | Yun |
| 6,582,436 B2 | 6/2003 | Schlapfer et al. |
| 6,582,466 B1 | 6/2003 | Gauchet |
| 6,585,740 B2 | 7/2003 | Schlapfer et al. |
| 6,589,243 B1 | 7/2003 | Viart et al. |
| 6,592,585 B2 | 7/2003 | Lee et al. |
| 6,592,624 B1 | 7/2003 | Fraser et al. |
| 6,595,992 B1 | 7/2003 | Wagner et al. |
| 6,595,993 B2 | 7/2003 | Donno et al. |
| 6,595,995 B2 | 7/2003 | Zdeblick et al. |
| 6,599,240 B2 | 7/2003 | Puchovsky et al. |
| 6,599,290 B2 | 7/2003 | Bailey et al. |
| 6,599,292 B1 | 7/2003 | Ray |
| 6,599,294 B2 | 7/2003 | Fuss et al. |
| 6,599,295 B1 | 7/2003 | Tornier et al. |
| 6,599,320 B1 | 7/2003 | Kuslich et al. |
| 6,599,321 B2 | 7/2003 | Hyde, Jr. |
| 6,602,254 B2 | 8/2003 | Gertzbein et al. |
| 6,602,255 B1 | 8/2003 | Campbell et al. |
| 6,602,256 B1 | 8/2003 | Hayes |
| 6,602,257 B1 | 8/2003 | Thramann |
| 6,605,089 B1 | 8/2003 | Michelson |
| 6,607,530 B1 | 8/2003 | Carl et al. |
| 6,607,558 B2 | 8/2003 | Kuras |

(56) References Cited

U.S. PATENT DOCUMENTS

| | | | |
|---|---|---|---|
| 6,610,063 | B2 | 8/2003 | Kumar et al. |
| 6,610,089 | B1 | 8/2003 | Liu et al. |
| 6,610,093 | B1 | 8/2003 | Pisharodi |
| 6,613,050 | B1 | 9/2003 | Wagner et al. |
| 6,613,089 | B1 | 9/2003 | Estes et al. |
| 6,613,091 | B1 | 9/2003 | Zdeblick et al. |
| 6,613,278 | B1 | 9/2003 | Mills et al. |
| 6,616,664 | B2 | 9/2003 | Walulik et al. |
| 6,616,665 | B2 | 9/2003 | Grafton et al. |
| 6,616,667 | B1 | 9/2003 | Steiger et al. |
| 6,616,669 | B2 | 9/2003 | Ogilvie et al. |
| 6,616,695 | B1 | 9/2003 | Crozet et al. |
| 6,620,163 | B1 | 9/2003 | Michelson |
| 6,622,344 | B1 | 9/2003 | Lu |
| 6,623,485 | B2 | 9/2003 | Doubler et al. |
| 6,626,347 | B2 | 9/2003 | Ng |
| 6,626,904 | B1 | 9/2003 | Jammet et al. |
| 6,626,906 | B1 | 9/2003 | Young |
| 6,626,907 | B2 | 9/2003 | Campbell et al. |
| 6,626,908 | B2 | 9/2003 | Cooper et al. |
| 6,635,059 | B2 | 10/2003 | Randall et al. |
| 6,635,060 | B2 | 10/2003 | Hanson et al. |
| 6,635,086 | B2 | 10/2003 | Lin |
| 6,635,087 | B2 | 10/2003 | Angelucci et al. |
| 6,638,276 | B2 | 10/2003 | Sharkey et al. |
| 6,638,310 | B2 | 10/2003 | Lin et al. |
| 6,641,583 | B2 | 11/2003 | Shluzas et al. |
| 6,641,585 | B2 | 11/2003 | Sato et al. |
| 6,641,586 | B2 | 11/2003 | Varieur |
| 6,641,614 | B1 | 11/2003 | Wagner et al. |
| 6,645,206 | B1 | 11/2003 | Zdeblick et al. |
| 6,645,207 | B2 | 11/2003 | Dixon et al. |
| 6,645,208 | B2 | 11/2003 | Apfelbaum et al. |
| 6,645,249 | B2 | 11/2003 | Ralph et al. |
| 6,648,885 | B1 | 11/2003 | Friesem |
| 6,648,887 | B2 | 11/2003 | Ashman |
| 6,648,888 | B1 | 11/2003 | Shluzas |
| 6,648,891 | B2 | 11/2003 | Kim |
| 6,648,894 | B2 | 11/2003 | Abdelgany et al. |
| 6,648,895 | B2 | 11/2003 | Burkus et al. |
| 6,648,917 | B2 | 11/2003 | Gerbec et al. |
| 6,652,525 | B1 | 11/2003 | Assaker et al. |
| 6,652,526 | B1 | 11/2003 | Arafiles |
| 6,652,533 | B2 | 11/2003 | O'Neil |
| 6,652,584 | B2 | 11/2003 | Michelson |
| 6,652,586 | B2 | 11/2003 | Hunter et al. |
| 6,652,765 | B1 | 11/2003 | Beaty |
| 6,652,818 | B1 | 11/2003 | Mills et al. |
| 6,656,179 | B1 | 12/2003 | Schaefer et al. |
| 6,656,181 | B2 | 12/2003 | Dixon et al. |
| 6,656,224 | B2 | 12/2003 | Middleton |
| 6,660,004 | B2 | 12/2003 | Barker et al. |
| 6,660,006 | B2 | 12/2003 | Markworth et al. |
| 6,663,631 | B2 | 12/2003 | Kuntz |
| 6,663,632 | B1 | 12/2003 | Frigg |
| 6,663,635 | B2 | 12/2003 | Frigg et al. |
| 6,663,642 | B2 | 12/2003 | Beyar et al. |
| 6,665,555 | B2 | 12/2003 | Henderson et al. |
| 6,666,612 | B2 | 12/2003 | Lorigny et al. |
| 6,666,866 | B2 | 12/2003 | Martz et al. |
| 6,666,867 | B2 | 12/2003 | Ralph et al. |
| 6,666,890 | B2 | 12/2003 | Michelson |
| 6,666,891 | B2 | 12/2003 | Boehm et al. |
| 6,668,688 | B2 | 12/2003 | Zhao et al. |
| 6,669,700 | B1 | 12/2003 | Farris et al. |
| 6,669,730 | B2 | 12/2003 | Ralph et al. |
| 6,673,073 | B1 | 1/2004 | Schaefer |
| 6,673,113 | B2 | 1/2004 | Ralph et al. |
| 6,673,362 | B2 | 1/2004 | Calhoun et al. |
| 6,675,805 | B1 | 1/2004 | Graether |
| 6,676,661 | B1 | 1/2004 | Martin et al. |
| 6,676,703 | B2 | 1/2004 | Biscup |
| 6,679,833 | B2 | 1/2004 | Smith et al. |
| 6,679,883 | B2 | 1/2004 | Hawkes et al. |
| 6,679,887 | B2 | 1/2004 | Nicholson et al. |
| 6,679,915 | B1 | 1/2004 | Cauthen |
| 6,682,529 | B2 | 1/2004 | Stahurski |
| 6,682,530 | B2 | 1/2004 | Dixon et al. |
| 6,682,533 | B1 | 1/2004 | Dinsdale et al. |
| 6,682,562 | B2 | 1/2004 | Viart et al. |
| 6,683,690 | B1 | 1/2004 | Tobias |
| 6,685,705 | B1 | 2/2004 | Taylor |
| 6,689,133 | B2 | 2/2004 | Morrison et al. |
| 6,689,134 | B2 | 2/2004 | Ralph et al. |
| 6,692,495 | B1 | 2/2004 | Zacouto |
| 6,695,842 | B2 | 2/2004 | Zucherman et al. |
| 6,695,843 | B2 | 2/2004 | Biedermann et al. |
| 6,695,846 | B2 | 2/2004 | Richelsoph et al. |
| 6,695,851 | B2 | 2/2004 | Zdeblick et al. |
| 6,699,246 | B2 | 3/2004 | Zucherman et al. |
| 6,699,247 | B2 | 3/2004 | Zucherman et al. |
| 6,699,249 | B2 | 3/2004 | Schlaepfer et al. |
| 6,702,814 | B2 | 3/2004 | Walulik et al. |
| 6,706,045 | B2 | 3/2004 | Lin et al. |
| 6,706,067 | B2 | 3/2004 | Shimp et al. |
| 6,706,068 | B2 | 3/2004 | Ferree |
| 6,706,070 | B1 | 3/2004 | Wagner et al. |
| 6,706,922 | B2 | 3/2004 | Wolff et al. |
| 6,709,389 | B2 | 3/2004 | Farascioni |
| 6,709,458 | B2 | 3/2004 | Michelson |
| 6,709,461 | B2 | 3/2004 | O'Neil et al. |
| 6,712,795 | B1 | 3/2004 | Cohen |
| 6,712,818 | B1 | 3/2004 | Michelson |
| 6,712,819 | B2 | 3/2004 | Zucherman et al. |
| 6,712,852 | B1 | 3/2004 | Chung et al. |
| 6,716,212 | B1 | 4/2004 | Pickens |
| 6,716,213 | B2 | 4/2004 | Shitoto |
| 6,716,214 | B1 | 4/2004 | Jackson |
| 6,716,247 | B2 | 4/2004 | Michelson |
| 6,719,794 | B2 | 4/2004 | Gerber et al. |
| 6,719,795 | B1 | 4/2004 | Cornwall et al. |
| 6,723,043 | B2 | 4/2004 | Kleeman et al. |
| 6,723,096 | B1 | 4/2004 | Dorchak et al. |
| 6,723,100 | B2 | 4/2004 | Biedermann et al. |
| 6,723,126 | B1 | 4/2004 | Berry |
| 6,723,127 | B2 | 4/2004 | Ralph et al. |
| 6,723,128 | B2 | 4/2004 | Uk |
| 6,726,685 | B2 | 4/2004 | To et al. |
| 6,726,687 | B2 | 4/2004 | Jackson |
| 6,726,720 | B2 | 4/2004 | Ross et al. |
| 6,730,093 | B2 | 5/2004 | Saint |
| 6,730,126 | B2 | 5/2004 | Boehm, Jr. et al. |
| 6,730,127 | B2 | 5/2004 | Michelson |
| 6,733,444 | B2 | 5/2004 | Phillips |
| 6,733,496 | B2 | 5/2004 | Sharkey et al. |
| 6,733,502 | B2 | 5/2004 | Altarac et al. |
| 6,733,531 | B1 | 5/2004 | Trieu |
| 6,733,534 | B2 | 5/2004 | Sherman |
| 6,733,535 | B2 | 5/2004 | Michelson |
| 6,736,816 | B2 | 5/2004 | Ritland |
| 6,736,817 | B2 | 5/2004 | Troxell et al. |
| 6,736,820 | B2 | 5/2004 | Biedermann et al. |
| 6,739,068 | B1 | 5/2004 | Rinner |
| 6,740,086 | B2 | 5/2004 | Richelsoph |
| 6,740,087 | B2 | 5/2004 | Knox |
| 6,740,090 | B1 | 5/2004 | Cragg et al. |
| 6,740,118 | B2 | 5/2004 | Eisermann et al. |
| 6,743,231 | B1 | 6/2004 | Gray et al. |
| 6,743,255 | B2 | 6/2004 | Ferree |
| 6,743,256 | B2 | 6/2004 | Mason |
| 6,743,257 | B2 | 6/2004 | Castro |
| 6,746,449 | B2 | 6/2004 | Jones et al. |
| 6,746,454 | B2 | 6/2004 | Winterbottom et al. |
| 6,749,613 | B1 | 6/2004 | Conchy et al. |
| 6,749,614 | B2 | 6/2004 | Teitelbaum et al. |
| 6,749,635 | B1 | 6/2004 | Bryan |
| 6,749,636 | B2 | 6/2004 | Michelson |
| 6,752,832 | B2 | 6/2004 | Neumann |
| 6,755,829 | B1 | 6/2004 | Bono et al. |
| 6,755,830 | B2 | 6/2004 | Minfelde et al. |
| 6,755,833 | B1 | 6/2004 | Paul et al. |
| 6,755,835 | B2 | 6/2004 | Schultheiss et al. |
| 6,755,836 | B1 | 6/2004 | Lewis |
| 6,755,841 | B2 | 6/2004 | Fraser et al. |

(56) References Cited

U.S. PATENT DOCUMENTS

| | | |
|---|---|---|
| 6,758,861 B2 | 7/2004 | Ralph et al. |
| 6,761,719 B2 | 7/2004 | Justis et al. |
| 6,761,720 B1 | 7/2004 | Senegas |
| 6,761,721 B2 | 7/2004 | Burgess et al. |
| 6,761,723 B2 | 7/2004 | Buttermann et al. |
| 6,761,738 B1 | 7/2004 | Boyd |
| 6,764,515 B2 | 7/2004 | Ralph et al. |
| 6,767,351 B2 | 7/2004 | Orbay et al. |
| 6,767,367 B1 | 7/2004 | Michelson |
| 6,770,074 B2 | 8/2004 | Michelson |
| 6,770,075 B2 | 8/2004 | Howland |
| 6,770,096 B2 | 8/2004 | Bolger et al. |
| 6,778,861 B1 | 8/2004 | Liebrecht et al. |
| 6,780,186 B2 | 8/2004 | Errico et al. |
| 6,780,192 B2 | 8/2004 | McKay et al. |
| 6,783,527 B2 | 8/2004 | Drewry et al. |
| 6,783,547 B2 | 8/2004 | Castro |
| 6,790,209 B2 | 9/2004 | Beale et al. |
| 6,790,210 B1 | 9/2004 | Cragg et al. |
| 6,793,658 B2 | 9/2004 | Lehuec et al. |
| 6,802,844 B2 | 10/2004 | Ferree |
| 6,805,697 B1 | 10/2004 | Helm et al. |
| 6,805,713 B1 | 10/2004 | Carter et al. |
| 6,805,714 B2 | 10/2004 | Sutcliffe |
| 6,808,493 B1 | 10/2004 | Bookwalter et al. |
| 6,808,537 B2 | 10/2004 | Michelson |
| 6,811,567 B2 | 11/2004 | Reiley |
| 6,814,737 B2 | 11/2004 | Cauthen |
| 6,821,277 B2 | 11/2004 | Teitelbaum |
| 6,824,565 B2 | 11/2004 | Muhanna et al. |
| 6,827,719 B2 | 12/2004 | Ralph et al. |
| 6,827,722 B1 | 12/2004 | Schoenefeld |
| 6,830,570 B1 | 12/2004 | Frey et al. |
| 6,830,571 B2 | 12/2004 | Lenke et al. |
| 6,830,589 B2 | 12/2004 | Erickson |
| 6,832,997 B2 | 12/2004 | Uchida et al. |
| 6,832,999 B2 | 12/2004 | Ueyama et al. |
| 6,835,196 B2 | 12/2004 | Biedermann et al. |
| 6,835,206 B2 | 12/2004 | Jackson |
| 6,837,884 B2 | 1/2005 | Woloszko |
| 6,837,889 B2 | 1/2005 | Shluzas |
| 6,840,940 B2 | 1/2005 | Ralph et al. |
| 6,843,791 B2 | 1/2005 | Serhan |
| 6,849,076 B2 | 2/2005 | Blunn et al. |
| 6,849,093 B2 | 2/2005 | Michelson |
| 6,852,127 B2 | 2/2005 | Varga et al. |
| 6,852,128 B2 | 2/2005 | Lange |
| 6,852,129 B2 | 2/2005 | Gerbec et al. |
| 6,855,147 B2 | 2/2005 | Harrington et al. |
| 6,857,343 B1 | 2/2005 | Easterbrooks et al. |
| 6,858,030 B2 | 2/2005 | Martin et al. |
| 6,858,031 B2 | 2/2005 | Morrison et al. |
| 6,860,850 B2 | 3/2005 | Phillips et al. |
| 6,863,673 B2 | 3/2005 | Gerbec et al. |
| 6,869,398 B2 | 3/2005 | Obenchain et al. |
| 6,869,432 B2 | 3/2005 | Schlapfer et al. |
| 6,869,433 B2 | 3/2005 | Glascott |
| 6,872,208 B1 | 3/2005 | McBride et al. |
| 6,875,211 B2 | 4/2005 | Nichols et al. |
| 6,881,228 B2 | 4/2005 | Zdeblick et al. |
| 6,884,241 B2 | 4/2005 | Bertranou et al. |
| 6,884,242 B2 | 4/2005 | Lehuec et al. |
| 6,884,243 B2 | 4/2005 | Sellers |
| 6,885,243 B2 | 4/2005 | Burstein et al. |
| D505,205 S | 5/2005 | Freid |
| 6,887,242 B2 | 5/2005 | Doubler et al. |
| 6,890,355 B2 | 5/2005 | Michelson |
| 6,893,444 B2 | 5/2005 | Orbay |
| 6,896,675 B2 | 5/2005 | Leung et al. |
| 6,896,676 B2 | 5/2005 | Zubok et al. |
| 6,896,677 B1 | 5/2005 | Lin |
| 6,896,680 B2 | 5/2005 | Michelson |
| 6,899,714 B2 | 5/2005 | Vaughan |
| 6,899,716 B2 | 5/2005 | Cragg |
| 6,902,566 B2 | 6/2005 | Zucherman et al. |
| 6,902,580 B2 | 6/2005 | Fallin et al. |
| 6,911,045 B2 | 6/2005 | Shimp |
| 6,916,320 B2 | 7/2005 | Michelson |
| 6,916,340 B2 | 7/2005 | Metzger et al. |
| 6,918,910 B2 | 7/2005 | Smith et al. |
| 6,918,911 B2 | 7/2005 | Biedermann et al. |
| 6,921,403 B2 | 7/2005 | Cragg et al. |
| 6,923,811 B1 | 8/2005 | Carl et al. |
| 6,923,830 B2 | 8/2005 | Michelson |
| 6,926,658 B2 | 8/2005 | Farnan |
| 6,926,737 B2 | 8/2005 | Jackson |
| 6,929,606 B2 | 8/2005 | Ritland |
| 6,929,640 B1 | 8/2005 | Underwood et al. |
| 6,932,817 B2 | 8/2005 | Baynham et al. |
| 6,932,820 B2 | 8/2005 | Osman |
| 6,936,071 B1 | 8/2005 | Marnay et al. |
| 6,945,933 B2 | 9/2005 | Branch et al. |
| 6,945,972 B2 | 9/2005 | Frigg et al. |
| 6,945,973 B2 | 9/2005 | Bray |
| 6,945,975 B2 | 9/2005 | Dalton |
| 6,947,967 B2 | 9/2005 | Ferris et al. |
| 6,949,100 B1 | 9/2005 | Venturini |
| 6,949,105 B2 | 9/2005 | Bryan et al. |
| 6,951,538 B2 | 10/2005 | Ritland |
| 6,951,561 B2 | 10/2005 | Warren et al. |
| 6,953,462 B2 | 10/2005 | Lieberman |
| 6,953,477 B2 | 10/2005 | Berry |
| 6,955,677 B2 | 10/2005 | Dahners |
| 6,958,065 B2 | 10/2005 | Ueyama et al. |
| 6,964,664 B2 | 11/2005 | Freid et al. |
| 6,964,665 B2 | 11/2005 | Thomas et al. |
| 6,964,666 B2 | 11/2005 | Jackson |
| 6,964,667 B2 | 11/2005 | Shaolian et al. |
| 6,964,687 B1 | 11/2005 | Bernard et al. |
| 6,966,910 B2 | 11/2005 | Ritland |
| 6,966,929 B2 | 11/2005 | Mitchell |
| 6,972,019 B2 | 12/2005 | Michelson |
| 6,972,035 B2 | 12/2005 | Michelson |
| 6,974,460 B2 | 12/2005 | Carbone et al. |
| 6,979,334 B2 | 12/2005 | Dalton |
| 6,980,862 B2 | 12/2005 | Fredricks et al. |
| 6,981,973 B2 | 1/2006 | McKinley |
| 6,981,975 B2 | 1/2006 | Michelson |
| 6,984,234 B2 | 1/2006 | Bray |
| 6,984,245 B2 | 1/2006 | McGahan et al. |
| 6,986,771 B2 | 1/2006 | Paul et al. |
| 6,986,772 B2 | 1/2006 | Michelson |
| 6,989,011 B2 | 1/2006 | Paul et al. |
| 6,989,044 B2 | 1/2006 | Zhang et al. |
| 6,991,632 B2 | 1/2006 | Ritland |
| 6,991,654 B2 | 1/2006 | Foley |
| 6,994,688 B2 | 2/2006 | Brauckman et al. |
| 6,997,929 B2 | 2/2006 | Manzi et al. |
| 6,997,941 B2 | 2/2006 | Sharkey et al. |
| 7,001,385 B2 | 2/2006 | Bonutti |
| 7,001,432 B2 | 2/2006 | Keller et al. |
| 7,004,947 B2 | 2/2006 | Shluzas et al. |
| RE39,035 E | 3/2006 | Finn et al. |
| 7,008,422 B2 | 3/2006 | Foley et al. |
| 7,008,424 B2 | 3/2006 | Teitelbaum |
| 7,008,426 B2 | 3/2006 | Paul |
| 7,008,453 B1 | 3/2006 | Michelson |
| 7,011,619 B1 | 3/2006 | Lewis et al. |
| 7,011,658 B2 | 3/2006 | Young |
| 7,011,660 B2 | 3/2006 | Sherman et al. |
| 7,014,608 B2 | 3/2006 | Larson et al. |
| 7,014,633 B2 | 3/2006 | Cragg |
| 7,018,378 B2 | 3/2006 | Biedermann et al. |
| 7,018,379 B2 | 3/2006 | Drewry et al. |
| 7,018,412 B2 | 3/2006 | Ferreira et al. |
| 7,018,415 B1 | 3/2006 | McKay |
| 7,018,416 B2 | 3/2006 | Hanson et al. |
| 7,022,122 B2 | 4/2006 | Amrein et al. |
| 7,025,716 B1 | 4/2006 | Meloul et al. |
| 7,025,787 B2 | 4/2006 | Bryan et al. |
| 7,029,472 B1 | 4/2006 | Fortin |
| 7,029,475 B2 | 4/2006 | Panjabi |
| 7,033,362 B2 | 4/2006 | McGahan et al. |
| RE39,089 E | 5/2006 | Ralph et al. |

(56) References Cited

U.S. PATENT DOCUMENTS

| | | |
|---|---|---|
| 7,037,339 B2 | 5/2006 | Houfburg |
| 7,041,135 B2 | 5/2006 | Michelson |
| 7,041,136 B2 | 5/2006 | Goble et al. |
| 7,044,971 B2 | 5/2006 | Suddaby |
| 7,048,736 B2 | 5/2006 | Robinson et al. |
| 7,052,497 B2 | 5/2006 | Sherman et al. |
| 7,056,321 B2 | 6/2006 | Pagliuca et al. |
| 7,056,344 B2 | 6/2006 | Huppert et al. |
| 7,060,066 B2 | 6/2006 | Zhao et al. |
| 7,060,097 B2 | 6/2006 | Fraser et al. |
| 7,063,702 B2 | 6/2006 | Michelson |
| 7,066,062 B2 | 6/2006 | Flesher |
| 7,066,937 B2 | 6/2006 | Shluzas |
| 7,066,961 B2 | 6/2006 | Michelson |
| 7,070,598 B2 | 7/2006 | Lim et al. |
| 7,074,237 B2 | 7/2006 | Goble et al. |
| 7,081,116 B1 | 7/2006 | Carly |
| 7,083,621 B2 | 8/2006 | Shaolian et al. |
| 7,083,622 B2 | 8/2006 | Simonson |
| 7,083,625 B2 | 8/2006 | Berry |
| 7,083,649 B2 | 8/2006 | Zucherman et al. |
| 7,087,057 B2 | 8/2006 | Konieczynski et al. |
| 7,087,058 B2 | 8/2006 | Cragg |
| 7,087,083 B2 | 8/2006 | Pasquet et al. |
| 7,090,674 B2 | 8/2006 | Doubler et al. |
| 7,090,679 B2 | 8/2006 | Saint-Martin et al. |
| 7,090,680 B2 | 8/2006 | Bonati et al. |
| 7,094,242 B2 | 8/2006 | Ralph et al. |
| 7,094,258 B2 | 8/2006 | Lambrecht et al. |
| 7,097,648 B1 | 8/2006 | Globerman et al. |
| 7,101,375 B2 | 9/2006 | Zucherman et al. |
| 7,101,399 B2 | 9/2006 | Errico et al. |
| 7,105,024 B2 | 9/2006 | Richelsoph |
| 7,108,698 B2 | 9/2006 | Robbins et al. |
| 7,112,206 B2 | 9/2006 | Michelson |
| 7,118,576 B2 | 10/2006 | Gitis et al. |
| 7,118,579 B2 | 10/2006 | Michelson |
| 7,118,580 B1 | 10/2006 | Beyersdorff et al. |
| 7,118,598 B2 | 10/2006 | Michelson |
| 7,121,755 B2 | 10/2006 | Schlapfer et al. |
| 7,122,629 B2 | 10/2006 | Bejanin et al. |
| 7,125,410 B2 | 10/2006 | Freudiger |
| 7,125,425 B2 | 10/2006 | Simonton et al. |
| 7,125,426 B2 | 10/2006 | Moumene et al. |
| 7,128,743 B2 | 10/2006 | Metz-Stavenhagen |
| 7,128,760 B2 | 10/2006 | Michelson |
| 7,128,761 B2 | 10/2006 | Kuras et al. |
| 7,137,985 B2 | 11/2006 | Jahng |
| 7,137,986 B2 | 11/2006 | Troxell et al. |
| 7,141,051 B2 | 11/2006 | Janowski et al. |
| 7,144,396 B2 | 12/2006 | Shluzas |
| 7,144,397 B2 | 12/2006 | Lambrecht et al. |
| 7,147,599 B2 | 12/2006 | Phillips et al. |
| 7,150,714 B2 | 12/2006 | Myles |
| 7,153,281 B2 | 12/2006 | Holmes |
| 7,153,325 B2 | 12/2006 | Kim et al. |
| 7,156,806 B2 | 1/2007 | Dobrovolny |
| 7,160,300 B2 | 1/2007 | Jackson |
| 7,163,538 B2 | 1/2007 | Altarac et al. |
| 7,163,539 B2 | 1/2007 | Abdelgany et al. |
| 7,163,558 B2 | 1/2007 | Senegas et al. |
| 7,163,561 B2 | 1/2007 | Michelson |
| 7,166,073 B2 | 1/2007 | Ritland |
| 7,166,107 B2 | 1/2007 | Anderson |
| 7,166,108 B2 | 1/2007 | Mazda et al. |
| 7,166,121 B2 | 1/2007 | Reiley et al. |
| 7,169,183 B2 | 1/2007 | Liu et al. |
| 7,179,261 B2 | 2/2007 | Sicvol et al. |
| 7,182,729 B2 | 2/2007 | Abdelgany et al. |
| 7,186,255 B2 | 3/2007 | Baynham et al. |
| 7,188,626 B2 | 3/2007 | Foley et al. |
| 7,198,644 B2 | 4/2007 | Schultz et al. |
| 7,201,751 B2 | 4/2007 | Zucherman et al. |
| 7,204,851 B2 | 4/2007 | Trieu et al. |
| 7,204,852 B2 | 4/2007 | Marnay et al. |
| 7,204,853 B2 | 4/2007 | Gordon et al. |
| 7,207,949 B2 | 4/2007 | Miles et al. |
| 7,207,991 B2 | 4/2007 | Michelson |
| 7,207,992 B2 | 4/2007 | Ritland |
| 7,211,085 B2 | 5/2007 | Michelson |
| 7,211,086 B2 | 5/2007 | Biedermann et al. |
| 7,211,087 B2 | 5/2007 | Young |
| 7,211,112 B2 | 5/2007 | Baynham et al. |
| 7,214,186 B2 | 5/2007 | Ritland |
| 7,214,227 B2 | 5/2007 | Colleran et al. |
| 7,217,291 B2 | 5/2007 | Zucherman et al. |
| 7,223,268 B2 | 5/2007 | Biedermann |
| 7,223,289 B2 | 5/2007 | Trieu et al. |
| 7,227,477 B2 | 6/2007 | Ye |
| 7,229,441 B2 | 6/2007 | Trieu et al. |
| 7,232,441 B2 | 6/2007 | Altarac et al. |
| 7,232,463 B2 | 6/2007 | Falahee |
| 7,232,464 B2 | 6/2007 | Mathieu et al. |
| 7,235,048 B2 | 6/2007 | Rein et al. |
| 7,235,105 B2 | 6/2007 | Jackson |
| 7,241,297 B2 | 7/2007 | Shaolian et al. |
| 7,250,052 B2 | 7/2007 | Landry et al. |
| 7,252,673 B2 | 8/2007 | Lim |
| 7,264,621 B2 | 9/2007 | Coates et al. |
| 7,270,665 B2 | 9/2007 | Morrison et al. |
| 7,273,496 B2 | 9/2007 | Mitchell |
| 7,276,081 B1 | 10/2007 | Coates et al. |
| 7,276,082 B2 | 10/2007 | Zdeblick et al. |
| 7,282,063 B2 | 10/2007 | Cohen et al. |
| 7,282,064 B2 | 10/2007 | Chin |
| 7,282,065 B2 | 10/2007 | Kirschman |
| 7,285,121 B2 | 10/2007 | Braun et al. |
| 7,291,149 B1 | 11/2007 | Michelson |
| 7,291,151 B2 | 11/2007 | Alvarez |
| 7,291,152 B2 | 11/2007 | Abdou |
| 7,291,153 B2 | 11/2007 | Glascott |
| 7,294,128 B2 | 11/2007 | Alleyne et al. |
| 7,294,129 B2 | 11/2007 | Hawkins et al. |
| 7,300,441 B2 | 11/2007 | Haid et al. |
| 7,303,563 B2 | 12/2007 | Poyner et al. |
| 7,306,603 B2 | 12/2007 | Boehm, Jr. et al. |
| 7,306,604 B2 | 12/2007 | Carli |
| 7,306,606 B2 | 12/2007 | Sasing |
| 7,306,628 B2 | 12/2007 | Zucherman et al. |
| 7,309,338 B2 | 12/2007 | Cragg |
| 7,311,734 B2 | 12/2007 | Hoeck et al. |
| 7,314,467 B2 | 1/2008 | Howland |
| 7,316,684 B1 | 1/2008 | Baccelli et al. |
| 7,316,714 B2 | 1/2008 | Gordon et al. |
| 7,318,817 B2 | 1/2008 | Hamada |
| 7,318,840 B2 | 1/2008 | McKay |
| 7,322,979 B2 | 1/2008 | Crandall et al. |
| 7,326,216 B2 | 2/2008 | Bertagnoli et al. |
| 7,329,258 B2 | 2/2008 | Studer |
| 7,331,961 B2 | 2/2008 | Abdou |
| 7,331,995 B2 | 2/2008 | Eisermann et al. |
| 7,335,201 B2 | 2/2008 | Doubler et al. |
| 7,335,202 B2 | 2/2008 | Matthis et al. |
| 7,335,203 B2 | 2/2008 | Winslow et al. |
| 7,338,490 B2 | 3/2008 | Ogilvie et al. |
| 7,338,491 B2 | 3/2008 | Baker et al. |
| 7,338,527 B2 | 3/2008 | Blatt et al. |
| 7,341,587 B2 | 3/2008 | Molz et al. |
| 7,347,874 B2 | 3/2008 | Disilvestro |
| 7,361,179 B2 | 4/2008 | Rousseau et al. |
| 7,361,196 B2 | 4/2008 | Fallin et al. |
| 7,374,534 B2 | 5/2008 | Dalton |
| 7,377,921 B2 | 5/2008 | Studer et al. |
| 7,377,942 B2 | 5/2008 | Berry |
| 7,396,328 B2 | 7/2008 | Penenberg |
| 7,396,360 B2 | 7/2008 | Lieberman |
| 7,410,501 B2 | 8/2008 | Michelson |
| 7,419,505 B2 | 9/2008 | Fleischmann et al. |
| 7,431,735 B2 | 10/2008 | Liu et al. |
| 7,435,262 B2 | 10/2008 | Michelson |
| 7,442,209 B2 | 10/2008 | Michelson |
| 7,445,635 B2 | 11/2008 | Fallin et al. |
| 7,445,637 B2 | 11/2008 | Taylor |
| 7,455,639 B2 | 11/2008 | Ritland |

(56) References Cited

U.S. PATENT DOCUMENTS

| | | |
|---|---|---|
| 7,455,685 B2 | 11/2008 | Justis |
| 7,465,306 B2 | 12/2008 | Pond, Jr. et al. |
| 7,473,223 B2 | 1/2009 | Fetzer |
| 7,473,276 B2 | 1/2009 | Aebi et al. |
| 7,476,228 B2 | 1/2009 | Abdou |
| 7,476,238 B2 | 1/2009 | Panjabi |
| 7,479,160 B2 | 1/2009 | Branch et al. |
| 7,485,132 B1 | 2/2009 | McBride et al. |
| 7,491,205 B1 | 2/2009 | Michelson |
| 7,491,208 B2 | 2/2009 | Pond, Jr. et al. |
| 7,494,508 B2 | 2/2009 | Zeegers |
| 7,497,859 B2 | 3/2009 | Zucherman et al. |
| 7,503,918 B2 | 3/2009 | Baccelli et al. |
| 7,503,933 B2 | 3/2009 | Michelson |
| 7,520,888 B2 | 4/2009 | Trieu |
| 7,527,640 B2 | 5/2009 | Ziolo et al. |
| 7,534,265 B1 | 5/2009 | Boyd et al. |
| 7,537,565 B2 | 5/2009 | Bass |
| 7,537,616 B1 | 5/2009 | Branch et al. |
| 7,540,882 B2 | 6/2009 | Michelson |
| 7,547,308 B2 | 6/2009 | Bertagnoli et al. |
| 7,547,325 B2 | 6/2009 | Biedermann et al. |
| 7,556,639 B2 | 7/2009 | Rothman et al. |
| 7,559,930 B2 | 7/2009 | Allard et al. |
| 7,559,942 B2 | 7/2009 | Paul et al. |
| 7,563,274 B2 | 7/2009 | Justis et al. |
| 7,563,283 B2 | 7/2009 | Kwak |
| 7,566,345 B1 | 7/2009 | Fallin et al. |
| 7,569,014 B2 | 8/2009 | Bass et al. |
| 7,572,276 B2 | 8/2009 | Lim et al. |
| 7,575,580 B2 | 8/2009 | Lim et al. |
| 7,575,587 B2 | 8/2009 | Rezach et al. |
| 7,578,820 B2 | 8/2009 | Moore et al. |
| 7,578,834 B2 | 8/2009 | Abdou et al. |
| 7,578,849 B2 | 8/2009 | Trieu |
| 7,582,058 B1 | 9/2009 | Miles et al. |
| 7,582,107 B2 | 9/2009 | Trail et al. |
| 7,585,316 B2 | 9/2009 | Trieu |
| 7,588,537 B2 | 9/2009 | Bass |
| 7,588,579 B2 | 9/2009 | Mommaerts |
| 7,588,589 B2 | 9/2009 | Falahee |
| 7,588,593 B2 | 9/2009 | Aferzon |
| 7,591,839 B2 | 9/2009 | Biedermann et al. |
| 7,591,851 B2 | 9/2009 | Winslow et al. |
| 7,594,919 B2 | 9/2009 | Peterman |
| 7,594,931 B2 | 9/2009 | Louis et al. |
| 7,594,932 B2 | 9/2009 | Aferzon et al. |
| 7,597,694 B2 | 10/2009 | Lim et al. |
| 7,601,166 B2 | 10/2009 | Biedermann et al. |
| 7,601,170 B2 | 10/2009 | Winslow et al. |
| 7,604,643 B2 | 10/2009 | Ciccone et al. |
| 7,604,654 B2 | 10/2009 | Fallin et al. |
| 7,611,518 B2 | 11/2009 | Walder et al. |
| 7,618,423 B1 | 11/2009 | Valentine et al. |
| 7,618,443 B2 | 11/2009 | Abdou |
| 7,618,455 B2 | 11/2009 | Goble et al. |
| 7,618,456 B2 | 11/2009 | Mathieu et al. |
| 7,621,912 B2 | 11/2009 | Harms et al. |
| 7,621,939 B2 | 11/2009 | Zucherman et al. |
| 7,621,940 B2 | 11/2009 | Harms et al. |
| 7,621,942 B2 | 11/2009 | Piehl |
| 7,621,953 B2 | 11/2009 | Braddock et al. |
| 7,621,955 B2 | 11/2009 | Goble et al. |
| 7,621,957 B2 | 11/2009 | Errico et al. |
| 7,625,379 B2 | 12/2009 | Puno et al. |
| 7,625,380 B2 | 12/2009 | Drewry et al. |
| 7,625,393 B2 | 12/2009 | Fallin et al. |
| 7,625,396 B2 | 12/2009 | Jackson |
| 7,628,799 B2 | 12/2009 | Richelsoph et al. |
| 7,632,292 B2 | 12/2009 | Sengupta et al. |
| 7,635,366 B2 | 12/2009 | Abdou |
| 7,635,371 B2 | 12/2009 | McGahan et al. |
| 7,641,673 B2 | 1/2010 | Le et al. |
| 7,641,690 B2 | 1/2010 | Abdou |
| 7,641,693 B2 | 1/2010 | Gutlin et al. |
| 7,645,281 B2 | 1/2010 | Marik |
| 7,651,515 B2 | 1/2010 | Mack et al. |
| 7,654,954 B1 | 2/2010 | Phillips et al. |
| 7,655,026 B2 | 2/2010 | Justis et al. |
| 7,655,027 B2 | 2/2010 | Michelson |
| 7,655,028 B2 | 2/2010 | Kirschman |
| 7,655,042 B2 | 2/2010 | Foley et al. |
| 7,658,739 B2 | 2/2010 | Shluzas |
| 7,658,752 B2 | 2/2010 | Labrom et al. |
| 7,658,766 B2 | 2/2010 | Melkent et al. |
| 7,682,375 B2 | 3/2010 | Ritland |
| 7,682,396 B2 | 3/2010 | Beaurain et al. |
| 7,686,809 B2 | 3/2010 | Triplett et al. |
| 7,691,057 B2 | 4/2010 | Miles et al. |
| 7,691,129 B2 | 4/2010 | Felix |
| 7,695,496 B2 | 4/2010 | Labrom et al. |
| 7,695,498 B2 | 4/2010 | Ritland |
| 7,695,514 B2 | 4/2010 | Kwak |
| 7,695,516 B2 | 4/2010 | Zeegers |
| 7,695,517 B2 | 4/2010 | Benzel et al. |
| 7,704,271 B2 | 4/2010 | Abdou |
| 7,708,743 B2 | 5/2010 | Anderson et al. |
| 7,708,765 B2 | 5/2010 | Carl et al. |
| 7,722,618 B2 | 5/2010 | Estes et al. |
| 7,727,233 B2 | 6/2010 | Blackwell et al. |
| 7,727,280 B2 | 6/2010 | McLuen |
| 7,738,968 B2 | 6/2010 | Bleich |
| 7,744,635 B2 | 6/2010 | Sweeney et al. |
| 7,749,231 B2 | 7/2010 | Bonvallet et al. |
| 7,749,251 B2 | 7/2010 | Obenchain et al. |
| 7,749,252 B2 | 7/2010 | Zucherman et al. |
| 7,749,269 B2 | 7/2010 | Peterman et al. |
| 7,749,270 B2 | 7/2010 | Peterman |
| 7,749,274 B2 | 7/2010 | Razian |
| 7,753,844 B2 | 7/2010 | Sharratt et al. |
| 7,753,937 B2 | 7/2010 | Chervitz et al. |
| 7,753,938 B2 | 7/2010 | Aschmann et al. |
| 7,753,958 B2 | 7/2010 | Gordon et al. |
| 7,758,274 B2 | 7/2010 | Paul |
| 7,758,501 B2 | 7/2010 | Frasier et al. |
| 7,758,644 B2 | 7/2010 | Trieu et al. |
| 7,758,645 B2 | 7/2010 | Studer et al. |
| 7,758,648 B2 | 7/2010 | Castleman et al. |
| 7,763,074 B2 | 7/2010 | Altarac et al. |
| 7,763,078 B2 | 7/2010 | Peterman et al. |
| 7,766,918 B2 | 8/2010 | Allard et al. |
| 7,771,432 B2 | 8/2010 | Schwab et al. |
| 7,771,473 B2 | 8/2010 | Thramann |
| 7,771,475 B2 | 8/2010 | Michelson |
| 7,776,049 B1 | 8/2010 | Curran et al. |
| 7,776,067 B2 | 8/2010 | Jackson |
| 7,776,090 B2 | 8/2010 | Winslow et al. |
| 7,780,670 B2 | 8/2010 | Bonutti |
| 7,780,732 B2 | 8/2010 | Abernathie et al. |
| 7,789,914 B2 | 9/2010 | Michelson |
| 7,794,501 B2 | 9/2010 | Edie et al. |
| 7,799,053 B2 | 9/2010 | Haid, Jr. et al. |
| 7,799,081 B2 | 9/2010 | McKinley |
| 7,806,911 B2 | 10/2010 | Peckham |
| 7,806,913 B2 | 10/2010 | Fanger et al. |
| 7,811,326 B2 | 10/2010 | Braddock, Jr. et al. |
| 7,815,683 B2 | 10/2010 | Melkent et al. |
| 7,819,801 B2 | 10/2010 | Miles et al. |
| 7,819,903 B2 | 10/2010 | Fraser et al. |
| 7,824,445 B2 | 11/2010 | Biro et al. |
| 7,828,807 B2 | 11/2010 | Lehuec et al. |
| 7,828,847 B2 | 11/2010 | Abdou |
| 7,828,849 B2 | 11/2010 | Lim |
| 7,837,688 B2 | 11/2010 | Boyer, II et al. |
| 7,837,714 B2 | 11/2010 | Drewry et al. |
| 7,837,732 B2 | 11/2010 | Zucherman et al. |
| 7,837,734 B2 | 11/2010 | Zucherman et al. |
| 7,842,074 B2 | 11/2010 | Abdou |
| 7,846,186 B2 | 12/2010 | Taylor |
| 7,846,207 B2 | 12/2010 | Lechmann et al. |
| 7,850,608 B2 | 12/2010 | Hamada |
| 7,850,731 B2 | 12/2010 | Brittan et al. |
| 7,850,732 B2 | 12/2010 | Heinz |
| 7,850,733 B2 | 12/2010 | Baynham et al. |

(56) References Cited

U.S. PATENT DOCUMENTS

| | | |
|---|---|---|
| 7,854,752 B2 | 12/2010 | Colleran et al. |
| 7,857,818 B2 | 12/2010 | Trieu et al. |
| 7,857,833 B2 | 12/2010 | Abdou |
| 7,862,588 B2 | 1/2011 | Abdou et al. |
| 7,871,426 B2 | 1/2011 | Chin et al. |
| 7,875,034 B2 | 1/2011 | Josse et al. |
| 7,875,076 B2 | 1/2011 | Mathieu et al. |
| 7,875,078 B2 | 1/2011 | Wysocki et al. |
| 7,879,074 B2 | 2/2011 | Kwak et al. |
| 7,883,532 B2 | 2/2011 | Biscup et al. |
| 7,883,542 B2 | 2/2011 | Zipnick et al. |
| 7,887,591 B2 | 2/2011 | Aebi et al. |
| 7,892,173 B2 | 2/2011 | Miles et al. |
| 7,892,174 B2 | 2/2011 | Hestad et al. |
| 7,892,261 B2 | 2/2011 | Bonutti |
| 7,892,286 B2 | 2/2011 | Michelson |
| 7,901,409 B2 | 3/2011 | Canaveral et al. |
| 7,901,458 B2 | 3/2011 | DeRidder et al. |
| 7,905,840 B2 | 3/2011 | Pimenta et al. |
| 7,905,886 B1 | 3/2011 | Curran et al. |
| 7,909,829 B2 | 3/2011 | Patel et al. |
| 7,909,848 B2 | 3/2011 | Patel et al. |
| 7,909,870 B2 | 3/2011 | Kraus |
| 7,909,871 B2 | 3/2011 | Abdou |
| 7,914,558 B2 | 3/2011 | Landry et al. |
| 7,918,792 B2 | 4/2011 | Drzyzga et al. |
| 7,922,658 B2 | 4/2011 | Cohen et al. |
| 7,922,745 B2 | 4/2011 | Hestad et al. |
| 7,922,750 B2 | 4/2011 | Trautwein et al. |
| 7,927,337 B2 | 4/2011 | Keller |
| 7,931,589 B2 | 4/2011 | Cohen et al. |
| 7,931,674 B2 | 4/2011 | Zucherman et al. |
| 7,935,134 B2 | 5/2011 | Reglos et al. |
| 7,935,147 B2 | 5/2011 | Wales |
| 7,935,149 B2 | 5/2011 | Michelson |
| 7,938,848 B2 | 5/2011 | Sweeney |
| 7,946,982 B2 | 5/2011 | Hamada |
| 7,951,153 B2 | 5/2011 | Abdou et al. |
| 7,951,198 B2 | 5/2011 | Sucec et al. |
| 7,955,390 B2 | 6/2011 | Fallin et al. |
| 7,955,392 B2 | 6/2011 | Dewey et al. |
| 7,959,564 B2 | 6/2011 | Ritland |
| 7,959,677 B2 | 6/2011 | Landry et al. |
| 7,972,363 B2 | 7/2011 | Moskowitz et al. |
| 7,976,566 B2 | 7/2011 | Michelson |
| 7,981,031 B2 | 7/2011 | Frasier et al. |
| 7,985,258 B2 | 7/2011 | Zdeblick et al. |
| 7,988,699 B2 | 8/2011 | Martz et al. |
| 8,002,802 B2 | 8/2011 | Abdou |
| 8,002,833 B2 | 8/2011 | Fabris et al. |
| 8,002,842 B2 | 8/2011 | Ronk |
| 8,012,207 B2 | 9/2011 | Kim |
| 8,021,393 B2 | 9/2011 | Seifert et al. |
| 8,021,401 B2 | 9/2011 | Carl et al. |
| 8,021,429 B2 | 9/2011 | Viker |
| 8,025,680 B2 | 9/2011 | Hayes et al. |
| 8,025,697 B2 | 9/2011 | McClellan, III et al. |
| 8,034,109 B2 | 10/2011 | Zwirkoski |
| 8,034,110 B2 | 10/2011 | Garner et al. |
| 8,038,716 B2 | 10/2011 | Duggal et al. |
| 8,043,334 B2 | 10/2011 | Fisher et al. |
| 8,043,343 B2 | 10/2011 | Miller et al. |
| 8,043,376 B2 | 10/2011 | Falahee |
| 8,043,380 B1 | 10/2011 | Park et al. |
| 8,048,120 B1 | 11/2011 | Fallin et al. |
| 8,062,299 B2 | 11/2011 | McGahan et al. |
| 8,062,336 B2 | 11/2011 | Triplett et al. |
| 8,062,337 B2 | 11/2011 | Bruneau et al. |
| 8,066,710 B2 | 11/2011 | Estes et al. |
| 8,066,714 B2 | 11/2011 | Shipp et al. |
| 8,066,741 B2 | 11/2011 | Fallin et al. |
| 8,066,742 B2 | 11/2011 | Anderson et al. |
| 8,066,749 B2 | 11/2011 | Winslow et al. |
| 8,070,749 B2 | 12/2011 | Stern |
| 8,070,816 B2 | 12/2011 | Taylor |
| 8,075,593 B2 | 12/2011 | Hess |
| 8,075,618 B2 | 12/2011 | Trieu et al. |
| 8,075,621 B2 | 12/2011 | Michelson |
| 8,080,046 B2 | 12/2011 | Suddaby |
| 8,083,798 B2 | 12/2011 | Allard et al. |
| 8,097,018 B2 | 1/2012 | Malandain et al. |
| 8,100,828 B2 | 1/2012 | Frey et al. |
| 8,105,358 B2 | 1/2012 | Phan |
| 8,114,131 B2 | 2/2012 | Kohm et al. |
| 8,123,807 B2 | 2/2012 | Kim |
| 8,128,659 B2 | 3/2012 | Ginsberg et al. |
| 8,128,664 B2 | 3/2012 | Pasquet |
| 8,137,284 B2 | 3/2012 | Miles et al. |
| 8,142,479 B2 | 3/2012 | Hess |
| 8,157,840 B2 | 4/2012 | Zucherman et al. |
| 8,163,026 B2 | 4/2012 | Gray |
| 8,167,887 B2 | 5/2012 | McLean |
| 8,167,908 B2 | 5/2012 | Ely et al. |
| 8,167,915 B2 | 5/2012 | Ferree et al. |
| 8,167,946 B2 | 5/2012 | Michelson |
| 8,167,949 B2 | 5/2012 | Tyber et al. |
| 8,172,855 B2 | 5/2012 | Abdou |
| 8,182,423 B2 | 5/2012 | Miles et al. |
| 8,192,358 B2 | 6/2012 | Leahy |
| 8,197,514 B2 | 6/2012 | Maas et al. |
| 8,197,522 B2 | 6/2012 | Park et al. |
| 8,206,420 B2 | 6/2012 | Patel et al. |
| 8,216,312 B2 | 7/2012 | Gray |
| 8,226,690 B2 | 7/2012 | Altarac et al. |
| 8,231,623 B1 | 7/2012 | Jordan |
| 8,241,329 B2 | 8/2012 | Abdou |
| 8,241,330 B2 | 8/2012 | Lamborne et al. |
| 8,241,359 B2 | 8/2012 | Davis et al. |
| 8,241,362 B2 | 8/2012 | Voorhies |
| 8,251,997 B2 | 8/2012 | Michelson |
| 8,268,004 B2 | 9/2012 | Castleman et al. |
| 8,273,005 B2 | 9/2012 | Abdou et al. |
| 8,277,489 B2 | 10/2012 | Saidha et al. |
| 8,287,569 B1 | 10/2012 | Powell |
| 8,292,896 B2 | 10/2012 | Abdou et al. |
| 8,303,629 B1 | 11/2012 | Abdou |
| 8,303,630 B2 | 11/2012 | Abdou et al. |
| 8,303,660 B1 | 11/2012 | Abdou |
| 8,308,776 B2 | 11/2012 | Abdou et al. |
| 8,308,804 B2 | 11/2012 | Krueger |
| 8,343,046 B2 | 1/2013 | Miles et al. |
| 8,343,190 B1 | 1/2013 | Mueller et al. |
| 8,349,012 B2 | 1/2013 | McKay |
| 8,353,826 B2 | 1/2013 | Weiman et al. |
| 8,361,108 B2 | 1/2013 | Gold et al. |
| 8,382,801 B2 | 2/2013 | Lamborne et al. |
| 8,388,660 B1 | 3/2013 | Abdou |
| 8,388,687 B2 | 3/2013 | Gimbel et al. |
| 8,397,522 B2 | 3/2013 | Springer et al. |
| 8,398,689 B2 | 3/2013 | Abdou |
| 8,403,959 B2 | 3/2013 | Doellinger |
| 8,409,208 B2 | 4/2013 | Abdou |
| 8,419,738 B2 | 4/2013 | Smisson, III et al. |
| 8,419,772 B2 | 4/2013 | Thompson et al. |
| 8,425,602 B2 | 4/2013 | Guyer et al. |
| 8,435,268 B2 | 5/2013 | Thompson et al. |
| 8,435,269 B2 | 5/2013 | Woolley et al. |
| 8,439,953 B2 | 5/2013 | Mitchell et al. |
| 8,454,621 B2 | 6/2013 | DeRidder et al. |
| 8,454,661 B2 | 6/2013 | Rathbun et al. |
| 8,454,694 B2 | 6/2013 | Armstrong et al. |
| 8,465,547 B2 | 6/2013 | Melkent et al. |
| RE44,380 E | 7/2013 | De La Torre et al. |
| 8,475,497 B2 | 7/2013 | Grizzard |
| 8,480,712 B1 | 7/2013 | Samuel et al. |
| 8,480,747 B2 | 7/2013 | Melkent et al. |
| 8,486,147 B2 | 7/2013 | De Villiers et al. |
| 8,491,471 B2 | 7/2013 | Deshmukh et al. |
| 8,500,814 B2 | 8/2013 | Abdou |
| 8,506,629 B2 | 8/2013 | Weiland |
| 8,512,343 B2 | 8/2013 | Dziedzic et al. |
| 8,529,611 B2 | 9/2013 | Champagne et al. |
| 8,545,538 B2 | 10/2013 | Abdou et al. |
| 8,562,650 B2 | 10/2013 | Dace |

(56) References Cited

U.S. PATENT DOCUMENTS

| | | |
|---|---|---|
| 8,568,453 B2 | 10/2013 | Abdou et al. |
| 8,574,267 B2 | 11/2013 | Linares |
| 8,603,143 B2 | 12/2013 | Robinson |
| 8,623,055 B2 | 1/2014 | Abdou |
| 8,623,088 B1 | 1/2014 | Tohmeh et al. |
| 8,636,655 B1 | 1/2014 | Childs |
| 8,636,772 B2 | 1/2014 | Schmierer et al. |
| 8,657,855 B2 | 2/2014 | Zhang |
| 8,663,331 B2 | 3/2014 | McClellan, III et al. |
| 8,673,013 B2 | 3/2014 | Abdou |
| 8,685,065 B1 | 4/2014 | Taber et al. |
| 8,685,093 B2 | 4/2014 | Anderson et al. |
| 8,690,917 B2 | 4/2014 | Suh et al. |
| 8,690,950 B2 | 4/2014 | Refai et al. |
| 8,696,709 B2 | 4/2014 | Dinville et al. |
| 8,696,751 B2 | 4/2014 | Ashley et al. |
| 8,702,756 B2 | 4/2014 | Reimels |
| 8,721,686 B2 | 5/2014 | Gordon et al. |
| 8,721,689 B2 | 5/2014 | Butler et al. |
| 8,764,806 B2 | 7/2014 | Abdou |
| 8,771,318 B2 | 7/2014 | Triplett et al. |
| 8,771,355 B2 | 7/2014 | Abdou |
| 8,771,360 B2 | 7/2014 | Jimenez et al. |
| 8,795,335 B1 | 8/2014 | Abdou et al. |
| 8,795,375 B2 | 8/2014 | Malberg |
| 8,801,757 B2 | 8/2014 | Abdou et al. |
| 8,808,379 B2 | 8/2014 | Abdou et al. |
| 8,827,900 B1 | 9/2014 | Pimenta |
| 8,828,055 B2 | 9/2014 | Blain et al. |
| 8,828,056 B2 | 9/2014 | Buss et al. |
| 8,828,061 B2 | 9/2014 | Scrantz et al. |
| 8,845,688 B2 | 9/2014 | Abdou et al. |
| 8,845,696 B1 | 9/2014 | Abdou |
| 8,845,701 B2 | 9/2014 | Abdou |
| 8,845,728 B1 | 9/2014 | Abdou |
| 8,870,920 B2 | 10/2014 | Abdou et al. |
| 8,876,874 B2 | 11/2014 | Abdou et al. |
| 8,876,904 B2 | 11/2014 | Pimenta et al. |
| 8,900,137 B1 | 12/2014 | Lovell et al. |
| 8,906,092 B2 | 12/2014 | Abdou |
| 8,911,441 B2 | 12/2014 | Dace et al. |
| 8,940,019 B2 | 1/2015 | Gordon et al. |
| 8,940,051 B2 | 1/2015 | Gimbel et al. |
| 8,940,052 B2 | 1/2015 | Lechmann et al. |
| 8,956,415 B2 | 2/2015 | Cowan |
| 8,974,381 B1 | 3/2015 | Lovell et al. |
| 8,974,461 B2 | 3/2015 | Abdou |
| 8,998,905 B2 | 4/2015 | Marik et al. |
| 9,005,248 B2 | 4/2015 | Taber et al. |
| 9,011,538 B2 | 4/2015 | Allard et al. |
| 9,044,280 B1 | 6/2015 | Arambula et al. |
| 9,060,816 B2 | 6/2015 | Abdou |
| 9,060,873 B2 | 6/2015 | Abdou |
| 9,101,491 B2 | 8/2015 | Rodgers et al. |
| 9,107,705 B2 | 8/2015 | Abdou et al. |
| 9,113,853 B1 | 8/2015 | Casey et al. |
| 9,135,059 B2 | 9/2015 | Ballard et al. |
| 9,179,903 B2 | 11/2015 | Cianfrani et al. |
| 9,198,767 B2 | 12/2015 | Abdou |
| 9,211,147 B2 | 12/2015 | Gordon et al. |
| 9,247,968 B2 | 2/2016 | Taber et al. |
| 9,265,526 B1 | 2/2016 | Abdou |
| 9,308,099 B2 | 4/2016 | Triplett et al. |
| 9,314,350 B1 | 4/2016 | Abdou |
| 9,320,506 B2 | 4/2016 | Bertagnoli et al. |
| 9,320,610 B2 | 4/2016 | Alheidt et al. |
| 9,320,617 B2 | 4/2016 | Abdou et al. |
| 9,345,464 B2 | 5/2016 | Abdou et al. |
| 9,364,338 B2 | 6/2016 | Malberg |
| 9,375,239 B2 | 6/2016 | Abdou |
| 9,408,596 B2 | 8/2016 | Blain |
| 9,408,717 B2 | 8/2016 | Perrow et al. |
| 9,445,918 B1 | 9/2016 | Lin et al. |
| 9,451,940 B2 | 9/2016 | Spann |
| 9,486,328 B2 | 11/2016 | Jimenez et al. |
| 9,610,176 B1 | 4/2017 | Abdou |
| 9,622,795 B2 | 4/2017 | Reitblat et al. |
| 9,655,505 B1 | 5/2017 | Gharib et al. |
| 9,675,389 B2 | 6/2017 | Abdou |
| 9,687,356 B1 | 6/2017 | Spangler et al. |
| 9,687,357 B2 | 6/2017 | Bannigan et al. |
| 9,717,601 B2 | 8/2017 | Miller |
| 9,730,737 B2 | 8/2017 | Baynham et al. |
| 9,730,802 B1 | 8/2017 | Harvey |
| 9,795,367 B1 | 10/2017 | Lee et al. |
| 9,795,370 B2 | 10/2017 | O'Connell et al. |
| RE46,647 E | 12/2017 | Messerli et al. |
| 9,867,714 B1 | 1/2018 | Abdou |
| 9,901,458 B1 | 2/2018 | Abdou |
| 9,937,052 B2 | 4/2018 | Abdou et al. |
| 10,092,330 B2 | 10/2018 | Abdou et al. |
| 10,111,757 B2 | 10/2018 | Abdou et al. |
| 10,166,018 B2 | 1/2019 | Hunt et al. |
| 10,188,529 B2 | 1/2019 | Abdou |
| 10,426,450 B2 | 10/2019 | Vogel et al. |
| 10,470,892 B2 | 11/2019 | Abdou |
| 10,543,107 B2 | 1/2020 | Abdou |
| 10,548,740 B1 | 2/2020 | Abdou |
| 10,575,961 B1 | 3/2020 | Abdou |
| 10,610,380 B2 | 4/2020 | Abdou |
| 10,695,105 B2 | 6/2020 | Abdou |
| 10,744,000 B1 | 8/2020 | Abdou |
| 10,857,003 B1 | 12/2020 | Abdou |
| 10,857,004 B2 | 12/2020 | Abdou |
| 10,918,498 B2 | 2/2021 | Abdou |
| 10,945,861 B2 * | 3/2021 | Abdou ............... A61B 17/7032 |
| 10,973,648 B1 | 4/2021 | Abdou |
| 11,006,982 B2 | 5/2021 | Abdou |
| 11,058,548 B1 | 7/2021 | Abdou |
| 11,096,799 B2 | 8/2021 | Abdou |
| 11,259,935 B1 | 3/2022 | Abdou |
| 2001/0001129 A1 | 5/2001 | McKay et al. |
| 2001/0012938 A1 | 8/2001 | Zucherman et al. |
| 2001/0021850 A1 | 9/2001 | Zucherman et al. |
| 2001/0031965 A1 | 10/2001 | Zucherman et al. |
| 2001/0039452 A1 | 11/2001 | Zucherman et al. |
| 2001/0047172 A1 | 11/2001 | Foley et al. |
| 2001/0053914 A1 | 12/2001 | Landry et al. |
| 2001/0056219 A1 | 12/2001 | Brauckman et al. |
| 2002/0016595 A1 | 2/2002 | Michelson |
| 2002/0019626 A1 | 2/2002 | Sharkey et al. |
| 2002/0019637 A1 | 2/2002 | Frey et al. |
| 2002/0026101 A1 | 2/2002 | Bookwalter et al. |
| 2002/0032484 A1 | 3/2002 | Hyde |
| 2002/0045899 A1 | 4/2002 | Errico et al. |
| 2002/0045904 A1 | 4/2002 | Fuss et al. |
| 2002/0045945 A1 | 4/2002 | Liu et al. |
| 2002/0049394 A1 | 4/2002 | Roy et al. |
| 2002/0049444 A1 | 4/2002 | Knox |
| 2002/0049446 A1 | 4/2002 | Harkey et al. |
| 2002/0055738 A1 | 5/2002 | Lieberman |
| 2002/0055741 A1 | 5/2002 | Schlapfer et al. |
| 2002/0058944 A1 | 5/2002 | Michelson |
| 2002/0065558 A1 | 5/2002 | Varga et al. |
| 2002/0077530 A1 | 6/2002 | Velikaris et al. |
| 2002/0082602 A1 | 6/2002 | Biedermann et al. |
| 2002/0082700 A1 | 6/2002 | Bianchi et al. |
| 2002/0099386 A1 | 7/2002 | Beger et al. |
| 2002/0111628 A1 | 8/2002 | Ralph et al. |
| 2002/0120268 A1 | 8/2002 | Berger |
| 2002/0128713 A1 | 9/2002 | Ferree |
| 2002/0138146 A1 | 9/2002 | Jackson |
| 2002/0143328 A1 | 10/2002 | Shluzas et al. |
| 2002/0143332 A1 | 10/2002 | Lin et al. |
| 2002/0143341 A1 | 10/2002 | Biedermann et al. |
| 2002/0147449 A1 | 10/2002 | Yun |
| 2002/0161368 A1 | 10/2002 | Foley et al. |
| 2002/0165550 A1 | 11/2002 | Frey et al. |
| 2002/0165612 A1 | 11/2002 | Gerber et al. |
| 2002/0169450 A1 | 11/2002 | Lange |
| 2002/0169453 A1 | 11/2002 | Berger |
| 2002/0183748 A1 | 12/2002 | Martin et al. |
| 2002/0183755 A1 | 12/2002 | Michelson |
| 2002/0183761 A1 | 12/2002 | Johnson et al. |

(56) References Cited

U.S. PATENT DOCUMENTS

| | | |
|---|---|---|
| 2002/0183848 A1 | 12/2002 | Ray et al. |
| 2002/0188296 A1 | 12/2002 | Michelson |
| 2003/0000350 A1 | 1/2003 | Zhao et al. |
| 2003/0004572 A1 | 1/2003 | Goble et al. |
| 2003/0014068 A1 | 1/2003 | Bonutti et al. |
| 2003/0014123 A1 | 1/2003 | Copf et al. |
| 2003/0018389 A1 | 1/2003 | Castro et al. |
| 2003/0023240 A1 | 1/2003 | Amrein et al. |
| 2003/0023243 A1 | 1/2003 | Biedermann et al. |
| 2003/0023305 A1 | 1/2003 | McKay |
| 2003/0023306 A1 | 1/2003 | Liu et al. |
| 2003/0023308 A1 | 1/2003 | Leroux et al. |
| 2003/0028251 A1 | 2/2003 | Mathews |
| 2003/0040746 A1 | 2/2003 | Mitchell et al. |
| 2003/0040798 A1 | 2/2003 | Michelson |
| 2003/0045878 A1 | 3/2003 | Petit et al. |
| 2003/0045935 A1 | 3/2003 | Angelucci et al. |
| 2003/0055430 A1 | 3/2003 | Kim |
| 2003/0060826 A1 | 3/2003 | Foley et al. |
| 2003/0065330 A1 | 4/2003 | Zucherman et al. |
| 2003/0065395 A1 | 4/2003 | Ralph et al. |
| 2003/0065396 A1 | 4/2003 | Michelson |
| 2003/0073997 A1 | 4/2003 | Doubler et al. |
| 2003/0074001 A1 | 4/2003 | Apfelbaum et al. |
| 2003/0074005 A1 | 4/2003 | Roth et al. |
| 2003/0078583 A1 | 4/2003 | Biedermann et al. |
| 2003/0078662 A1 | 4/2003 | Ralph et al. |
| 2003/0078664 A1 | 4/2003 | Ralph et al. |
| 2003/0083747 A1 | 5/2003 | Winterbottom et al. |
| 2003/0088251 A1 | 5/2003 | Braun et al. |
| 2003/0093153 A1 | 5/2003 | Banick et al. |
| 2003/0094812 A1 | 5/2003 | Balsells |
| 2003/0100896 A1 | 5/2003 | Biedermann et al. |
| 2003/0105460 A1 | 6/2003 | Crandall et al. |
| 2003/0109880 A1 | 6/2003 | Shirado et al. |
| 2003/0114852 A1 | 6/2003 | Biedermann et al. |
| 2003/0125741 A1 | 7/2003 | Biedermann et al. |
| 2003/0125742 A1 | 7/2003 | Yuan et al. |
| 2003/0139813 A1 | 7/2003 | Messerli et al. |
| 2003/0149341 A1 | 8/2003 | Clifton |
| 2003/0149431 A1 | 8/2003 | Varieur |
| 2003/0149432 A1 | 8/2003 | Frigg et al. |
| 2003/0149484 A1 | 8/2003 | Michelson |
| 2003/0153911 A1 | 8/2003 | Shluzas |
| 2003/0153913 A1 | 8/2003 | Altarac et al. |
| 2003/0163133 A1 | 8/2003 | Altarac et al. |
| 2003/0163199 A1 | 8/2003 | Boehm et al. |
| 2003/0167058 A1 | 9/2003 | Shluzas |
| 2003/0171749 A1 | 9/2003 | Le Couedic et al. |
| 2003/0171751 A1 | 9/2003 | Ritland |
| 2003/0176862 A1 | 9/2003 | Taylor et al. |
| 2003/0176864 A1 | 9/2003 | Ueyama et al. |
| 2003/0176923 A1 | 9/2003 | Keller et al. |
| 2003/0181975 A1 | 9/2003 | Ishii et al. |
| 2003/0187436 A1 | 10/2003 | Bolger et al. |
| 2003/0187510 A1 | 10/2003 | Hyde |
| 2003/0191470 A1 | 10/2003 | Ritland |
| 2003/0195518 A1 | 10/2003 | Cragg |
| 2003/0195633 A1 | 10/2003 | Hyde |
| 2003/0199873 A1 | 10/2003 | Richelsoph |
| 2003/0199981 A1 | 10/2003 | Ferree |
| 2003/0208202 A1 | 11/2003 | Falahee |
| 2003/0208203 A1 | 11/2003 | Lim et al. |
| 2003/0208204 A1 | 11/2003 | Bailey et al. |
| 2003/0208273 A1 | 11/2003 | Eisermann et al. |
| 2003/0212398 A1 | 11/2003 | Jackson |
| 2003/0216735 A1 | 11/2003 | Altarac et al. |
| 2003/0216736 A1 | 11/2003 | Robinson et al. |
| 2003/0216737 A1 | 11/2003 | Biscup |
| 2003/0217809 A1 | 11/2003 | Morishige |
| 2003/0220642 A1 | 11/2003 | Freudiger |
| 2003/0220643 A1 | 11/2003 | Ferree |
| 2003/0225408 A1 | 12/2003 | Nichols et al. |
| 2003/0229347 A1 | 12/2003 | Sherman et al. |
| 2003/0233136 A1 | 12/2003 | Williams et al. |
| 2003/0236472 A1 | 12/2003 | Van Hoeck et al. |
| 2003/0236572 A1 | 12/2003 | Bertram |
| 2004/0002708 A1 | 1/2004 | Ritland |
| 2004/0006342 A1 | 1/2004 | Altarac et al. |
| 2004/0006391 A1 | 1/2004 | Reiley |
| 2004/0010253 A1 | 1/2004 | Morrison |
| 2004/0012938 A1 | 1/2004 | Sylvester et al. |
| 2004/0018228 A1 | 1/2004 | Fischell et al. |
| 2004/0019263 A1 | 1/2004 | Jutras et al. |
| 2004/0030338 A1 | 2/2004 | Paul |
| 2004/0030346 A1 | 2/2004 | Frey et al. |
| 2004/0039387 A1 | 2/2004 | Gause et al. |
| 2004/0044412 A1 | 3/2004 | Lambrecht et al. |
| 2004/0049189 A1 | 3/2004 | Le Couedic et al. |
| 2004/0049190 A1 | 3/2004 | Biedermann et al. |
| 2004/0049271 A1 | 3/2004 | Biedermann et al. |
| 2004/0049280 A1 | 3/2004 | Cauthen |
| 2004/0054412 A1 | 3/2004 | Gerbec et al. |
| 2004/0059318 A1 | 3/2004 | Zhang et al. |
| 2004/0068261 A1 | 4/2004 | Fourcault et al. |
| 2004/0068318 A1 | 4/2004 | Coates et al. |
| 2004/0073215 A1 | 4/2004 | Carli |
| 2004/0073216 A1 | 4/2004 | Lieberman |
| 2004/0078079 A1 | 4/2004 | Foley |
| 2004/0078082 A1 | 4/2004 | Lange |
| 2004/0087947 A1 | 5/2004 | Lim et al. |
| 2004/0087948 A1 | 5/2004 | Suddaby |
| 2004/0087949 A1 | 5/2004 | Bono et al. |
| 2004/0087952 A1 | 5/2004 | Borgstrom et al. |
| 2004/0092930 A1 | 5/2004 | Petit et al. |
| 2004/0092933 A1 | 5/2004 | Shaolian et al. |
| 2004/0092934 A1 | 5/2004 | Howland |
| 2004/0093083 A1 | 5/2004 | Branch et al. |
| 2004/0097933 A1 | 5/2004 | Lourdel et al. |
| 2004/0097935 A1 | 5/2004 | Richelsoph et al. |
| 2004/0097940 A1 | 5/2004 | Paul |
| 2004/0098129 A1 | 5/2004 | Lin |
| 2004/0102780 A1 | 5/2004 | West |
| 2004/0106927 A1 | 6/2004 | Ruffner et al. |
| 2004/0106995 A1 | 6/2004 | Le Couedic et al. |
| 2004/0106996 A1 | 6/2004 | Liu et al. |
| 2004/0111136 A1 | 6/2004 | Sharkey et al. |
| 2004/0111141 A1 | 6/2004 | Brabec et al. |
| 2004/0116929 A1 | 6/2004 | Barker et al. |
| 2004/0116965 A1 | 6/2004 | Falkenberg |
| 2004/0122518 A1 | 6/2004 | Rhoda |
| 2004/0127963 A1 | 7/2004 | Uchida et al. |
| 2004/0127990 A1 | 7/2004 | Bartish et al. |
| 2004/0127994 A1 | 7/2004 | Kast et al. |
| 2004/0133207 A1 | 7/2004 | Abdou |
| 2004/0138662 A1 | 7/2004 | Landry et al. |
| 2004/0138671 A1 | 7/2004 | Zander et al. |
| 2004/0143264 A1 | 7/2004 | McAfee |
| 2004/0143265 A1 | 7/2004 | Landry et al. |
| 2004/0143270 A1 | 7/2004 | Zucherman et al. |
| 2004/0143332 A1 | 7/2004 | Krueger et al. |
| 2004/0147928 A1 | 7/2004 | Landry et al. |
| 2004/0147929 A1 | 7/2004 | Biedermann et al. |
| 2004/0153065 A1 | 8/2004 | Lim |
| 2004/0153070 A1 | 8/2004 | Barker et al. |
| 2004/0158247 A1 | 8/2004 | Sitiso et al. |
| 2004/0158254 A1 | 8/2004 | Eisermann |
| 2004/0162558 A1 | 8/2004 | Hegde et al. |
| 2004/0162560 A1 | 8/2004 | Raynor et al. |
| 2004/0167520 A1 | 8/2004 | Zucherman et al. |
| 2004/0167625 A1 | 8/2004 | Beyar et al. |
| 2004/0167626 A1 | 8/2004 | Geremakis et al. |
| 2004/0172022 A1 | 9/2004 | Landry et al. |
| 2004/0172025 A1 | 9/2004 | Drewry et al. |
| 2004/0172134 A1 | 9/2004 | Berry |
| 2004/0176766 A1 | 9/2004 | Shluzas |
| 2004/0181226 A1 | 9/2004 | Michelson |
| 2004/0181285 A1 | 9/2004 | Simonson |
| 2004/0186473 A1 | 9/2004 | Cournoyer et al. |
| 2004/0186572 A1 | 9/2004 | Lange et al. |
| 2004/0193151 A1 | 9/2004 | To et al. |
| 2004/0193159 A1 | 9/2004 | Zucherman et al. |
| 2004/0195089 A1 | 10/2004 | O'Brien |
| 2004/0204712 A1 | 10/2004 | Kolb et al. |

(56) References Cited

U.S. PATENT DOCUMENTS

| | | |
|---|---|---|
| 2004/0204713 A1 | 10/2004 | Abdou |
| 2004/0210216 A1 | 10/2004 | Farris et al. |
| 2004/0215190 A1 | 10/2004 | Nguyen et al. |
| 2004/0220567 A1 | 11/2004 | Eisermann et al. |
| 2004/0220670 A1 | 11/2004 | Eisermann et al. |
| 2004/0220671 A1 | 11/2004 | Ralph et al. |
| 2004/0225289 A1 | 11/2004 | Biedermann et al. |
| 2004/0225291 A1 | 11/2004 | Schwammberger et al. |
| 2004/0225364 A1 | 11/2004 | Richelsoph et al. |
| 2004/0225365 A1 | 11/2004 | Eisermann et al. |
| 2004/0225366 A1 | 11/2004 | Eisermann et al. |
| 2004/0230309 A1 | 11/2004 | DiMauro et al. |
| 2004/0236327 A1 | 11/2004 | Paul et al. |
| 2004/0236328 A1 | 11/2004 | Paul et al. |
| 2004/0236329 A1 | 11/2004 | Panjabi |
| 2004/0236330 A1 | 11/2004 | Purcell et al. |
| 2004/0236333 A1 | 11/2004 | Lin |
| 2004/0236425 A1 | 11/2004 | Huang |
| 2004/0243240 A1 | 12/2004 | Beaurain et al. |
| 2004/0249377 A1 | 12/2004 | Kaes et al. |
| 2004/0249379 A1 | 12/2004 | Winslow et al. |
| 2004/0249380 A1 | 12/2004 | Glascott |
| 2004/0249461 A1 | 12/2004 | Ferree |
| 2004/0254574 A1 | 12/2004 | Morrison et al. |
| 2004/0254575 A1 | 12/2004 | Obenchain et al. |
| 2004/0260283 A1 | 12/2004 | Wu et al. |
| 2004/0260291 A1 | 12/2004 | Jensen |
| 2004/0267264 A1 | 12/2004 | Konieczynski et al. |
| 2004/0267369 A1 | 12/2004 | Lyons et al. |
| 2005/0004573 A1 | 1/2005 | Abdou |
| 2005/0010227 A1 | 1/2005 | Paul |
| 2005/0010291 A1 | 1/2005 | Stinson et al. |
| 2005/0010301 A1 | 1/2005 | Disilvestro et al. |
| 2005/0012506 A1 | 1/2005 | Yudahira |
| 2005/0015149 A1 | 1/2005 | Michelson |
| 2005/0021029 A1 | 1/2005 | Trieu et al. |
| 2005/0021031 A1 | 1/2005 | Foley et al. |
| 2005/0021040 A1 | 1/2005 | Bertagnoli |
| 2005/0021041 A1 | 1/2005 | Michelson |
| 2005/0027296 A1 | 2/2005 | Thramann et al. |
| 2005/0027360 A1 | 2/2005 | Webb et al. |
| 2005/0033296 A1 | 2/2005 | Bono et al. |
| 2005/0033298 A1 | 2/2005 | Hawkes et al. |
| 2005/0033431 A1 | 2/2005 | Gordon et al. |
| 2005/0033432 A1 | 2/2005 | Gordon et al. |
| 2005/0033434 A1 | 2/2005 | Berry |
| 2005/0038432 A1 | 2/2005 | Shaolian et al. |
| 2005/0038511 A1 | 2/2005 | Martz et al. |
| 2005/0043800 A1 | 2/2005 | Paul et al. |
| 2005/0043802 A1 | 2/2005 | Eisermann et al. |
| 2005/0049705 A1 | 3/2005 | Hale et al. |
| 2005/0049708 A1 | 3/2005 | Atkinson et al. |
| 2005/0055026 A1 | 3/2005 | Biedermann et al. |
| 2005/0055031 A1 | 3/2005 | Lim |
| 2005/0065514 A1 | 3/2005 | Studer |
| 2005/0065515 A1 | 3/2005 | Jahng |
| 2005/0065516 A1 | 3/2005 | Jahng |
| 2005/0065517 A1 | 3/2005 | Chin |
| 2005/0069701 A1 | 3/2005 | Watanabe et al. |
| 2005/0070899 A1 | 3/2005 | Doubler et al. |
| 2005/0070901 A1 | 3/2005 | David |
| 2005/0071007 A1 | 3/2005 | Malek |
| 2005/0075636 A1 | 4/2005 | Gotzen |
| 2005/0080320 A1 | 4/2005 | Lee et al. |
| 2005/0080415 A1 | 4/2005 | Keyer et al. |
| 2005/0085812 A1 | 4/2005 | Sherman et al. |
| 2005/0085813 A1 | 4/2005 | Spitler et al. |
| 2005/0085815 A1 | 4/2005 | Harms et al. |
| 2005/0085816 A1 | 4/2005 | Michelson |
| 2005/0085909 A1 | 4/2005 | Eisermann |
| 2005/0096652 A1 | 5/2005 | Burton |
| 2005/0096653 A1 | 5/2005 | Doubler et al. |
| 2005/0096654 A1 | 5/2005 | Lin |
| 2005/0096745 A1 | 5/2005 | Andre et al. |
| 2005/0107788 A1 | 5/2005 | Beaurain et al. |
| 2005/0113830 A1 | 5/2005 | Rezach et al. |
| 2005/0113833 A1 | 5/2005 | Davison |
| 2005/0113927 A1 | 5/2005 | Malek |
| 2005/0113928 A1 | 5/2005 | Cragg et al. |
| 2005/0119663 A1 | 6/2005 | Keyer et al. |
| 2005/0119747 A1 | 6/2005 | Fabris et al. |
| 2005/0119748 A1 | 6/2005 | Reiley et al. |
| 2005/0124991 A1 | 6/2005 | Jahng |
| 2005/0125061 A1 | 6/2005 | Zucherman et al. |
| 2005/0125066 A1 | 6/2005 | McAfee |
| 2005/0126576 A1 | 6/2005 | Ferree |
| 2005/0131404 A1 | 6/2005 | Mazda et al. |
| 2005/0131406 A1 | 6/2005 | Reiley et al. |
| 2005/0131407 A1 | 6/2005 | Sicvol et al. |
| 2005/0131409 A1 | 6/2005 | Chervitz et al. |
| 2005/0131413 A1 | 6/2005 | O'Driscoll et al. |
| 2005/0131420 A1 | 6/2005 | Techiera et al. |
| 2005/0131421 A1 | 6/2005 | Anderson et al. |
| 2005/0137597 A1 | 6/2005 | Butler et al. |
| 2005/0137604 A1 | 6/2005 | Assell et al. |
| 2005/0143737 A1 | 6/2005 | Pafford et al. |
| 2005/0143822 A1 | 6/2005 | Paul |
| 2005/0143823 A1 | 6/2005 | Boyd et al. |
| 2005/0149020 A1 | 7/2005 | Jahng |
| 2005/0149023 A1 | 7/2005 | Ritland |
| 2005/0149035 A1* | 7/2005 | Pimenta ............... A61B 17/02 606/86 R |
| 2005/0149188 A1 | 7/2005 | Cook et al. |
| 2005/0149196 A1 | 7/2005 | Zucherman et al. |
| 2005/0154389 A1 | 7/2005 | Selover et al. |
| 2005/0154390 A1 | 7/2005 | Biedermann et al. |
| 2005/0154391 A1 | 7/2005 | Doherty et al. |
| 2005/0154461 A1 | 7/2005 | Humphreys et al. |
| 2005/0159750 A1 | 7/2005 | Doherty |
| 2005/0159756 A1 | 7/2005 | Ray |
| 2005/0159813 A1 | 7/2005 | Molz |
| 2005/0159815 A1 | 7/2005 | Kamimura et al. |
| 2005/0165396 A1 | 7/2005 | Fortin et al. |
| 2005/0165398 A1 | 7/2005 | Reiley |
| 2005/0165400 A1 | 7/2005 | Fernandez |
| 2005/0165487 A1 | 7/2005 | Muhanna et al. |
| 2005/0171540 A1 | 8/2005 | Lim et al. |
| 2005/0171541 A1 | 8/2005 | Boehm et al. |
| 2005/0171543 A1 | 8/2005 | Timm et al. |
| 2005/0171608 A1 | 8/2005 | Peterman et al. |
| 2005/0171609 A1 | 8/2005 | Humphreys et al. |
| 2005/0171610 A1 | 8/2005 | Humphreys et al. |
| 2005/0177156 A1 | 8/2005 | Timm et al. |
| 2005/0177157 A1 | 8/2005 | Jahng |
| 2005/0177163 A1 | 8/2005 | Abdou et al. |
| 2005/0177164 A1 | 8/2005 | Walters et al. |
| 2005/0177166 A1 | 8/2005 | Timm et al. |
| 2005/0177167 A1 | 8/2005 | Muckter |
| 2005/0177209 A1 | 8/2005 | Leung et al. |
| 2005/0177210 A1 | 8/2005 | Leung et al. |
| 2005/0177211 A1 | 8/2005 | Leung et al. |
| 2005/0177240 A1 | 8/2005 | Blain |
| 2005/0182401 A1 | 8/2005 | Timm et al. |
| 2005/0182404 A1 | 8/2005 | Lauryssen et al. |
| 2005/0187548 A1 | 8/2005 | Butler et al. |
| 2005/0187555 A1 | 8/2005 | Biedermann et al. |
| 2005/0187628 A1 | 8/2005 | Michelson |
| 2005/0192571 A1 | 9/2005 | Abdelgany |
| 2005/0192577 A1 | 9/2005 | Mosca et al. |
| 2005/0192580 A1 | 9/2005 | Dalton |
| 2005/0192589 A1 | 9/2005 | Raymond et al. |
| 2005/0192671 A1 | 9/2005 | Bao et al. |
| 2005/0197660 A1 | 9/2005 | Haid et al. |
| 2005/0197702 A1 | 9/2005 | Coppes et al. |
| 2005/0203511 A1 | 9/2005 | Wilson-MacDonald et al. |
| 2005/0203512 A1 | 9/2005 | Hawkins et al. |
| 2005/0203513 A1 | 9/2005 | Jahng et al. |
| 2005/0203514 A1 | 9/2005 | Jahng et al. |
| 2005/0203516 A1 | 9/2005 | Biedermann et al. |
| 2005/0203517 A1 | 9/2005 | Jahng et al. |
| 2005/0203518 A1 | 9/2005 | Biedermann et al. |
| 2005/0203519 A1 | 9/2005 | Harms et al. |
| 2005/0203533 A1 | 9/2005 | Ferguson et al. |
| 2005/0203604 A1 | 9/2005 | Brabec et al. |

(56) References Cited

U.S. PATENT DOCUMENTS

| | | |
|---|---|---|
| 2005/0203624 A1 | 9/2005 | Serhan et al. |
| 2005/0209694 A1 | 9/2005 | Loeb |
| 2005/0215999 A1 | 9/2005 | Birkmeyer et al. |
| 2005/0216001 A1 | 9/2005 | David |
| 2005/0216003 A1 | 9/2005 | Biedermann et al. |
| 2005/0216083 A1 | 9/2005 | Michelson |
| 2005/0222682 A1 | 10/2005 | Link et al. |
| 2005/0222683 A1 | 10/2005 | Berry |
| 2005/0228376 A1 | 10/2005 | Boomer et al. |
| 2005/0228377 A1 | 10/2005 | Chao et al. |
| 2005/0228395 A1 | 10/2005 | Auxepaules et al. |
| 2005/0228400 A1 | 10/2005 | Chao et al. |
| 2005/0228501 A1 | 10/2005 | Miller et al. |
| 2005/0234449 A1 | 10/2005 | Aferzon |
| 2005/0234450 A1 | 10/2005 | Barker |
| 2005/0234451 A1 | 10/2005 | Markworth |
| 2005/0234452 A1 | 10/2005 | Malandain |
| 2005/0234453 A1 | 10/2005 | Shaolian et al. |
| 2005/0234454 A1 | 10/2005 | Chin |
| 2005/0234456 A1 | 10/2005 | Malandain |
| 2005/0234555 A1 | 10/2005 | Sutton et al. |
| 2005/0240181 A1 | 10/2005 | Boomer et al. |
| 2005/0240183 A1 | 10/2005 | Vaughan |
| 2005/0240265 A1 | 10/2005 | Kuiper et al. |
| 2005/0240273 A1 | 10/2005 | Khandkar et al. |
| 2005/0245928 A1 | 11/2005 | Colleran et al. |
| 2005/0245930 A1 | 11/2005 | Timm et al. |
| 2005/0251137 A1 | 11/2005 | Ball |
| 2005/0251139 A1 | 11/2005 | Roh |
| 2005/0251140 A1 | 11/2005 | Shaolian et al. |
| 2005/0251141 A1 | 11/2005 | Frigg et al. |
| 2005/0251258 A1 | 11/2005 | Jackson |
| 2005/0256576 A1 | 11/2005 | Moskowitz et al. |
| 2005/0256578 A1 | 11/2005 | Blatt et al. |
| 2005/0260058 A1 | 11/2005 | Cassagne, III |
| 2005/0261685 A1 | 11/2005 | Fortin et al. |
| 2005/0261687 A1 | 11/2005 | Garamszegi et al. |
| 2005/0261768 A1 | 11/2005 | Trieu |
| 2005/0267470 A1 | 12/2005 | McBride |
| 2005/0267471 A1 | 12/2005 | Biedermann et al. |
| 2005/0267474 A1 | 12/2005 | Dalton |
| 2005/0267477 A1 | 12/2005 | Jackson |
| 2005/0267579 A1 | 12/2005 | Reiley et al. |
| 2005/0267580 A1 | 12/2005 | Suddaby |
| 2005/0273099 A1 | 12/2005 | Baccelli et al. |
| 2005/0273101 A1 | 12/2005 | Schumacher |
| 2005/0273120 A1 | 12/2005 | Abdou et al. |
| 2005/0273171 A1 | 12/2005 | Gordon et al. |
| 2005/0277919 A1 | 12/2005 | Slivka et al. |
| 2005/0277921 A1 | 12/2005 | Eisermann et al. |
| 2005/0277922 A1 | 12/2005 | Trieu et al. |
| 2005/0277923 A1 | 12/2005 | Sweeney |
| 2005/0277924 A1 | 12/2005 | Roychowdhury |
| 2005/0277925 A1 | 12/2005 | Mujwid |
| 2005/0277927 A1 | 12/2005 | Guenther et al. |
| 2005/0277928 A1 | 12/2005 | Boschert |
| 2005/0277931 A1 | 12/2005 | Sweeney et al. |
| 2005/0277934 A1 | 12/2005 | Vardiman |
| 2005/0278026 A1 | 12/2005 | Gordon et al. |
| 2005/0283152 A1 | 12/2005 | Lindemann et al. |
| 2005/0283153 A1 | 12/2005 | Poyner et al. |
| 2005/0283157 A1 | 12/2005 | Coates et al. |
| 2005/0283236 A1 | 12/2005 | Razian |
| 2005/0283238 A1 | 12/2005 | Reiley |
| 2005/0283241 A1 | 12/2005 | Keller et al. |
| 2005/0283244 A1 | 12/2005 | Gordon et al. |
| 2005/0283245 A1 | 12/2005 | Gordon et al. |
| 2005/0288669 A1 | 12/2005 | Abdou et al. |
| 2005/0288670 A1 | 12/2005 | Panjabi et al. |
| 2005/0288671 A1 | 12/2005 | Yuan et al. |
| 2005/0288672 A1 | 12/2005 | Ferree |
| 2005/0288673 A1 | 12/2005 | Catbagan et al. |
| 2006/0004357 A1 | 1/2006 | Lee et al. |
| 2006/0004359 A1 | 1/2006 | Kramer et al. |
| 2006/0004360 A1 | 1/2006 | Kramer et al. |
| 2006/0004363 A1 | 1/2006 | Brockmeyer et al. |
| 2006/0004367 A1 | 1/2006 | Alamin et al. |
| 2006/0004453 A1 | 1/2006 | Bartish et al. |
| 2006/0009767 A1 | 1/2006 | Kiester |
| 2006/0009768 A1 | 1/2006 | Ritland |
| 2006/0009769 A1 | 1/2006 | Lieberman |
| 2006/0009770 A1 | 1/2006 | Speirs et al. |
| 2006/0009775 A1 | 1/2006 | Dec et al. |
| 2006/0009780 A1 | 1/2006 | Foley et al. |
| 2006/0009846 A1 | 1/2006 | Trieu et al. |
| 2006/0015099 A1 | 1/2006 | Cannon et al. |
| 2006/0015104 A1 | 1/2006 | Dalton |
| 2006/0015181 A1 | 1/2006 | Elberg |
| 2006/0015183 A1 | 1/2006 | Gilbert et al. |
| 2006/0020342 A1 | 1/2006 | Ferree et al. |
| 2006/0024614 A1 | 2/2006 | Williamson |
| 2006/0025767 A1 | 2/2006 | Khalili |
| 2006/0025768 A1 | 2/2006 | Iott et al. |
| 2006/0025770 A1 | 2/2006 | Schlapfer et al. |
| 2006/0030839 A1 | 2/2006 | Park et al. |
| 2006/0030850 A1 | 2/2006 | Keegan et al. |
| 2006/0030943 A1 | 2/2006 | Peterman |
| 2006/0036240 A1 | 2/2006 | Colleran et al. |
| 2006/0036242 A1 | 2/2006 | Nilsson et al. |
| 2006/0036244 A1 | 2/2006 | Spitler et al. |
| 2006/0036246 A1 | 2/2006 | Carl et al. |
| 2006/0036250 A1 | 2/2006 | Lange et al. |
| 2006/0036252 A1 | 2/2006 | Baynham et al. |
| 2006/0036254 A1 | 2/2006 | Lim |
| 2006/0036255 A1 | 2/2006 | Pond et al. |
| 2006/0036256 A1 | 2/2006 | Carl et al. |
| 2006/0036258 A1 | 2/2006 | Zucherman et al. |
| 2006/0036259 A1 | 2/2006 | Carl et al. |
| 2006/0036260 A1 | 2/2006 | Runco et al. |
| 2006/0036323 A1 | 2/2006 | Carl et al. |
| 2006/0036324 A1 | 2/2006 | Sachs et al. |
| 2006/0041259 A1 | 2/2006 | Paul et al. |
| 2006/0052780 A1 | 3/2006 | Errico et al. |
| 2006/0052783 A1 | 3/2006 | Dant et al. |
| 2006/0052784 A1 | 3/2006 | Dant et al. |
| 2006/0052786 A1 | 3/2006 | Dant et al. |
| 2006/0052870 A1 | 3/2006 | Ferree |
| 2006/0052872 A1 | 3/2006 | Studer et al. |
| 2006/0058788 A1 | 3/2006 | Hammer et al. |
| 2006/0058790 A1 | 3/2006 | Carl et al. |
| 2006/0058791 A1 | 3/2006 | Broman et al. |
| 2006/0058800 A1 | 3/2006 | Ainsworth et al. |
| 2006/0058878 A1 | 3/2006 | Michelson |
| 2006/0064090 A1 | 3/2006 | Park |
| 2006/0064091 A1 | 3/2006 | Ludwig et al. |
| 2006/0064092 A1 | 3/2006 | Howland |
| 2006/0064095 A1 | 3/2006 | Senn et al. |
| 2006/0069315 A1 | 3/2006 | Miles et al. |
| 2006/0069390 A1 | 3/2006 | Frigg et al. |
| 2006/0069436 A1 | 3/2006 | Sutton et al. |
| 2006/0069438 A1 | 3/2006 | Zucherman et al. |
| 2006/0074419 A1 | 4/2006 | Taylor et al. |
| 2006/0074445 A1* | 4/2006 | Gerber ............... A61B 17/7076 606/191 |
| 2006/0074488 A1 | 4/2006 | Abdou et al. |
| 2006/0079894 A1 | 4/2006 | Colleran et al. |
| 2006/0079895 A1 | 4/2006 | McLeer |
| 2006/0079896 A1 | 4/2006 | Kwak et al. |
| 2006/0079898 A1 | 4/2006 | Ainsworth et al. |
| 2006/0079899 A1 | 4/2006 | Ritland |
| 2006/0079903 A1 | 4/2006 | Wong |
| 2006/0079905 A1 | 4/2006 | Beyar et al. |
| 2006/0084844 A1 | 4/2006 | Nehls |
| 2006/0084976 A1 | 4/2006 | Borgstrom et al. |
| 2006/0084977 A1 | 4/2006 | Lieberman |
| 2006/0084981 A1 | 4/2006 | Shluzas |
| 2006/0084982 A1 | 4/2006 | Kim |
| 2006/0084983 A1 | 4/2006 | Kim |
| 2006/0084984 A1 | 4/2006 | Kim |
| 2006/0084985 A1 | 4/2006 | Kim |
| 2006/0084986 A1 | 4/2006 | Grinberg et al. |
| 2006/0084987 A1 | 4/2006 | Kim |
| 2006/0084988 A1 | 4/2006 | Kim |
| 2006/0084989 A1 | 4/2006 | Dickinson et al. |

(56) References Cited

U.S. PATENT DOCUMENTS

| | | |
|---|---|---|
| 2006/0084991 A1 | 4/2006 | Borgstrom et al. |
| 2006/0084993 A1 | 4/2006 | Landry et al. |
| 2006/0084995 A1 | 4/2006 | Biedermann et al. |
| 2006/0085069 A1 | 4/2006 | Kim |
| 2006/0085076 A1 | 4/2006 | Krishna et al. |
| 2006/0088398 A1 | 4/2006 | Lund |
| 2006/0089643 A1 | 4/2006 | Mujwid |
| 2006/0089644 A1 | 4/2006 | Felix |
| 2006/0089646 A1 | 4/2006 | Bonutti |
| 2006/0089647 A1 | 4/2006 | Culbert et al. |
| 2006/0089656 A1 | 4/2006 | Allard et al. |
| 2006/0089718 A1 | 4/2006 | Zucherman et al. |
| 2006/0095037 A1 | 5/2006 | Jones et al. |
| 2006/0106380 A1 | 5/2006 | Colleran et al. |
| 2006/0106381 A1 | 5/2006 | Ferree et al. |
| 2006/0106383 A1 | 5/2006 | Biedermann et al. |
| 2006/0106387 A1 | 5/2006 | Fanger et al. |
| 2006/0106395 A1 | 5/2006 | Link et al. |
| 2006/0106397 A1 | 5/2006 | Lins |
| 2006/0111714 A1 | 5/2006 | Foley |
| 2006/0111715 A1 | 5/2006 | Jackson |
| 2006/0111728 A1 | 5/2006 | Abdou |
| 2006/0116677 A1 | 6/2006 | Burd et al. |
| 2006/0116768 A1 | 6/2006 | Krueger et al. |
| 2006/0122597 A1 | 6/2006 | Jones et al. |
| 2006/0122599 A1 | 6/2006 | Drewry et al. |
| 2006/0122604 A1 | 6/2006 | Gorhan et al. |
| 2006/0122607 A1 | 6/2006 | Kolb |
| 2006/0122625 A1 | 6/2006 | Truckai et al. |
| 2006/0122701 A1 | 6/2006 | Kiester |
| 2006/0129147 A1 | 6/2006 | Biedermann et al. |
| 2006/0129149 A1 | 6/2006 | Iott et al. |
| 2006/0129239 A1 | 6/2006 | Kwak |
| 2006/0129244 A1 | 6/2006 | Ensign |
| 2006/0136060 A1 | 6/2006 | Taylor |
| 2006/0136062 A1 | 6/2006 | DiNello et al. |
| 2006/0142758 A1 | 6/2006 | Petit |
| 2006/0142760 A1 | 6/2006 | McDonnell |
| 2006/0142761 A1 | 6/2006 | Landry et al. |
| 2006/0142858 A1 | 6/2006 | Colleran et al. |
| 2006/0149228 A1 | 7/2006 | Schlapfer et al. |
| 2006/0149229 A1 | 7/2006 | Kwak et al. |
| 2006/0149232 A1 | 7/2006 | Sasing |
| 2006/0149234 A1 | 7/2006 | de Coninck |
| 2006/0149238 A1 | 7/2006 | Sherman et al. |
| 2006/0149240 A1 | 7/2006 | Jackson |
| 2006/0149241 A1 | 7/2006 | Richelsoph et al. |
| 2006/0149244 A1 | 7/2006 | Amrein et al. |
| 2006/0149245 A1 | 7/2006 | Sweeney |
| 2006/0149278 A1 | 7/2006 | Abdou |
| 2006/0149284 A1 | 7/2006 | McCormack et al. |
| 2006/0149385 A1 | 7/2006 | McKay |
| 2006/0155277 A1 | 7/2006 | Metz-Stavenhagen |
| 2006/0155278 A1 | 7/2006 | Warnick |
| 2006/0155284 A1 | 7/2006 | Doherty et al. |
| 2006/0161152 A1 | 7/2006 | Ensign et al. |
| 2006/0161154 A1 | 7/2006 | McAfee |
| 2006/0167454 A1 | 7/2006 | Ludwig et al. |
| 2006/0167455 A1 | 7/2006 | Clement et al. |
| 2006/0173454 A1 | 8/2006 | Spitler et al. |
| 2006/0173456 A1 | 8/2006 | Hawkes et al. |
| 2006/0178746 A1 | 8/2006 | Bartish et al. |
| 2006/0184112 A1 | 8/2006 | Horn et al. |
| 2006/0184171 A1 | 8/2006 | Biedermann et al. |
| 2006/0184180 A1 | 8/2006 | Augostino et al. |
| 2006/0184247 A1 | 8/2006 | Edidin et al. |
| 2006/0187562 A1 | 8/2006 | Mounnarat et al. |
| 2006/0189983 A1 | 8/2006 | Fallin et al. |
| 2006/0189984 A1 | 8/2006 | Fallin et al. |
| 2006/0189985 A1 | 8/2006 | Lewis |
| 2006/0189999 A1 | 8/2006 | Zwirkoski |
| 2006/0190082 A1 | 8/2006 | Keller et al. |
| 2006/0190083 A1 | 8/2006 | Arnin et al. |
| 2006/0195089 A1 | 8/2006 | Lehuec et al. |
| 2006/0195090 A1 | 8/2006 | Suddaby |
| 2006/0195093 A1 | 8/2006 | Jahng |
| 2006/0195096 A1 | 8/2006 | Lee et al. |
| 2006/0195098 A1 | 8/2006 | Schumacher |
| 2006/0195102 A1 | 8/2006 | Malandain |
| 2006/0195192 A1 | 8/2006 | Gordon et al. |
| 2006/0200121 A1 | 9/2006 | Mowery |
| 2006/0200128 A1 | 9/2006 | Mueller |
| 2006/0200130 A1 | 9/2006 | Hawkins et al. |
| 2006/0200131 A1 | 9/2006 | Chao et al. |
| 2006/0200132 A1 | 9/2006 | Chao et al. |
| 2006/0200135 A1 | 9/2006 | Sherman et al. |
| 2006/0200138 A1 | 9/2006 | Michelson |
| 2006/0200139 A1 | 9/2006 | Michelson |
| 2006/0200149 A1 | 9/2006 | Hoy et al. |
| 2006/0210494 A1 | 9/2006 | Rabiei et al. |
| 2006/0212033 A1 | 9/2006 | Rothman et al. |
| 2006/0212034 A1 | 9/2006 | Triplett et al. |
| 2006/0217710 A1 | 9/2006 | Abdou |
| 2006/0217712 A1 | 9/2006 | Mueller et al. |
| 2006/0217713 A1 | 9/2006 | Serhan et al. |
| 2006/0217714 A1 | 9/2006 | Serhan et al. |
| 2006/0217716 A1 | 9/2006 | Baker et al. |
| 2006/0217719 A1 | 9/2006 | Albert et al. |
| 2006/0217731 A1 | 9/2006 | Gil et al. |
| 2006/0217809 A1 | 9/2006 | Albert et al. |
| 2006/0224159 A1 | 10/2006 | Anderson |
| 2006/0224241 A1 | 10/2006 | Butler et al. |
| 2006/0229608 A1 | 10/2006 | Foster et al. |
| 2006/0229609 A1 | 10/2006 | Wang |
| 2006/0229610 A1 | 10/2006 | Piehl |
| 2006/0229612 A1 | 10/2006 | Rothman et al. |
| 2006/0229613 A1 | 10/2006 | Timm et al. |
| 2006/0229614 A1 | 10/2006 | Foley et al. |
| 2006/0229615 A1 | 10/2006 | Abdou et al. |
| 2006/0229627 A1 | 10/2006 | Hunt et al. |
| 2006/0229629 A1 | 10/2006 | Manzi et al. |
| 2006/0229715 A1 | 10/2006 | Istephanous et al. |
| 2006/0229729 A1 | 10/2006 | Gordon et al. |
| 2006/0235387 A1 | 10/2006 | Peterman |
| 2006/0235389 A1 | 10/2006 | Albert et al. |
| 2006/0235391 A1 | 10/2006 | Sutterlin, III |
| 2006/0235392 A1 | 10/2006 | Hammer et al. |
| 2006/0235393 A1 | 10/2006 | Bono et al. |
| 2006/0235403 A1 | 10/2006 | Blain |
| 2006/0235411 A1 | 10/2006 | Blain et al. |
| 2006/0235414 A1 | 10/2006 | Lim et al. |
| 2006/0235426 A1 | 10/2006 | Lim et al. |
| 2006/0235520 A1 | 10/2006 | Pannu |
| 2006/0235532 A1 | 10/2006 | Meunier et al. |
| 2006/0241593 A1 | 10/2006 | Sherman et al. |
| 2006/0241595 A1 | 10/2006 | Molz, IV et al. |
| 2006/0241599 A1 | 10/2006 | Konieczynski et al. |
| 2006/0241600 A1 | 10/2006 | Ensign et al. |
| 2006/0241601 A1 | 10/2006 | Trautwein et al. |
| 2006/0241610 A1 | 10/2006 | Lim et al. |
| 2006/0241614 A1 | 10/2006 | Bruneau et al. |
| 2006/0241615 A1 | 10/2006 | Melkent |
| 2006/0241641 A1 | 10/2006 | Albans et al. |
| 2006/0241761 A1 | 10/2006 | Gately |
| 2006/0241769 A1 | 10/2006 | Gordon et al. |
| 2006/0241771 A1 | 10/2006 | Gordon et al. |
| 2006/0247624 A1 | 11/2006 | Banouskou et al. |
| 2006/0247630 A1 | 11/2006 | Iott et al. |
| 2006/0247631 A1 | 11/2006 | Ahn et al. |
| 2006/0247632 A1 | 11/2006 | Winslow et al. |
| 2006/0247633 A1 | 11/2006 | Winslow et al. |
| 2006/0247634 A1 | 11/2006 | Warner et al. |
| 2006/0247635 A1 | 11/2006 | Gordon et al. |
| 2006/0247636 A1 | 11/2006 | Yuan et al. |
| 2006/0247637 A1 | 11/2006 | Colleran et al. |
| 2006/0247640 A1 | 11/2006 | Blackwell et al. |
| 2006/0247655 A1 | 11/2006 | Francis et al. |
| 2006/0247679 A1 | 11/2006 | Peterman |
| 2006/0247772 A1 | 11/2006 | McKay |
| 2006/0247778 A1 | 11/2006 | Ferree et al. |
| 2006/0247779 A1 | 11/2006 | Gordon et al. |
| 2006/0247781 A1 | 11/2006 | Francis |
| 2006/0247782 A1 | 11/2006 | Molz, IV et al. |
| 2006/0253198 A1 | 11/2006 | Myint et al. |

(56) References Cited

U.S. PATENT DOCUMENTS

| | | |
|---|---|---|
| 2006/0253201 A1 | 11/2006 | McLuen |
| 2006/0264933 A1 | 11/2006 | Baker et al. |
| 2006/0264934 A1 | 11/2006 | Fallin |
| 2006/0264935 A1 | 11/2006 | White |
| 2006/0264936 A1 | 11/2006 | Partin et al. |
| 2006/0264937 A1 | 11/2006 | White |
| 2006/0264940 A1 | 11/2006 | Hartmann |
| 2006/0264942 A1 | 11/2006 | Lim et al. |
| 2006/0264962 A1 | 11/2006 | Chin et al. |
| 2006/0265077 A1 | 11/2006 | Zwirkoski |
| 2006/0269940 A1 | 11/2006 | Li et al. |
| 2006/0271046 A1 | 11/2006 | Kwak et al. |
| 2006/0276787 A1 | 12/2006 | Zubok et al. |
| 2006/0276789 A1 | 12/2006 | Jackson |
| 2006/0276791 A1 | 12/2006 | Shluzas |
| 2006/0276792 A1 | 12/2006 | Ensign et al. |
| 2006/0276793 A1 | 12/2006 | Berry |
| 2006/0276803 A1 | 12/2006 | Salerni |
| 2006/0276900 A1 | 12/2006 | Carpenter |
| 2006/0282074 A1 | 12/2006 | Renaud et al. |
| 2006/0282075 A1 | 12/2006 | Labrom et al. |
| 2006/0282076 A1 | 12/2006 | Labrom et al. |
| 2006/0282078 A1 | 12/2006 | Labrom et al. |
| 2006/0282079 A1 | 12/2006 | Labrom et al. |
| 2006/0287583 A1 | 12/2006 | Mangiardi |
| 2006/0293662 A1 | 12/2006 | Boyer, II et al. |
| 2007/0010889 A1 | 1/2007 | Francis |
| 2007/0016218 A1 | 1/2007 | Winslow et al. |
| 2007/0016298 A1 | 1/2007 | Recoules-Arche et al. |
| 2007/0021836 A1 | 1/2007 | Doty |
| 2007/0027542 A1 | 2/2007 | Xu |
| 2007/0032790 A1 | 2/2007 | Aschmann et al. |
| 2007/0039837 A1 | 2/2007 | Hanina et al. |
| 2007/0043356 A1 | 2/2007 | Timm et al. |
| 2007/0043442 A1 | 2/2007 | Abernathie et al. |
| 2007/0049935 A1 | 3/2007 | Edidin et al. |
| 2007/0050030 A1 | 3/2007 | Kim |
| 2007/0050032 A1 | 3/2007 | Gittings et al. |
| 2007/0055236 A1 | 3/2007 | Hudgins et al. |
| 2007/0055377 A1 | 3/2007 | Hanson et al. |
| 2007/0067035 A1 | 3/2007 | Falahee |
| 2007/0073111 A1 | 3/2007 | Bass |
| 2007/0073398 A1 | 3/2007 | Fabian et al. |
| 2007/0083266 A1 | 4/2007 | Lang |
| 2007/0090238 A1 | 4/2007 | Justis |
| 2007/0093817 A1 | 4/2007 | Barrus et al. |
| 2007/0093823 A1 | 4/2007 | Booth et al. |
| 2007/0093825 A1 | 4/2007 | Ferree et al. |
| 2007/0093828 A1 | 4/2007 | Abdou et al. |
| 2007/0093829 A1 | 4/2007 | Abdou |
| 2007/0093901 A1 | 4/2007 | Grotz et al. |
| 2007/0100212 A1 | 5/2007 | Pimenta et al. |
| 2007/0100340 A1 | 5/2007 | Lange et al. |
| 2007/0100341 A1 | 5/2007 | Reglos et al. |
| 2007/0106298 A1 | 5/2007 | Carli et al. |
| 2007/0106383 A1 | 5/2007 | Abdou et al. |
| 2007/0108383 A1 | 5/2007 | Combes et al. |
| 2007/0118121 A1 | 5/2007 | Purcell et al. |
| 2007/0118122 A1 | 5/2007 | Butler et al. |
| 2007/0118123 A1 | 5/2007 | Strausbaugh et al. |
| 2007/0118132 A1 | 5/2007 | Culbert et al. |
| 2007/0123867 A1 | 5/2007 | Kirschman |
| 2007/0123869 A1 | 5/2007 | Chin et al. |
| 2007/0123884 A1 | 5/2007 | Abdou |
| 2007/0129804 A1 | 6/2007 | Bentley et al. |
| 2007/0142916 A1 | 6/2007 | Olson et al. |
| 2007/0149978 A1 | 6/2007 | Shezifi et al. |
| 2007/0151116 A1 | 7/2007 | Malandain |
| 2007/0156233 A1 | 7/2007 | Kapadia et al. |
| 2007/0161962 A1 | 7/2007 | Edie et al. |
| 2007/0161992 A1 | 7/2007 | Kwak et al. |
| 2007/0162000 A1 | 7/2007 | Perkins |
| 2007/0162001 A1 | 7/2007 | Chin et al. |
| 2007/0162005 A1 | 7/2007 | Peterson et al. |
| 2007/0162127 A1 | 7/2007 | Peterman et al. |
| 2007/0162133 A1 | 7/2007 | Doubler et al. |
| 2007/0162138 A1 | 7/2007 | Heinz |
| 2007/0167948 A1 | 7/2007 | Abdou |
| 2007/0168036 A1 | 7/2007 | Ainsworth et al. |
| 2007/0173831 A1 | 7/2007 | Abdou |
| 2007/0173842 A1 | 7/2007 | Abdou |
| 2007/0179493 A1 | 8/2007 | Kim |
| 2007/0179500 A1 | 8/2007 | Chin et al. |
| 2007/0179614 A1 | 8/2007 | Heinz et al. |
| 2007/0185367 A1 | 8/2007 | Abdou |
| 2007/0185376 A1 | 8/2007 | Wilson et al. |
| 2007/0185489 A1 | 8/2007 | Abdou |
| 2007/0191834 A1 | 8/2007 | Bruneau et al. |
| 2007/0191861 A1 | 8/2007 | Allard et al. |
| 2007/0191946 A1 | 8/2007 | Heinz et al. |
| 2007/0191951 A1 | 8/2007 | Branch et al. |
| 2007/0191958 A1 | 8/2007 | Abdou |
| 2007/0198090 A1 | 8/2007 | Abdou |
| 2007/0208227 A1 | 9/2007 | Smith et al. |
| 2007/0213597 A1 | 9/2007 | Wooster |
| 2007/0213732 A1 | 9/2007 | Khanna et al. |
| 2007/0225724 A1 | 9/2007 | Edmond |
| 2007/0225726 A1 | 9/2007 | Dye et al. |
| 2007/0225807 A1 | 9/2007 | Phan et al. |
| 2007/0225808 A1 | 9/2007 | Warnick |
| 2007/0225812 A1 | 9/2007 | Gill |
| 2007/0233074 A1 | 10/2007 | Anderson et al. |
| 2007/0233077 A1 | 10/2007 | Khalili |
| 2007/0233082 A1 | 10/2007 | Chin et al. |
| 2007/0233083 A1 | 10/2007 | Abdou |
| 2007/0233084 A1 | 10/2007 | Betz et al. |
| 2007/0233088 A1 | 10/2007 | Edmond |
| 2007/0233089 A1 | 10/2007 | DiPoto et al. |
| 2007/0233118 A1 | 10/2007 | McLain |
| 2007/0233129 A1 | 10/2007 | Bertagnoli et al. |
| 2007/0233247 A1 | 10/2007 | Schwab |
| 2007/0233251 A1 | 10/2007 | Abdou |
| 2007/0255389 A1 | 11/2007 | Oberti et al. |
| 2007/0255415 A1 | 11/2007 | Edie et al. |
| 2007/0260314 A1 | 11/2007 | Biyani |
| 2007/0270812 A1 | 11/2007 | Peckham |
| 2007/0270813 A1 | 11/2007 | Garamszegi |
| 2007/0270824 A1 | 11/2007 | Lim et al. |
| 2007/0270827 A1 | 11/2007 | Lim et al. |
| 2007/0270838 A1 | 11/2007 | Bruneau et al. |
| 2007/0270840 A1 | 11/2007 | Chin et al. |
| 2007/0270874 A1 | 11/2007 | Anderson |
| 2007/0270963 A1 | 11/2007 | Melkent et al. |
| 2007/0270968 A1 | 11/2007 | Baynham et al. |
| 2007/0274772 A1 | 11/2007 | Tiberghien et al. |
| 2007/0276370 A1 | 11/2007 | Altarac et al. |
| 2007/0282448 A1 | 12/2007 | Abdou |
| 2007/0293949 A1 | 12/2007 | Salerni et al. |
| 2007/0299445 A1 | 12/2007 | Shadduck et al. |
| 2007/0299521 A1 | 12/2007 | Glenn et al. |
| 2008/0009880 A1 | 1/2008 | Warnick et al. |
| 2008/0015580 A1 | 1/2008 | Chao |
| 2008/0015597 A1 | 1/2008 | Whipple |
| 2008/0015698 A1 | 1/2008 | Marino et al. |
| 2008/0021466 A1 | 1/2008 | Shadduck et al. |
| 2008/0021559 A1 | 1/2008 | Thramann |
| 2008/0027432 A1 | 1/2008 | Strauss et al. |
| 2008/0027438 A1 | 1/2008 | Abdou |
| 2008/0027458 A1 | 1/2008 | Aikins et al. |
| 2008/0027544 A1 | 1/2008 | Melkent |
| 2008/0027545 A1 | 1/2008 | Zucherman et al. |
| 2008/0027550 A1 | 1/2008 | Link et al. |
| 2008/0039837 A1 | 2/2008 | Gambale |
| 2008/0039843 A1 | 2/2008 | Abdou |
| 2008/0045963 A1 | 2/2008 | Abdou |
| 2008/0045968 A1 | 2/2008 | Yu et al. |
| 2008/0045983 A1 | 2/2008 | To et al. |
| 2008/0051783 A1 | 2/2008 | Null et al. |
| 2008/0051896 A1 | 2/2008 | Suddaby |
| 2008/0058606 A1 | 3/2008 | Miles et al. |
| 2008/0058810 A1 | 3/2008 | Abdou |
| 2008/0065219 A1 | 3/2008 | Dye |
| 2008/0065222 A1 | 3/2008 | Hamada |
| 2008/0081951 A1 | 4/2008 | Frasier et al. |

(56) References Cited

U.S. PATENT DOCUMENTS

| | | |
|---|---|---|
| 2008/0086080 A1 | 4/2008 | Mastri et al. |
| 2008/0091211 A1 | 4/2008 | Gately |
| 2008/0108993 A1 | 5/2008 | Bennett et al. |
| 2008/0114401 A1 | 5/2008 | Liu et al. |
| 2008/0114455 A1 | 5/2008 | Lange et al. |
| 2008/0119853 A1 | 5/2008 | Felt et al. |
| 2008/0119935 A1 | 5/2008 | Alvarez |
| 2008/0125813 A1 | 5/2008 | Erickson et al. |
| 2008/0125865 A1 | 5/2008 | Abdelgany |
| 2008/0126813 A1 | 5/2008 | Kawakami |
| 2008/0132951 A1 | 6/2008 | Reiley et al. |
| 2008/0133012 A1 | 6/2008 | McGuckin |
| 2008/0133014 A1 | 6/2008 | Gately et al. |
| 2008/0133016 A1 | 6/2008 | Heinz |
| 2008/0133017 A1 | 6/2008 | Beyar et al. |
| 2008/0139879 A1 | 6/2008 | Olson et al. |
| 2008/0140085 A1 | 6/2008 | Gately et al. |
| 2008/0140125 A1 | 6/2008 | Mitchell et al. |
| 2008/0140204 A1 | 6/2008 | Heinz |
| 2008/0140207 A1 | 6/2008 | Olmos et al. |
| 2008/0147123 A1 | 6/2008 | Schermerhorn |
| 2008/0147190 A1 | 6/2008 | Dewey et al. |
| 2008/0154308 A1 | 6/2008 | Sherman et al. |
| 2008/0154374 A1 | 6/2008 | Labrom |
| 2008/0161818 A1 | 7/2008 | Kloss et al. |
| 2008/0161821 A1 | 7/2008 | Heinz |
| 2008/0161853 A1 | 7/2008 | Arnold et al. |
| 2008/0161856 A1 | 7/2008 | Liu et al. |
| 2008/0167655 A1 | 7/2008 | Wang et al. |
| 2008/0167657 A1 | 7/2008 | Greenhalgh |
| 2008/0177271 A1 | 7/2008 | Yeh |
| 2008/0177298 A1 | 7/2008 | Zucherman et al. |
| 2008/0177306 A1 | 7/2008 | Lamborne et al. |
| 2008/0177312 A1 | 7/2008 | Perez-Cruet et al. |
| 2008/0177326 A1 | 7/2008 | Thompson |
| 2008/0177391 A1 | 7/2008 | Mitchell et al. |
| 2008/0183204 A1 | 7/2008 | Greenhalgh et al. |
| 2008/0183209 A1 | 7/2008 | Robinson et al. |
| 2008/0183211 A1 | 7/2008 | Lamborne et al. |
| 2008/0183218 A1 | 7/2008 | Mueller et al. |
| 2008/0188898 A1 | 8/2008 | Jackson |
| 2008/0188941 A1 | 8/2008 | Grotz |
| 2008/0195152 A1 | 8/2008 | Altarac et al. |
| 2008/0234735 A1 | 9/2008 | Joshi |
| 2008/0243185 A1 | 10/2008 | Felix et al. |
| 2008/0243186 A1 | 10/2008 | Abdou |
| 2008/0243188 A1 | 10/2008 | Walder et al. |
| 2008/0243189 A1 | 10/2008 | Purcell et al. |
| 2008/0243255 A1 | 10/2008 | Butler et al. |
| 2008/0249622 A1 | 10/2008 | Gray |
| 2008/0249628 A1 | 10/2008 | Altarac et al. |
| 2008/0262318 A1 | 10/2008 | Gorek et al. |
| 2008/0262554 A1 | 10/2008 | Hayes et al. |
| 2008/0269904 A1 | 10/2008 | Voorhies |
| 2008/0281346 A1 | 11/2008 | Greenhalgh et al. |
| 2008/0281358 A1 | 11/2008 | Abdou |
| 2008/0281359 A1 | 11/2008 | Abdou |
| 2008/0281424 A1 | 11/2008 | Parry et al. |
| 2008/0281425 A1 | 11/2008 | Thalgott et al. |
| 2008/0288073 A1 | 11/2008 | Renganath et al. |
| 2008/0294199 A1 | 11/2008 | Kohm et al. |
| 2008/0294200 A1 | 11/2008 | Kohm et al. |
| 2008/0300598 A1 | 12/2008 | Barreiro et al. |
| 2008/0300601 A1 | 12/2008 | Fabian et al. |
| 2008/0300685 A1 | 12/2008 | Carls et al. |
| 2008/0300686 A1 | 12/2008 | Khoo |
| 2008/0306601 A1 | 12/2008 | Dreyfuss |
| 2008/0312655 A1 | 12/2008 | Kirschman et al. |
| 2008/0312692 A1 | 12/2008 | Brennan et al. |
| 2008/0312741 A1 | 12/2008 | Lee et al. |
| 2008/0312743 A1 | 12/2008 | Vila et al. |
| 2008/0319487 A1 | 12/2008 | Fielding et al. |
| 2008/0319549 A1 | 12/2008 | Greenhalgh et al. |
| 2009/0012566 A1 | 1/2009 | Fauth |
| 2009/0012623 A1 | 1/2009 | Sack et al. |
| 2009/0024166 A1 | 1/2009 | Carl et al. |
| 2009/0024217 A1 | 1/2009 | Levy et al. |
| 2009/0030423 A1 | 1/2009 | Puno |
| 2009/0030457 A1 | 1/2009 | Janowski et al. |
| 2009/0030465 A1 | 1/2009 | Altarac et al. |
| 2009/0030519 A1 | 1/2009 | Falahee |
| 2009/0030520 A1 | 1/2009 | Biedermann et al. |
| 2009/0036746 A1 | 2/2009 | Blackwell et al. |
| 2009/0036927 A1 | 2/2009 | Vestgaarden |
| 2009/0036929 A1 | 2/2009 | Reglos et al. |
| 2009/0036988 A1 | 2/2009 | Peckham |
| 2009/0048668 A1 | 2/2009 | Wilson et al. |
| 2009/0054931 A1 | 2/2009 | Metz-Stavenhagen |
| 2009/0062869 A1 | 3/2009 | Claverie et al. |
| 2009/0062915 A1 | 3/2009 | Kohm et al. |
| 2009/0062918 A1 | 3/2009 | Wang et al. |
| 2009/0062920 A1 | 3/2009 | Tauber |
| 2009/0076333 A1 | 3/2009 | Bjork |
| 2009/0076516 A1 | 3/2009 | Lowry et al. |
| 2009/0076615 A1 | 3/2009 | Duggal et al. |
| 2009/0082808 A1 | 3/2009 | Butler et al. |
| 2009/0082813 A1 | 3/2009 | Long et al. |
| 2009/0093884 A1 | 4/2009 | Bass |
| 2009/0099601 A1 | 4/2009 | Aferzon et al. |
| 2009/0105547 A1 | 4/2009 | Vayser et al. |
| 2009/0105761 A1 | 4/2009 | Robie |
| 2009/0105768 A1 | 4/2009 | Cragg et al. |
| 2009/0105773 A1 | 4/2009 | Lange et al. |
| 2009/0105830 A1 | 4/2009 | Jones et al. |
| 2009/0105831 A1 | 4/2009 | Jones et al. |
| 2009/0118766 A1 | 5/2009 | Park et al. |
| 2009/0118771 A1 | 5/2009 | Gonzalez-Hernandez |
| 2009/0124861 A1 | 5/2009 | Fetzer |
| 2009/0125062 A1 | 5/2009 | Arnin |
| 2009/0125071 A1 | 5/2009 | Skinlo et al. |
| 2009/0132054 A1 | 5/2009 | Zeegers |
| 2009/0143859 A1 | 6/2009 | McClellan, III et al. |
| 2009/0149956 A1 | 6/2009 | Greenhalgh et al. |
| 2009/0149959 A1 | 6/2009 | Conner et al. |
| 2009/0157186 A1 | 6/2009 | Magerl |
| 2009/0157188 A1 | 6/2009 | Zeegers |
| 2009/0163920 A1 | 6/2009 | Hochschuler et al. |
| 2009/0163957 A1 | 6/2009 | St Clair et al. |
| 2009/0163961 A1 | 6/2009 | Kirschman |
| 2009/0164020 A1 | 6/2009 | Janowski et al. |
| 2009/0171394 A1 | 7/2009 | Abdou |
| 2009/0177238 A1 | 7/2009 | Abdou |
| 2009/0177262 A1 | 7/2009 | Oberti et al. |
| 2009/0182429 A1 | 7/2009 | Humphreys et al. |
| 2009/0182430 A1 | 7/2009 | Tyber et al. |
| 2009/0186333 A1 | 7/2009 | Mills et al. |
| 2009/0187249 A1 | 7/2009 | Osman |
| 2009/0192613 A1 | 7/2009 | Wing et al. |
| 2009/0192615 A1 | 7/2009 | Tyber et al. |
| 2009/0198211 A1 | 8/2009 | Thorne, Jr. et al. |
| 2009/0198277 A1 | 8/2009 | Gordon et al. |
| 2009/0204151 A1 | 8/2009 | Bracken |
| 2009/0204154 A1 | 8/2009 | Kiester |
| 2009/0204218 A1 | 8/2009 | Richelsoph |
| 2009/0204219 A1 | 8/2009 | Beaurain et al. |
| 2009/0210007 A1 | 8/2009 | Levy et al. |
| 2009/0210015 A1 | 8/2009 | Cermak et al. |
| 2009/0210062 A1 | 8/2009 | Thalgott et al. |
| 2009/0216234 A1 | 8/2009 | Farr et al. |
| 2009/0216241 A1 | 8/2009 | Dinville |
| 2009/0222046 A1 | 9/2009 | Gorek |
| 2009/0222092 A1 | 9/2009 | Davis et al. |
| 2009/0222100 A1 | 9/2009 | Cipoletti et al. |
| 2009/0227845 A1 | 9/2009 | Lo et al. |
| 2009/0228045 A1 | 9/2009 | Hayes et al. |
| 2009/0228108 A1 | 9/2009 | Keller |
| 2009/0228110 A1 | 9/2009 | McClintock |
| 2009/0234364 A1 | 9/2009 | Crook |
| 2009/0234455 A1 | 9/2009 | Moskowitz et al. |
| 2009/0240334 A1 | 9/2009 | Richelsoph |
| 2009/0240335 A1 | 9/2009 | Arcenio et al. |
| 2009/0247819 A1 | 10/2009 | Wilson et al. |
| 2009/0248078 A1 | 10/2009 | Dant |
| 2009/0248089 A1 | 10/2009 | Jacofsky et al. |

(56) References Cited

U.S. PATENT DOCUMENTS

| | | |
|---|---|---|
| 2009/0254125 A1 | 10/2009 | Predick |
| 2009/0259257 A1 | 10/2009 | Prevost |
| 2009/0259316 A1 | 10/2009 | Ginn et al. |
| 2009/0265007 A1 | 10/2009 | Colleran |
| 2009/0270918 A1 | 10/2009 | Attia et al. |
| 2009/0270989 A1 | 10/2009 | Conner et al. |
| 2009/0270990 A1 | 10/2009 | Louis et al. |
| 2009/0276040 A1 | 11/2009 | Rowe et al. |
| 2009/0276049 A1 | 11/2009 | Weiland |
| 2009/0281628 A1 | 11/2009 | Oglaza et al. |
| 2009/0290316 A1 | 11/2009 | Kariya |
| 2009/0292361 A1 | 11/2009 | Lopez |
| 2009/0299478 A1 | 12/2009 | Carls et al. |
| 2009/0326538 A1 | 12/2009 | Sennett et al. |
| 2009/0326581 A1 | 12/2009 | Galley et al. |
| 2009/0326584 A1 | 12/2009 | Slivka et al. |
| 2010/0004664 A1 | 1/2010 | Boyajian et al. |
| 2010/0009929 A1 | 1/2010 | Cheng et al. |
| 2010/0016897 A1 | 1/2010 | Le Couedic et al. |
| 2010/0016906 A1 | 1/2010 | Abdou |
| 2010/0023061 A1 | 1/2010 | Randol et al. |
| 2010/0023064 A1 | 1/2010 | Brunger et al. |
| 2010/0036423 A1 | 2/2010 | Hayes et al. |
| 2010/0036495 A1 | 2/2010 | Daum et al. |
| 2010/0042149 A1 | 2/2010 | Chao et al. |
| 2010/0049324 A1 | 2/2010 | Valdevit et al. |
| 2010/0069929 A1 | 3/2010 | Abdou |
| 2010/0069962 A1 | 3/2010 | Harms et al. |
| 2010/0069965 A1 | 3/2010 | Abdou |
| 2010/0070041 A1 | 3/2010 | Peterman et al. |
| 2010/0076448 A1 | 3/2010 | Abdou |
| 2010/0082109 A1 | 4/2010 | Greenhalgh et al. |
| 2010/0087858 A1 | 4/2010 | Abdou |
| 2010/0087869 A1 | 4/2010 | Abdou |
| 2010/0087878 A1 | 4/2010 | Abdou |
| 2010/0087923 A1 | 4/2010 | Abdou |
| 2010/0094422 A1 | 4/2010 | Hansell et al. |
| 2010/0100137 A1 | 4/2010 | Justis et al. |
| 2010/0106250 A1 | 4/2010 | Abdou |
| 2010/0121384 A1 | 5/2010 | Abdou |
| 2010/0130827 A1 | 5/2010 | Pimenta et al. |
| 2010/0152603 A1* | 6/2010 | Miles .................. A61B 17/02 600/210 |
| 2010/0152778 A1 | 6/2010 | Saint |
| 2010/0174315 A1 | 7/2010 | Scodary et al. |
| 2010/0179657 A1 | 7/2010 | Greenhalgh et al. |
| 2010/0185291 A1 | 7/2010 | Jimenez et al. |
| 2010/0191336 A1 | 7/2010 | Greenhalgh |
| 2010/0191337 A1 | 7/2010 | Zamani et al. |
| 2010/0198140 A1 | 8/2010 | Lawson |
| 2010/0204795 A1 | 8/2010 | Greenhalgh |
| 2010/0211101 A1 | 8/2010 | Blackwell et al. |
| 2010/0211176 A1 | 8/2010 | Greenhalgh |
| 2010/0211177 A1 | 8/2010 | Abdou |
| 2010/0217382 A1 | 8/2010 | Chau et al. |
| 2010/0222644 A1 | 9/2010 | Sebastian et al. |
| 2010/0222816 A1 | 9/2010 | Gabelberger et al. |
| 2010/0222884 A1 | 9/2010 | Greenhalgh et al. |
| 2010/0234889 A1 | 9/2010 | Hess |
| 2010/0234952 A1 | 9/2010 | Peterman |
| 2010/0234956 A1 | 9/2010 | Attia et al. |
| 2010/0241168 A1 | 9/2010 | Franck et al. |
| 2010/0249933 A1 | 9/2010 | Trieu |
| 2010/0256759 A1 | 10/2010 | Hansell et al. |
| 2010/0256760 A1 | 10/2010 | Hansell |
| 2010/0262245 A1 | 10/2010 | Alfaro et al. |
| 2010/0262248 A1 | 10/2010 | Sournac et al. |
| 2010/0268281 A1 | 10/2010 | Abdou |
| 2010/0280622 A1 | 11/2010 | McKinley |
| 2010/0286483 A1 | 11/2010 | Bettuchi et al. |
| 2010/0286779 A1 | 11/2010 | Thibodeau |
| 2010/0286780 A1 | 11/2010 | Dryer et al. |
| 2010/0292796 A1 | 11/2010 | Greenhalgh et al. |
| 2010/0305705 A1 | 12/2010 | Butler et al. |
| 2010/0312282 A1 | 12/2010 | Abdou |
| 2010/0312347 A1 | 12/2010 | Arramon et al. |
| 2010/0318128 A1 | 12/2010 | Abdou |
| 2010/0331883 A1 | 12/2010 | Schmitz et al. |
| 2010/0331887 A1 | 12/2010 | Jackson et al. |
| 2010/0331889 A1 | 12/2010 | Abdou |
| 2010/0331981 A1 | 12/2010 | Mohammed |
| 2010/0331985 A1 | 12/2010 | Gordon et al. |
| 2011/0004248 A1 | 1/2011 | Abdou |
| 2011/0009969 A1 | 1/2011 | Puno |
| 2011/0009970 A1 | 1/2011 | Puno |
| 2011/0022090 A1 | 1/2011 | Gordon et al. |
| 2011/0029083 A1 | 2/2011 | Hynes et al. |
| 2011/0029085 A1 | 2/2011 | Hynes et al. |
| 2011/0035011 A1 | 2/2011 | Cain |
| 2011/0046679 A1 | 2/2011 | Chow et al. |
| 2011/0046740 A1 | 2/2011 | Chen et al. |
| 2011/0054531 A1 | 3/2011 | Lamborne et al. |
| 2011/0060366 A1 | 3/2011 | Heim et al. |
| 2011/0066186 A1 | 3/2011 | Boyer, II et al. |
| 2011/0082551 A1 | 4/2011 | Kraus |
| 2011/0082553 A1 | 4/2011 | Abdou |
| 2011/0093074 A1 | 4/2011 | Glerum et al. |
| 2011/0098749 A1 | 4/2011 | Boomer et al. |
| 2011/0106163 A1 | 5/2011 | Hochschuler et al. |
| 2011/0106259 A1 | 5/2011 | Lindenmann et al. |
| 2011/0118552 A1 | 5/2011 | Fischvogt |
| 2011/0125266 A1 | 5/2011 | Rodgers et al. |
| 2011/0130793 A1* | 6/2011 | Woolley .............. A61B 17/7076 606/279 |
| 2011/0137353 A1 | 6/2011 | Buttermann |
| 2011/0144692 A1 | 6/2011 | Saladin et al. |
| 2011/0166600 A1 | 7/2011 | Lamborne et al. |
| 2011/0172720 A1 | 7/2011 | Metcalf, Jr. et al. |
| 2011/0172772 A1 | 7/2011 | Abdou |
| 2011/0184471 A1 | 7/2011 | Foley et al. |
| 2011/0190825 A1 | 8/2011 | Thalgott et al. |
| 2011/0196492 A1 | 8/2011 | Lambrecht et al. |
| 2011/0213465 A1 | 9/2011 | Landry et al. |
| 2011/0224496 A1 | 9/2011 | Weiman |
| 2011/0224497 A1 | 9/2011 | Weiman et al. |
| 2011/0238181 A1 | 9/2011 | Trieu |
| 2011/0251693 A1 | 10/2011 | Barreiro et al. |
| 2011/0264218 A1 | 10/2011 | Asaad |
| 2011/0264228 A1 | 10/2011 | Johnson et al. |
| 2011/0276099 A1 | 11/2011 | Champagne et al. |
| 2011/0276142 A1 | 11/2011 | Niemiec et al. |
| 2011/0282459 A1 | 11/2011 | McClellan, III et al. |
| 2011/0288588 A1 | 11/2011 | Chin et al. |
| 2011/0288594 A1 | 11/2011 | Woolley et al. |
| 2011/0288644 A1 | 11/2011 | Gray et al. |
| 2011/0288645 A1 | 11/2011 | Braddock, Jr. et al. |
| 2011/0301710 A1 | 12/2011 | Mather et al. |
| 2011/0301712 A1 | 12/2011 | Palmatier et al. |
| 2011/0307011 A1 | 12/2011 | Moskowitz et al. |
| 2011/0307012 A1 | 12/2011 | Mir et al. |
| 2011/0319941 A1 | 12/2011 | Bar et al. |
| 2011/0319995 A1 | 12/2011 | Voellmicke et al. |
| 2012/0010472 A1 | 1/2012 | Spann |
| 2012/0010658 A1 | 1/2012 | Kirschman |
| 2012/0016481 A1 | 1/2012 | Zwirkoski |
| 2012/0029565 A1 | 2/2012 | Seifert et al. |
| 2012/0029639 A1 | 2/2012 | Blackwell et al. |
| 2012/0035424 A1 | 2/2012 | Schulte |
| 2012/0041272 A1 | 2/2012 | Dietze, Jr. et al. |
| 2012/0071980 A1 | 3/2012 | Purcell et al. |
| 2012/0078301 A1 | 3/2012 | Hess |
| 2012/0089184 A1 | 4/2012 | Yeh |
| 2012/0095512 A1 | 4/2012 | Nihalani |
| 2012/0101528 A1 | 4/2012 | Souza et al. |
| 2012/0109206 A1 | 5/2012 | Abdou |
| 2012/0123546 A1 | 5/2012 | Medina |
| 2012/0136442 A1 | 5/2012 | Kleiner |
| 2012/0150229 A1 | 6/2012 | Hess |
| 2012/0150302 A1 | 6/2012 | Gray |
| 2012/0158060 A1 | 6/2012 | Abrahams et al. |
| 2012/0158140 A1 | 6/2012 | Miller et al. |
| 2012/0158150 A1 | 6/2012 | Siegal |
| 2012/0179260 A1 | 7/2012 | Nottingham |
| 2012/0185045 A1 | 7/2012 | Morris et al. |

(56) References Cited

U.S. PATENT DOCUMENTS

| | | |
|---|---|---|
| 2012/0190933 A1 | 7/2012 | Kleyman |
| 2012/0191135 A1 | 7/2012 | Abdou |
| 2012/0197297 A1 | 8/2012 | Bootwala et al. |
| 2012/0197401 A1 | 8/2012 | Duncan et al. |
| 2012/0197402 A1 | 8/2012 | Blackwell et al. |
| 2012/0203279 A1 | 8/2012 | Walters et al. |
| 2012/0209271 A1 | 8/2012 | Cohen et al. |
| 2012/0209383 A1 | 8/2012 | Tsuang et al. |
| 2012/0215316 A1 | 8/2012 | Mohr et al. |
| 2012/0221049 A1 | 8/2012 | Blain et al. |
| 2012/0226313 A1 | 9/2012 | Dace |
| 2012/0232592 A1 | 9/2012 | Massoudi |
| 2012/0232658 A1 | 9/2012 | Morgenstern et al. |
| 2012/0238825 A1 | 9/2012 | Smith |
| 2012/0245425 A1 | 9/2012 | Okoniewski |
| 2012/0245431 A1 | 9/2012 | Baudouin et al. |
| 2012/0245432 A1 | 9/2012 | Karpowicz et al. |
| 2012/0245704 A1 | 9/2012 | Childs et al. |
| 2012/0253393 A1 | 10/2012 | Fiorella |
| 2012/0253396 A1 | 10/2012 | Stern et al. |
| 2012/0259416 A1 | 10/2012 | Blackwell et al. |
| 2012/0265021 A1 | 10/2012 | Nottmeier |
| 2012/0271119 A1 | 10/2012 | White |
| 2012/0277864 A1 | 11/2012 | Brodke et al. |
| 2012/0283521 A1 | 11/2012 | Smith et al. |
| 2012/0290017 A1 | 11/2012 | Haidukewych |
| 2012/0290096 A1 | 11/2012 | Messerli |
| 2012/0296171 A1 | 11/2012 | Lovell et al. |
| 2012/0296377 A1 | 11/2012 | Ferree et al. |
| 2012/0310282 A1 | 12/2012 | Abdou |
| 2013/0018467 A1 | 1/2013 | Suh |
| 2013/0023933 A1 | 1/2013 | Haas |
| 2013/0023937 A1 | 1/2013 | Biedermann et al. |
| 2013/0030467 A1 | 1/2013 | Karas et al. |
| 2013/0030469 A1 | 1/2013 | Karas et al. |
| 2013/0030470 A1 | 1/2013 | Karas et al. |
| 2013/0041471 A1 | 2/2013 | Siegal et al. |
| 2013/0053896 A1 | 2/2013 | Voyadzis |
| 2013/0060284 A1 | 3/2013 | Abdou |
| 2013/0066374 A1 | 3/2013 | Galley et al. |
| 2013/0079883 A1 | 3/2013 | Butler et al. |
| 2013/0090691 A1 | 4/2013 | Zhang et al. |
| 2013/0103088 A1 | 4/2013 | Karahalios et al. |
| 2013/0103089 A1 | 4/2013 | Gordon et al. |
| 2013/0123849 A1 | 5/2013 | Abdou |
| 2013/0123924 A1 | 5/2013 | Butler et al. |
| 2013/0131738 A1 | 5/2013 | Powell et al. |
| 2013/0144339 A1 | 6/2013 | Choi et al. |
| 2013/0144340 A1 | 6/2013 | Sheffer et al. |
| 2013/0144387 A1 | 6/2013 | Walker et al. |
| 2013/0144391 A1 | 6/2013 | Siegal et al. |
| 2013/0150886 A1 | 6/2013 | Altarac et al. |
| 2013/0150970 A1 | 6/2013 | Thaiyananthan |
| 2013/0158359 A1 | 6/2013 | Predick et al. |
| 2013/0165982 A1 | 6/2013 | Ek et al. |
| 2013/0172736 A1 | 7/2013 | Abdou |
| 2013/0172932 A1 | 7/2013 | Altarac et al. |
| 2013/0172933 A1 | 7/2013 | Altarac et al. |
| 2013/0172934 A1 | 7/2013 | Walker et al. |
| 2013/0178903 A1 | 7/2013 | Abdou |
| 2013/0184752 A1 | 7/2013 | Binder |
| 2013/0184758 A1 | 7/2013 | Karim |
| 2013/0190573 A1 | 7/2013 | Smith |
| 2013/0190575 A1 | 7/2013 | Mast et al. |
| 2013/0197587 A1 | 8/2013 | Abdou |
| 2013/0197588 A1 | 8/2013 | Abdou |
| 2013/0197647 A1 | 8/2013 | Wolters et al. |
| 2013/0204091 A1 | 8/2013 | Menendez et al. |
| 2013/0218166 A1 | 8/2013 | Elmore |
| 2013/0226240 A1 | 8/2013 | Abdou |
| 2013/0245383 A1 | 9/2013 | Friedrich et al. |
| 2013/0253585 A1 | 9/2013 | Garcia et al. |
| 2013/0253586 A1 | 9/2013 | Rathbun et al. |
| 2013/0261401 A1 | 10/2013 | Hawkins et al. |
| 2013/0261666 A1 | 10/2013 | Gundanna |
| 2013/0274883 A1 | 10/2013 | McLuen et al. |
| 2013/0274884 A1 | 10/2013 | Matsumoto et al. |
| 2013/0296939 A1 | 11/2013 | Perkins |
| 2013/0296940 A1 | 11/2013 | Northcutt et al. |
| 2013/0310942 A1 | 11/2013 | Abdou |
| 2013/0325128 A1 | 12/2013 | Perloff et al. |
| 2014/0005484 A1 | 1/2014 | Charles |
| 2014/0031874 A1 | 1/2014 | Kucharzyk et al. |
| 2014/0058512 A1 | 2/2014 | Petersheim |
| 2014/0058513 A1 | 2/2014 | Gahman et al. |
| 2014/0067070 A1 | 3/2014 | Abdou |
| 2014/0081331 A1 | 3/2014 | Zappacosta et al. |
| 2014/0094922 A1 | 4/2014 | Abdou |
| 2014/0107783 A1 | 4/2014 | Abdou |
| 2014/0114137 A1 | 4/2014 | Reglos et al. |
| 2014/0114138 A1 | 4/2014 | Fedorov et al. |
| 2014/0114139 A1 | 4/2014 | Ziolo et al. |
| 2014/0121705 A1 | 5/2014 | Abdou |
| 2014/0128917 A1 | 5/2014 | Abdou |
| 2014/0135584 A1 | 5/2014 | Lee et al. |
| 2014/0148652 A1 | 5/2014 | Weiman |
| 2014/0148856 A1 | 5/2014 | Ibarra et al. |
| 2014/0155939 A1 | 6/2014 | Sugawara |
| 2014/0172002 A1 | 6/2014 | Predick |
| 2014/0172105 A1 | 6/2014 | Frasier et al. |
| 2014/0172107 A1 | 6/2014 | Thirugnanasambanda et al. |
| 2014/0188223 A1 | 7/2014 | Jensen et al. |
| 2014/0188233 A1 | 7/2014 | Mutchler et al. |
| 2014/0249631 A1 | 9/2014 | Weiman |
| 2014/0257466 A1 | 9/2014 | Board et al. |
| 2014/0277143 A1 | 9/2014 | Zappacosta |
| 2014/0277486 A1 | 9/2014 | Abdou et al. |
| 2014/0277490 A1 | 9/2014 | Perloff et al. |
| 2014/0277499 A1 | 9/2014 | Ainsworth et al. |
| 2014/0277502 A1 | 9/2014 | Schiffman et al. |
| 2014/0288480 A1 | 9/2014 | Zimmerman et al. |
| 2014/0309741 A1 | 10/2014 | Ganter et al. |
| 2014/0336471 A1 | 11/2014 | Pfabe et al. |
| 2014/0343608 A1 | 11/2014 | Whiton et al. |
| 2014/0343678 A1 | 11/2014 | Suddaby et al. |
| 2014/0350347 A1 | 11/2014 | Karpowicz et al. |
| 2014/0379032 A1 | 12/2014 | Hennard |
| 2014/0379086 A1 | 12/2014 | Elahinia et al. |
| 2015/0005882 A1 | 1/2015 | Abdou |
| 2015/0018829 A1 | 1/2015 | Woodburn, Sr. et al. |
| 2015/0057755 A1 | 2/2015 | Suddaby et al. |
| 2015/0080973 A1 | 3/2015 | Eastlack et al. |
| 2015/0094814 A1 | 4/2015 | Emerick et al. |
| 2015/0190242 A1 | 7/2015 | Blain et al. |
| 2015/0202053 A1 | 7/2015 | Willis et al. |
| 2015/0257894 A1 | 9/2015 | Levy et al. |
| 2015/0305785 A1 | 10/2015 | Taber et al. |
| 2015/0313585 A1 | 11/2015 | Abidin et al. |
| 2015/0313650 A1 | 11/2015 | Taber et al. |
| 2015/0351738 A1 | 12/2015 | Perrow |
| 2015/0351925 A1 | 12/2015 | Emerick et al. |
| 2015/0359640 A1 | 12/2015 | Taber et al. |
| 2016/0000419 A1 | 1/2016 | Weisshaupt et al. |
| 2016/0030030 A1 | 2/2016 | Bass |
| 2016/0045333 A1 | 2/2016 | Baynham |
| 2016/0081681 A1 | 3/2016 | Waugh et al. |
| 2016/0089247 A1 | 3/2016 | Nichols et al. |
| 2016/0103689 A1 | 4/2016 | Sanghi et al. |
| 2016/0143747 A1 | 5/2016 | Agarwal et al. |
| 2016/0199195 A1 | 7/2016 | Hauck et al. |
| 2016/0213443 A1 | 7/2016 | Lueck et al. |
| 2016/0270772 A1 | 9/2016 | Beale et al. |
| 2016/0287236 A1 | 10/2016 | Garcia-Bengochea et al. |
| 2016/0310294 A1 | 10/2016 | McConnell et al. |
| 2016/0317323 A1 | 11/2016 | Cho et al. |
| 2016/0317324 A1 | 11/2016 | Cho et al. |
| 2016/0354210 A1 | 12/2016 | Tran |
| 2016/0361177 A1 | 12/2016 | Biedermann et al. |
| 2017/0007226 A1 | 1/2017 | Fehling |
| 2017/0014117 A1 | 1/2017 | Capote |
| 2017/0042527 A1 | 2/2017 | Farley et al. |
| 2017/0056194 A1 | 3/2017 | Biedermann et al. |
| 2017/0065269 A1 | 3/2017 | Thommen et al. |
| 2017/0112635 A1 | 4/2017 | Ty et al. |

(56) References Cited

U.S. PATENT DOCUMENTS

| | | | |
|---|---|---|---|
| 2017/0143325 A1 | 5/2017 | Lynn et al. |
| 2017/0172759 A1 | 6/2017 | Kukkar et al. |
| 2017/0172760 A1 | 6/2017 | Loebl et al. |
| 2017/0231613 A1 | 8/2017 | Casey et al. |
| 2017/0245997 A1 | 8/2017 | Trischler et al. |
| 2017/0340451 A1 | 11/2017 | McCormack et al. |
| 2018/0021149 A1 | 1/2018 | Boehm et al. |
| 2018/0085105 A1 | 3/2018 | Kim |
| 2018/0193165 A1 | 7/2018 | Abdou |
| 2018/0206834 A1 | 7/2018 | Villamil et al. |
| 2018/0235724 A1 | 8/2018 | Nowatschin et al. |
| 2018/0249992 A1 | 9/2018 | Truckey |
| 2018/0256363 A1 | 9/2018 | Moon |
| 2018/0289506 A1 | 10/2018 | Kim et al. |
| 2018/0303624 A1 | 10/2018 | Shoshtaev |
| 2018/0310927 A1 | 11/2018 | Garcia-Bengochea et al. |
| 2018/0333061 A1 | 11/2018 | Pracyk et al. |
| 2018/0344481 A1 | 12/2018 | Garcia-Bengochea |
| 2018/0360621 A1 | 12/2018 | Moon |
| 2019/0021875 A1 | 1/2019 | Abdou et al. |
| 2019/0091037 A1 | 3/2019 | Abdou et al. |
| 2019/0192312 A1 | 6/2019 | Ullrich, Jr. et al. |
| 2019/0209154 A1 | 7/2019 | Richter et al. |
| 2019/0216450 A1 | 7/2019 | Bjork et al. |
| 2019/0216453 A1 | 7/2019 | Predick et al. |
| 2019/0307439 A1 | 10/2019 | Chhit et al. |
| 2019/0321022 A1 | 10/2019 | Karpowicz et al. |
| 2020/0000497 A1 | 1/2020 | Abdou |
| 2020/0085530 A1 | 3/2020 | Sauer, Md |
| 2020/0100914 A1 | 4/2020 | Abdou et al. |
| 2020/0113713 A1 | 4/2020 | LaMarca et al. |
| 2020/0229943 A1 | 7/2020 | Abdou |
| 2020/0330244 A1 | 10/2020 | Abdou |
| 2020/0337861 A1 | 10/2020 | Abdou |
| 2020/0360155 A1 | 11/2020 | Abdou |
| 2022/0211517 A1 | 7/2022 | Abdou et al. |

FOREIGN PATENT DOCUMENTS

| | | |
|---|---|---|
| BR | PI0512056 A | 2/2008 |
| CH | 1814474 | 9/2011 |
| DE | 3114872 A1 | 10/1982 |
| DE | 3741493 A1 | 6/1989 |
| DE | 29911422 U1 | 8/1999 |
| DE | 10035182 A1 | 2/2002 |
| DE | 20320454 U1 | 10/2004 |
| DE | 10323363 A1 | 12/2004 |
| DE | 602005030074 | 9/2011 |
| EP | 0077159 A1 | 4/1983 |
| EP | 0274713 A1 | 7/1988 |
| EP | 0301489 A1 | 2/1989 |
| EP | 0317972 A1 | 5/1989 |
| EP | 0333990 A2 | 9/1989 |
| EP | 0356112 A1 | 2/1990 |
| EP | 0418387 A1 | 3/1991 |
| EP | 0512529 A1 | 11/1992 |
| EP | 0560141 A1 | 9/1993 |
| EP | 0566810 A1 | 10/1993 |
| EP | 0611116 A1 | 8/1994 |
| EP | 0614649 A1 | 9/1994 |
| EP | 0637439 A1 | 2/1995 |
| EP | 0697200 A1 | 2/1996 |
| EP | 0611116 B1 | 7/1996 |
| EP | 0566810 B1 | 8/1996 |
| EP | 0747025 A1 | 12/1996 |
| EP | 0951879 A2 | 10/1999 |
| EP | 0955021 A1 | 11/1999 |
| EP | 0965313 A1 | 12/1999 |
| EP | 1180348 A2 | 2/2002 |
| EP | 1192910 A2 | 4/2002 |
| EP | 1222903 A1 | 7/2002 |
| EP | 1254640 A2 | 11/2002 |
| EP | 1287795 A1 | 3/2003 |
| EP | 1442715 A2 | 8/2004 |
| EP | 1504733 A1 | 2/2005 |
| EP | 1374808 B1 | 12/2005 |
| EP | 1758511 A2 | 3/2007 |
| EP | 1848352 A2 | 10/2007 |
| EP | 1872731 A1 | 1/2008 |
| EP | 1942816 A2 | 7/2008 |
| EP | 1942838 A2 | 7/2008 |
| EP | 1968466 A2 | 9/2008 |
| EP | 1980222 A1 | 10/2008 |
| EP | 1988854 A2 | 11/2008 |
| EP | 1389978 B1 | 1/2009 |
| EP | 2032086 A2 | 3/2009 |
| EP | 2101691 A2 | 9/2009 |
| EP | 2113228 A1 | 11/2009 |
| EP | 2327375 A1 | 6/2011 |
| EP | 2340788 A1 | 7/2011 |
| EP | 1814474 B1 | 9/2011 |
| EP | 2363080 A1 | 9/2011 |
| EP | 2131790 B1 | 10/2012 |
| EP | 2729081 A1 | 5/2014 |
| EP | 3111896 A1 | 1/2017 |
| FR | 1037262 A | 9/1953 |
| FR | 2124815 A5 | 9/1972 |
| FR | 2632516 A1 | 12/1989 |
| FR | 2659226 A1 | 9/1991 |
| FR | 2703239 A1 | 10/1994 |
| FR | 2703580 A1 | 10/1994 |
| FR | 2723841 A1 | 3/1996 |
| FR | 2724108 A1 | 3/1996 |
| FR | 2730159 A1 | 8/1996 |
| FR | 2733413 A1 | 10/1996 |
| FR | 2747034 A1 | 10/1997 |
| FR | 2781359 A1 | 1/2000 |
| FR | 2787021 A1 | 6/2000 |
| FR | 2788958 A1 | 8/2000 |
| FR | 2806614 A1 | 9/2001 |
| FR | 2808995 A1 | 11/2001 |
| FR | 2813782 A1 | 3/2002 |
| FR | 2824261 A1 | 11/2002 |
| FR | 2827156 A1 | 1/2003 |
| FR | 2831796 A1 | 5/2003 |
| FR | 2846550 A1 | 5/2004 |
| FR | 2856271 A1 | 12/2004 |
| FR | 2861582 A1 | 5/2005 |
| FR | 2865629 A1 | 8/2005 |
| FR | 2879436 A1 | 6/2006 |
| FR | 2880795 A1 | 7/2006 |
| FR | 2887762 A1 | 1/2007 |
| FR | 2891135 A1 | 3/2007 |
| FR | 2893838 A1 | 6/2007 |
| FR | 2897259 A1 | 8/2007 |
| FR | 2902639 A1 | 12/2007 |
| FR | 2916956 A1 | 12/2008 |
| FR | 2930718 A1 | 11/2009 |
| FR | 1814474 | 11/2011 |
| GB | 780652 A | 8/1957 |
| GB | 2178323 A | 2/1987 |
| GB | 1814474 | 9/2011 |
| JP | H02261446 A | 10/1990 |
| JP | H0998983 A | 4/1997 |
| KR | 100858306 B1 | 9/2008 |
| WO | WO-9000037 A1 | 1/1990 |
| WO | WO-9107931 A1 | 6/1991 |
| WO | WO-9301771 A1 | 2/1993 |
| WO | WO-9307823 A1 | 4/1993 |
| WO | WO-9314721 A1 | 8/1993 |
| WO | WO-9404100 A1 | 3/1994 |
| WO | WO-9420048 A1 | 9/1994 |
| WO | WO-9508306 A1 | 3/1995 |
| WO | WO-9510240 A1 | 4/1995 |
| WO | WO-9515133 A1 | 6/1995 |
| WO | WO-9525474 A1 | 9/1995 |
| WO | WO-9715248 A1 | 5/1997 |
| WO | WO-9723174 A1 | 7/1997 |
| WO | WO-9730666 A2 | 8/1997 |
| WO | WO-9737620 A1 | 10/1997 |
| WO | WO-9801091 A1 | 1/1998 |
| WO | WO-9817209 A2 | 4/1998 |
| WO | WO-9855052 A1 | 12/1998 |
| WO | WO-9900065 A1 | 1/1999 |

(56) References Cited

FOREIGN PATENT DOCUMENTS

| | | |
|---|---|---|
| WO | WO-9904718 A1 | 2/1999 |
| WO | WO-9909914 A1 | 3/1999 |
| WO | WO-9921500 A1 | 5/1999 |
| WO | WO-9921502 A1 | 5/1999 |
| WO | WO-9933405 A1 | 7/1999 |
| WO | WO-9938463 A2 | 8/1999 |
| WO | WO-9953871 A1 | 10/1999 |
| WO | WO-9956653 A1 | 11/1999 |
| WO | WO-9956675 A1 | 11/1999 |
| WO | WO-9956676 A1 | 11/1999 |
| WO | WO-9963914 A1 | 12/1999 |
| WO | WO-9965412 A1 | 12/1999 |
| WO | WO-9966864 A1 | 12/1999 |
| WO | WO-0015125 A1 | 3/2000 |
| WO | WO-0018312 A1 | 4/2000 |
| WO | WO-0023015 A1 | 4/2000 |
| WO | WO-0024325 A1 | 5/2000 |
| WO | WO-0024327 A2 | 5/2000 |
| WO | WO-0053127 A1 | 9/2000 |
| WO | WO-0064362 A1 | 11/2000 |
| WO | WO-0072770 A1 | 12/2000 |
| WO | WO-0074606 A1 | 12/2000 |
| WO | WO-0078238 A1 | 12/2000 |
| WO | WO-0101874 A1 | 1/2001 |
| WO | WO-0103592 A1 | 1/2001 |
| WO | WO-0106940 A1 | 2/2001 |
| WO | WO-0119295 A1 | 3/2001 |
| WO | WO-0126566 A1 | 4/2001 |
| WO | WO-0128465 A2 | 4/2001 |
| WO | WO-0141680 A1 | 6/2001 |
| WO | WO-0143620 A2 | 6/2001 |
| WO | WO-0145577 A2 | 6/2001 |
| WO | WO-0160270 A1 | 8/2001 |
| WO | WO-0162191 A2 | 8/2001 |
| WO | WO-0170141 A1 | 9/2001 |
| WO | WO-0187194 A1 | 11/2001 |
| WO | WO-0211633 A2 | 2/2002 |
| WO | WO-0213732 A2 | 2/2002 |
| WO | WO-0228299 A1 | 4/2002 |
| WO | WO-0230307 A2 | 4/2002 |
| WO | WO-02051326 A1 | 7/2002 |
| WO | WO-02058599 A2 | 8/2002 |
| WO | WO-02058600 A2 | 8/2002 |
| WO | WO-02071960 A1 | 9/2002 |
| WO | WO-02076315 A1 | 10/2002 |
| WO | WO-02080788 A1 | 10/2002 |
| WO | WO-02089701 A2 | 11/2002 |
| WO | WO-03005939 A2 | 1/2003 |
| WO | WO-03007829 A1 | 1/2003 |
| WO | WO-03015646 A2 | 2/2003 |
| WO | WO-03024298 A2 | 3/2003 |
| WO | WO-03026522 A2 | 4/2003 |
| WO | WO-03032850 A1 | 4/2003 |
| WO | WO-03032851 A1 | 4/2003 |
| WO | WO-03037200 A2 | 5/2003 |
| WO | WO-03039400 A2 | 5/2003 |
| WO | WO-03045262 A2 | 6/2003 |
| WO | WO-03049629 A1 | 6/2003 |
| WO | WO-03051212 A2 | 6/2003 |
| WO | WO-03059212 A1 | 7/2003 |
| WO | WO-03075803 A1 | 9/2003 |
| WO | WO-03075804 A1 | 9/2003 |
| WO | WO-2004016217 A2 | 2/2004 |
| WO | WO-2004032726 A2 | 4/2004 |
| WO | WO-2004034935 A1 | 4/2004 |
| WO | WO-2004039283 A2 | 5/2004 |
| WO | WO-2004039291 A1 | 5/2004 |
| WO | WO-2004041129 A1 | 5/2004 |
| WO | WO-2004049915 A2 | 6/2004 |
| WO | WO-2004062482 A2 | 7/2004 |
| WO | WO-2004084774 A1 | 10/2004 |
| WO | WO-2004093702 A2 | 11/2004 |
| WO | WO-2004105577 A2 | 12/2004 |
| WO | WO-2005007040 A1 | 1/2005 |
| WO | WO-2005009262 A1 | 2/2005 |
| WO | WO-2005011522 A2 | 2/2005 |
| WO | WO-2005020829 A1 | 3/2005 |
| WO | WO-2005044119 A2 | 5/2005 |
| WO | WO-2005046534 A1 | 5/2005 |
| WO | WO-2005051243 A2 | 6/2005 |
| WO | WO-2005074839 A1 | 8/2005 |
| WO | WO-2005077288 A1 | 8/2005 |
| WO | WO-2005104996 A1 | 11/2005 |
| WO | WO-2005117728 A1 | 12/2005 |
| WO | WO-2005122922 A2 | 12/2005 |
| WO | WO-2006016384 A2 | 2/2006 |
| WO | WO-2006041963 A2 | 4/2006 |
| WO | WO-2006042335 A1 | 4/2006 |
| WO | WO-2006045089 A2 | 4/2006 |
| WO | WO-2006047587 A2 | 5/2006 |
| WO | WO-2006058221 A2 | 6/2006 |
| WO | WO-2006062960 A2 | 6/2006 |
| WO | WO-2006086241 A2 | 8/2006 |
| WO | WO-2006089292 A2 | 8/2006 |
| WO | WO-2006096756 A2 | 9/2006 |
| WO | WO-2006106268 A2 | 10/2006 |
| WO | WO-2006110578 A2 | 10/2006 |
| WO | WO-2006120505 A1 | 11/2006 |
| WO | WO-2006130460 A2 | 12/2006 |
| WO | WO-2006136760 A2 | 12/2006 |
| WO | WO-2007000634 A1 | 1/2007 |
| WO | WO-2007000654 A2 | 1/2007 |
| WO | WO-2007034310 A1 | 3/2007 |
| WO | WO-2007038475 A2 | 4/2007 |
| WO | WO-2007041648 A2 | 4/2007 |
| WO | WO-2007044705 A2 | 4/2007 |
| WO | WO-2007044836 A2 | 4/2007 |
| WO | WO-2007056516 A2 | 5/2007 |
| WO | WO-2007059207 A1 | 5/2007 |
| WO | WO-2007063398 A2 | 6/2007 |
| WO | WO-2007064695 A2 | 6/2007 |
| WO | WO-2007075843 A2 | 7/2007 |
| WO | WO-2007078978 A2 | 7/2007 |
| WO | WO-2007087535 A2 | 8/2007 |
| WO | WO-2007089975 A1 | 8/2007 |
| WO | WO-2007093900 A2 | 8/2007 |
| WO | WO-2007095333 A2 | 8/2007 |
| WO | WO-2007106573 A2 | 9/2007 |
| WO | WO-2007075843 A3 | 12/2007 |
| WO | WO-2007140382 A2 | 12/2007 |
| WO | WO-2008013960 A2 | 1/2008 |
| WO | WO-2008021319 A2 | 2/2008 |
| WO | WO-2008024373 A2 | 2/2008 |
| WO | WO-2008067452 A1 | 6/2008 |
| WO | WO-2008073447 A2 | 6/2008 |
| WO | WO-2008082836 A1 | 7/2008 |
| WO | WO-2008085521 A1 | 7/2008 |
| WO | WO-2008099277 A2 | 8/2008 |
| WO | WO-2008106140 A2 | 9/2008 |
| WO | WO-2008131084 A2 | 10/2008 |
| WO | WO-2008149223 A2 | 12/2008 |
| WO | WO-2009033100 A1 | 3/2009 |
| WO | WO-2009064787 A2 | 5/2009 |
| WO | WO-2009135208 A1 | 11/2009 |
| WO | WO-2009152126 A1 | 12/2009 |
| WO | WO-2010057980 A1 | 5/2010 |
| WO | WO-2013006830 A1 | 1/2013 |
| WO | WO-2020072600 A1 | 4/2020 |
| WO | WO-2021158571 A1 | 8/2021 |

OTHER PUBLICATIONS

Abstract for French Patent Publication FR2856271, Published Dec. 24, 2004, Osteo-Synthesis Vertebral Column Plate, has Connection Head Integrated with Plate and Movable in Three Directions of Space So as to Adapt itself to Connection Rod, and Including Opening to Facilitate Introduction of Rod. Accession No. 14694557, (Derwent Information Ltd.).

Abstract for German Patent No. DE10035182. (Derwent Information Ltd.), publication date Feb. 7, 2002.

Andersen T., et al., "Pain 5 years After Instrumented and Non-Instrumented Posterolateral Lumbar Spinal Fusion," European Spine Journal, 2003, vol. 12 (4), pp. 393-399.

(56) References Cited

OTHER PUBLICATIONS

Asazuma T., et al., "Intersegmental Spinal Flexibility With Lumbosacral Instrumentation. An In Vitro Biomechanical Investigation," Spine (Phila Pa 1976), 1990, vol. 15 (11), pp. 1153-1158.
Balderston R.A., et al., "Technique for Achievement and Maintenance of Reduction for Severe Spondylolisthesis Using Spinous Process Traction Wiring and External Fixation of the Pelvis," Spine (Phila Pa 1976), 1985, vol. 10 (4), pp. 376-382.
Barbre C.J.,, "Devices for Targeting the Needle," Neurosurgery Clinics of North America, 2009, vol. 20 (2), pp. 187-191.
Bendo J.A., et al., "Instrumented Posterior Arthrodesis of the Lumbar Spine in Patients with Diabetes Mellitus," American Journal of Orthopedics (Belle Mead, NJ), 2000, vol. 29 (8), pp. 617-620.
Benz R.J., et al., "Current Techniques of Decompression of the Lumbar Spine," Clinical Orthopaedics and Related Research, 2001, No. (384), pp. 75-81.
Bostman O., et al., "Posterior Spinal Fusion Using Internal Fixation with the Daab Plate," Acta Orthopaedica Scandinavica, 1984, vol. 55 (3), pp. 310-314.
Branch C.L., et al., "Posterior Lumbar Interbody Fusion with the Keystone Graft: Technique and Results," Surgical Neurology, 1987, vol. 27 (5), pp. 449-454.
Bridwell K. H., et al., "Decision Making Regarding Smith-Petersen vs. Pedicle Subtraction Osteotomy vs. Vertebral Column Resection for Spinal Deformity," Spine, 2006, vol. 31(19S), pp. S171-S178.
Chen W.J., et al., "Surgical Treatment of Adjacent Instability After Lumbar Spine Fusion," Spine (Phila Pa 1976), 2001, vol. 26 (22), pp. E519-E524.
Chiba M., et al., "Short-Segment Pedicle Instrumentation. Biomechanical Analysis of Supplemental Hook Fixation," Spine (Phila Pa 1976), 1996, vol. 21 (3), pp. 288-294.
Cobo S.J., et al., "Predictors of Outcome After Decompressive Lumbar Surgery and Instrumented Posterolateral Fusion," European Spine Journal, 2010, vol. 19 (11), pp. 1841-1848.
Collins P., Carbon Multiwall Nanotubes: A High-Performance Conductive Additive for Demanding Plastics Applications, Materials Integrity Management Symposium, Jun. 2004, Retrieved from the Internet URL : (http://hyperioncatalysis.com/PDFs/CMWNT.pdf>).
"Curve, The Ultimate Control and Information Center" from https://www.brainlab.com/surgery-products/overview-platform-products/curve-image-guided-surgery/, 8 pages, downloaded from the Internet Mar. 27, 2014.
Dar G., et al., "The Epiphyses Ring: A Long Forgotten Anatomical Structure with Significant Physiological Function", Spine Anatomy, (PA 1976). May 15, 2011, vol. 36 (11), pp. 850-856.
Dawson E.G., et al., "Intertransverse Process Lumbararthodesis with Autogenous Bone Graft," Clinical Orthopaedics and Related Research, 1981, No. (154), pp. 90-96.
Deguchi M., et al., "Biomechanical Comparison of Spondylolysis Fixation Techniques," Spine (Phila Pa 1976), 1999, vol. 24 (4), pp. 328-333.
Denis, F., "The Three Column Spine and its Significance in the Classification of Acute Thoracolumbar Spinal Injuries," Spine (Phila Pa 1976), 1983, vol. 8 (8), pp. 817-831.
Dove J., "Internal Fixation of the Lumbar Spine. The Hartshill Rectangle," Clinical Orthopaedics and Related Research, 1986, No. (203), pp. 135-140.
Fischgrund J.S., et al., "1997 Volvo Award Winner in Clinical Studies. Degenerative Lumbar Spondylolisthesis with Spinal Stenosis: A Prospective, Randomized Study Comparing Decompressive Laminectomy and Arthrodesis with and without Spinal Instrumentation," Spine (Phila Pa 1976), 1997, vol. 22 (24), pp. 2807-2812.
"Flexural Pivot Bearings for Frictionless Applications" printout of web page as displayed from Feb. 10, 2010 accessed Sep. 16, 2019 via the Internet Wayback Machine.https://web.archive.org/web/20100210030115/http://www.flexpivots.com/.
Freeman B.J., et al., "Posterior Lumbar Interbody Fusion Combined with Instrumented Postero-Lateral Fusion: 5-year Results in 60 Patients," European Spine Journal, 2000, vol. 9 (1), pp. 42-46.

Frogley M.D., et al., "Mechanical Properties of Carbon Nanoparticle-Reinforced Elastomers," Composites Science and Technology, 2003, vol. 63 (11), pp. 1647-1654.
Gibson J.N., et al., "Surgery for Degenerative Lumbar Spondylosis," Cochrane Database of Systematic Reviews, 2005, No. (4), pp. CD001352.
Gill G.G., "Long-Term Follow-Up Evaluation of a Few Patients with Spondylolisthesis Treated by Excision of the Loose Lamina with Decompression of the Nerve Roots without Spinal Fusion," Clinical Orthopaedics and Related Research, 1984, No. (182), pp. 215-219.
Greenough C.G., et al., "Instrumented Posterolateral Lumbar Fusion. Results and Comparison with Anterior Interbody Fusion," Spine (Phila Pa 1976), 1998, vol. 23 (4), pp. 479-486.
Gunzburg R., et al., "The Conservative Surgical Treatment of Lumbar Spinal Stenosis in the Elderly," European Spine Journal, 2003, vol. 12 (Suppl. 2), pp. S176-S180.
Hajek P.D., et al., "Biomechanical Study of C1-C2 Posterior Arthrodesis Techniques," Spine (Phila Pa 1976), 1993, vol. 18 (2), pp. 173-177.
Heggeness M.H., et al., "Translaminar Facet Joint Screw Fixation for Lumbar and Lumbosacral Fusion. A Clinical and Biomechanical Study," Spine (Phila Pa 1976), 1991, vol. 16 (6 Suppl), pp. S266-S269.
Holland N.R., et al., "Intraoperative Electromyography During Thoracolumbar Spinal Surgery," Spine (Phila Pa 1976), 1998, vol. 23 (17), pp. 1915-1922.
Hoshide R., et al., "Cadaveric Analysis of the Kambin's Triangle" Cureus, Feb. 2, 2016, vol. 8 (2), pp. e475.
Katz J.N., et al., "Lumbar Laminectomy Alone or with Instrumented or Noninstrumented Arthrodesis in Degenerative Lumbar Spinal Stenosis. Patient Selection, Costs, and Surgical Outcomes," Spine (Phila Pa 1976), 1997, vol. 22 (10), pp. 1123-1131.
Kis A., et al., "Reinforcement of Single-Walled Carbon Nanotube Bundles by Intertube Bridging," Nature Materials, 2004, vol. 3 (3), pp. 153-157.
Korkala O., et al., "Reduction and Fixation of Late Diagnosed Lower Ccervical Spine Dislocations Using the Daab Plate. A Report of Two Cases," Archives of Orthopaedic and Trauma Surgery, 1984, vol. 103 (5), pp. 353-355.
Krag M.H., et al., "An Internal Fixator for Posterior Application to Short Segments of the Thoracic, Lumbar, or Lumbosacral Spine. Design and Testing," Clinical Orthopaedics and Related Research, 1986, No. 203, pp. 75-98.
Lin P.M., et al., "Internal Decompression for Multiple Levels of Lumbar Spinal Stenosis: A Technical Note," Neurosurgery, 1982, vol. 11 (4), pp. 546-549.
Liquidmetal Technologies product page from http://liquidmetal.com/our-products/product-parts/, What we Sell, 5 pages, downloaded from the internet Mar. 27, 2014.
Lorenz M., et al., "A Comparison of Single-Level Fusions with and without Hardware," Spine (Phila Pa 1976), 1991, vol. 16 (8 Suppl), pp. S455-S458.
Lowery G.L., "Orion Anterior Cervical Plate System" in: Spinal Instrumentation—Surgical Techniques, Kim D.H., et al., eds., Thieme Medical Publications (New York), 2005, pp. 116-122.
Luque E.R., "Segmental Spinal Instrumentation of the Lumbar Spine," Clinical Orthopaedics and Related Research, 1986, No. 203, pp. 126-134.
Madan S., et al., "Outcome of Posterior Lumbar Interbody Fusion Versus Posterolateral Fusion for Spondylolytic Spondylolisthesis," Spine (Phila Pa 1976), 2002, vol. 27 (14), pp. 1536-1542.
Madan S.S., et al., "Circumferential and Posterolateral Fusion for Lumbar Disc Disease," Clinical Orthopaedics and Related Research, 2003, No. 409, pp. 114-123.
Marotta N., et al., "A Novel Minimally Invasive Presacral Approach and Instrumentation Technique for Anterior L5-S1 Intervertebral Discectomy and Fusion: Technical Description and Case Presentations," Neurosurgical Focus, 2006, vol. 20 (1), pp. E9.
McInerney J., et al., "Frameless Stereotaxy of the Brain," The Mount Sinai Journal of Medicine, 2000, vol. 67 (4), pp. 300-310.
Moskowitz A., "Transforaminal Lumbar Interbody Fusion," Orthopedic Clinics of North America, 2002, vol. 33 (2), pp. 359-366.

(56) References Cited

OTHER PUBLICATIONS

Nardi P., et al., "Aperius PercLID Stand Alone Interspinous System for the Treatment of Degenerative Lumbar Stenosis: Experience on 152 Cases," Journal of Spinal Disorders & Techniques, 2010, vol. 23 (3), pp. 203-207.
Neo M., et al., "Spinous Process Plate Fixation As a Salvage Operation for Failed Anterior Cervical Fusion. Technical Note," Journal of Neurosurgery: Spine, 2006, vol. 4 (1), pp. 78-81.
Netter F., Atlas of Human Anatomy, 3rd Edition, Icon Learning Systems, Tegerboro, New Jersey (2004).
O'Leary P.F., et al., "Distraction Laminoplasty for Decompression of Lumbar Spinal Stenosis," Clinical Orthopaedics and Related Research, 2001, No. 384, pp. 26-34.
Ozgur B.M., et al., "Extreme Lateral Interbody Fusion (XLIF): A Novel Surgical Technique for Anterior Lumbar Interbody Fusion," Spine Journal, 2006, vol. 6 (4), pp. 435-443.
Polly D.W., et al., "Surgical Treatment for the Painful Motion Segment: Matching Technology with the Indications: Posterior Lumbar Fusion," Spine (Phila Pa 1976), 2005, vol. 30 (16 Suppl), pp. S44-S51.
Qian D., et al., "Mechanics of Carbon Nanotubes," Applied Mechanics Reviews, 2002, vol. 55 (2), pp. 495-533.
Rapoff A.J., et al., "Biomechanical Comparison of Posterior Lumbar Interbody Fusion Cages," Spine (Phila Pa 1976), 1997, vol. 22 (20), pp. 2375-2379.
Rompe J.D., et al., "Degenerative Lumbar Spinal Stenosis. Long-Term Results After Undercutting Decompression Compared with Decompressive Laminectomy Alone or with Instrumented Fusion," Neurosurgical Review, 1999, vol. 22 (2-3), pp. 102-106.
Rousseau M.A., et al., "Predictors of Outcomes After Posterior Decompression and Fusion in Degenerative Spondylolisthesis," European Spine Journal, 2005, vol. 14 (1), pp. 55-60.
Santoni BG., et al., "Cortical Bone Trajectory for Lumbar Pedicle Screws" The Spine Journal, 2009, vol. 9 (5), pp. 366-373.
Sasso R.C., et al., "Translaminar Facet Screw Fixation," World Spine Journal, 2006, vol. 1 (1), pp. 34-39.
Sidhu K.S., et al., "Spinal Instrumentation in the Management of Degenerative Disorders of the Lumbar Spine," Clinical Orthopaedics and Related Research, 1997, No. 335, pp. 39-53.
Smith M.D., et al., "A Biomechanical Analysis of Atlantoaxial Stabilization Methods Using a Bovine Model. C1/C2 Fixation Analysis," Clinical Orthopaedics and Related Research, 1993, No. 290, pp. 285-295.
Stambough J.L., et al., "Instrumented One and Two Level Posterolateral Fusions with Recombinant Human Bone Morphogenetic Protein-2 and Allograft: A Computed Tomography Study," Spine (Phila Pa 1976), 2010, vol. 35 (1), pp. 124-129.
Stambough J.L., "Lumbosacral Instrumented Fusion: Analysis of 124 Consecutive Cases," Journal of Spinal Disorders, 1999, vol. 12 (1), pp. 1-9.
Suzuki Y., "Shape Memory and Super-Elasticity Effects in NiTi Alloys," Titanium-Zirconium, 1982, vol. 30 (4), pp. 185-192.
Swanson K.E., et al., "The Effects of an Interspinous Implant on Intervertebral Disc Pressures," Spine (Phila Pa 1976), 2003, vol. 28 (1), pp. 26-32.
Thomsen K., et al., "1997 Volvo Award Winner in Clinical Studies. The Effect of Pedicle Screw Instrumentation on Functional Outcome and Fusion Rates in Posterolateral Lumbar Spinal Fusion: A Prospective, Randomized Clinical Study," Spine (Phila Pa 1976), 1997, vol. 22 (24), pp. 2813-2822.
Tseng Y.C., et al., "Monolithic Integration of Carbon Nanotube Devices with Silicon MOS Technology," Nano Letters, 2004, vol. 4 (1), pp. 123-127.
Vaccaro, et al., Principles of Practice of Spine Surgery; Mosby Press, Philadelphia, PA; 2003.
Vamvanij V., et al., "Surgical Treatment of Internal Disc Disruption: An Outcome Study of Four Fusion Techniques," Journal of Spinal Disorders, 1998, vol. 11 (5), pp. 375-382.
Voor M.J., et al., "Biomechanical Evaluation of Posterior and Anterior Lumbar Interbody Fusion Techniques," Journal of Spinal Disorders, 1998, vol. 11 (4), pp. 328-334.
Wang J.C., et al., "Comparison of CD Horizon Spire Spinous Process Plate Stabilization and Pedicle Screw Fixation after Anterior Lumbar Interbody Fusion. Invited Submission from the Joint Section Meeting On Disorders of the Spine and Peripheral Nerves, Mar. 2005," Journal of Neurosurgery: Spine, 2006, vol. 4 (2), pp. 132-136.
Wang J.C., et al., "Spire Spinous Process Stabilization Plate: Biomechanical Evaluation of a Novel Technology. Invited Submission from the Joint Section Meeting on Disorders of the Spine and Peripheral Nerves, Mar. 2005," Journal of Neurosurgery: Spine, 2006, vol. 4 (2), pp. 160-164.
Webster T.J., et al., "Increased Osteoblast Adhesion on Nanophase Metals: Ti, Ti6Al4V, and CoCrMo," Biomaterials, 2004, vol. 25 (19), pp. 4731-4739.
Willard, F. H., et al., "The Thoracolumbar Fascia: Anatomy, Function and Clinical Considerations." Journal of Anatomy, 2012, vol. 221(6), pp. 507-536.
Wohns R.N.W., et al., Day Surgery for Anterior Cervical Microdiskectomy: Experience with 75 Cases, Jul. 11, 2002, pp. 1-3.
Wood M.J., et al., "Improving Accuracy and Reducing Radiation Exposure in Minimally Invasive Lumbar Interbody Fusion," Journal of Neurosurgery: Spine, 2010, vol. 12 (5), pp. 533-539.
Yang C.K., et al., "Binding energies and electronic Structures of Adsorbed Titanium Chains on Carbon Nanotubes," Physical Review 66, 2002, 041403-1.
Yerby S., et al., "The Effect of Cutting Flute Design on the Insertion and Pullout Properties of Self-tapping Bone Screws," Jul. 2, 2002, pp. 1-2.

* cited by examiner

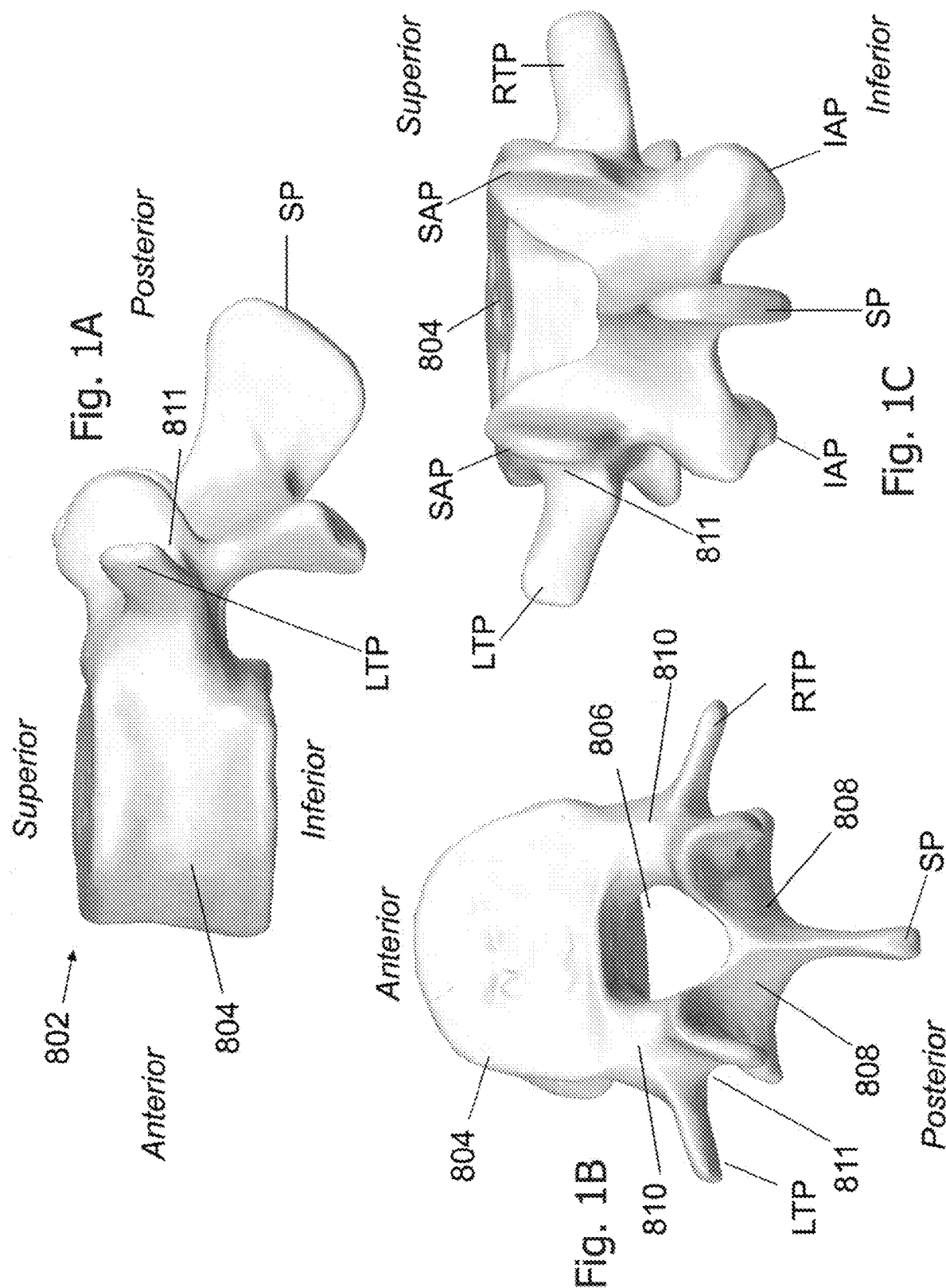

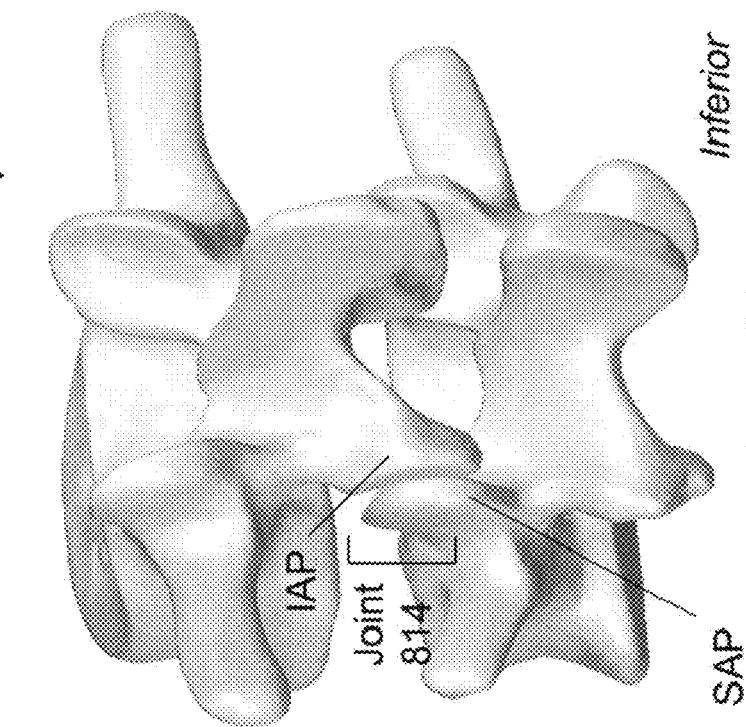
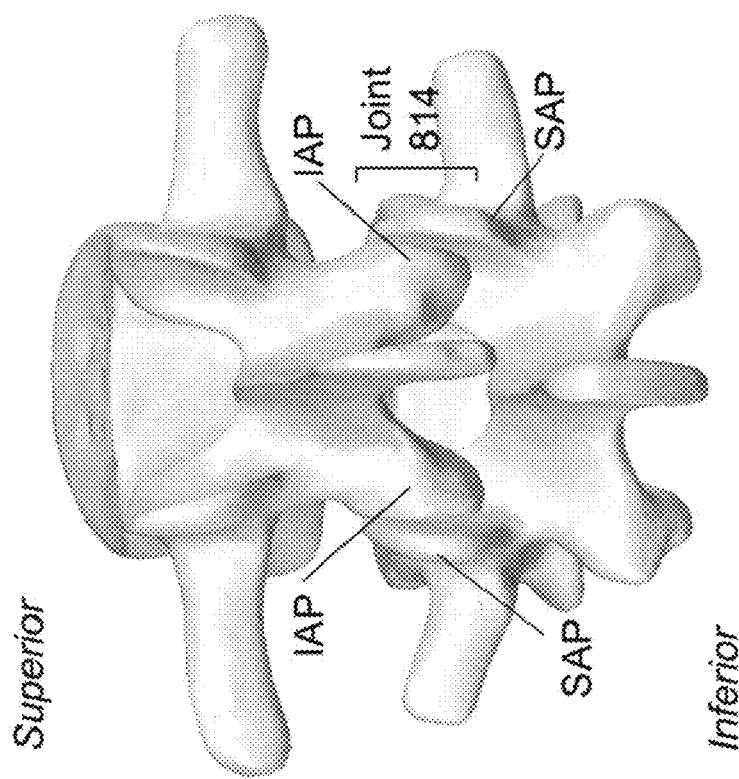
Fig. 2A
Fig. 2B

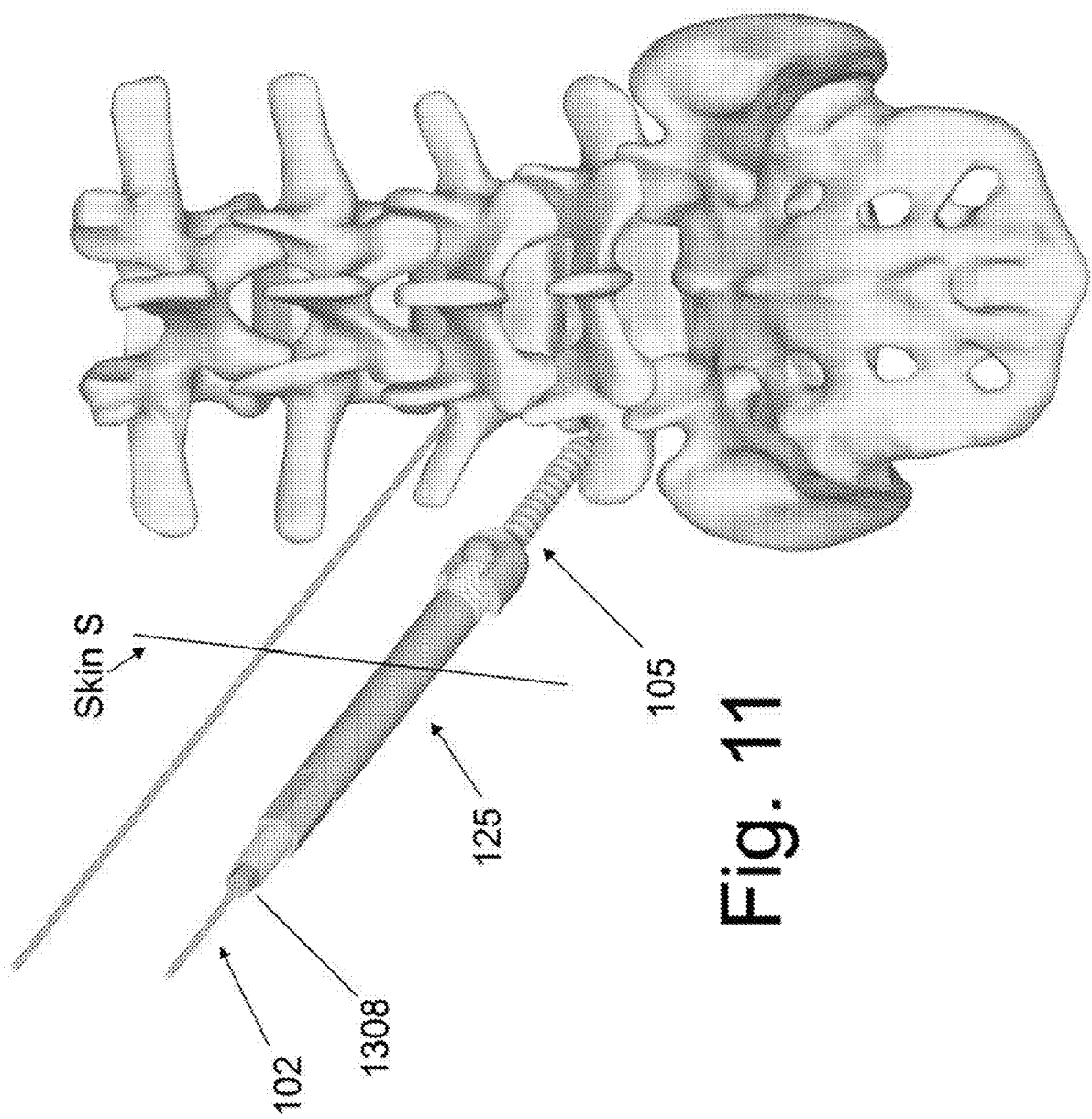

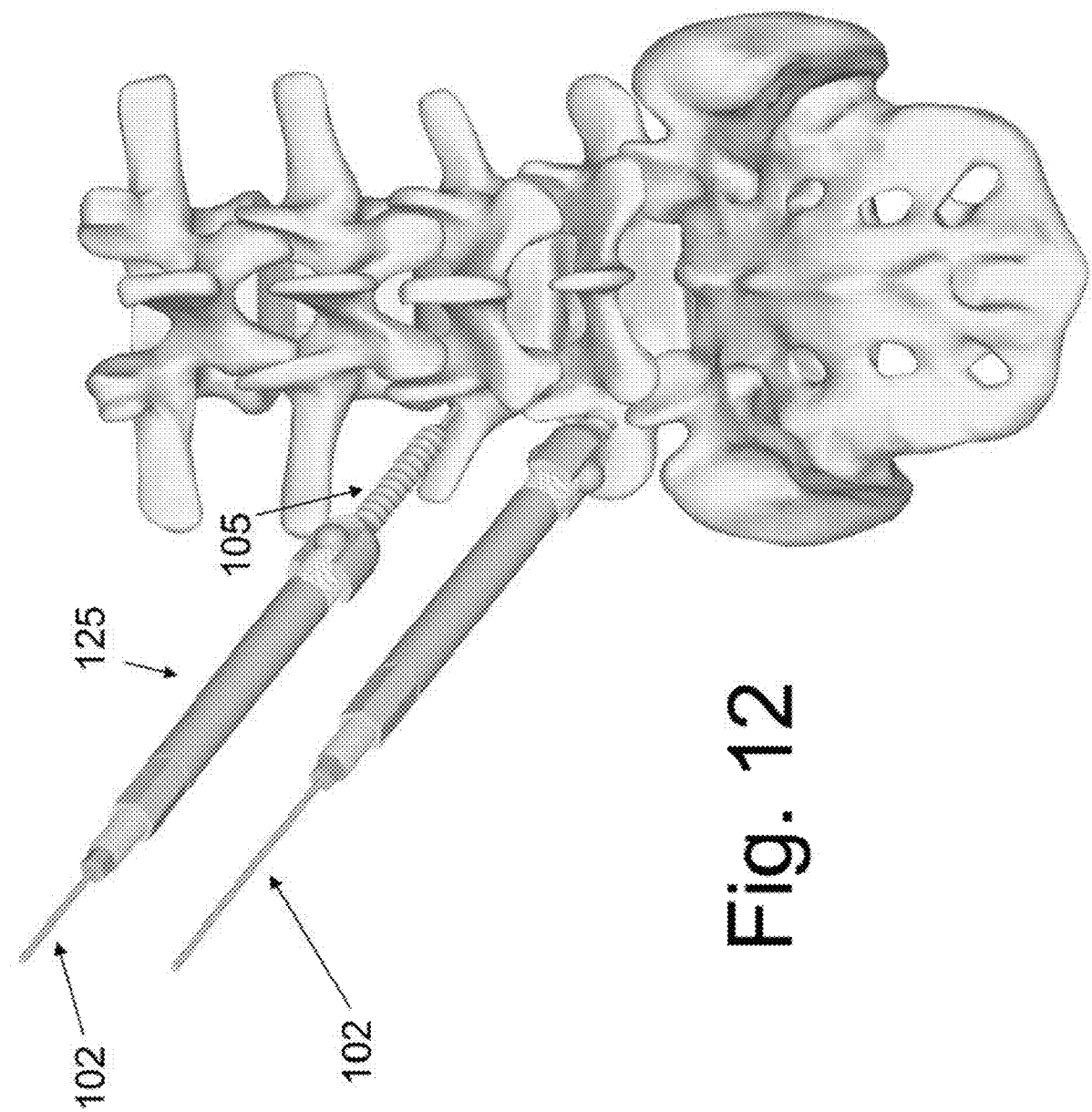

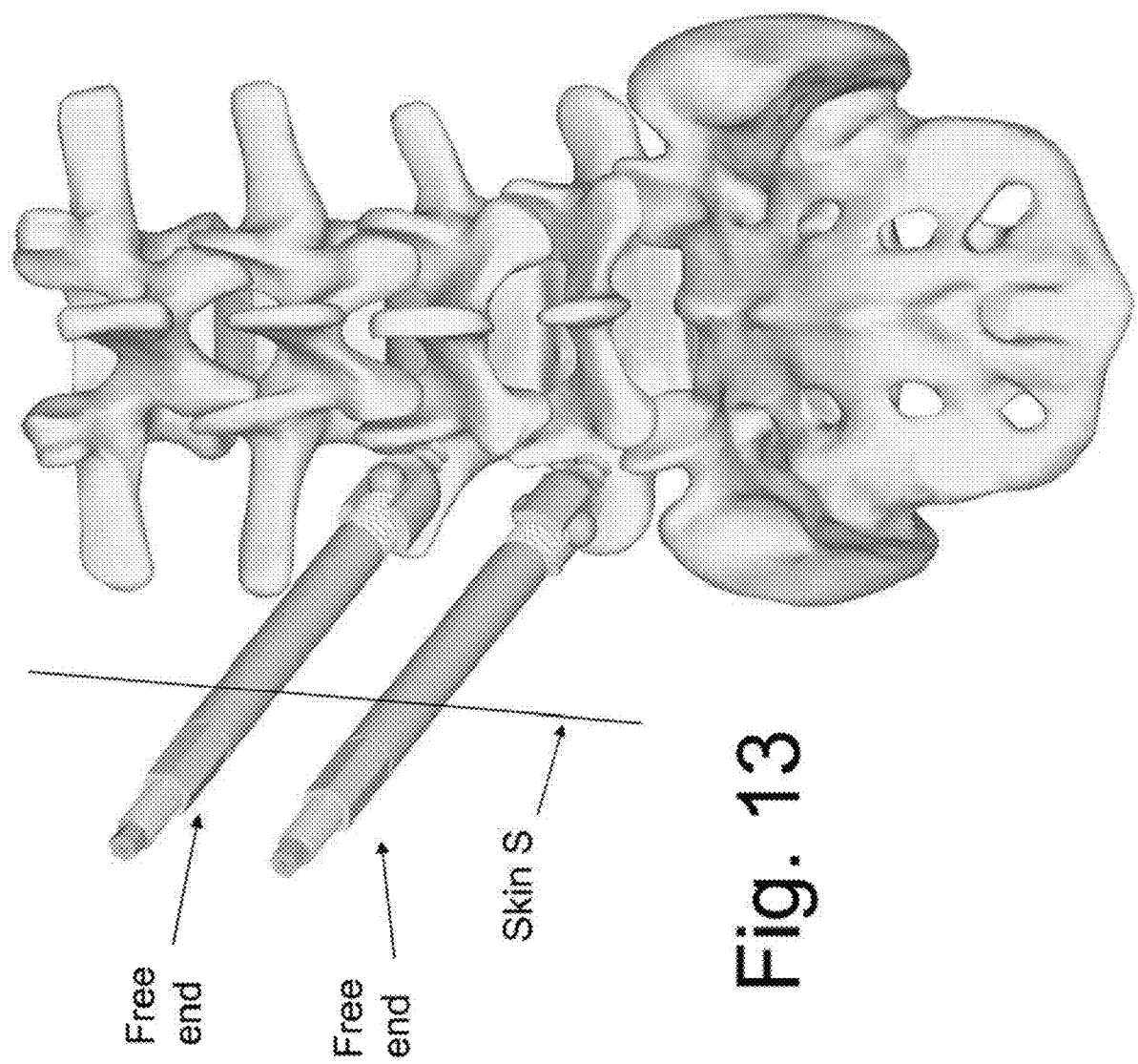

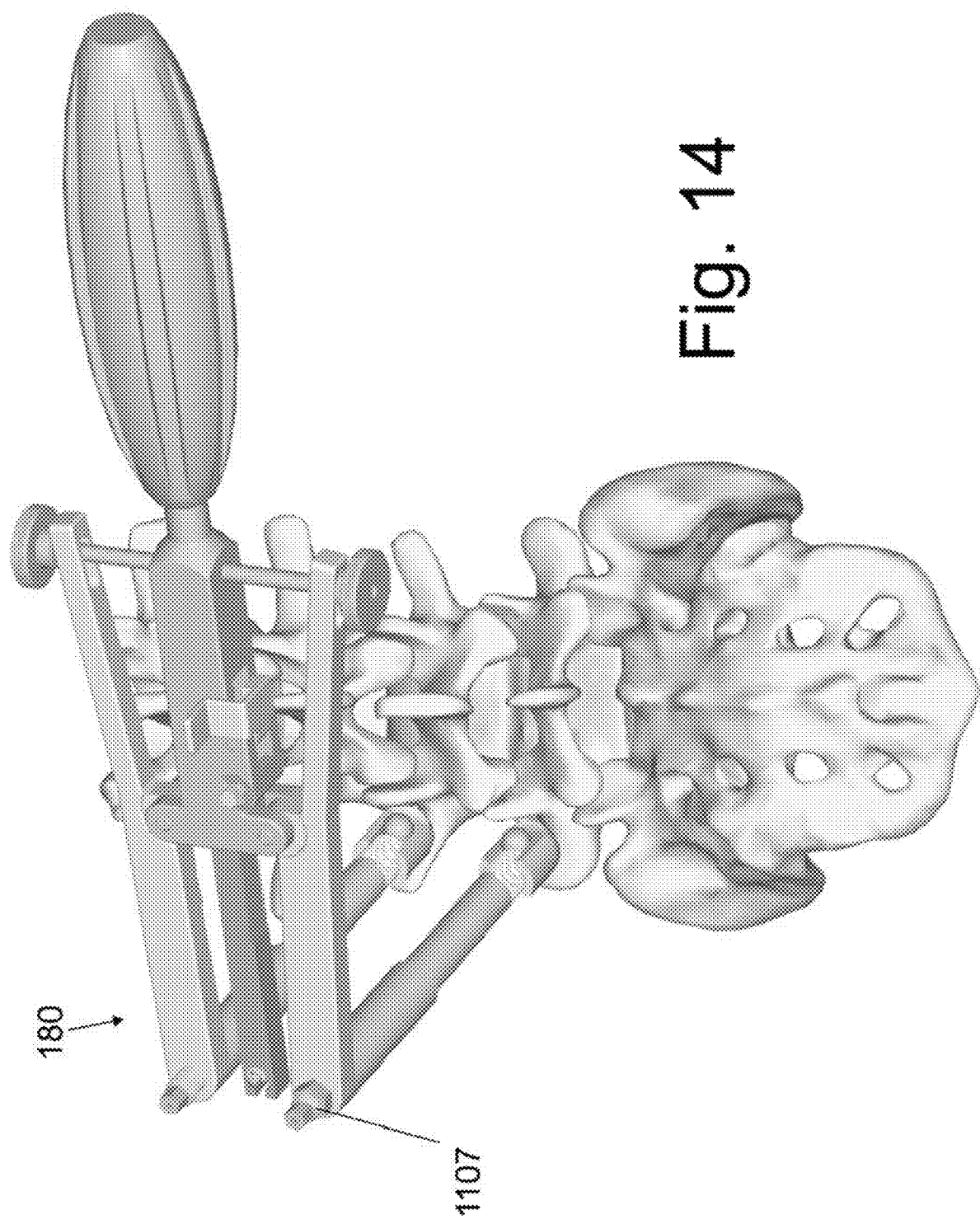

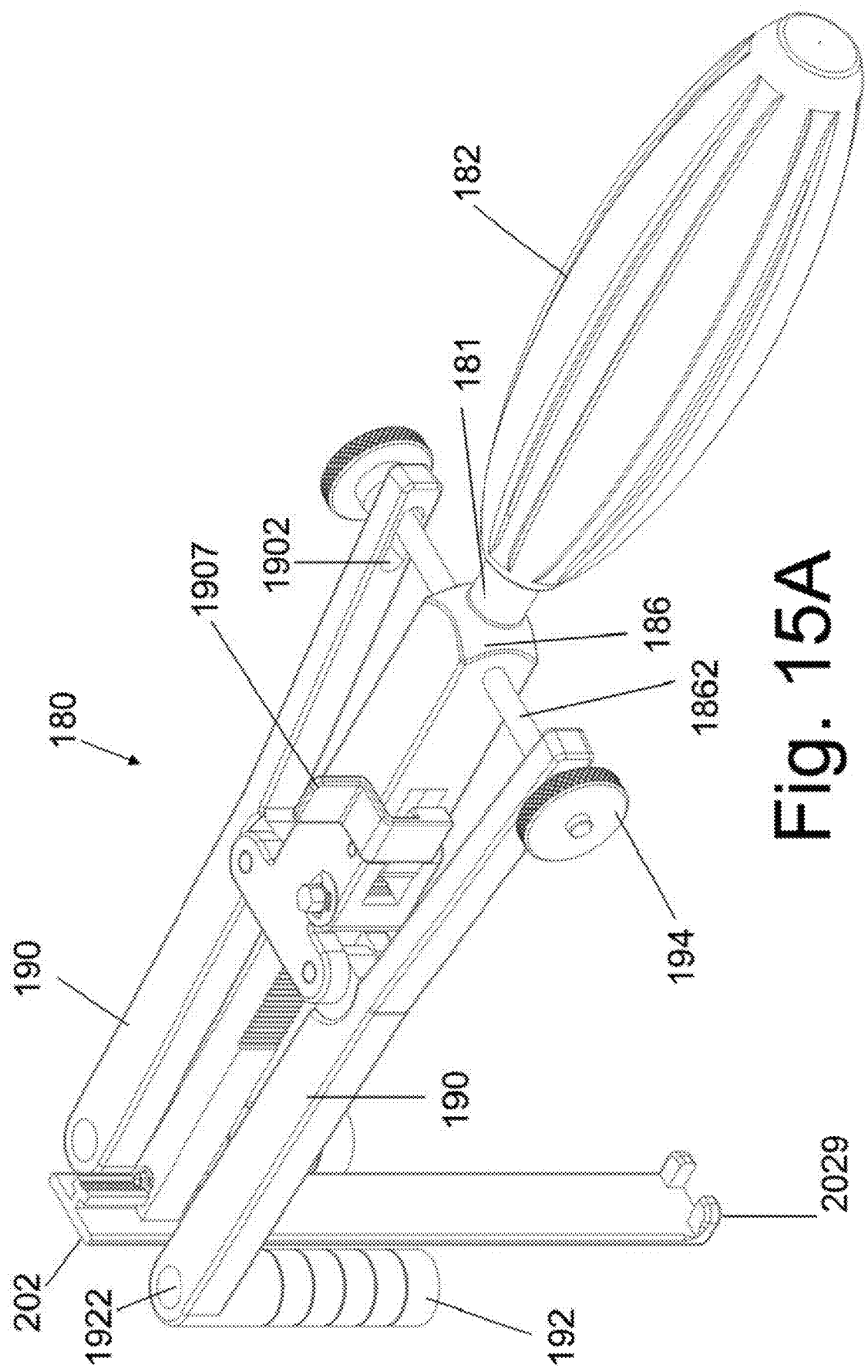

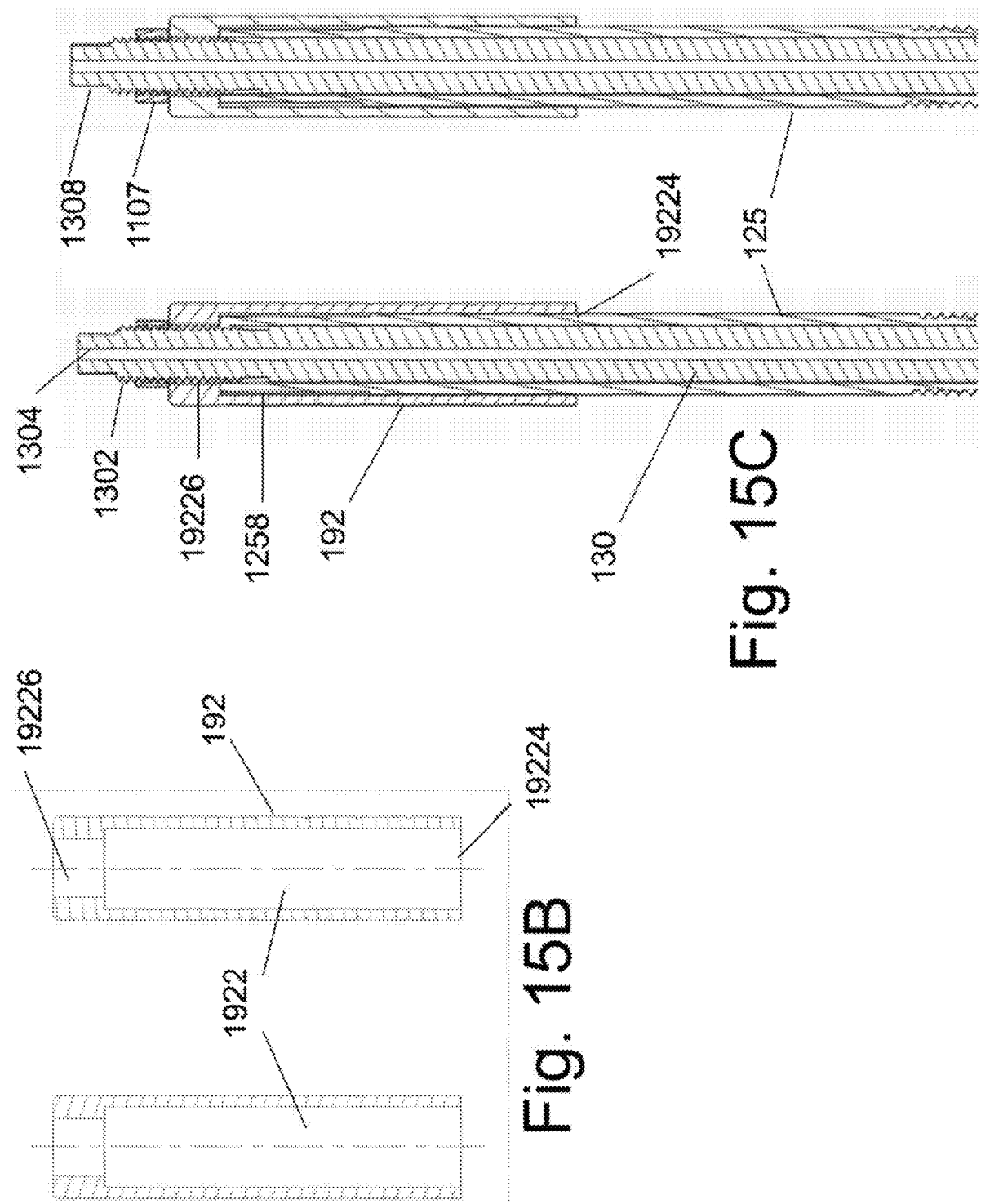

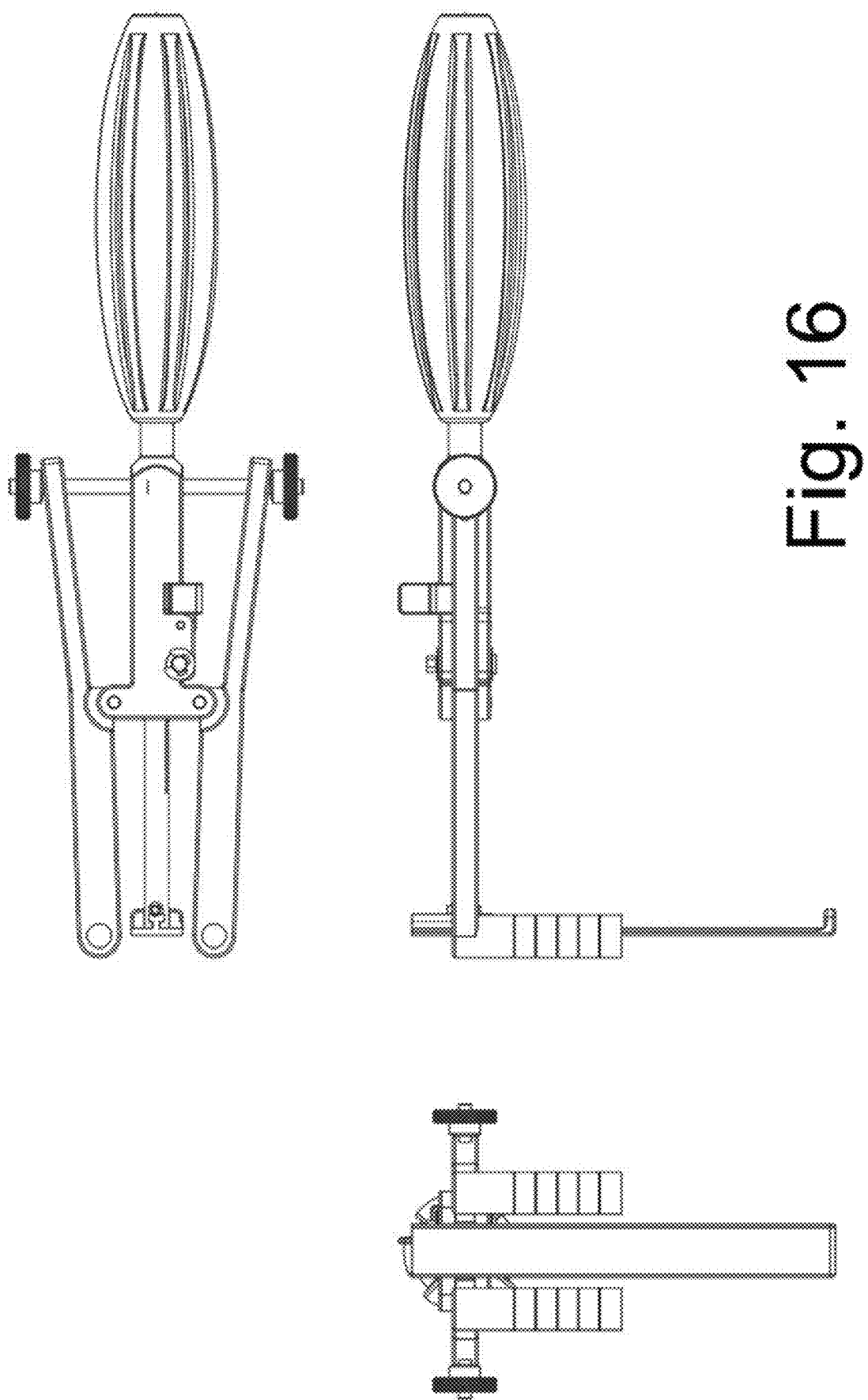

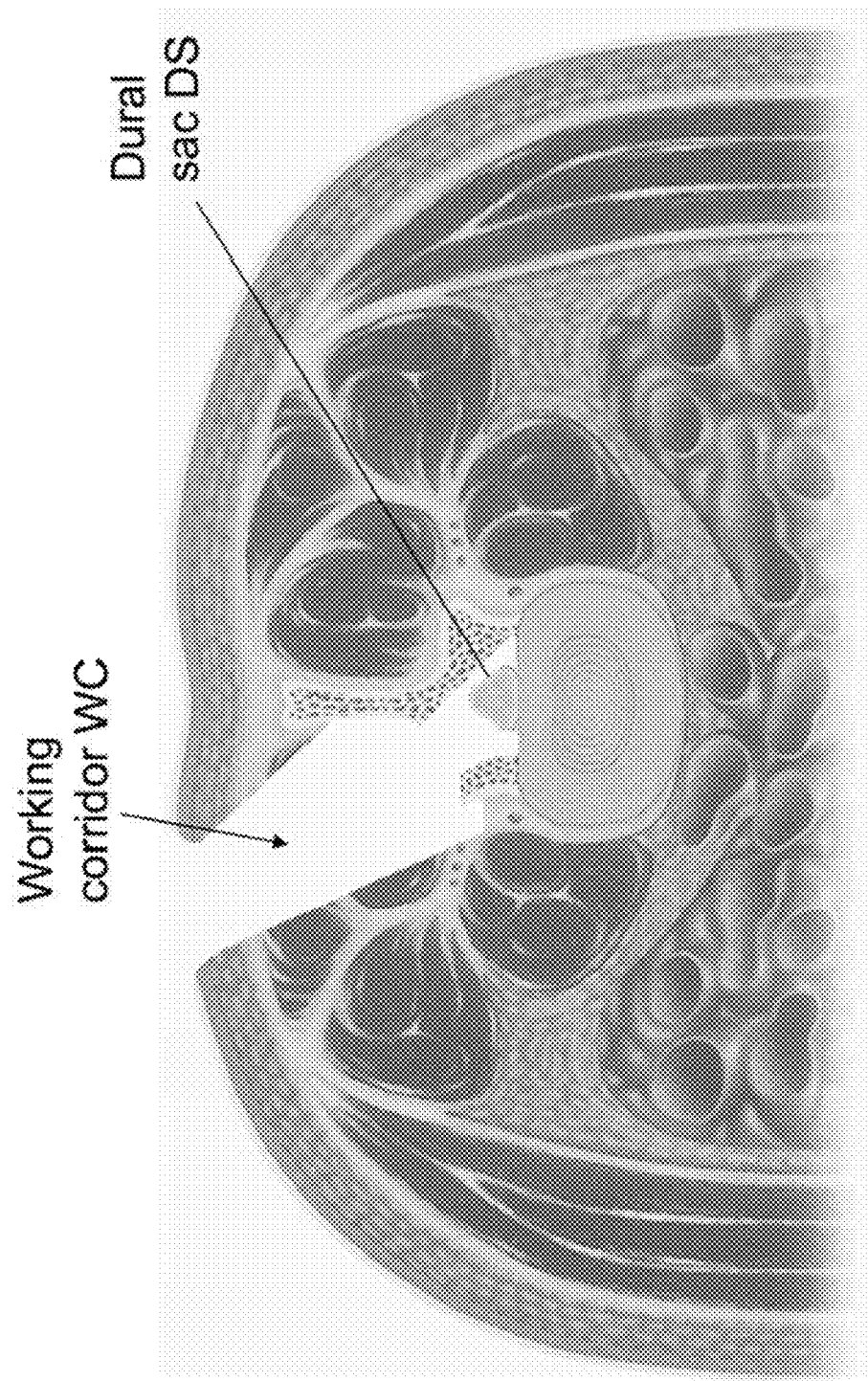

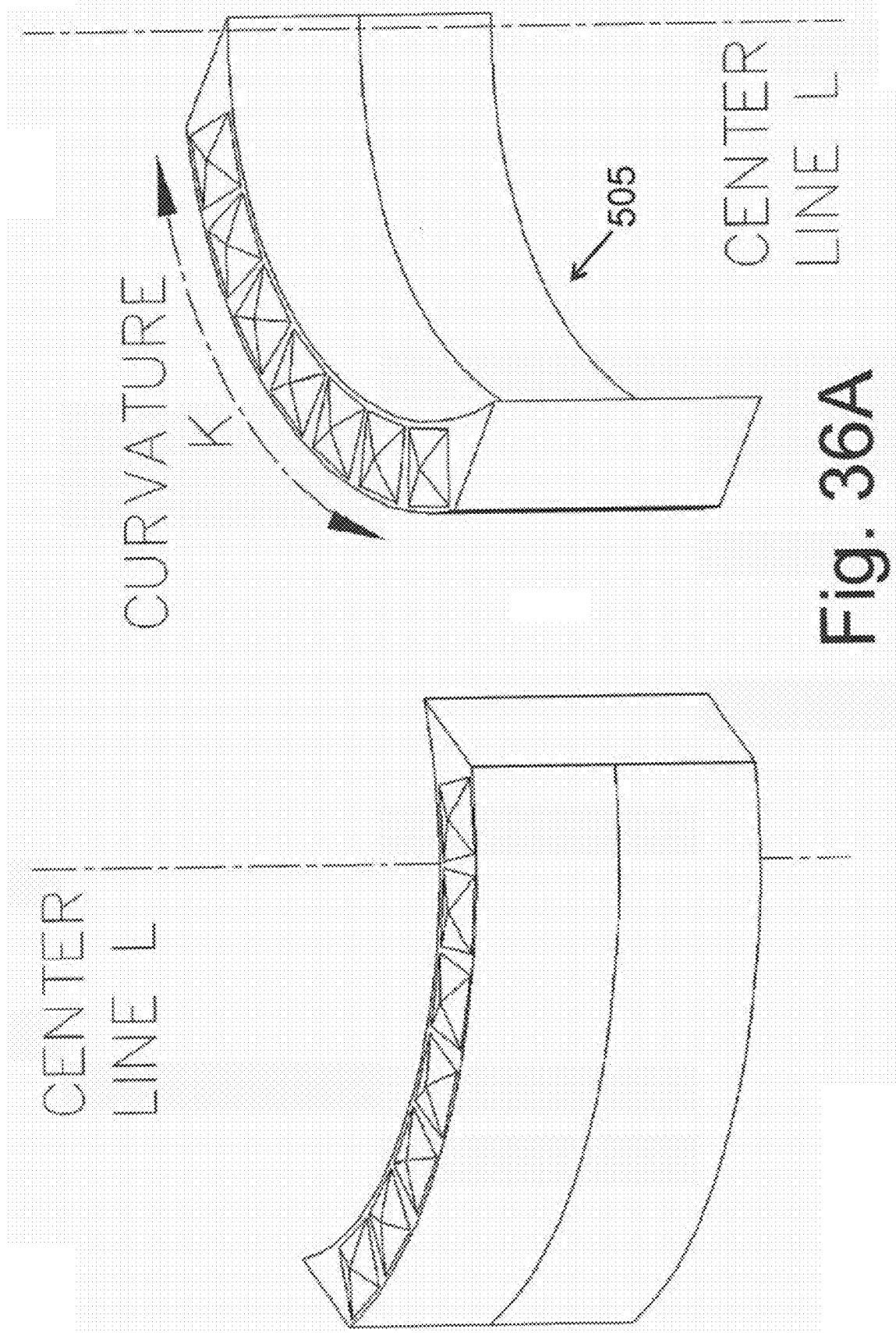

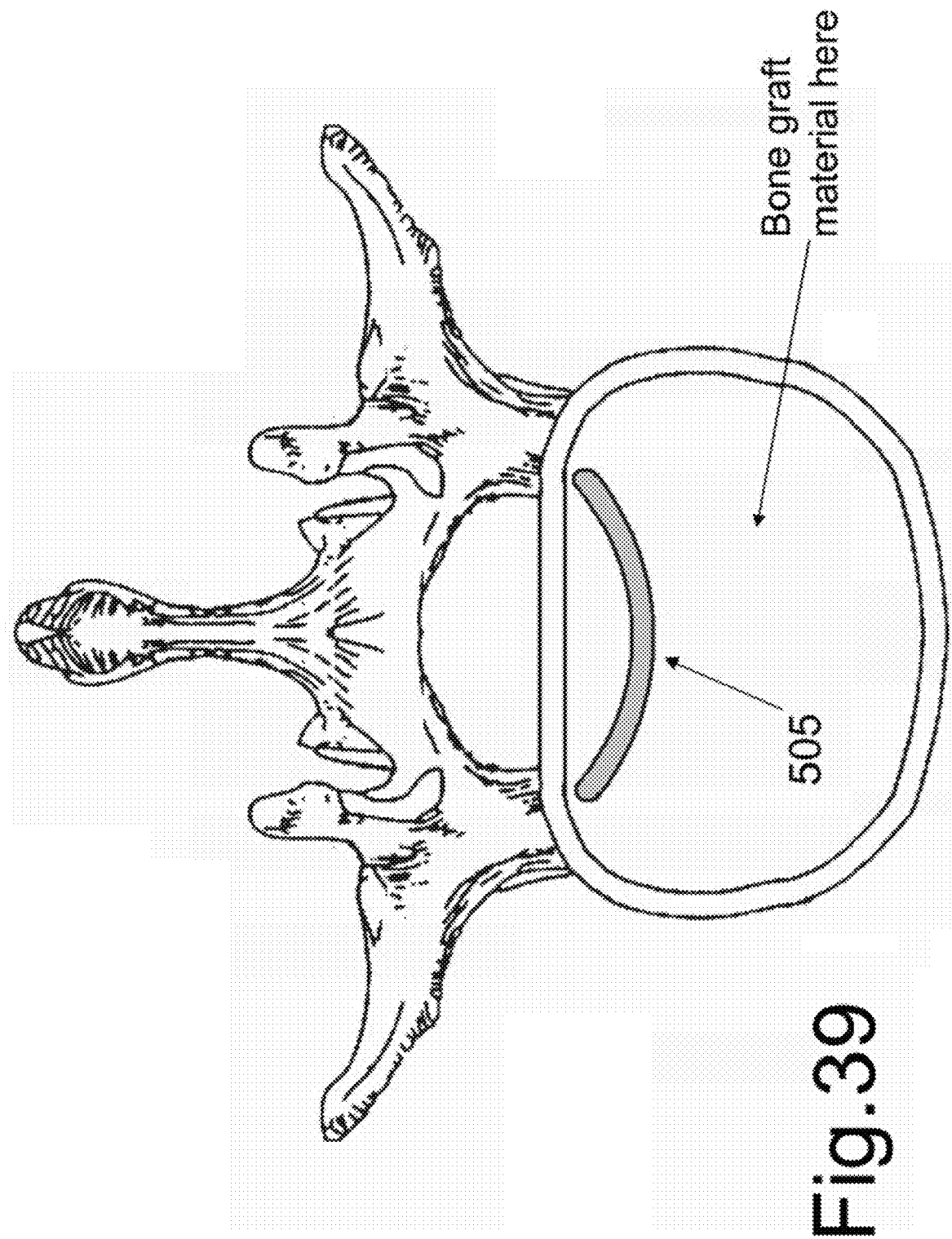

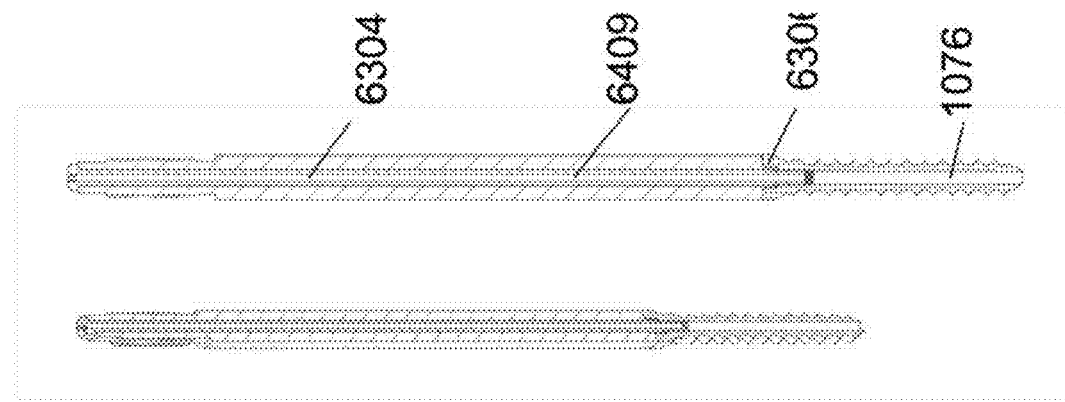
Fig. 43C
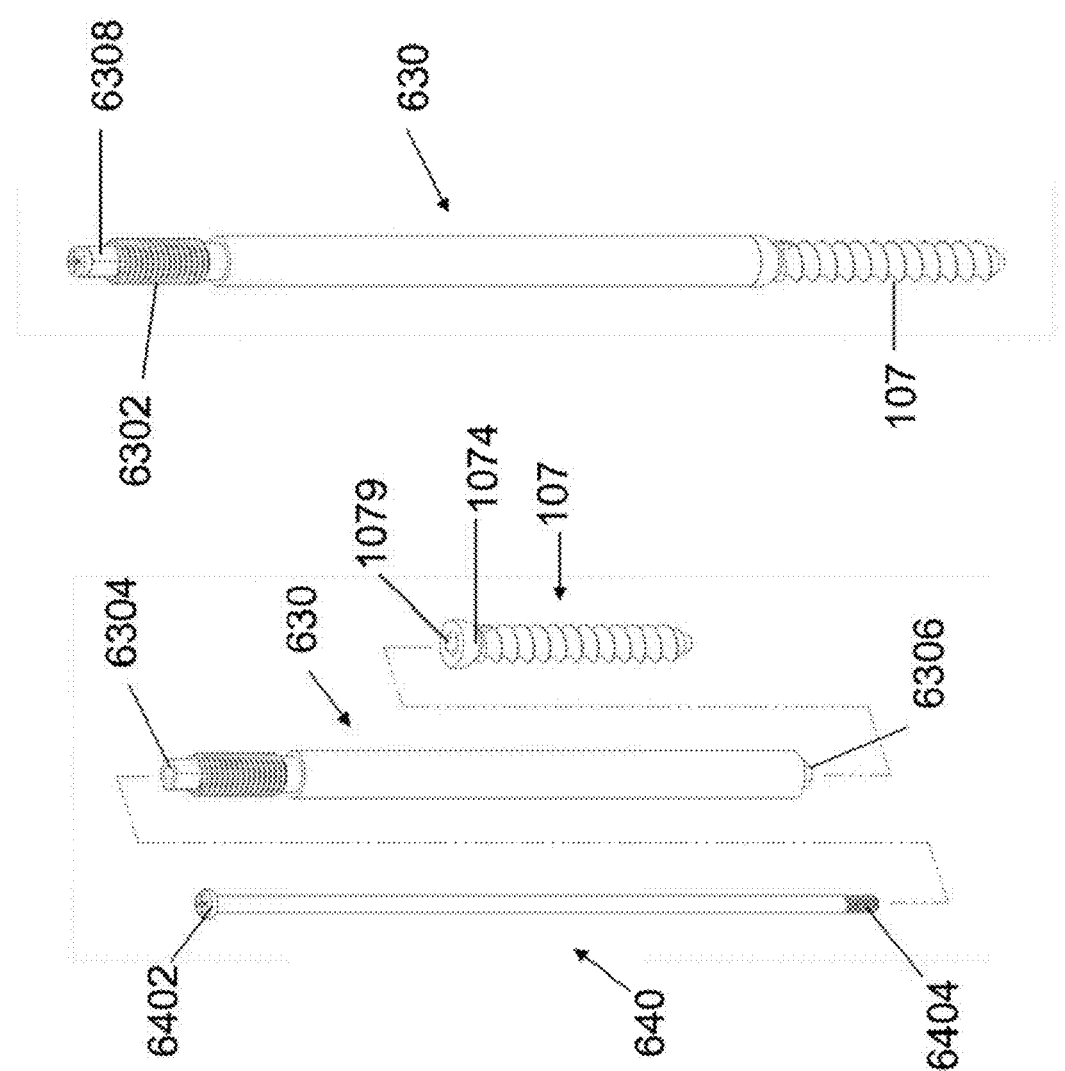
Fig. 43B
Fig. 43A

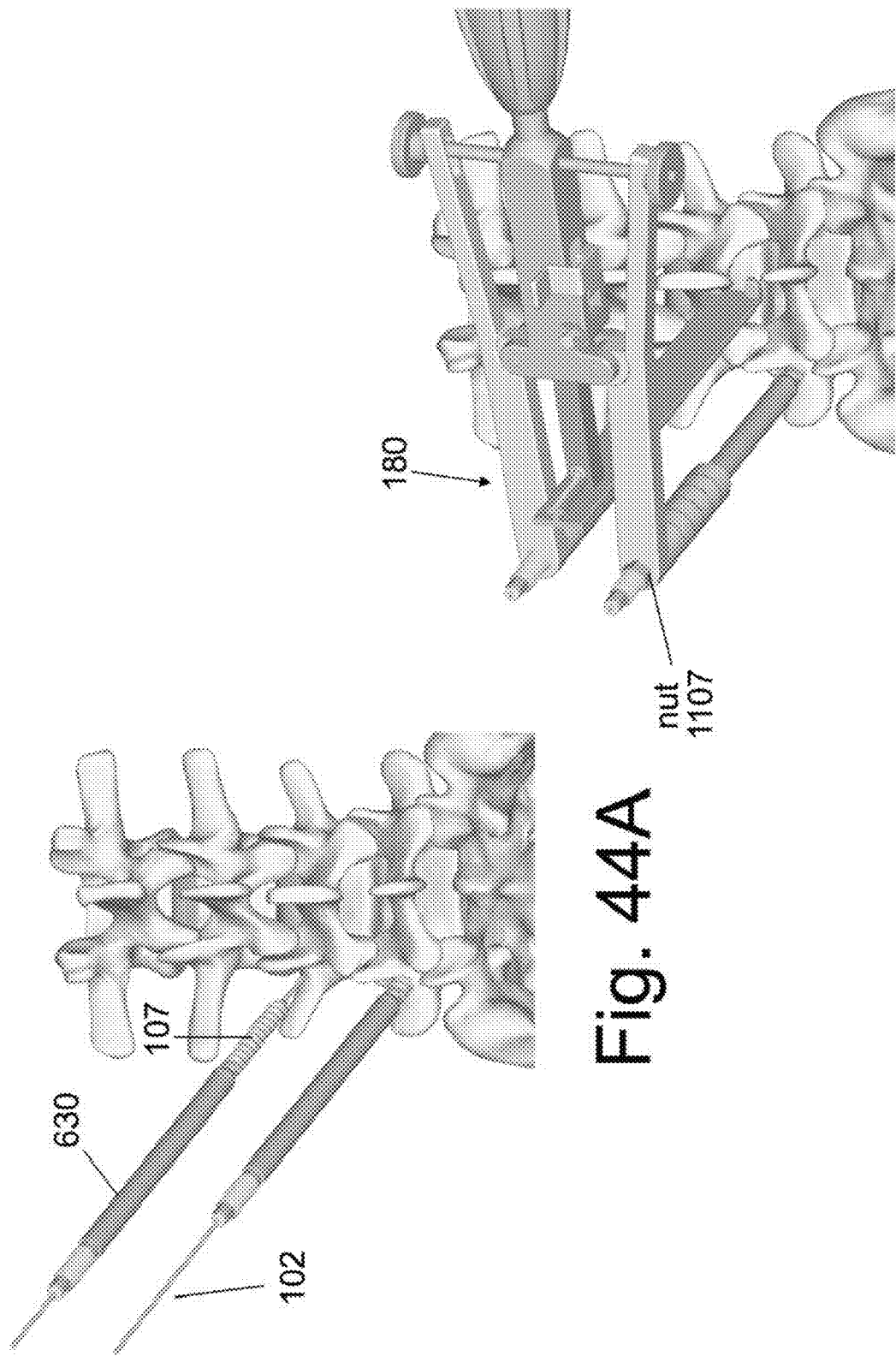

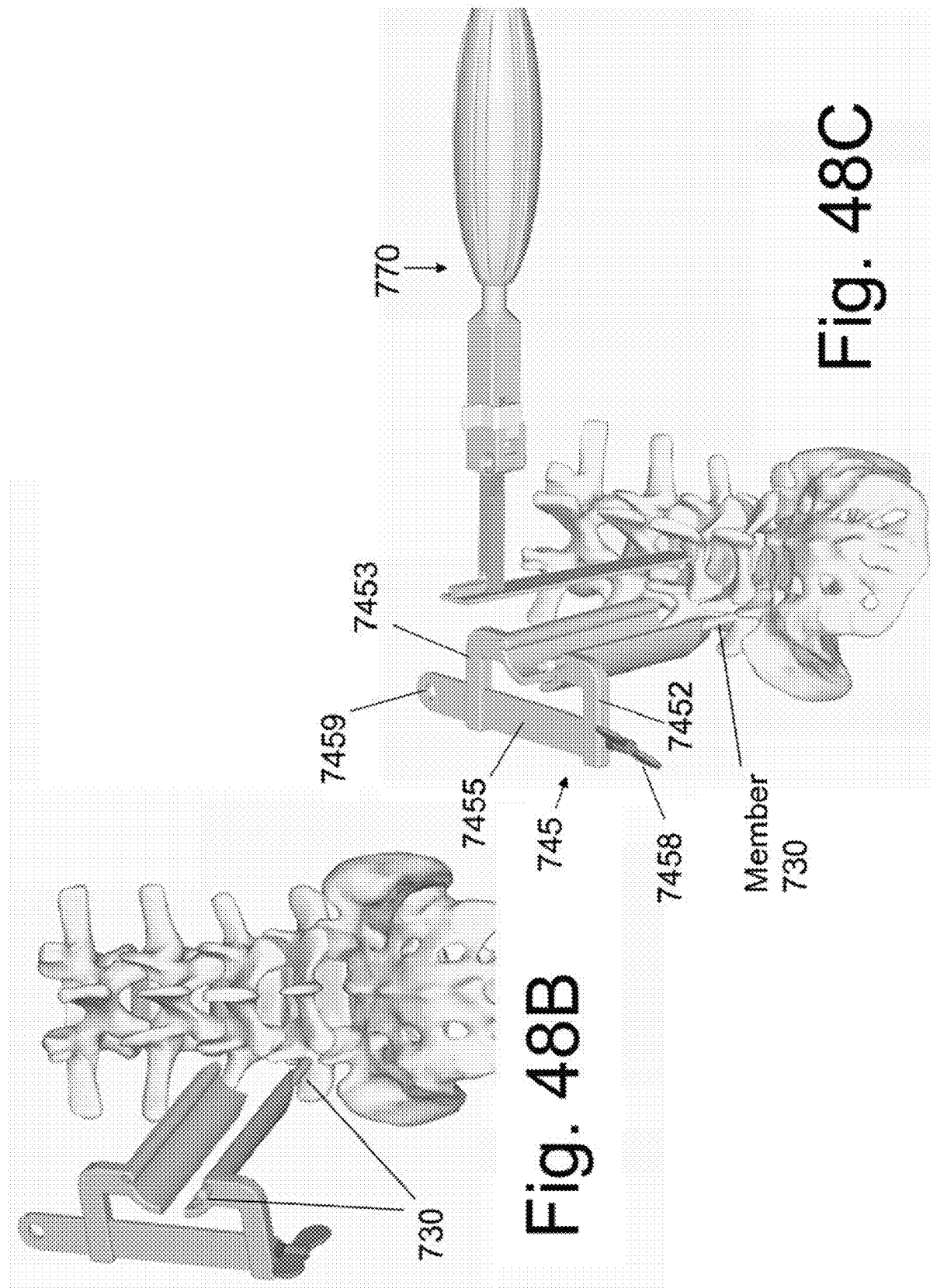

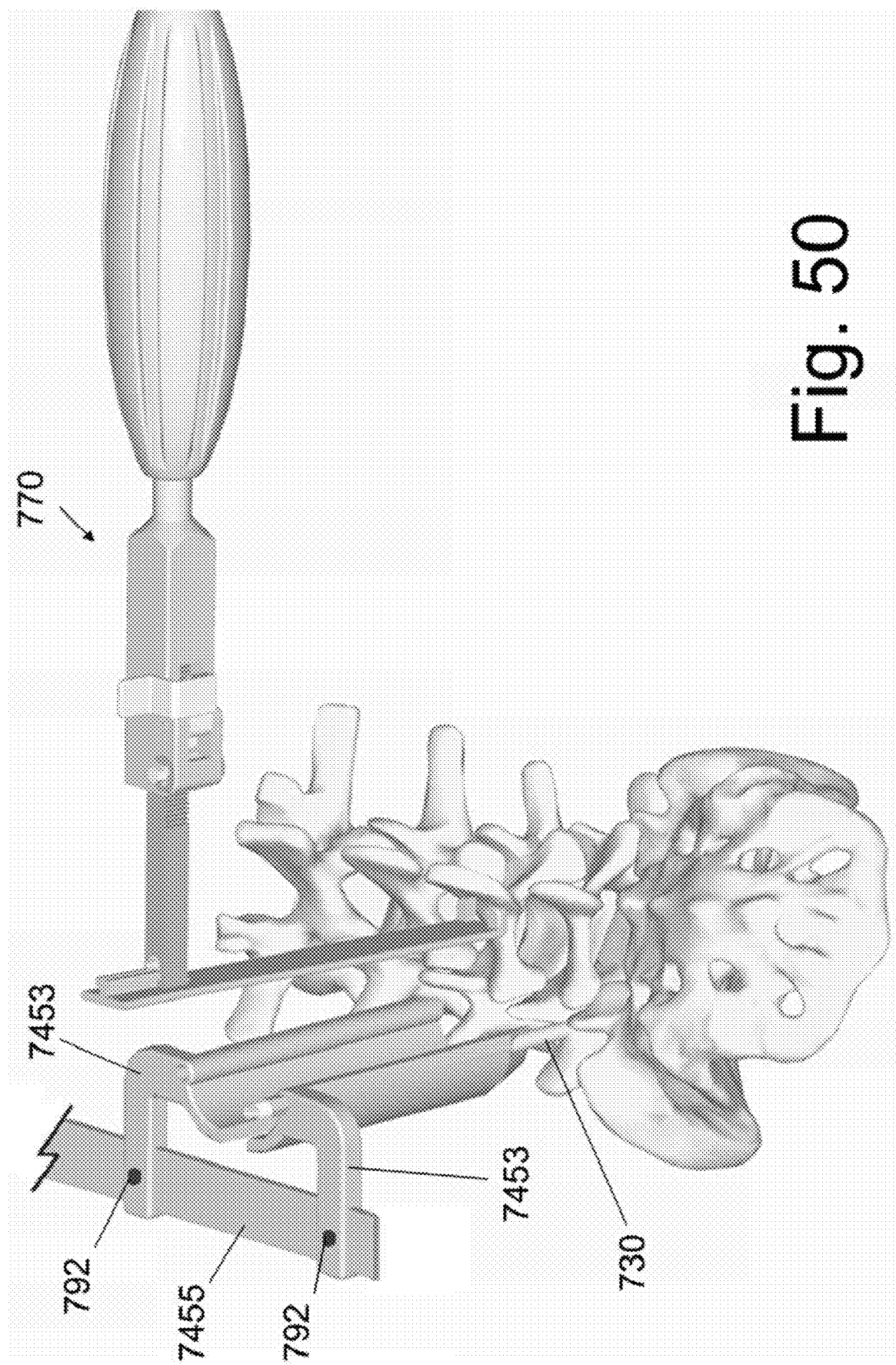

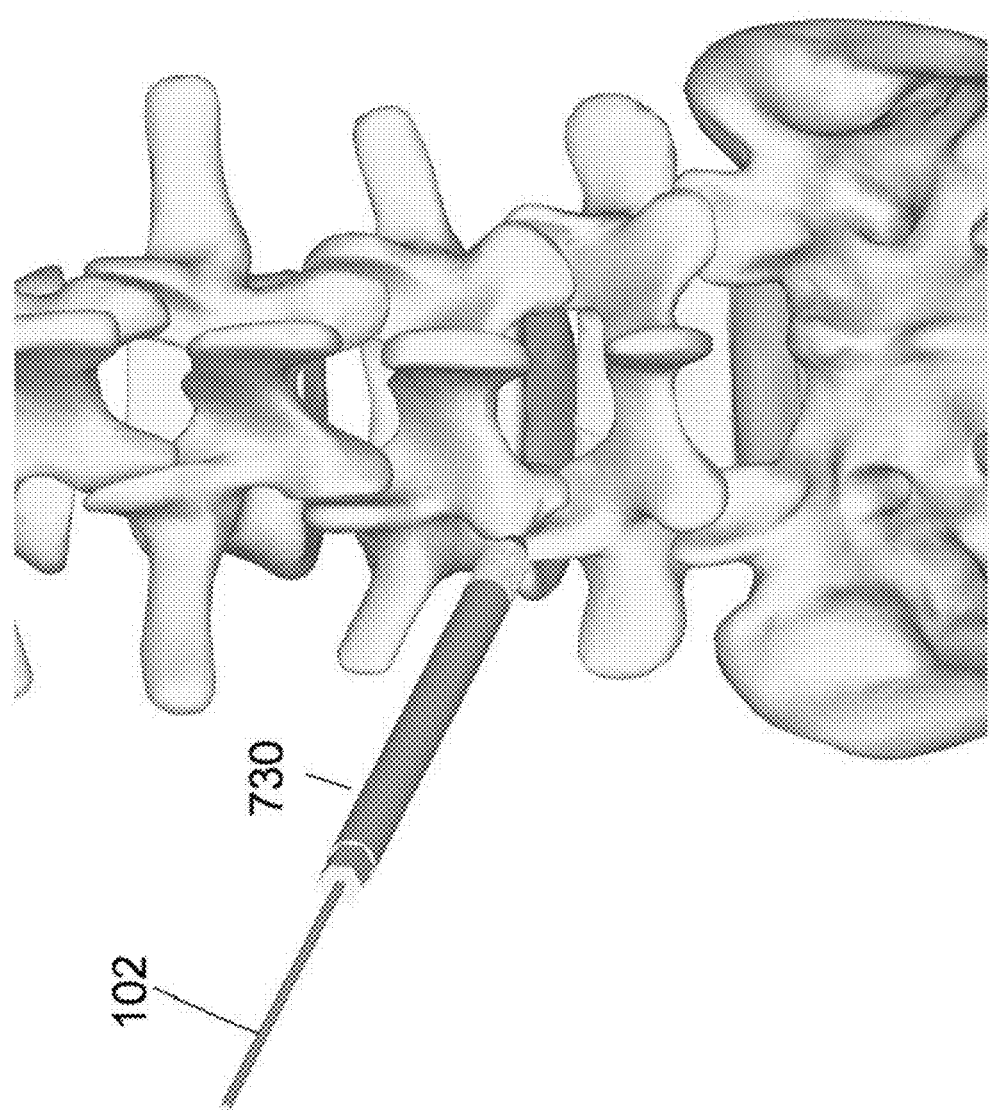

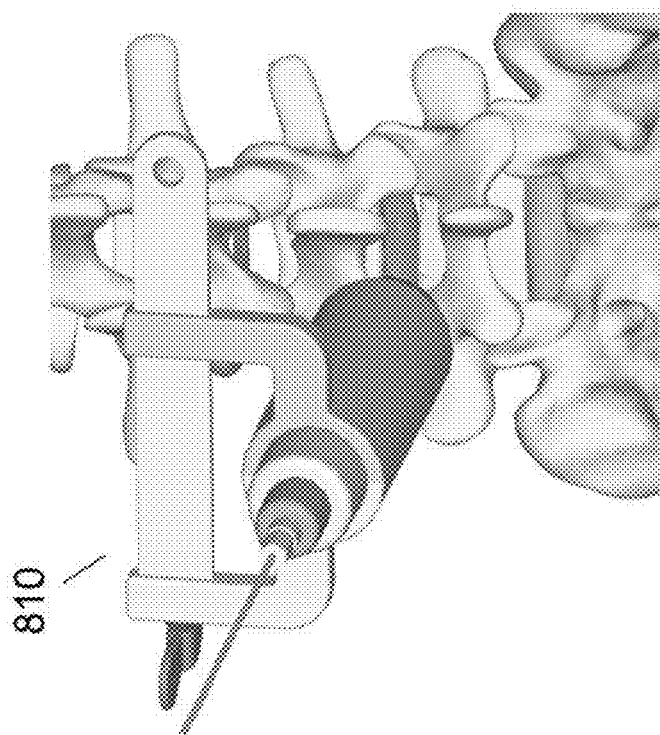
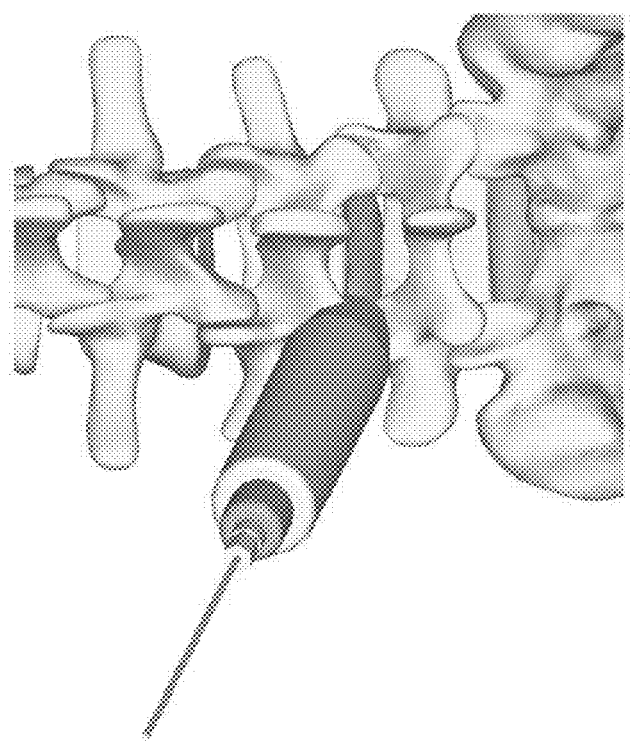
Fig. 52A
Fig. 52B

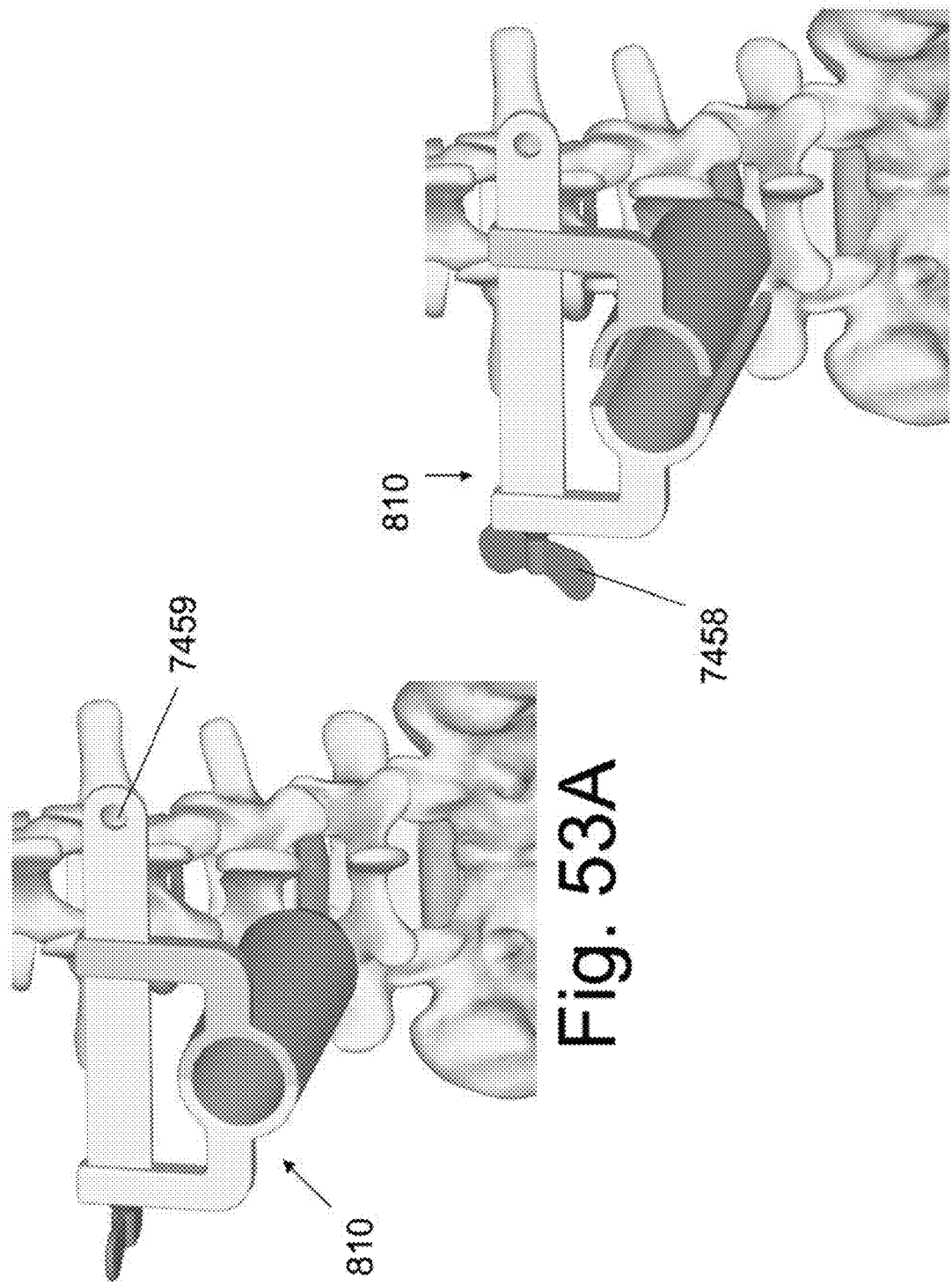

DEVICES AND METHODS FOR MINIMALLY INVASIVE SPINAL STABILIZATION AND INSTRUMENTATION

CROSS REFERENCE TO PRIORITY DOCUMENTS DOCUMENT

This application is a continuation of and claims the benefit of priority to co-owned U.S. patent application Ser. No. 15/887,854 of the same title filed on Feb. 2, 2018, issuing as U.S. Pat. No. 10,857,004 on Dec. 8, 2020, which is a continuation of and claims the benefit of priority to co-owned U.S. Patent application Ser. No. 15/620,633 of the same title filed on Jun. 12, 2017, issued as U.S. Pat. No. 10,543,107 on Jan. 28, 2020, which is a continuation of and claims the benefit of priority to co-owned U.S. patent application Ser. No. 15/162,468 of the same title filed on May 23, 2016, issued as U.S. Pat. No. 9,675,389 on Jun. 13, 2017, which is a continuation of and claims the benefit of priority to co-owned U.S. patent application Ser. No. 14/616,439 of the same title filed on Feb. 6, 2015, issued as U.S. Pat. No. 9,345,464 on May 24, 2016, which is a divisional of and claims the benefit of priority to co-owned U.S. Patent application Ser. No. 14/320,349 of the same title filed on Jun. 30, 2014, which is a continuation of and claims the benefit of priority to co-owned U.S. Patent application Ser. No. 13/875,228 of the same title filed on May 1, 2013, issued as U.S. Pat. No. 8,764,806 on Jul. 1, 2014, which is a continuation of and claims the benefit of priority to co-owned U.S. patent application Ser. No. 12/962,534 of the same title filed on Dec. 7, 2010, which claims the benefit of priority to co-owned U.S. Provisional Patent Application Ser. No. 61/283,745, entitled "Devices and Methods for Minimally Invasive Spinal Stabilization and Instrumentation", filed Dec. 7, 2009. Priority of the aforementioned filing date is hereby claimed and the disclosure of the provisional patent application is hereby incorporated by reference in its entirety.

This application is related to co-owned U.S. Patent Application Serial No. of the same titled filed Feb. 5, 2018, issued as U.S. Patent No. 10,610,380 on Apr. 6, 2020; and co-owned U.S. patent application Ser. No. 16/657,848 of the same title filed Oct. 17, 2019, each of which is incorporated herein by reference in its entirety.

BACKGROUND

Disclosed herein are devices, systems and methods of stabilization of the bony elements of the skeleton. These devices will permit adjustment and maintenance of the spatial relationship(s) between neighboring bones. Depending on the specifics of the design, the motion between skeletal segments may be immobilized completely or preserved.

Surgical reconstructions of the bony skeleton are common procedures in current medical practice. Regardless of the anatomical region or the specifics of the reconstructive procedure, many surgeons employ an implantable device that can adjust, align and maintain the spatial relationship(s) between adjacent bones.

Whether from degenerative disease, traumatic disruption, infection or neoplastic invasion, alteration in the anatomical relationships between the spinal vertebras can cause significant pain, deformity and disability. Spinal disease is a major health problem in the industrialized world and the surgical treatment of spinal pathology is an evolving discipline. The current surgical treatment of abnormal vertebral motion is the complete immobilization and bony fusion of the involved spinal segment. An extensive array of surgical techniques and implantable devices have been formulated to accomplish this goal.

Vertebral fusion may be accomplished by using an anterior, lateral or posterior approach and each has particular advantages and draw backs. Frequently, circumferential fusion of the unstable level with fixation of both the anterior and posterior aspect of the spine is desired. This requires that patients undergo a combination of the aforementioned approaches. The anterior or lateral approaches are used to insert the bone graft into the disc space between the adjacent vertebras while the posterior approach is used to place bone screws or similar fasteners that are used to immobilize the vertebral bodies.

A Trans-foraminal Lumbar Interbody Fusion (TLIF) is known in the art to permit circumferential fusion of the spine through a single surgical approach. (The procedure is described in several literature citations, including: *Transforaminal Lumbar Interbody Fusion by Alan Moskowitz, Orthop Clint N Am* 33 (2002) 359-366. The article is hereby incorporated by reference in its entirety.)

The procedure requires an oblique approach to the posterior aspect of the spine. Unfortunately, an oblique operative corridor is less familiar to surgeons and contains fewer recognizable anatomical landmarks—leading to a higher rate of intra-operative confusion and loss of direction among operating surgeons. This difficulty is compounded when the procedure is performed using minimally invasive or percutaneous surgical technique, wherein the extent of tissue exposure is purposefully minimized. With the lack of surgical landmarks, the probability of intra-operative misdirection and the consequent development of surgical complications are necessarily increased.

In the current execution of the trans-foraminal lumbar interbody fusion (TLIF), the surgeon makes a skin incision posterior to the spinal level that is to be fused, develops a dissection corridor through the soft tissues adjacent to the spine and arrives at a facet joint of the spinal level to be fused. The facet joint is then at least partially removed in order to provide access to the posterior surface of the disc space which is positioned immediately anterior to the facet joint. The disc space is entered, prepared to accept fusion (preparation of the disc space is a well known procedure in the art and will not be described in detail here) and then implanted with the desired implant and material. After disc space implantation, the surgeon frequently, but not necessarily, desires to add supplemental orthopedic instrumentation to rigidly fixate the operative level while the bony fusion matures. Most commonly, the supplemental fixation involves placement of bone anchors (usually screws) that are interconnected with an interconnecting members (usually one or more rods).

In the current execution of the trans-foraminal lumbar interbody fusion (TLIF), it is the development of a dissection corridor through the soft tissues from the skin incision to the facet joint that is most likely to create disorientation and confusion. The surgeon often arrives at a bony prominence of the underlying vertebral bones but may be unclear as to which segment of the bone it is or the precise orientation of the soft tissue corridor relative to the vertebral bones that must be fused. The lack of reliable surgical landmarks during development of the oblique soft tissue corridor adds to the uncertainly and this difficulty is compounded when the procedure is performed using minimally invasive or percutaneous surgical technique, wherein the extent of tissue exposure is purposefully minimized.

SUMMARY

Provided herein are devices and methods for the safe and reproducible placement of an orthopedic implant into the disc space of a desired spinal segment. The disclosed procedure is especially well adapted for performing minimally invasive or percutaneous trans-foraminal lumbar interbody fusion (TLIF) procedures. However, while described for a posterior fusion technique of the lumbar spine, it is nevertheless understood that the devices and methods described herein may be used with any other applicable surgical approach to any applicable spinal level. Further, the devices and method may be used to implant non-fusion implants (such as artificial discs, replacement nucleus pulposis, and the like) into a targeted disc space.

The disclosed devices and methods include identifying and targeting a portion of a vertebral bone adjacent to the disc space to be implanted in the initial operative steps. A marker is advanced into the identified bony segment and the marker is used as a reference to orient the surgical corridor and to correctly identify the segments of bone and disc to be removed and/or manipulated. In a preferred embodiment that is illustrated in a TLIF procedure, the pedicle portion of the vertebral bone is the targeted segment of bone that is identified and marked. Preferably the pedicle is marked with a bone screw that is anchored into it and the pedicle and screw are then used to define and orient the subsequent operative steps. In another embodiment that is illustrated in the performance of a TLIF procedure, the facet joint is the targeted segment that is identified and marker. Preferably, the facet joint is marked with a bone screw that is anchored into it and the screw is then used to define and orient the subsequent operative steps.

Disclosed is a method wherein a segment of bone of at least one vertebra that borders the disc space to be implanted is identified intra-operatively by imaging techniques (X-rays, CT, MRI and the like). A marker, such as a bone screw, is placed into the identified bone segment and the attached marker forms a readily identifiable surgical land mark for the surgeon during formation of the surgical corridor. When illustrated in the performance of a TLIF procedure, the marker is preferably positioned into the pedicle or facet portion of the vertebral bone. The marker is coupled to bone prior to resection of the facet joint. The marker is used to define the exposure and orient the surgeon during the subsequent bony manipulation.

In the preferred embodiment, it is the pedicle portion of the vertebral bone that is localized and marked. The devices and methods described herein are illustrated in the performance of a minimally invasive trans-foraminal lumbar interbody fusion (TLIF) procedure, wherein a bone screw is placed into the identified pedicle and the bone screw forms a readily identifiable surgical land mark for the surgeon during formation of the surgical corridor to the facet joint and its subsequent removal.

Disclosed are distractor platforms and methods of use for the exposure and resection of at least a portion of the facet joint in performance of a TLIF procedure. In an embodiment, the distractor platform contains at least a first receptacle and/or extension that are adapted to couple to the implanted screw/bone marker. Preferably, the distractor platform also contains at least one retractor blade that is adapted to retract and retain the soft tissues that rest posterior to the facet joint so as to expose the posterior aspect of the joint. The tissue retractor blade may be reversibly detachable from the distractor platform and, preferably, the distance from tissue-retracting blade tip to the distractor platform may be varied so that the distractor blade is, in effect, of variable in length.

Provided herein are instruments and methods for the unambiguous introduction of surgical landmarks and corridors for placement of an orthopedic implant into the disc space of a spinal segment. Described herein are instruments and methods for placement of an orthopedic implant into the disc space of spinal segment using a trans-foraminal lumbar interbody fusion (TLIF) procedure, wherein the TLIF procedure is preferably performed in a minimally invasive or percutaneous manner. While illustrated in the TLIF approach, it is understood that the illustrated embodiments are not restrictive and the instruments and methods may be used with any other applicable surgical approach and at any applicable spinal level.

In one aspect provided is a method for fusion of a first vertebral bone and a second adjacent vertebral bone of a subject. The method includes identifying a first pedicle of the first vertebral bone on radiographic imaging; identifying the second adjacent vertebral bone on radiographic imaging and a first facet joint. The first facet joint forms an articulation between the first vertebral bone and the second adjacent vertebral bone. The first facet joint resides on the same side of the vertebral midline as the identified first pedicle of the first vertebral bone. The method also includes advancing a first threaded segment of a first bone fastener assembly into the identified first pedicle of the first vertebral bone. The first bone fastener assembly further includes a second segment that is adapted to couple with a distraction platform. The method also includes coupling the distraction platform with the second segment of the first bone fastener assembly. The distraction platform is adapted to concurrently attach onto at least one tissue retention blade. The method further includes positioning the tissue retention blade in proximity to the first bone fastener assembly that is anchored to the pedicle of the first vertebral bone; exposing the first facet joint by applying a force to displace the tissue retention blade away from the first bone fastener assembly and towards the vertebral midline. The distraction platform is adapted to retain the tissue retention blade in the displaced position. The method also includes removing at least a segment of the first facet joint and exposing a posterior surface of an intervertebral disc space. The exposed disc space is positioned between the first and second vertebral bones. At least a portion of exposed disc surface is immediately anterior to the removed portion of the first facet joint. The method also includes entering the posterior aspect of the disc space through a trans-foraminal corridor and removing the distraction platform. The entry point of the posterior disc is at least partially in between the nerve root that exits the spinal canal beneath the pedicle of the superior vertebral bone and the pedicle of the inferior vertebral bone; positioning an implant into the disc space. The implant can bear at least some of the load transmitted across the disc space and maintain the superior and inferior vertebral bones separated by a desired distance.

In another aspect, there is disclosed a method for the fusion of a first vertebral bone and a second adjacent vertebral bone of a subject. The method includes identifying the first vertebral bone on radiographic imaging and a first facet joint, wherein the first facet joint forms an articulation between the first and second adjacent vertebral bones; advancing a first threaded segment of a first bone fastener into the identified first facet joint under radiographic guidance, wherein the bone fastener is threadedly anchored onto the first facet joint; using the anchored first bone fastener to guide and position a retraction platform; advancing a distraction platform over the anchored first bone fastener and onto the facet joint, wherein the distraction platform is coupled to at least two tissue retention extensions; detaching the first bone fastener from the facet joint in order to form a corridor between the tissue retention extensions of the distraction platform, wherein the corridor permits direct access to the posterior aspect of the first facet joint; identifying visually the first facet joint at the distal end of the corridor between the tissue retention extensions of the distraction platform; removing at least a segment of the first facet joint and exposing a posterior surface of an intervertebral disc space, wherein the exposed disc space is positioned between the first and second vertebral bones, wherein at least a portion of exposed disc surface is immediately anterior to the removed portion of the first facet joint; entering the posterior aspect of the disc space through a trans-foraminal corridor, wherein the entry point of the posterior disc is at least partially in between the nerve root that exits the spinal canal beneath the pedicle of the superior vertebral bone and the pedicle of the inferior vertebral bone; positioning an implant into the disc space, wherein the implant can bear at least some of the load transmitted across the disc space and maintain the superior and inferior vertebral bones separated by a desired distance; and removing the distraction platform.

Other features and advantages should be apparent from the following description of various embodiments, which illustrate, by way of example, the principles of the disclosed instruments and methods.

BRIEF DESCRIPTION OF THE DRAWINGS

FIGS. 1A-1C show diagrammatic representations of a spinal vertebral bone in multiple views.

FIGS. 2A and 2B illustrate a functional spinal unit (FSU), which includes two adjacent vertebrae and the intervertebral disc between them.

FIG. 11 shows a step in the advancement of fastener into the bone.

FIG. 12 shows a step in the advancement of fastener into the bone.

FIG. 13 shows a step in the advancement of fastener into the bone.

FIG. 14 shows an embodiment of a distraction platform.

FIGS. 15A-15C show various views of the platform.

FIG. 16 show various view of the platform.

FIG. 35 shows schematic view of the dural sac and contained nerve element decompressed on the posterior and lateral aspects.

FIGS. 36A-36B show an embodiment of a disc implant.

FIG. 39 shows bone graft material placed into the disc space adjacent the implant.

FIGS. 43A-43C show an example of a device adapted to perform the method.

FIGS. 44A-44B show steps in the assembly onto the distractor platform.

FIGS. 48A-48C show a retractor platform.

FIG. 50 shows another embodiment of a retractor.

FIGS. 51A-51C show placement of guide wire directly into facet joint space between the IAP of the superior vertebral bone and SAP of the interior vertebral bone.

FIGS. 52A-52B show cylindrical tubes of progressively greater diameter sequentially passed over member to dilate surrounding soft tissue and advancement of retractor platform.

FIGS. 53A-53B show tube removed leaving a working corridor within the central aspect of the semi-cylindrical retractor blades.

DETAILED DESCRIPTION

Figure 3:
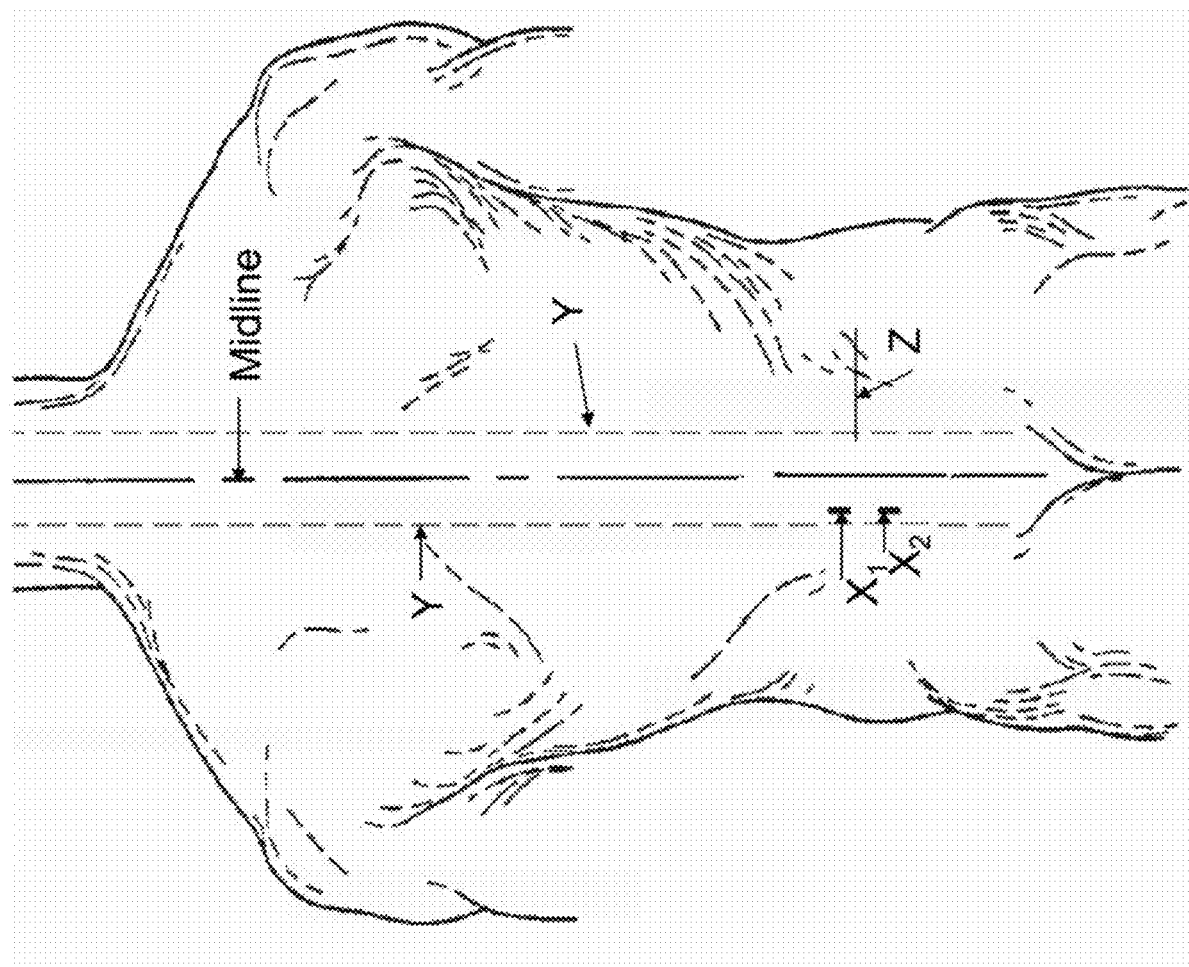
FIG. 3 shows a schematic representation of the posterior aspect of a patient who is positioned prone.

In order to promote an understanding of the principals of the disclosure, reference is made to the drawings and the embodiments illustrated therein. Nevertheless, it will be understood that the drawings are illustrative and no limitation of the scope of the invention is thereby intended. Any such alterations and further modifications in the illustrated embodiments, and any such further applications of the principles of the invention as illustrated herein are contemplated as would normally occur to one of ordinary skill in the art.

FIG. 1 shows a diagrammatic representation of a spinal vertebral bone 802 in multiple views. For clarity of illustration, the vertebral bone of FIG. 1 and those of other illustrations presented in this application are represented schematically and those skilled in the art will appreciate that actual vertebral bodies may include anatomical details that are not shown in these figures. Further, it is understood that the vertebral bones at a given level of the spinal column of a human or animal subject will contain anatomical features that may not be present at other levels of the same spinal column. The illustrated vertebral bones are intended to generically represent vertebral bones at any spinal level without limitation. Thus, the disclosed devices and methods may be applied at any applicable spinal level.

Vertebral bone 802 contains an anteriorly-placed vertebral body 804, a centrally placed spinal canal and 806 and posteriorly-placed lamina 808. The pedicle (810) segments of vertebral bone 802 form the lateral aspect of the spinal canal and connect the laminas 808 to the vertebral body 804. The spinal canal contains neural structures such as the spinal cord and/or nerves. A midline protrusion termed the spinous process (SP) extends posteriorly from the medial aspect of laminas 808. A protrusion extends laterally from each side of the posterior aspect of the vertebral bone and is termed the transverse process (TP). A right transverse process (RTP) extends to the right and a left transverse process (LTP) extends to the left. A superior protrusion extends superiorly above the lamina on each side of the vertebral midline and is termed the superior articulating process (SAP). An inferior protrusion extends inferiorly below the lamina on each side of the vertebral midline and is termed the inferior articulating process (IAP). Note that the posterior aspect of the pedicle can be accessed at an indentation 811 in the vertebral bone between the lateral aspect of the SAP and the medial aspect of the transverse process (TP). In surgery, it is common practice to anchor a bone fastener into the pedicle portion of a vertebral bone by inserting the fastener through indentation 811 and into the underlying pedicle.

Figure 28:
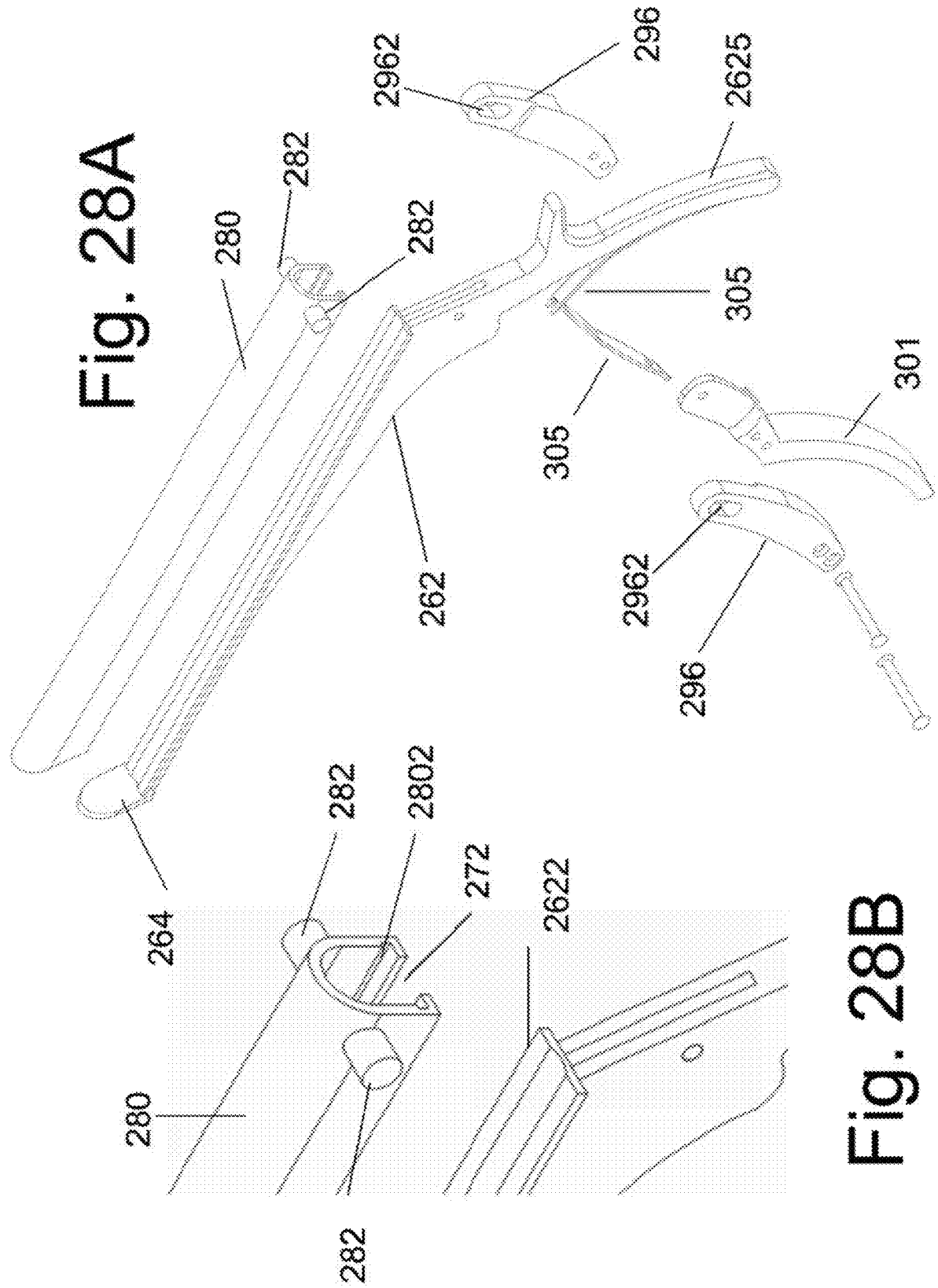
FIGS. 28A-28B show exploded views of the instrument.

FIGS. 2A and 2B illustrate a functional spinal unit (FSU), which includes two adjacent vertebrae and the intervertebral disc between them. The intervertebral disc resides between the inferior surface of the upper vertebral body and the superior surface of the lower vertebral body. (Note that a space is shown in FIGS. 2A and 2B where intervertebral disc would reside.) FIG. 2A shows the posterior surface of the adjacent vertebrae and the articulations between them while FIG. 28 shows an oblique view. Note that the FSU contains a three joint complex between the two vertebral bones, with the intervertebral disc comprising the anterior joint. The posterior joints include a facet joint 814 on each side of the midline, wherein the facet joint contains the articulation between the IAP of the superior vertebral bone and the SAP of the inferior bone.

The preceding illustrations and definitions of anatomical structures are known to those of ordinary skill in the art. They are described in more detail in *Atlas of Human Anatomy, by Frank Netter, third edition, Icon Learning Systems, Teterboro, New Jersey*. The text is hereby incorporated by reference in its entirety.

Illustrated are methods and devices that permit a surgeon to access the anterior column of the spine from a posterior skin incision through a transforaminal surgical approach. The "anterior column" is used here to designate that portion of the vertebral body and/or FSU that is situated anterior to the posterior longitudinal ligament (PLL)—and may include the PLL Thus, its use in this application encompasses both the anterior and middle column of Denis. (See *The three column spine and its significance in the classification of acute thoracolumbar spinal injuries*. By Denis, F. Spine 1983 Nov-Dec; 8(8):817-31. The article is incorporated by reference in its entirety.)

It is a purpose of the present invention to provide instruments and methods for the unambiguous introduction of surgical landmarks and corridors for placement of an orthopedic implant into the disc space of a spinal segment. It is a purpose of the present invention to specifically illustrate the instruments and methods for placement of an orthopedic implant into the disc space of spinal segment using a trans-foraminal lumbar interbody fusion (TLIF) procedure, wherein the TLIF procedure is preferably performed in a minimally invasive or percutaneous manner. While illustrated in the TLIF approach, it is understood that the illustrated embodiments are not restrictive and the instruments and methods may be applied at other spinal segments and to methods of implant placement other than TLIF.

For a functional spinal unit (FSU) that has been targeted for placement of an orthopedic implant into the intervening disc space, the trans-foraminal lumbar interbody fusion (TLIF) procedure requires removal of at least a portion of the IAP and SAP of a facet joint 814 that is immediately posterior to the disc space to be implanted. The facet joint removal may be performed on one side of the vertebral midline, the opposite side of the vertebral midline or on both sides of the vertebral midline. In the existing art, a TLIF procedure is started with development of an oblique soft tissue corridor from the skin incision site (which is posterior to the spine) to the facet joint that must be removed. Unfortunately, the soft tissue corridor lacks adequate surgical landmarks and its development can cause intra-operative confusion, misdirection and deviation into unintended structures. This difficulty is compounded when the procedure is performed using minimally invasive or percutaneous surgical technique.

It is a goal of the current invention to obviate any intra-operative confusion by placing bone markers and/or fasteners in at least one prescribed location of the vertebral bones of the targeted FSU. In a preferred embodiment, the pedicle portion of the upper and/or lower vertebral bones that border the disc space targeted for implantation are identified and localized on imaging (such as X-rays, CT, MRI and the like). Bone screws and/or other fasteners are then advanced in a percutaneous manner and under image guidance (such as X-rays, CT, MRI and the like) into the pedicle portion of the localized vertebrae through small skin incisions. Alternatively, a small posterior skin incision can be made overlying the posterior aspect of the disc space targeted for implantation. The bone screws and/or fasteners can then be advanced through the small incision, in a minimally invasive way, onto the bone insertion region 811 and into the underlying the pedicle. In another embodiment, the bone fasteners may be placed at the bone insertion site 811 with conventional surgical technique and a larger skin incision. The bone screws and/or fasteners are then used to guide the formation of the surgical corridor to the facet joint.

Placement of the bone fasteners before resection of the facet joint differs from the method of current art, wherein the facet joint is accessed/resected and an implant is positioned into the disc space without prior placement of the bone screws and/or fasteners. That is, in the current invention, bone markers are positioned to define the surgical corridor without prior resection of facet joint. In contrast, the current art does not use fasteners to define the surgical corridor to the facet joint nor are they used to guide implant placement.

After bone screw and/or fastener (hereinafter the terms are used interchangeably) placement, a distraction platform is used to couple and/or attach onto at least one of the bone screw assemblies. In a preferred embodiment, the distraction platform has at least one additional distraction arm that is adapted to retract soft tissues (skin, fat, muscle, etc). In specific, the distraction platform is coupled to each of the bone screws that have been advanced into the pedicle of the superior and inferior vertebral bones of the targeted FSU. Another arm member that is attached to the distraction platform is used to retract medially the soft tissues between the pedicle bone screws and the spinous process of the vertebrae of the targeted FSU. In this way, the facet joint 814 that lies immediately medial and between the two implanted pedicle bone screws is exposed. Using the bone screws as a coupling point for the distractor platform permits the pedicles and the anchored screws to be used as a surgical landmark in development of soft tissue corridor to the targeted facet joint. Use of another arm member that is coupled to the distraction platform to retract the soft tissues medially insures that the facet joint is readily and reproducibly exposed. It also obviates the possibility of intra-operative confusion by the surgeon.

The soft tissue retractor arm of the distraction is preferably, but not necessarily, removable. That is, the soft tissue retraction arm can be completely de-coupled and removed from the distraction platform. This provides maximal degree of versatility for the surgeon. After exposure of the facet joint 814 that is ipsilateral to the implanted bone screws, at least a portion of that facet joint is then removed. This is preferably, but not necessarily, performed by at least a combination of drill/burr removal and rongeur cutting of the bone so as to form a corridor within the facet joint that permits direct access of the segment of the disc space that is anterior to the removed joint. In an embodiment, the combination drilling and cutting of the facet joint may be performed by a single instrument. For example, the instrument may be adapted to permit bone removal by advancing a drill or burr through a central port of the instrument. The instrument may be further adapted to cut bone with sharpened edges—as would a bone rongeur.

After removal of the facet bone, the posterior disc space is accessed through a transforaminal corridor. The trans-foraminal corridor extends in the superior-inferior direction for a distance D1. Distance D1 extends from the inferior aspect of the nerve root that exits the spinal canal beneath the pedicle of the superior vertebral bone and the superior aspect of the pedicle of the inferior vertebral bone of the targeted FSU. The trans-foraminal corridor is bordered medially by the lateral aspect of the nerve root that exits the spinal canal beneath the pedicle of the inferior vertebral bone of the targeted FSU. A segment of the posterior aspect of the disc space that is exposed after facet resection is positioned immediately anterior to the trans-foraminal corridor. While described for completeness, the trans-foraminal corridor is known to those of ordinary skill in the art and may contain anatomical features that are not recounted here.

The posterior aspect of the disc space that is immediately anterior to the trans-foraminal corridor is entered by creation of a defect in the Annulus Fibrosus. At least partial removal of the disc material is performed and the bony endplate of each of the inferior surface of the superior vertebral bone and superior surface of the inferior vertebral bone are striped of cartilage material and then decorticated. Bone graft or bone graft substitute (hereafter collectively referred to as bone forming material) is then implanted into the evacuated disc space. Preferably, but not necessarily, an implant is concurrently implanted into the disc space that can bear at least some of the load transmitted across the disc space and maintain the superior and inferior vertebral bones separated by a desired distance. In an embodiment, the implant may be solid or it may contain a cavity adapted to house bone graft material, wherein the graft material is adapted to fuse with one or both of the vertebral bones.

After advancement of the implant into the targeted disc space, the distraction platform is removed. An inter-connecting member that is preferably, but not necessarily, a rod, is used to interconnect each of the superior and inferior bone fasteners. A locking element of each bone fastener is then deployed so that each bone fastener is rigidly attached to the interconnecting member. In this way, the fasteners and interconnecting rod member will rigidly interconnect and immobilize the superior and inferior vertebral bones that abut the implanted disc space. Additional immobilization may be produced by the implantation of fasteners/interconnecting member into the contra-lateral vertebral pedicles (i.e., on the contra-lateral side of the vertebral midline). A spinous process fastener that is adapted to rigidly affix to the spinous process of each of the superior and inferior vertebral bones and rigidly immobilize the FSU may be alternatively used instead of implantation of the contra-lateral pedicle bone screws and interconnecting rod. (spinous process fixation plates and fasteners are known in the art. Among others, U.S. Pat. Nos. 6,582,433, 7,048,736 and US patent application publication numbers US 2007/0270840 and US 2008/0183211 all disclose spinous process fixation implants that may be applicable. Each of these patents/applications is hereby incorporated by reference in its entirety.)

The preferred embodiment is now described in detail and reference is made to the accompanying drawings. While the disclosed devices may be positioned in an appropriate spinal level/segment using any appropriate surgical method and/or surgical corridor, the following disclosure illustrates implant placement into a disc space of a functional spinal unit (FSU) using a posterior skin incision (posterior to spine) and a transforaminal lumbar interbody fusion (TLIF) technique.

In preparation for the minimally invasive placement of the implant into a targeted spinal level, the patient is preferably, but not necessarily, placed in a prone position or in a lateral decubitus position. The level of the spine that is to be implanted is localized by imaging techniques (X-rays, CT, MRI and the like) in at least one plane. After the customary sterile preparation of the operative site, the surgeon localizes the incision points on the skin that are substantially lateral to vertebral midline and overlying the approximate spinal segment that will be implanted. FIG. 3 shows a schematic representation of the posterior aspect of a patient who is positioned prone. The skin overlying the back is shown. Lines Y illustrate a region that is approximately lateral to the midline and medial to the lateral extent of the transverse processes of the spinal column. Assuming that the spinal disc space to be accessed is skin line Z, the surgeon will access skin region $X_1$ that approximately overlies indentation 811 of the superior vertebral bone and skin region $X_2$ that approximately overlies indentation 811 of the inferior vertebral bone of the FSU that contains the targeted disc space. However, it is understood that one or more skin incisions of any sufficient length may be alternatively used.

Figure 4:
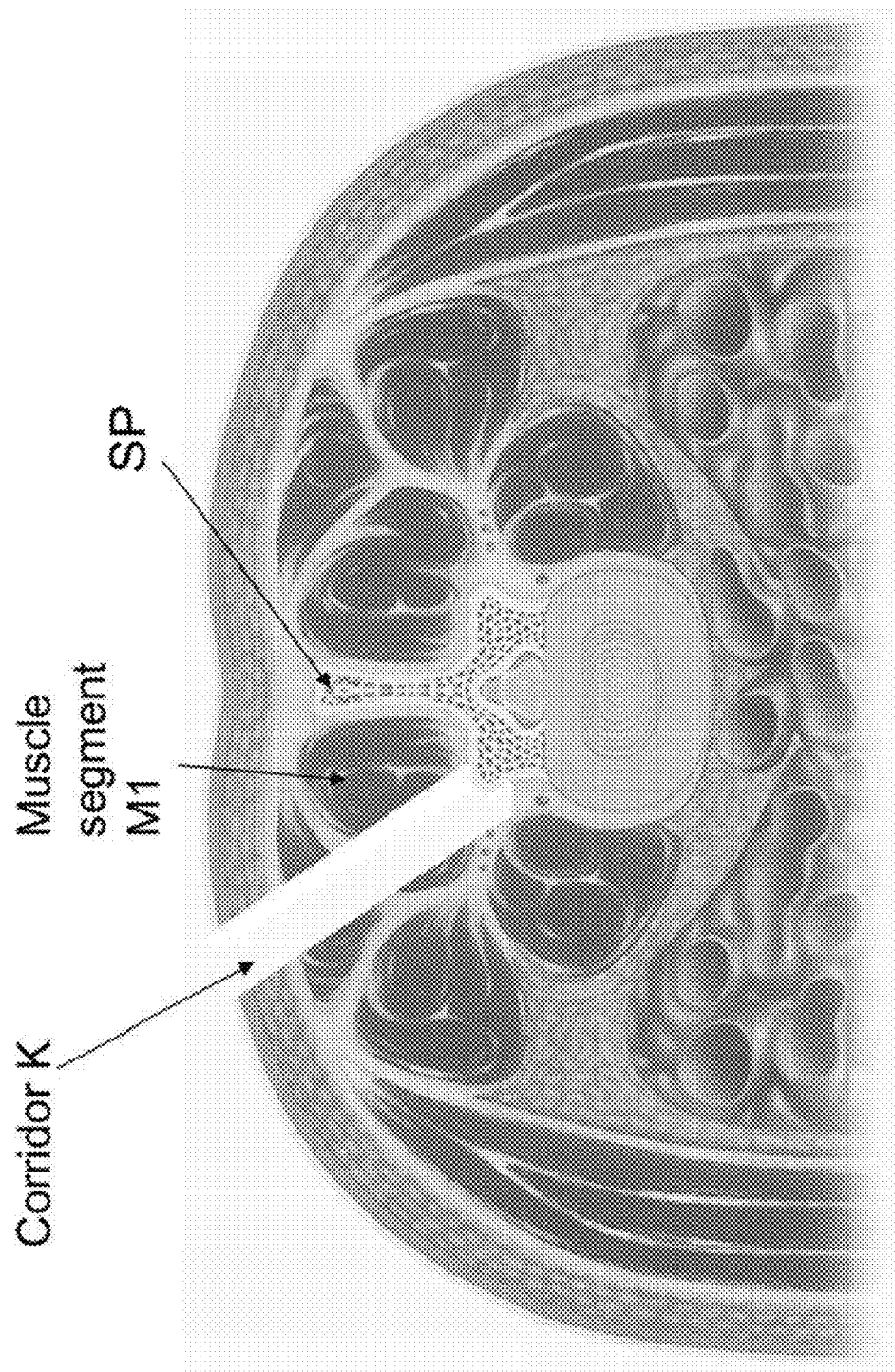
FIG. 4 illustrates a cross sectional view of the torso at the level of a targeted disc space in the lumbar spine.

Bone screws are placed into the pedicle portion of each of the superior and inferior vertebral bones by penetrating the bony surface at approximately indentation 811. In the preferred embodiment, the bone screw placement is performed in a percutaneous manner and under image guidance (such as X-ray, CT or MRI guidance and the like). Alternatively, the bone fasteners may be placed using a larger incision and minimally invasive surgery or full open (conventional) surgical technique. In general, each fastener follows an oblique corridor through the soft tissues between the skin entry site (wherein the skin entry site is posterior to the spine) and the bone entry point of indentation 811. An approximation of the soft tissue corridor K taken by the fasteners is shown in FIG. 4. FIG. 4 illustrates a cross sectional view of the torso at the level of a targeted disc space in the lumbar spine. For clarity of illustration, the contents are represented schematically and those skilled in the art will appreciate that an actual cross section of the human torso may include anatomical details not shown in FIG. 4.

Figure 5B:
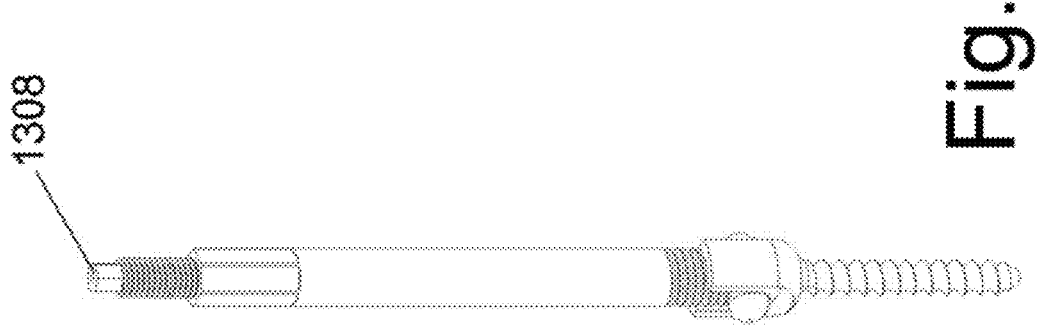
FIGS. 5A-B show representative bone screw assembly and coupling devices.
Figure 5A:
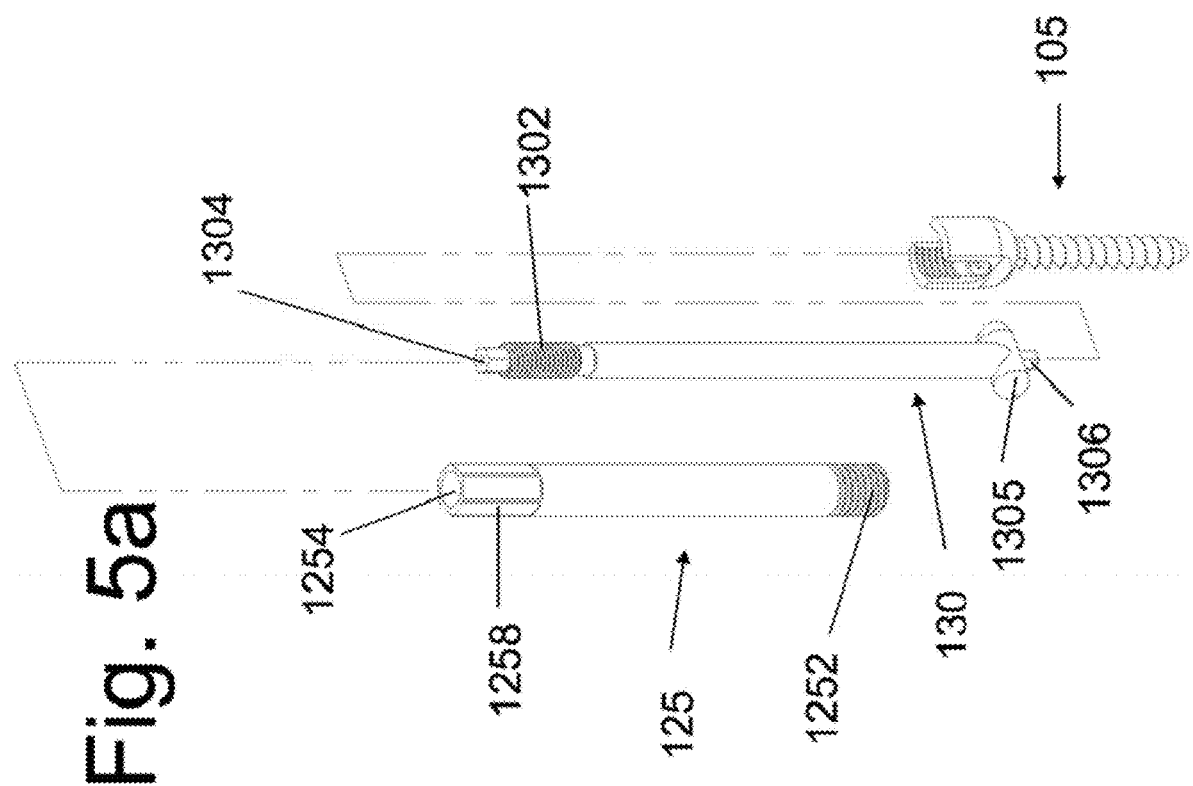
Figure 6:
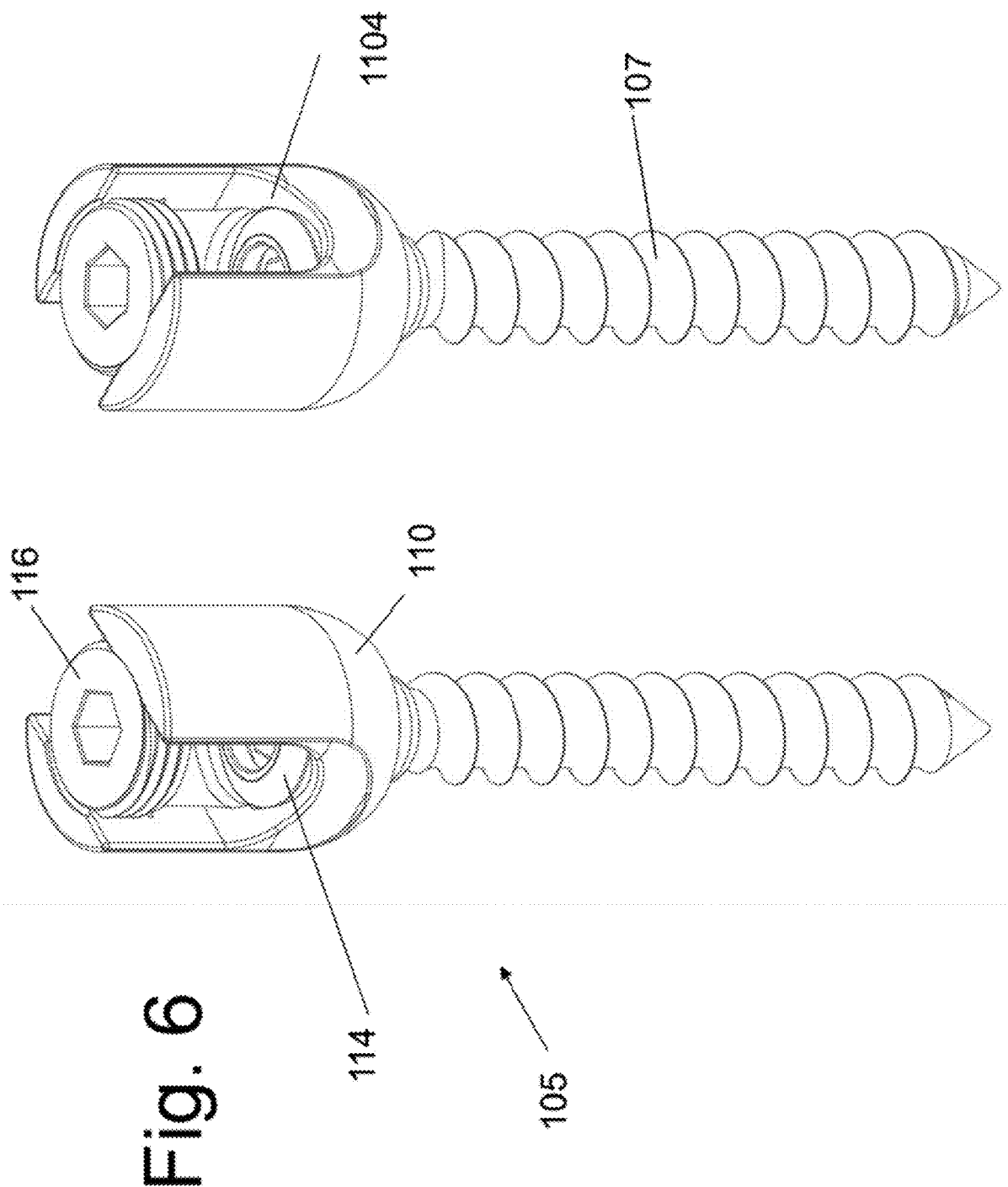
FIG. 6 shows perspective views of bone fastener.
Figure 7:
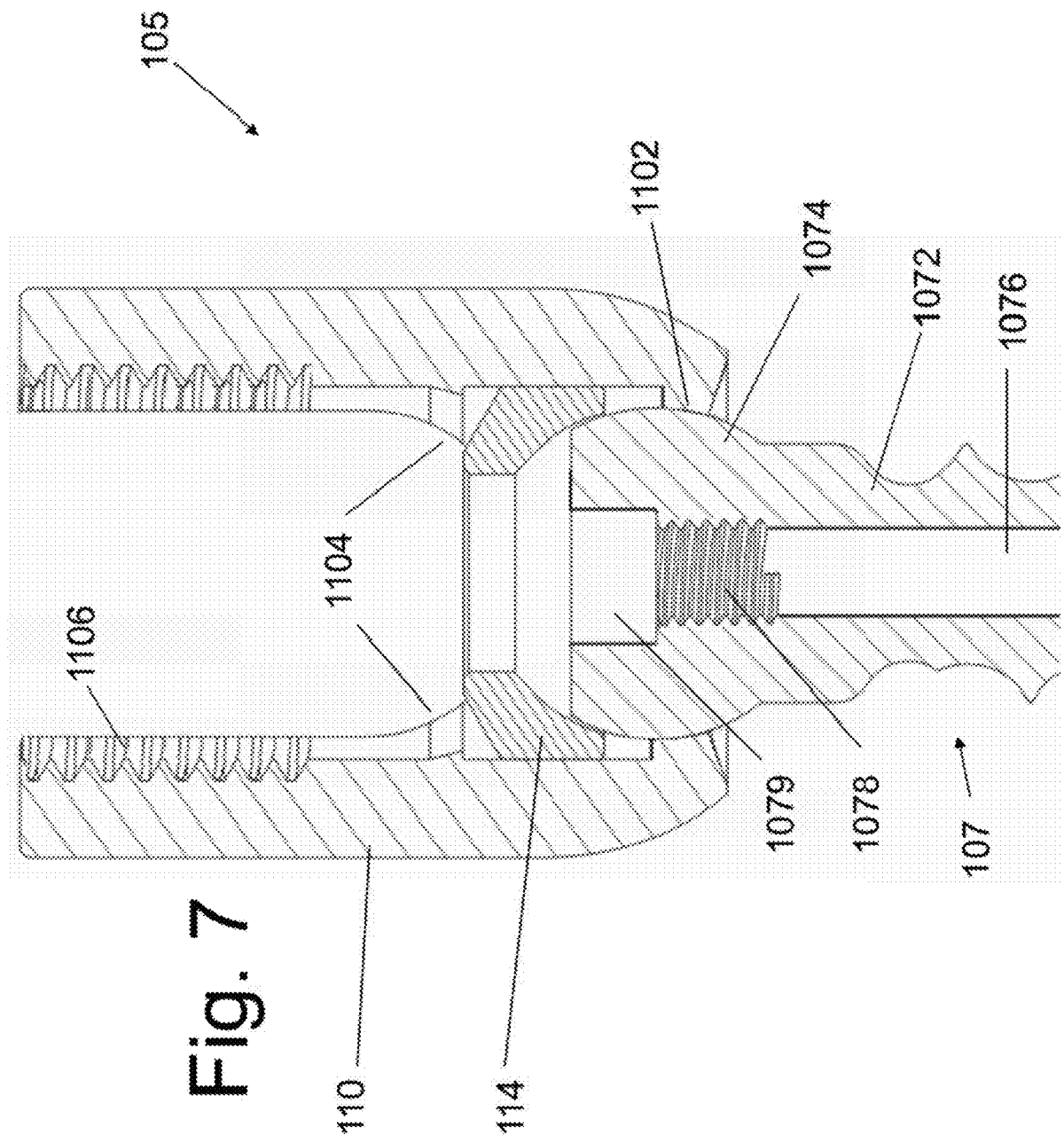
FIG. 7 shows a close-up section view of the fastener of FIG. 6.

FIGS. 5a and b show a representative bone screw assembly 105 and coupling device 125 and 130. FIG. 6 shows perspective views of bone fastener 105 while FIG. 7 shows a close-up section view of fastener 105. The bone fastener and coupling instruments are shown in additional detail in FIGS. 8 & 9. However, it should be appreciated that these embodiments are illustrative and there is known in the art many bone fasteners and couplers that may be alternatively used in the method disclosed in this application. (For example, U.S. RE37665, U.S. Pat. Nos. 6,248,105, 6,371, 957, 6,565,565 all discloses at least one bone screw assembly that may be used to accomplish the present method. Each citation is hereby incorporated by reference in its entirety.)

Assembly 105 contains a threaded bone screw 107 with threaded shaft 1072 and a spherical head 1074. An internal bore 1076 extends through out the internal aspect of the screw 107—extending from top of head 1074 to the tip of shaft 1072. The internal bore has a threaded portion 1078. A hex-shaped receptacle 1079 resides within head 1074. Receptacle 1079 is adapted to accept a screw driver (such as with a hex-shaped tip, or the like), wherein the driver can deliver a rotational force to screw 107 and drive the threaded shaft into bone.

An outer housing 110 has an internal seat 1102 that is adapt to seat head 1074 of screw 107. Housing 110 has an additional seat 1104 that is adapted to accept an interconnecting member, such as a rod. Threads 1106 are adapted to compliment and accept threaded locking nut 116. A pusher member 114 rests between the two seat portions 1104 and 1102 of housing 110 and transmits the downward force of the locking nut 116 onto head 1074 (when an interconnecting rod is positioned between the locking nut and pusher member 114).

In use, an interconnecting member, such as a rod, is positioned within seat 1104 of housing 110. The housing 110 and screw 107 are moved into the desired relative spatial orientation. Locking nut 116 is positioned above the seated interconnecting member and then threadedly advanced relative to threads 1106 of housing 110. As locking nut 116 is advanced, the interconnecting rod member is forced onto pusher member 114. The pusher 116 is forced downward onto head 1074 of screw 1074 and trapping the head between the pusher 116 and seat 1102. In this way, full advancement of locking nut 116 produces rigid immobilization of the interconnecting member, the housing 110 and the screw 107 relative to one another. (It should be appreciated that screw assembly 105 is an example of bone screw assembly that may be used. It is understood that other bone screw assemblies may be alternatively used. Multiple such screw assemblies are known in the art. For example, U.S. RE37665, U.S. Pat. Nos. 6,248,105, 6,371,957, 6,565,565, 6,641,586, 7,704,271 all disclose at least one bone screw assembly that may be used to accomplish the present method. Each citation is hereby incorporated by reference in its entirety.)

As shown in FIGS. 5, the assembly 105 can be coupled to coupler member 125 and 130. FIG. 5a shows the devices in an exploded state while FIG. 5b illustrates the assembled state. Outer member 125 has threaded end 1252 that is adapted to threadedly engage threads 1106 of housing 110. Member 125 has an elongated body with a central bore 1254 that extends there through from the top to the bottom surface of member 125. Central bore 1254 is adapted to accept member 130 within. At the top aspect of member 125, a hex-shaped segment 1258 is present. The segment 1258 is adapted to accept a hex-shaped driver (driver not shown) on the outer aspect of the member 125, wherein the driver, when engaged, is adapted to apply a rotational force to member 125.

Internal member 130 has an elongated body with a threaded segment 1302. Internal member 130 has a central bore 1304 that extends there through from the top to the bottom surface of member 130. A "T" shaped protrusion 1305 has a hex-shaped protrusion 1306 beneath it, wherein hex-shaped protrusion 1306 is adapted to snuggly rest within hex-shaped cut out 1079 of screw 107 such that rotation of member 130 produces rotation of screw 107. Further "T" shaped protrusion 1305 is adapted to rest within seat 1104 of housing 110. An additional hex-shaped protrusion 1308 is located at the top of member 130

Figure 8:
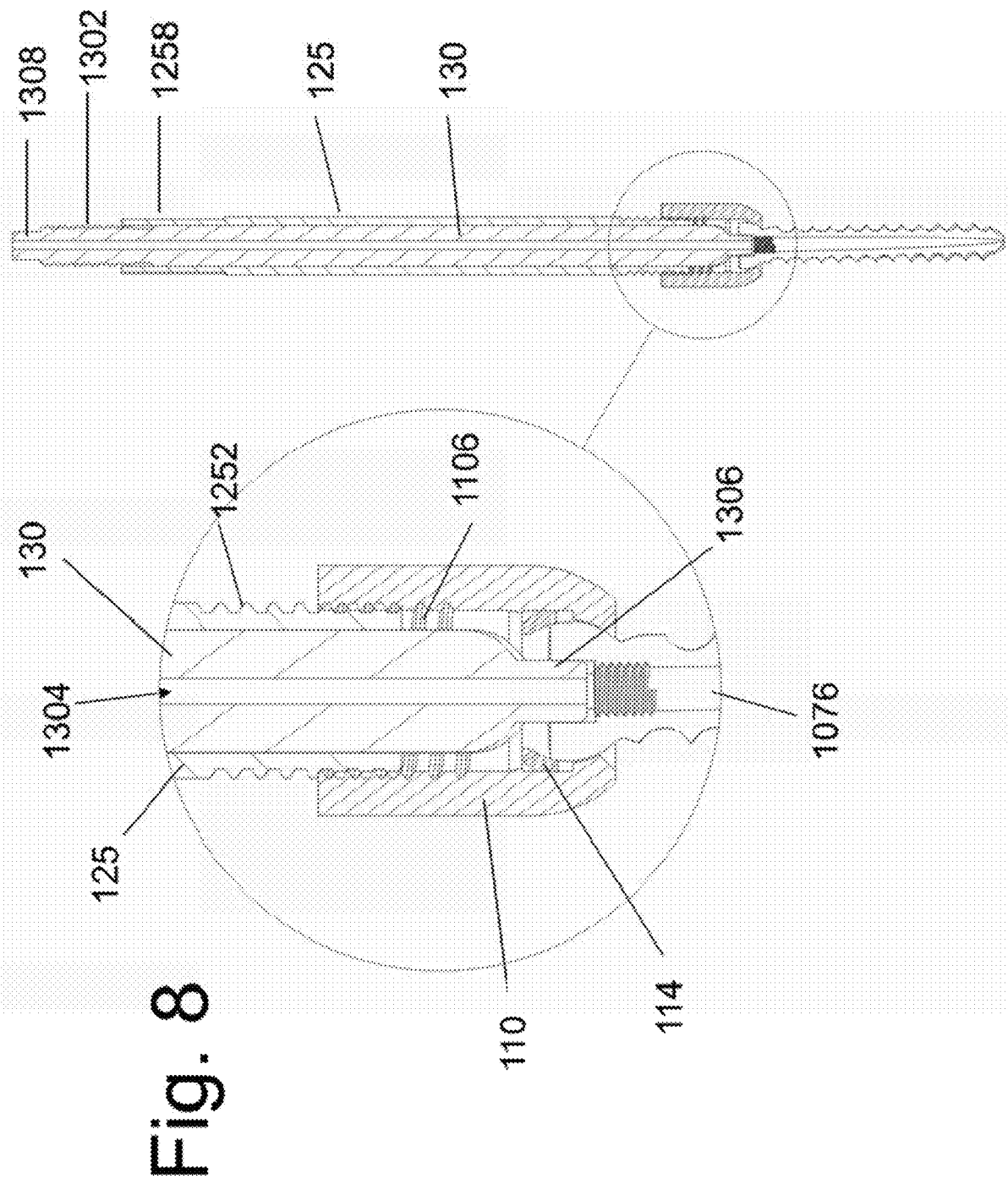
FIGS. 8 and 9 show section views through the device assembly of FIG. 5B.
Figure 9:
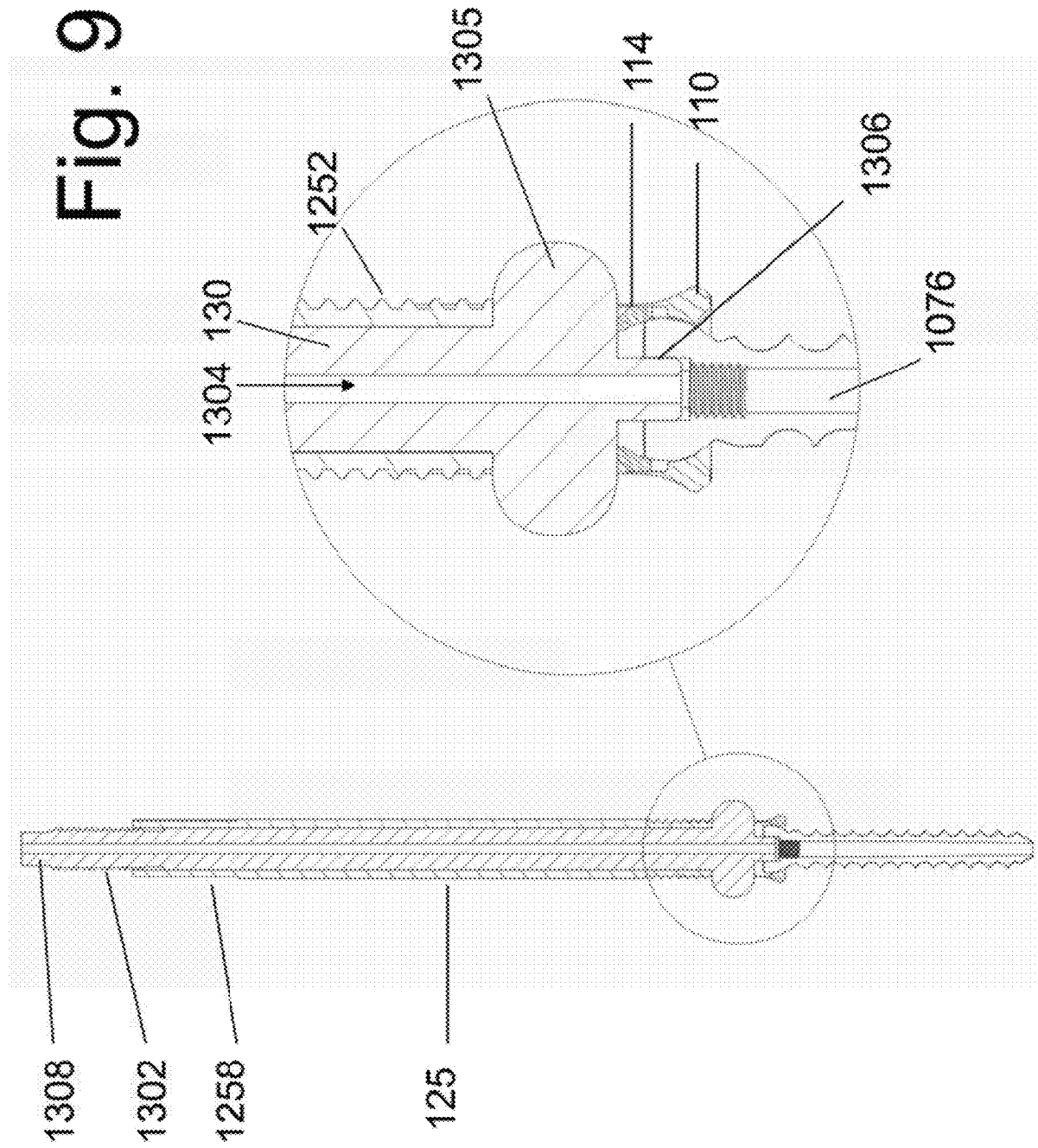

FIGS. 8 and 9 show section views through the device assembly of FIG. 5b. FIG. 8 shows a section view that is perpendicular to the "T" shaped protrusion 1305 of member 130. FIG. 9 illustrates a section view that is parallel to the "T" shaped protrusion 1305 of member 130. In FIGS. 8 and 9, member 130 is shown within bore 1254 of member 125. Protrusion 1306 rests within cut-out 1079, and aligns the long axis of screw 107 with that of housing 110, member 130 and member 125. Threads 1252 are driven into complimentary threads 1106 of housing 110 so that member 125 is threadedly locked to housing 110. In this way, member 110, 107, 130 and 125 are aligned and rigidly coupled to one another. Further, the application of a rotational force to hex-shaped protrusion 1308 (atop member 130), such as with a hex driver, caused rotation of the complete assembly and permits the advancement of threaded screw 107 into bone. Note that in the rigid assembly of FIG. 5b, bore 1304 of member 130 is aligned with bore 1076 of screw 107, thereby permitting passage of a guide needle from one end of the assembly through each of bore 1304 and bore 1076 and out the other end of the assembly.

Figure 10:
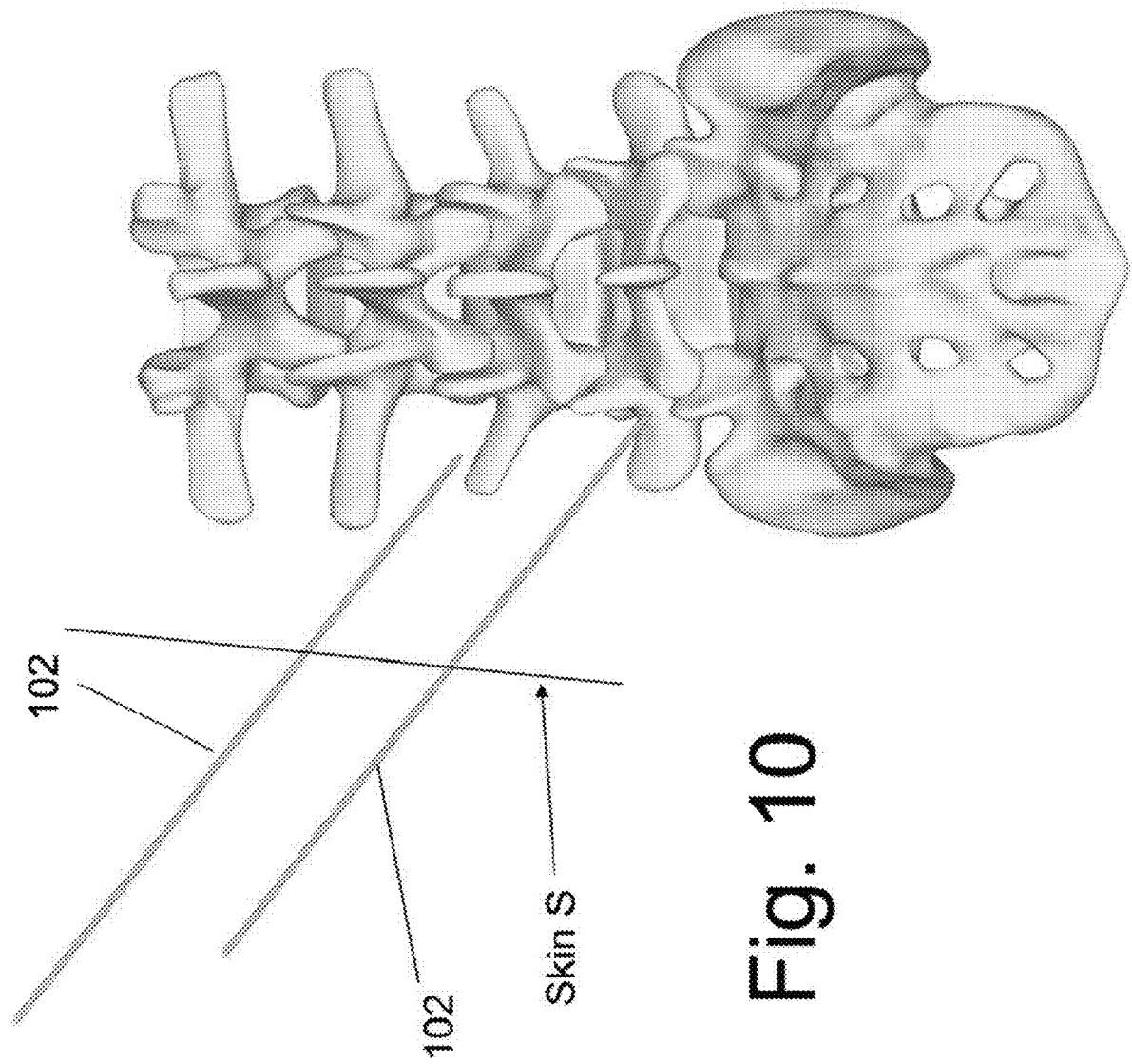
FIG. 10 shows schematically at least one wire advanced partially into the underlying pedicle of at least one vertebral bone.

An embodiment of the method of device use is now disclosed. The method illustration assumes that the L4 and L5 bones are to be fused and the L4/5 disc space is the target for implant placement. However, it is understood that the method may be alternatively used at any applicable spinal level. Under imaging guidance (X-ray, CT, MRI and the like), each of two guide wires 102 (substantially similar to elongated needles) is percutaneously passed through the skin (at or about skin region $X_1$ and $X_2$), and advanced to indentation 811 of each of the L4 and L5 vertebral bones. Each wire 102 preferably contains a threaded distal end with a sharpened tip. At least one wire 102 is then advanced (or threaded) at least partially into the underlying pedicle of at least one vertebral bone. This is schematically shown in FIG. 10 wherein the skin is schematically shown and labeled skin S. Those skilled in the art will appreciate that actual vertebral bodies may include anatomical details that are not shown in FIG. 10.

The skin entry site of and underlying soft tissue surrounding each wire is enlarged in preparation for bone screw placement. This can be performed using any applicable method but, in the preferred embodiment, serial cylindrical tubes of enlarging diameter are sequentially passed over the guide wire 102. This method of sequential tube dilatation of tissues over a guide wire is well known to those of ordinary skill in the art and will not be further detailed or illustrated. An assembly of bone fastener 105 and couplers 125/130 are assembled as shown in FIG. 5b and then advanced over a guide wire 102, wherein guide wire 102 extends through bores 1304 and 1076 of the assembly. The assembly is advanced until the threaded shank of screw 107 engages the vertebral bone at or about indentation 811. With rotation of protrusion 1308 (driver not shown) the bone screw is threadedly advanced into the pedicle portion of each vertebral bone. Preferably, the bone screw is advanced into the pedicle under radiographic visualization.

In actual use, a hole in the bone may need to be preformed with a tap instrument prior to screw placement. Further, the advancement of instruments (such as a tap or the bone screw) is preferably performed with the screw electrically connected to an electromyography (EMG) machine to minimize the possibility of nerve injury. (The technique is known in the art and is described in 1) *Intraoperative electromyography during thoracolumbar spinal surgery*. By Holland, NR. Spine 1998 Sep. 1: 23(17): 1915-22. and 2) *Improving accuracy and reducing radiation exposure in minimally invasive lumbar interbody fusion*. By Wood M J, Mannion R J. J Neurosurg Spine. 2010 May; 12(5): 533-9. Each article is hereby incorporated by reference in its entirety.)

The sequence is shown in FIGS. 11 and 12. After the fasteners are fully advanced into the bone, the guide wires 102 are removed—leaving the implanted fasteners and couplers as shown in FIG. 13. (An alternative method is further contemplated wherein a guide wire is not employed to guide the bone screw assembly. In this embodiment, a larger diameter tube is forcibly advanced through the skin and the soft tissue until indentation 811 of a targeted vertebral bone is reached. A cannula is removed from within an internal bore of the tube and bone screw assembly is advanced to indentation 811 through the internal bore of the tube.)

Note that the free end of each coupler 125/130 extends beyond the skin S so that free end of each coupler is physically located outside of the patient's body. Each coupler penetrates the skin S at a small incision (preferably a small "stab" wound) that surrounds the coupler. The segment of skin between each of the skin penetration sites of each coupler can be connected with a scalpel or other cutting instrument, so that a single skin incision starts immediately inferior to the inferior coupler, extends between the couplers and ends immediately superior to the superior coupler. If desired, the step of connecting the skin incision sites so as to form one larger incision may be performed earlier in the implantation procedure (such as, for example, at the start of the procedure, wherein one larger incision is placed instead of two smaller ones. Alternatively, two small stab wounds may be used to advance the guide wired 102 onto the bone. The incision may be then enlarged after guide wire placement.)

The skin incision segment between the couplers is then extended anteriorly from the level of the posterior skin incision, through the soft tissues that are posterior to (i.e., in back of) the spinal column until the posterior aspect of the vertebral bones are reached. That is, a corridor is developed between the couplers from the skin surface to the posterior aspect of the vertebral bone, wherein, in a preferred embodiment, the corridor developed is similar to that of Corridor K, which is schematically shown in FIG. 4.

Figure 17:
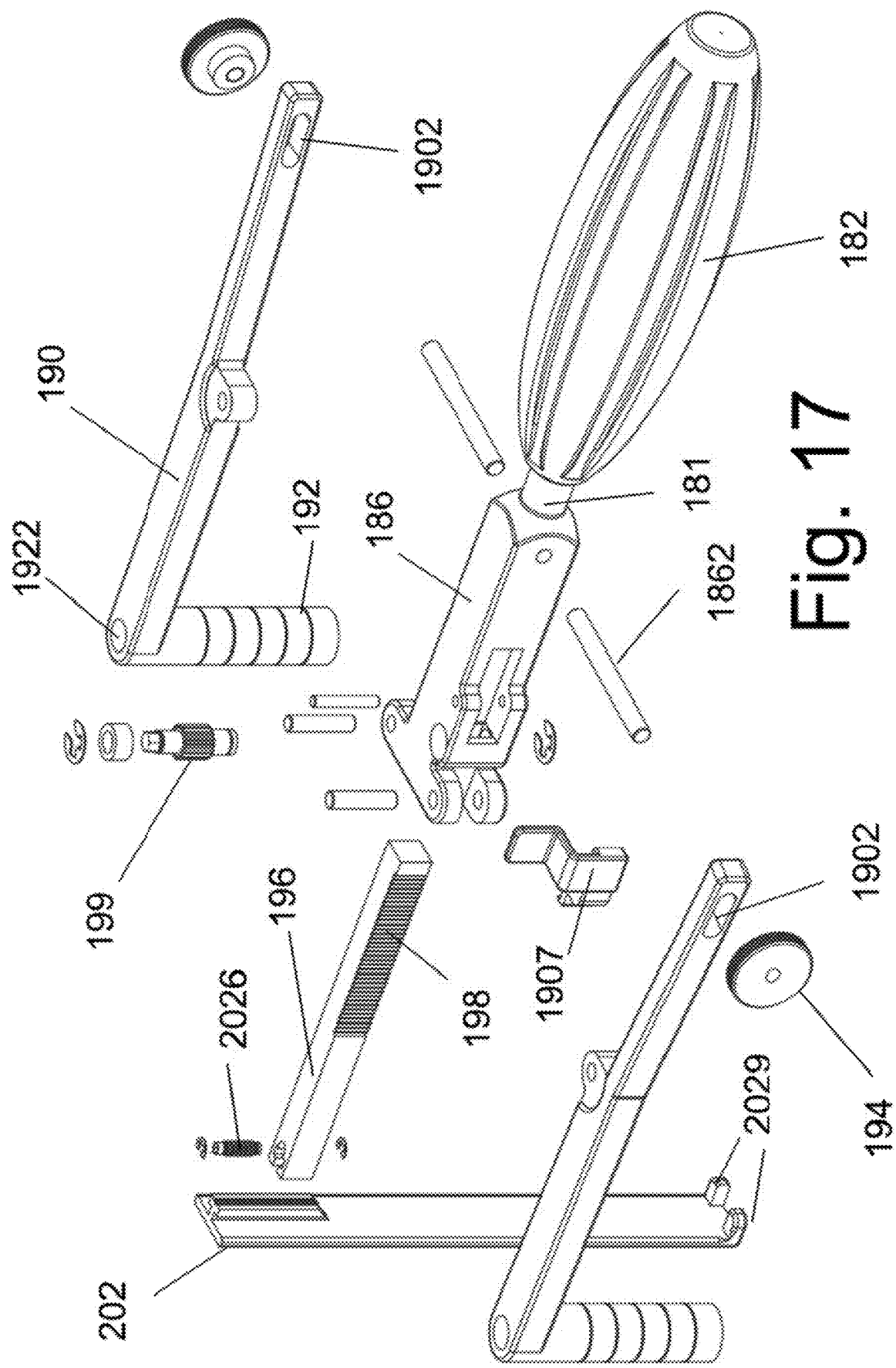
FIG. 17 shows an exploded view of the platform.
Figure 18:
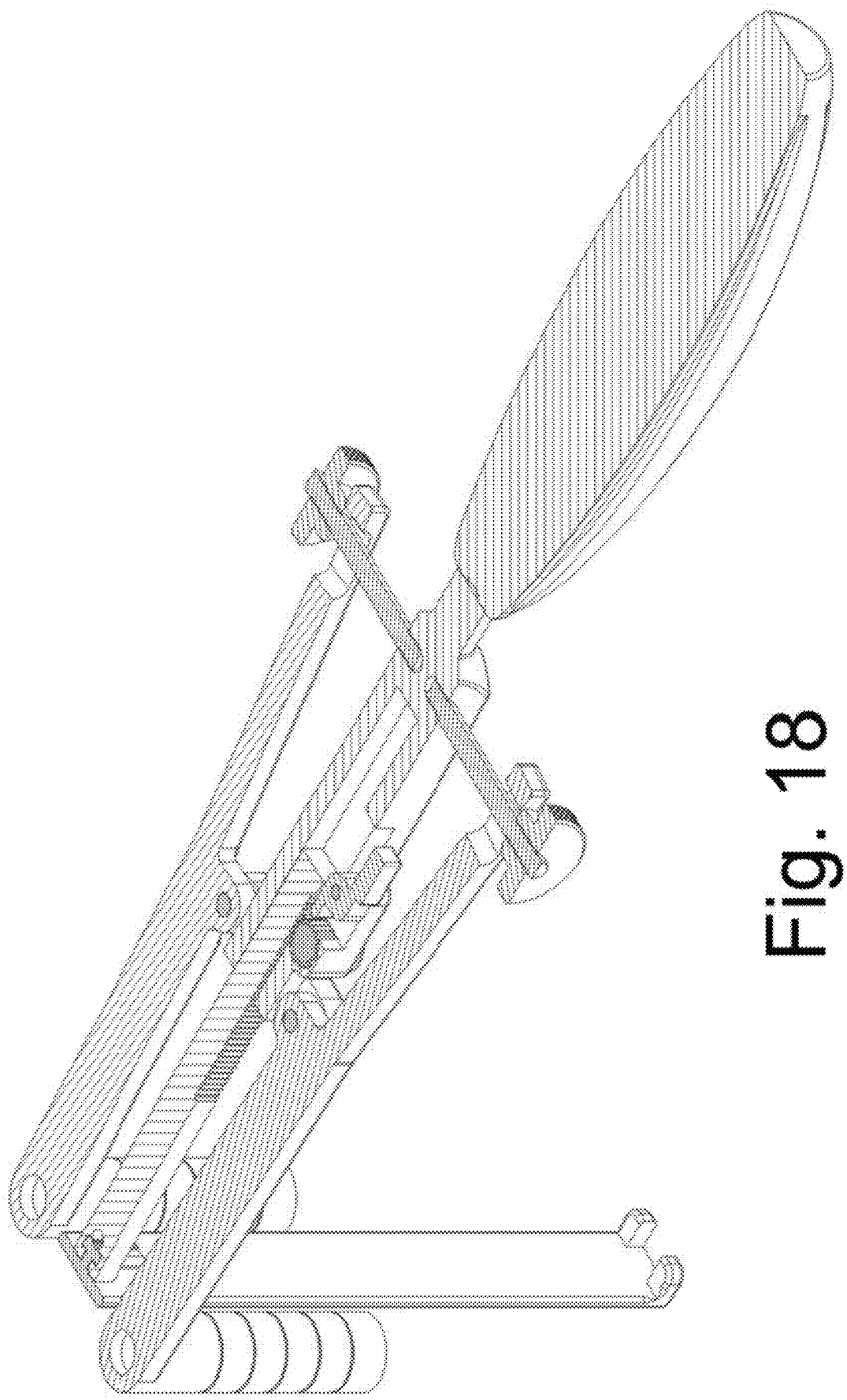
FIGS. 18 and 19 show cross section views of the platform.
Figure 19:
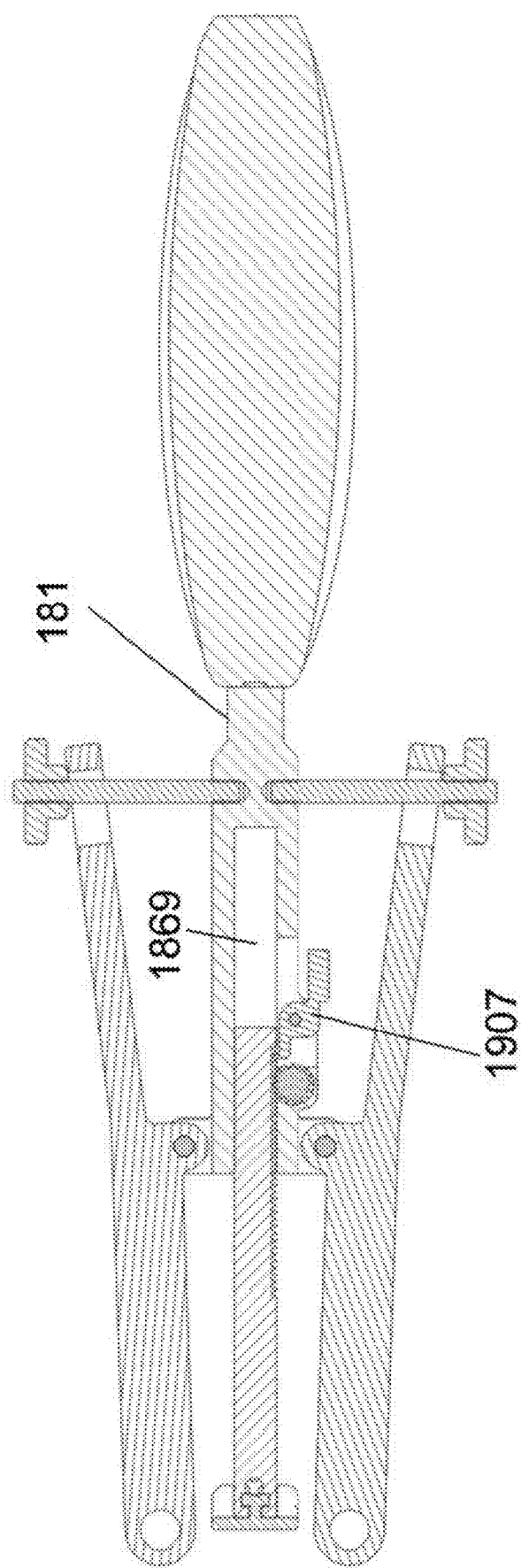

A distraction platform 180 is then attached onto each of the couplers 125/130 (each coupler being attached to a screw assembly 105), wherein the distraction platform is preferably, but not necessarily, adapted to distract the couplers towards or away from one another. An embodiment of a distraction platform is shown positioned in FIG. 14. Distraction platform 180 is an example of a platform that may be used and those of ordinary skill in the art will appreciate that any appropriate distraction platform may be alternatively used in the illustrated method. (An example of a distractor platform is disclosed in U.S. Pat. No. 7,819,801. The text is included by reference in its entirety). In the preferred embodiment, the distractor has members adapted to interact with the coupler 125/130 and at least one additional member adapted to retract soft tissues (such as muscle, fat and the like) away from the screw 105/coupler 125/130 assemblies. A perspective view of the platform is shown in FIG. 15A and multiple orthogonal views are shown in FIG. 16. An exploded view is shown in FIG. 17 and section views are shown in FIGS. 18 and 19.

The distraction platform 180 has handle 182 and central body member 186 that are interconnected by cylindrical region 181. Each of distraction arms 190 have an elongated member 192 that contains internal bore 1922, wherein bore 1922 extends the full length of the member 192. In a preferred embodiment, the internal bore 1922 of elongated member has a proximal (upper) opening 19226 and distal (lower) opening 19224, wherein the proximal opening is smaller than the distal opening. A section view through elongated members 192 is shown in FIG. 15B. Preferably, the external surface of elongated member 192 has markings that are labeled with numbers, letters, or other designation. In use, bore 1922 contains the proximal segment of coupler 125/130, wherein a segment of 1302 of member 130 emerges from the proximal (upper) opening 19226 of bore 1922. The smaller bore of opening 19226 permits segment 1302 of member 130 to exit bore 1922 but segment 1258 of member 125 is retained within member 192 (see FIG. 15C). A locking nut 1107 can be used to engage the threaded portion of segment 1302 that rests outside of member 192 and to lock the assembly of members 105, 125 and 130 relative to member 192 of distraction platform 180. When platform 180 engages couplers 125/130 and screw assembly 105, the skin rests at or between markings of the external surface of elongated member 192. In this way, the distance from skin to the bone fastener 105 can be easily read directly off of the external markings of member 192.

Distraction arm 190 articulates with body 186. Arm 190 has slot 1902 that is adapted to accept threaded post 1862 (threads not shown). Thumb wheel 194 has internal threads that threadedly interacted with threaded post 1862 and produce a compressive force onto the end of arm 190 that contains slot 1902. With advancement of wheel 194, the segment of distraction arm 190 that contains slot 1902 is urged towards body 186, and the segment of distraction arm 190 that contains member 192 is rotated outwardly and away from body 186. After platform 180 is attached to couplers 125/130 and screw assembly 105, thumb wheel(s) 194 may be actuated to impose a distractive force onto one or the other of the vertebral bones (or both). In this way, the vertebral bones may be moved away from one another in the vertical plane. Bony distraction may be performed before or after facet resection (or not at all). In a preferred embodiment, no distraction is performed prior to facet resection. In another preferred embodiment, distraction is performed prior to facet resection.

Arm 196 has side serrations 198. An end of arm 196 rests within bore 1869 of body 186. A spring-loaded (spring not shown) pawl 1907 and member 199 interact with serrations 198 of arm and serve as a mechanism to move arm into and out of bore 1869 of body 186. A removable tissue retractor 202 rests at the distal end of arm 196. Arm 202 has at least one distal extension 2029 that interact with the retracted tissue.

Figure 20:
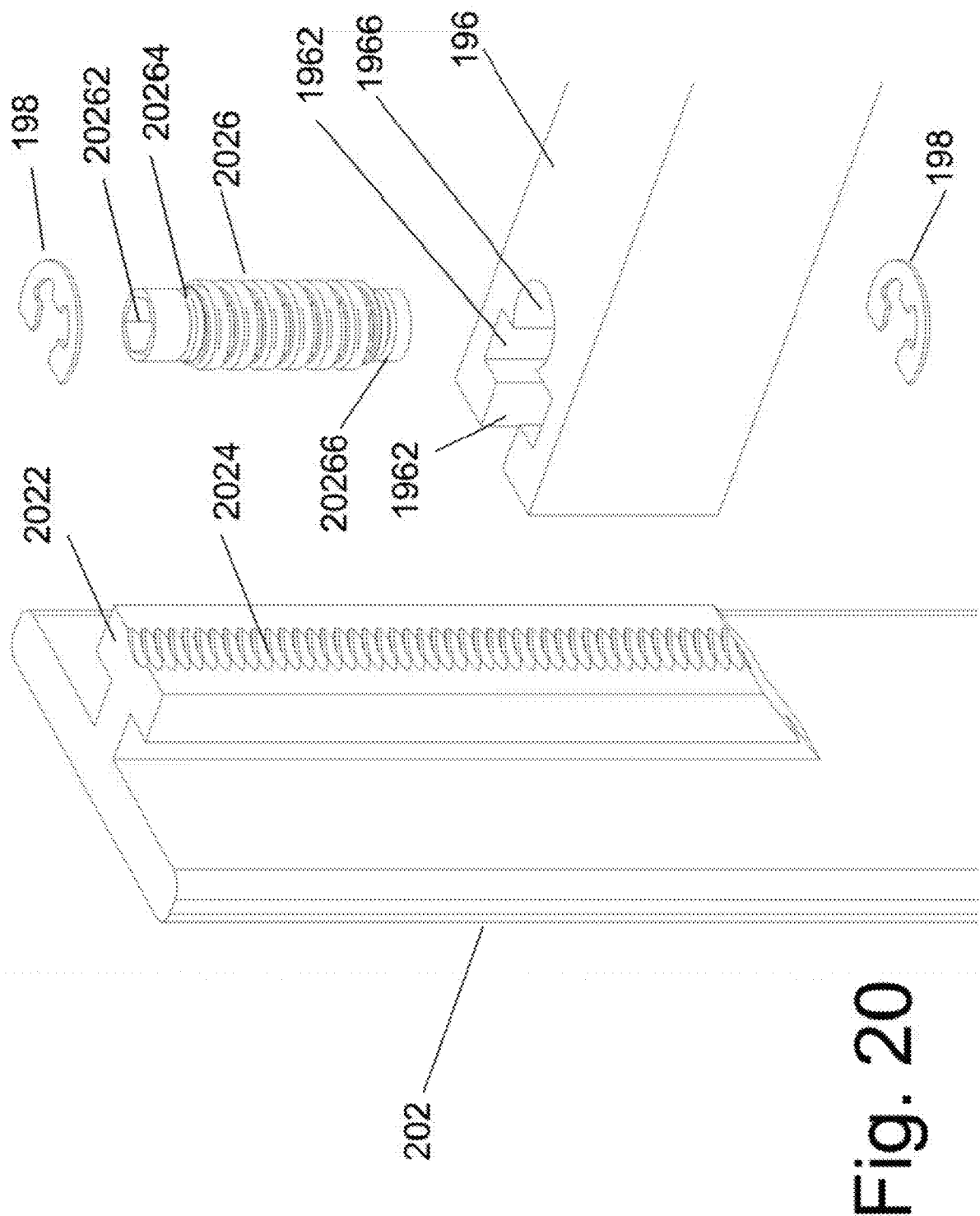
FIGS. 20-22 show close-up views of the proximal end of removable tissue distraction arm.
Figure 21:
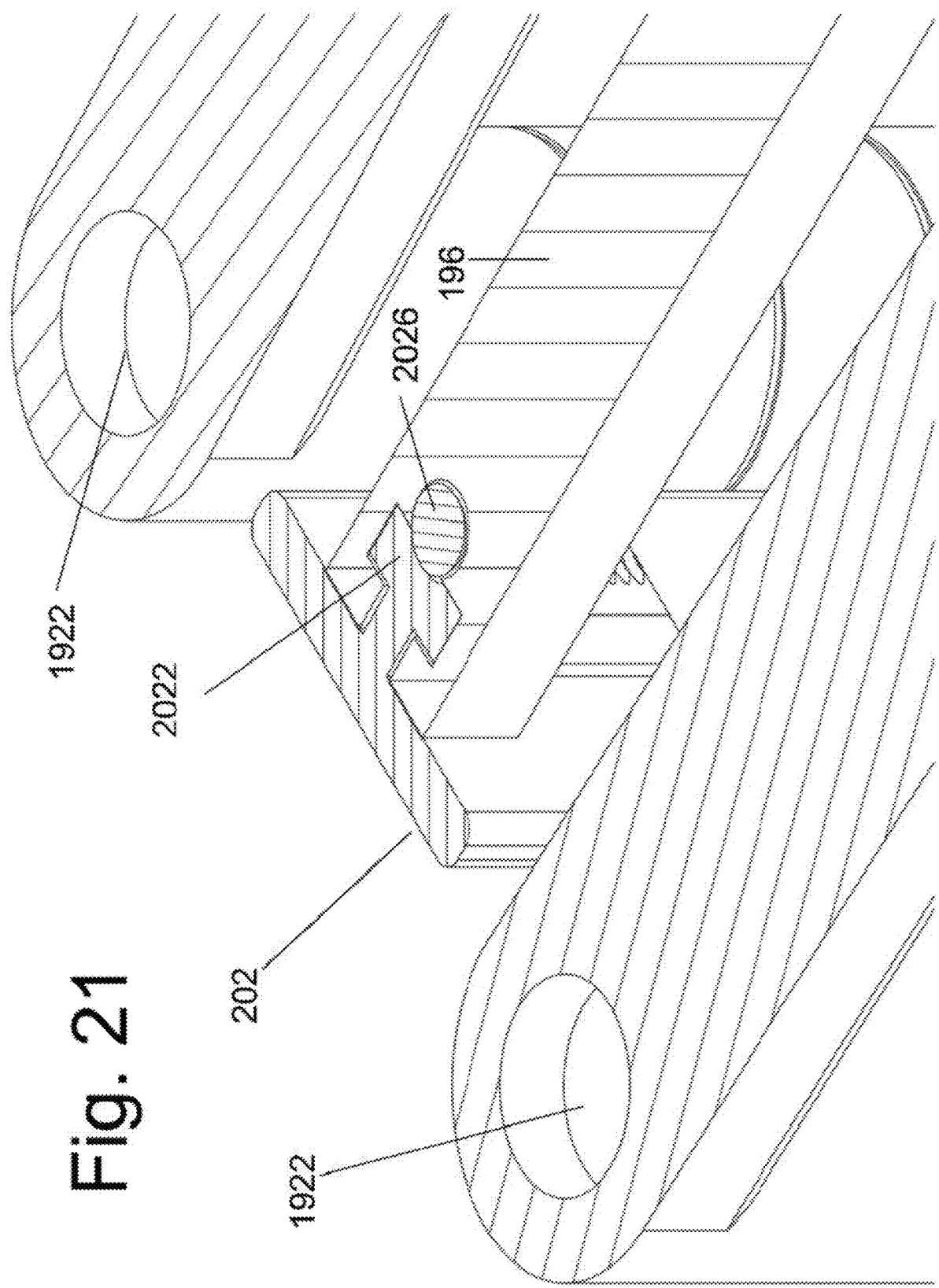
Figure 22:
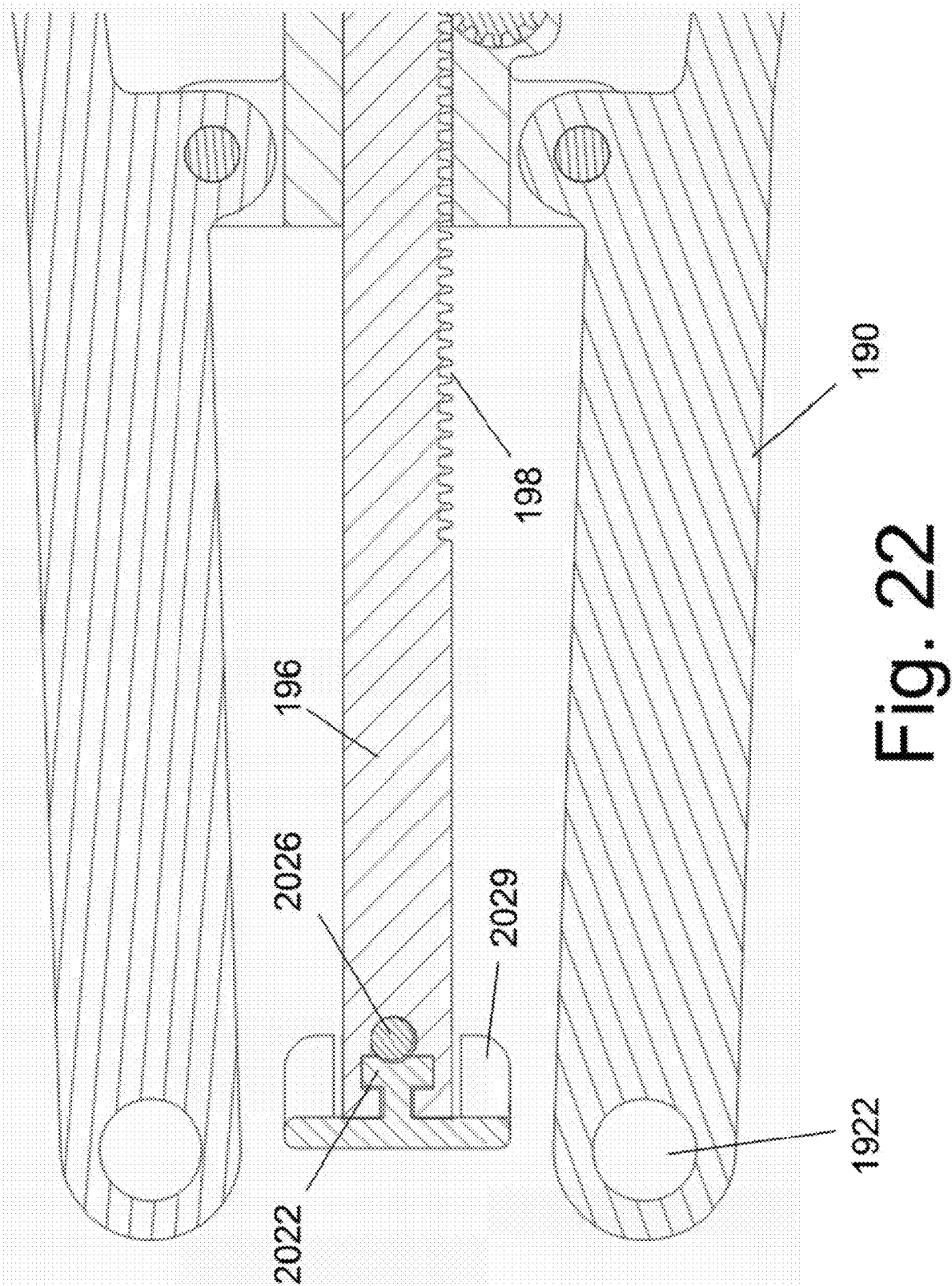

A close-up view of the proximal end of removable tissue distraction arm is shown in FIG. 20. Tissue distraction arm 202 has a protrusion 2022 with surface 2024 that contains partial threads (adapted to interact with threads of screw 2026). Protrusion 2022 rests within cut-out 1962 of arm 196. A threaded screw 2026 resides within bore 1966 of arm 196. A clip member 198 is adapted to rest within each of an upper channel 20264 and lower channel 20266 that rest on each side of the threads of screw 2026. The clip members 198 function to retain threaded screw 2026 within bore 1966. Screw 2026 has a hex-shaped cut out 20262 that is adapted to accept a complementary hex-drive screw driver.

As noted, distraction arm 202 is preferably removable in that the arm can be removed from cut-out 1962 of arm 196 by the surgeon at the time of surgery. Rotation of screw 2026 (through the action of a hex-drive positioned within cutout 20262) within bore 1966 will necessarily produce the interaction and movement of the threads of screw 2026 and the threads of surface 2024 of arm 202. Rotation of screw 2026 in a first direction will cause upward movement of arm 202, whereas rotation of screw 2026 in the opposite direction will produce downward movement of arm 202. With continued rotation of screw 2026 in one direction, the surgeon can produce sufficient movement of arm 202 such that protrusion 2022 exits cut-out 1962 of arm 196 and distraction arm 202 detaches from distraction platform 180. In this way, arm 202 is reversibly detachable (and mountable) relative to platform 180.

In the preferred embodiment, screw 2026 can be used to adjust the distance from arm 196 to protrusions 2029 of distraction arm 202. This is an important and notable feature of the preferred distraction platform. That is, in the preferred embodiment, distraction arm 202 is reversibly removable from distraction platform 180 and, when attached to the platform, the vertical distance from a horizontal surface of member 196 of platform 180 to the distal end (protrusions 2029) of arm 202 that engage the soft tissues may be varied by the operating surgeon. (While the variation in distance from platform 180 to protrusions 2029 of arm 202 may be accomplished by the movement of an end of a fixed length arm 202 relative to the platform, as illustrated, it may be alternatively accomplished by attachment of a variable length distraction arm 202 which is stationary relative to the platform 180 at the point of mutual attachment.)

Distraction arm 202 functions to retract muscle segment M1 (FIG. 4) medially towards spinous process SP and uncover the posterior aspect of the facet joint to be resected. After muscle retraction by arm 202, corridor K is expanded medially from that shown in Figure to approximately that represented by the schematic drawing of FIG. 258. In the preferred embodiment, the distraction platform 180 is coupled to the coupler 125/130 and bone screw as shown in FIG. 14.

The surgeon may elect to use locking nuts 1107 to rigidly lock one or more of the couplers 125/130 to platform 180. In addition, the platform 180 may be further immobilized relative to the spine and the patient by applying an articulated frame, wherein the frame is adapted to rigidly couple to platform 180 on a first end and to rigidly attach to the operating table at a second end. The frame further contains multiple segments that are adapted to reversibly transition from a first state, wherein there are relative movements between the segments, to a second state, wherein the segments are rigidly affixed to each other. Finally, the surgeon may elect not to lock the frame to the couplers or to the operating table.

Frame devices that anchor surgical retractors to the operating table are well known in the art. In the illustrated device (FIG. 25D), articulated frame 905 has member 9052 that reversibly attaches to the operating table onto which the patient is positioned. Member 9056 is adapted to reversibly and rigidly clamp onto a segment of platform 180. An end of member 9056 is adapted to clamp onto, for example, cylindrical segment 181 of platform 180, wherein locking member 9058 locks end segment 9056 after the latter is positioned onto segment 181. Member 9054 is adapted to reversibly transition the frame 905 from the first state (movably articulating frame segments) to the second state (articulated frame segments are rigidly locked to one another). While an example of an articulated frame 905 is illustrated, it is understood that any other applicable such device may be alternatively used. (For example, U.S. Pat. Nos. 4,254,763, 5,908,382, 6,302,843, 6,709,389, 7,156,806 and many other are known to disclose surgical retractor systems that anchor to the operating table. Each citation is hereby incorporated by reference in its entirety.)

In use, the distal tip of the tissue distraction must rest immediately posterior to the facet joint that will be resected. In selection of the proper distraction arm 202 to attach to the platform 180, the surgeon will need to know the distance from the skin edge of the incision to the posterior aspect of the facet joint. This distance can be measured directly with a ruler. Alternatively, the distance from the skin edge to the top of screw assembly 105 can be read directly off of the external surface markings of elongated member 192. In most patients, the distance from the skin edge to the posterior aspect of the facet joint is close to the distance from skin edge to the top of screw assembly 105 (of the inferior vertebral bone). The distance between the skin edge to the top of screw assembly 105 can be used a convenient approximation to the distance from skin to the posterior aspect of the facet joint. Since distraction arm 202 is movable relative to arm 196, any difference between the distance from skin edge to the top of screw assembly 105 and the distance from the skin edge to the posterior aspect of the facet joint can be easily corrected by the movement of distraction arm 202 relative to member 196 after attachment. However, if a distraction platform is used wherein the distraction arm is stationary relative to the attachment region of the platform, then the distance from skin to the posterior aspect of the facet joint is preferably measured directly with a ruler.

Figure 23:
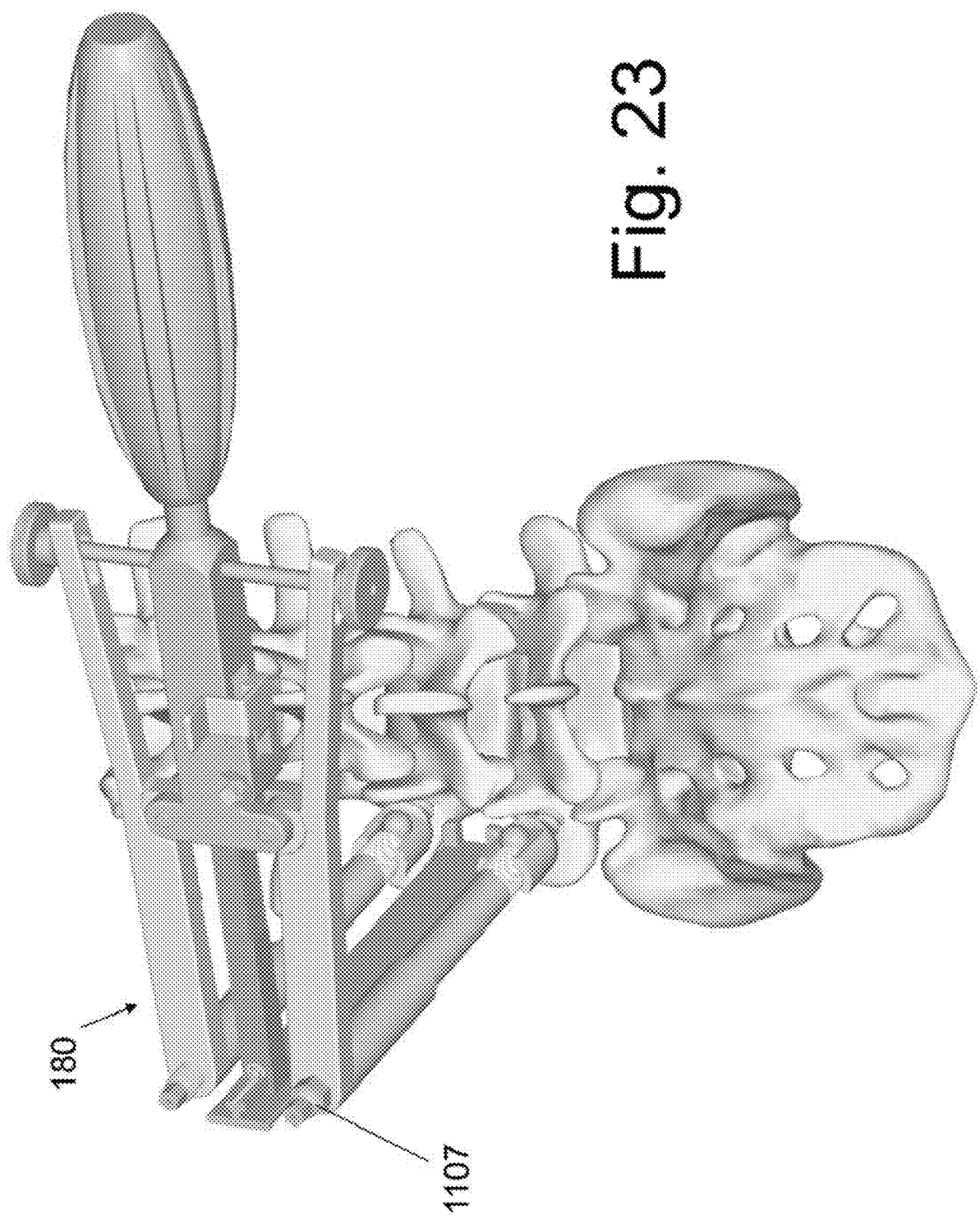
FIGS. 23-24 show distraction arms positioned within the incision between each of the fastener coupler members.
Figure 24:
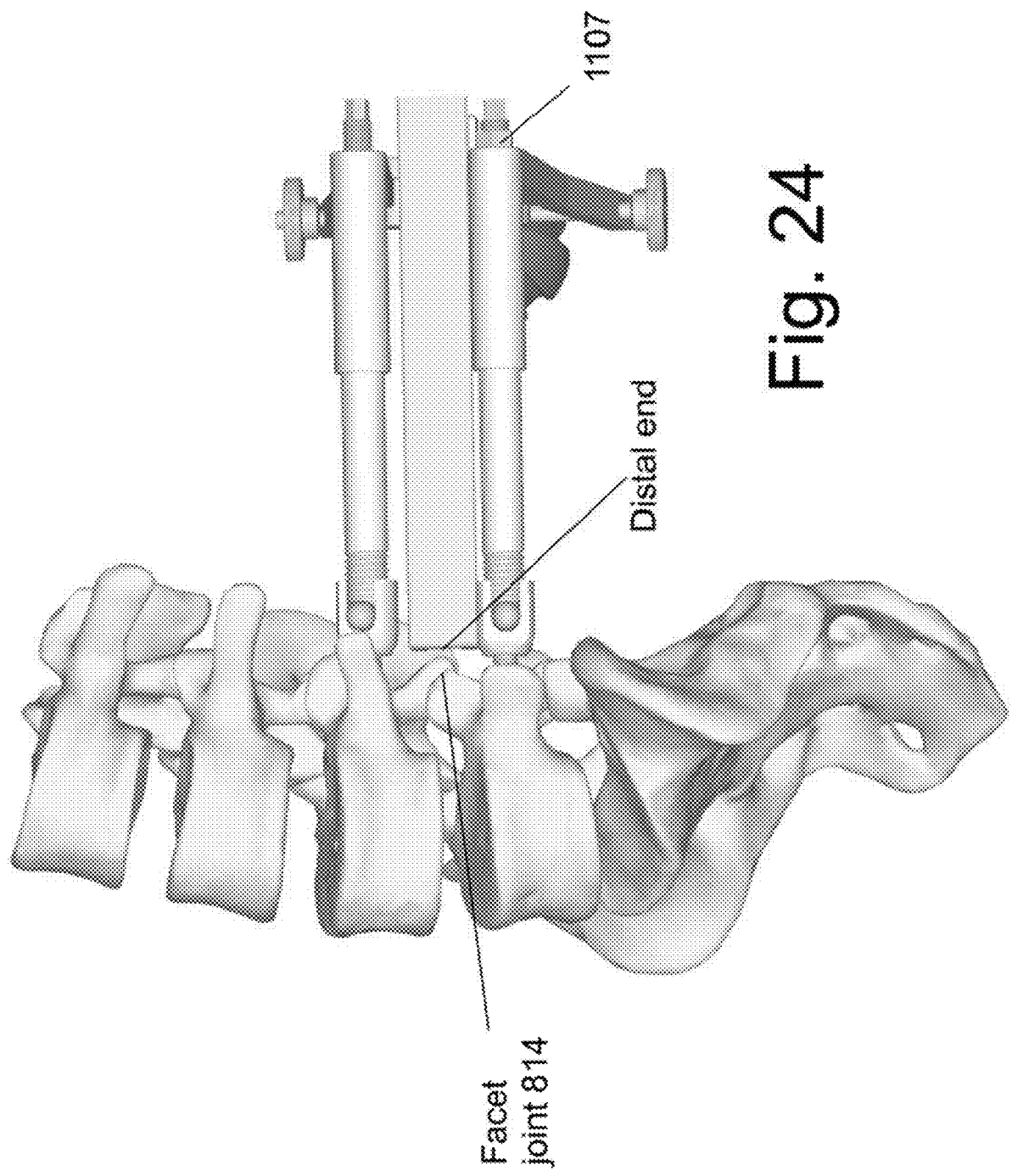
Figure 25A:
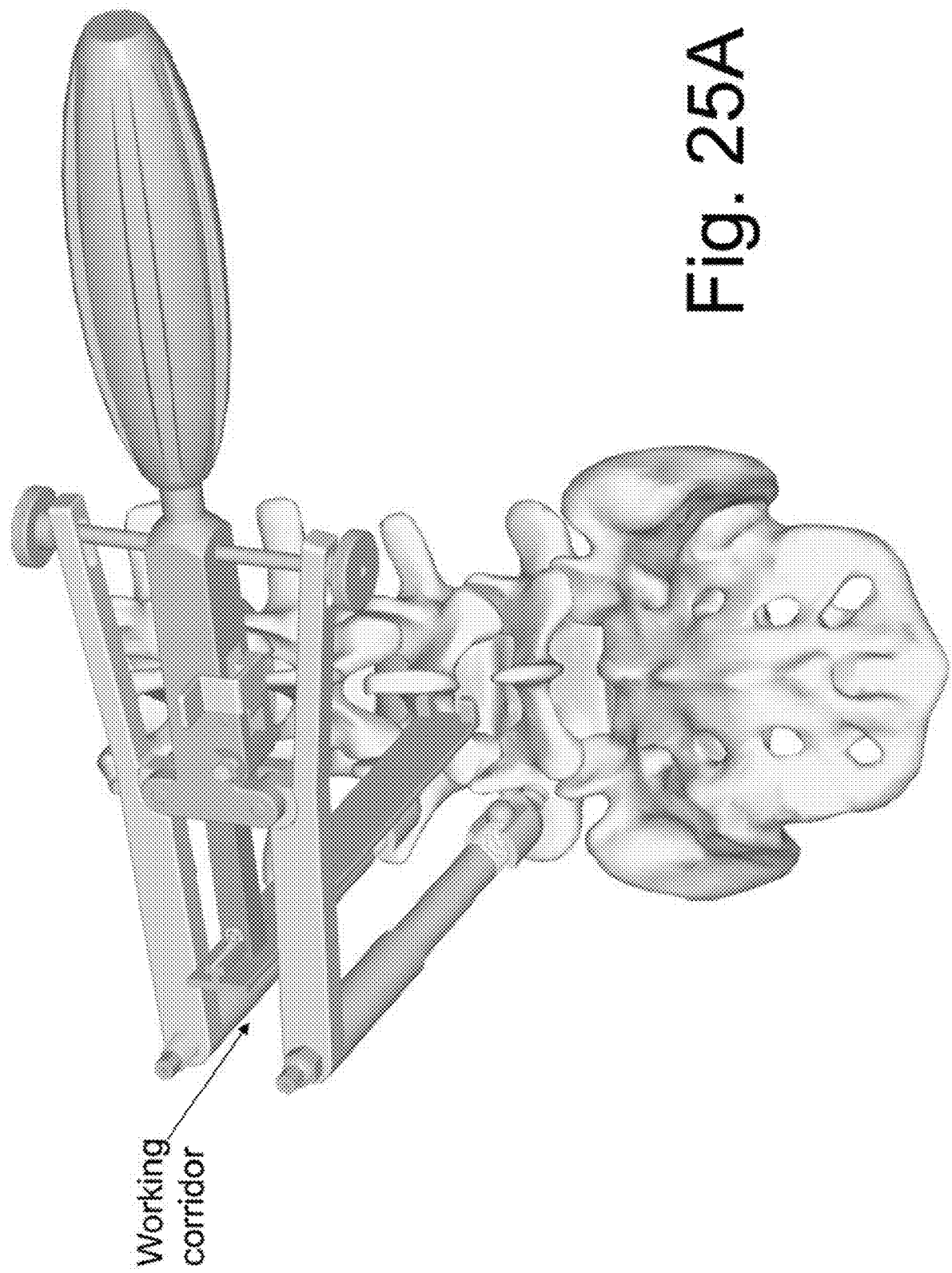
FIG. 25A-25D show various perspectives of the working corridor.

With the appropriate length tissue distraction arm 202 selected and positioned within the incision between each of the fastener coupler members—as shown in FIG. 23, a lateral X-ray is obtained. The distal end of the tissue distraction arm 202 is moved anterior/posteriorly by rotating screw 2026 until the distal end of arm 202 rests immediately in back of (i.e., posterior to) the facet joint 814 as shown in FIG. 24. The tissue distraction arm is moved medially by the rotation of member 199 and arm 202 retracts muscle segment M1 towards the spinous processes SP of the superior and inferior vertebral bones (FIG. 25A). In this way, a working corridor WC is formed between each of the coupler engagement members and tissue distraction arm of the distraction platform, wherein the posterior surface of the facet joint 814 is exposed and accessible within working corridor WC.

Figure 25B:
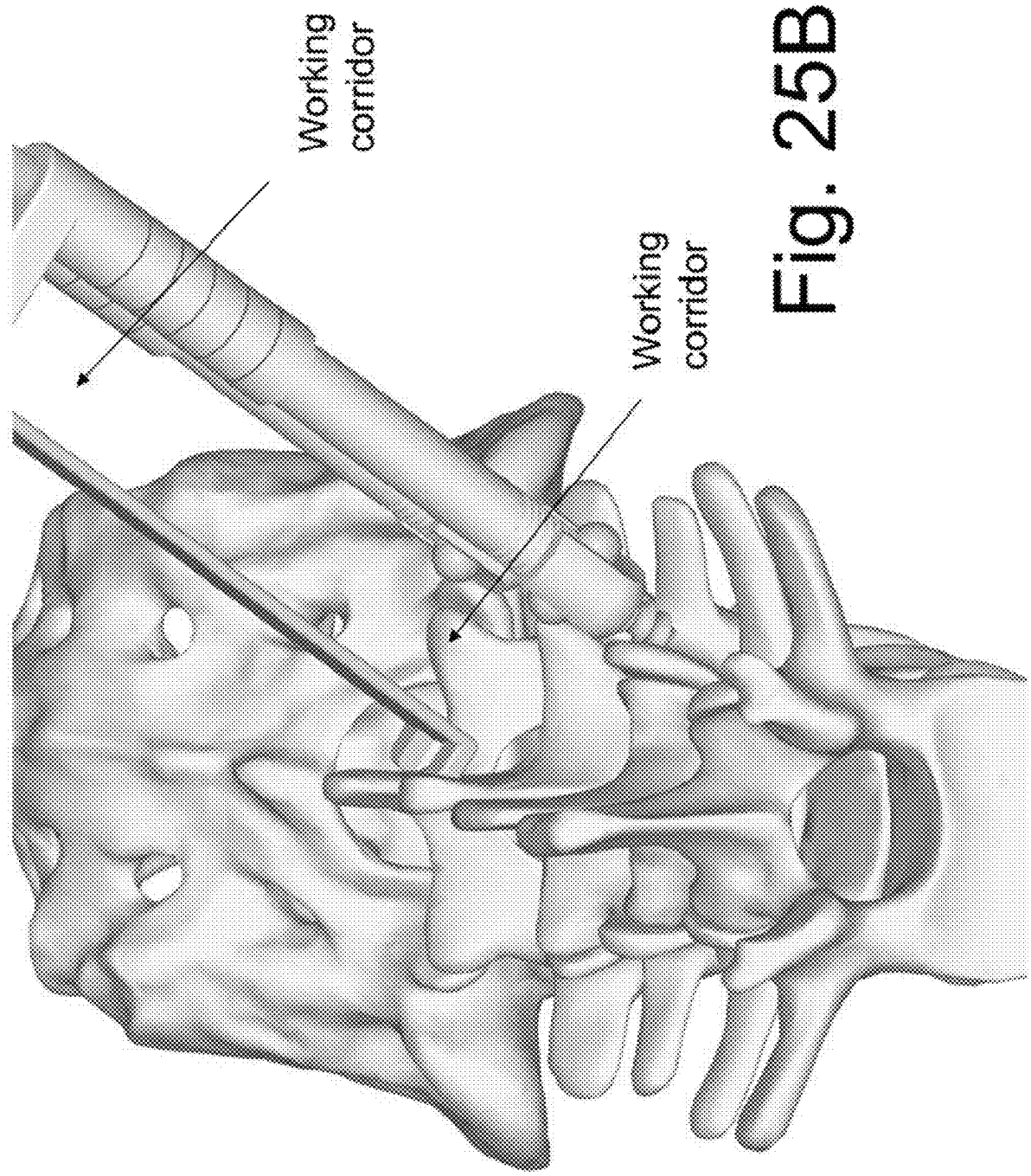
Figure 25C:
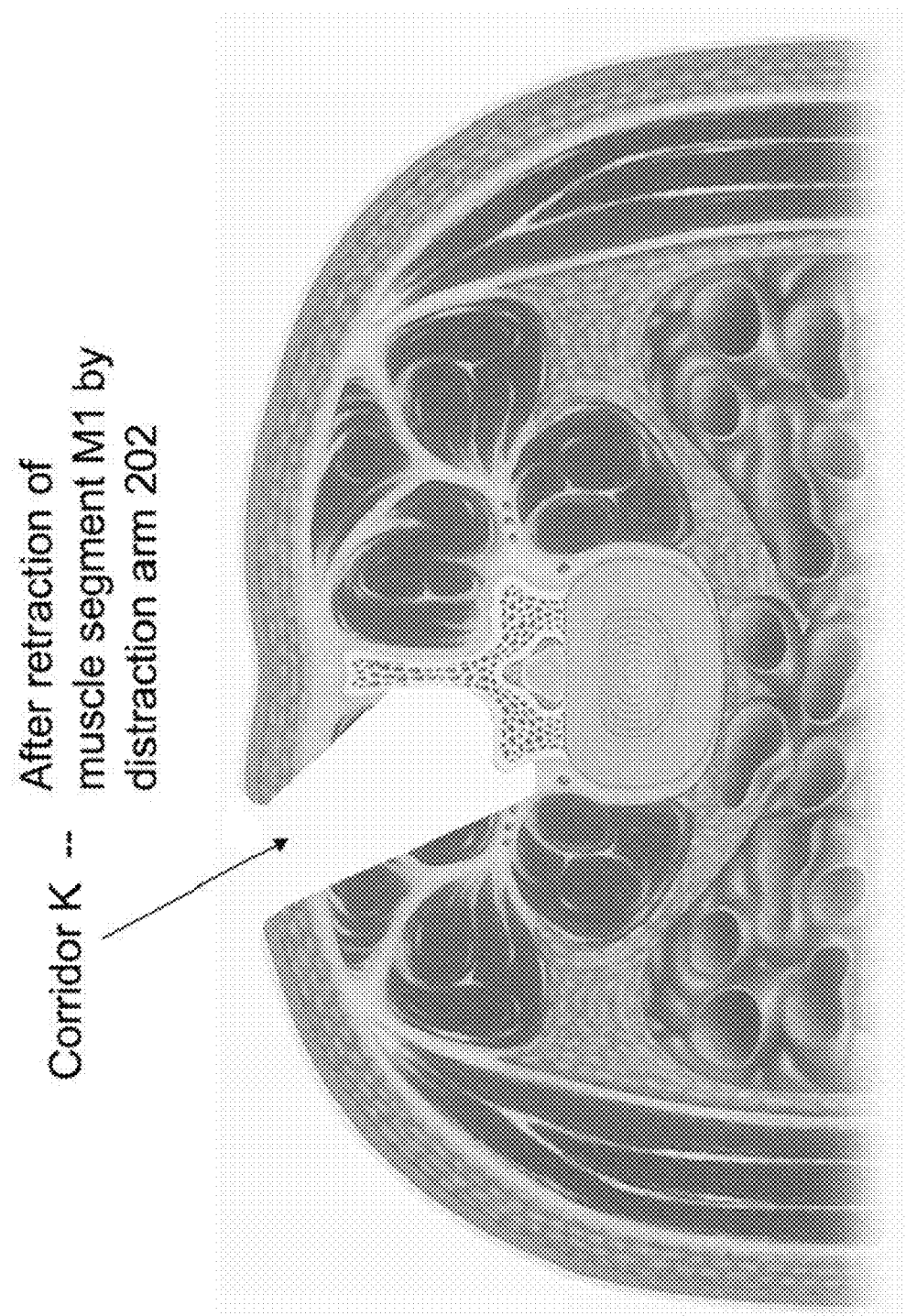

The working corridor is seen in a different perspective in FIG. 25B. Note that the distraction arm 202 rests in proximity to the spinous process and permits access, through the working channel, to the facet joint as well as the lamina portion of the vertebral bones. FIG. 25C illustrates an approximation of the soft tissue corridor K (first shown in FIG. 4) after placement of the distraction platform the medical retraction of distraction arm 202. (Note that corridor K is approximately equivalent to the working corridor WC. For clarity of illustration, the contents of the torso in FIG. 25C are represented schematically and those skilled in the art will appreciate that an actual cross section of the human torso may include anatomical details not shown in the illustration.)

After exposure of the facet joint, bone removing instruments are used to cut at least a segment of facet joint 814 and reveal the posterior aspect of the disc space that is immediately anterior to it. Preferably, the moved portion of the facet joint would include the lateral surface of the facet joint. The exposed portion of the disc space includes the segment of the posterior disc surface that rests immediately anterior to the neural foramen of the nerve root that exits the spinal canal beneath the pedicle portion of the superior vertebral bone. That is, at least a portion of the exposed posterior disc surface rests, in the superior/inferior plane, between the inferior aspect of the nerve root that exits the spinal canal beneath the pedicle of the superior vertebral bone and the superior aspect of the pedicle of the inferior vertebral bone of the targeted FSU. The exposed portion of the disc space is bordered medially by the lateral aspect of the nerve root that exits the spinal canal beneath the pedicle of the inferior vertebral bone of the targeted FSU.

While any instrument that is adapted to remove a portion of the facet joint may be used, the removal is preferably made with one or more instruments that collectively drill away a portion of the bone and rongeur away other joint fragments. In an embodiment, an instrument that is adapted to perform both the drill and rongeur function is shown in FIGS. 26 to 30. It is understood that the illustrated instrument is not restrictive in any way and any other instrument or combination of instruments that may remove bone by drilling and cutting the joint may be alternatively used.

Figure 26:
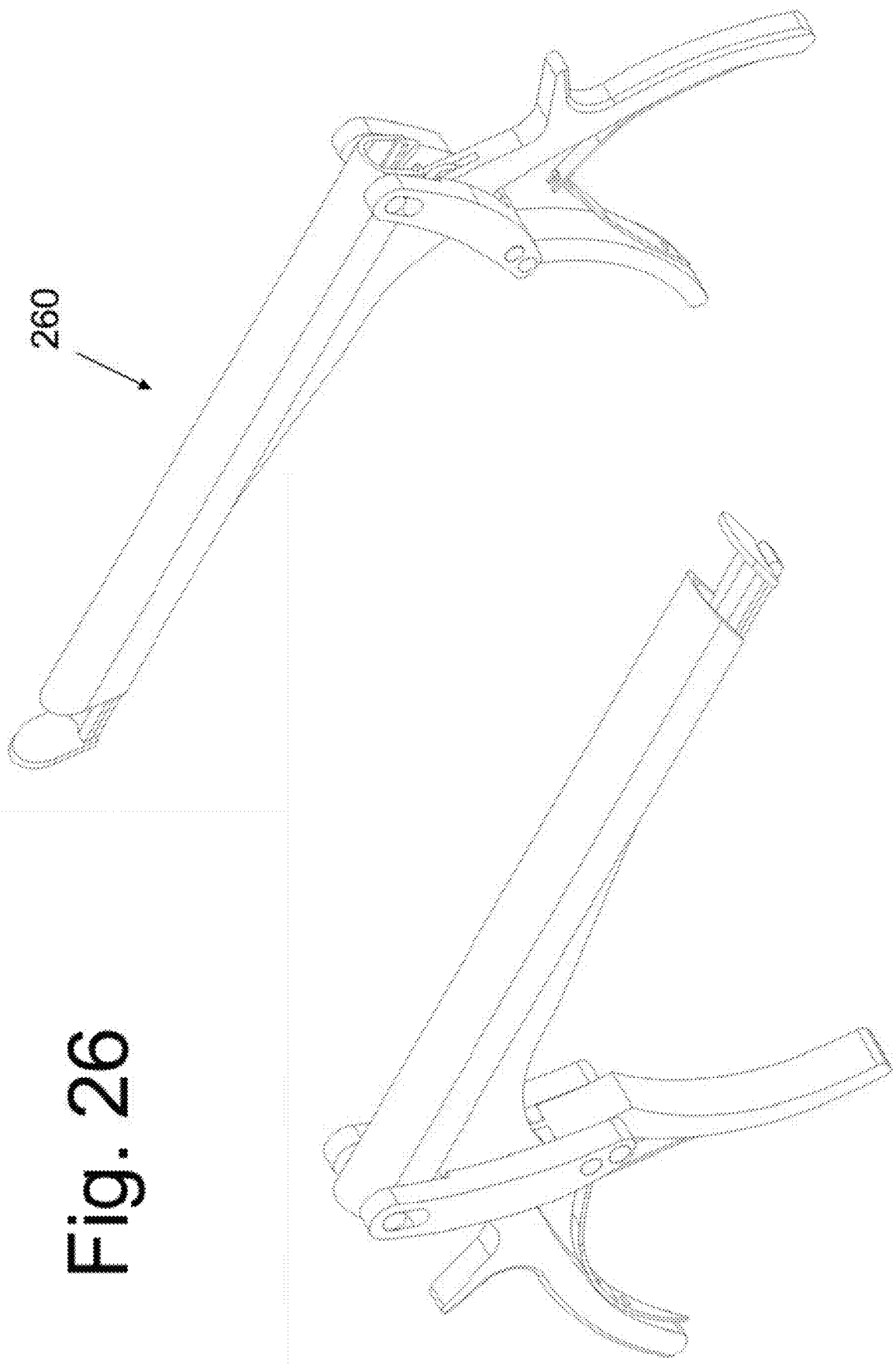
FIG. 26 shows an embodiment of an instrument adapted to perform both the drill and rongeur function.
Figure 27:
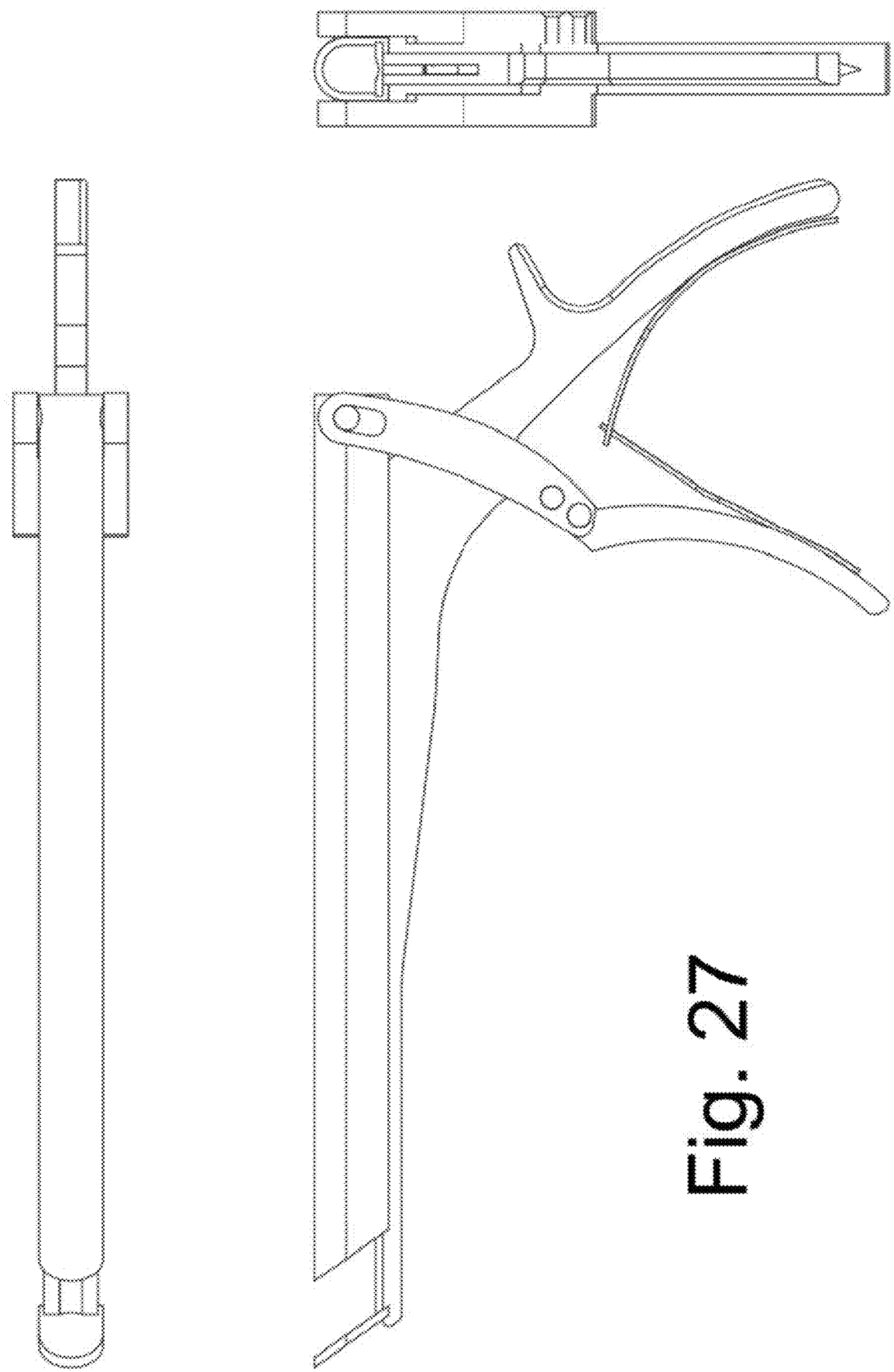
FIG. 27 shows another view of the instrument.
Figure 29:
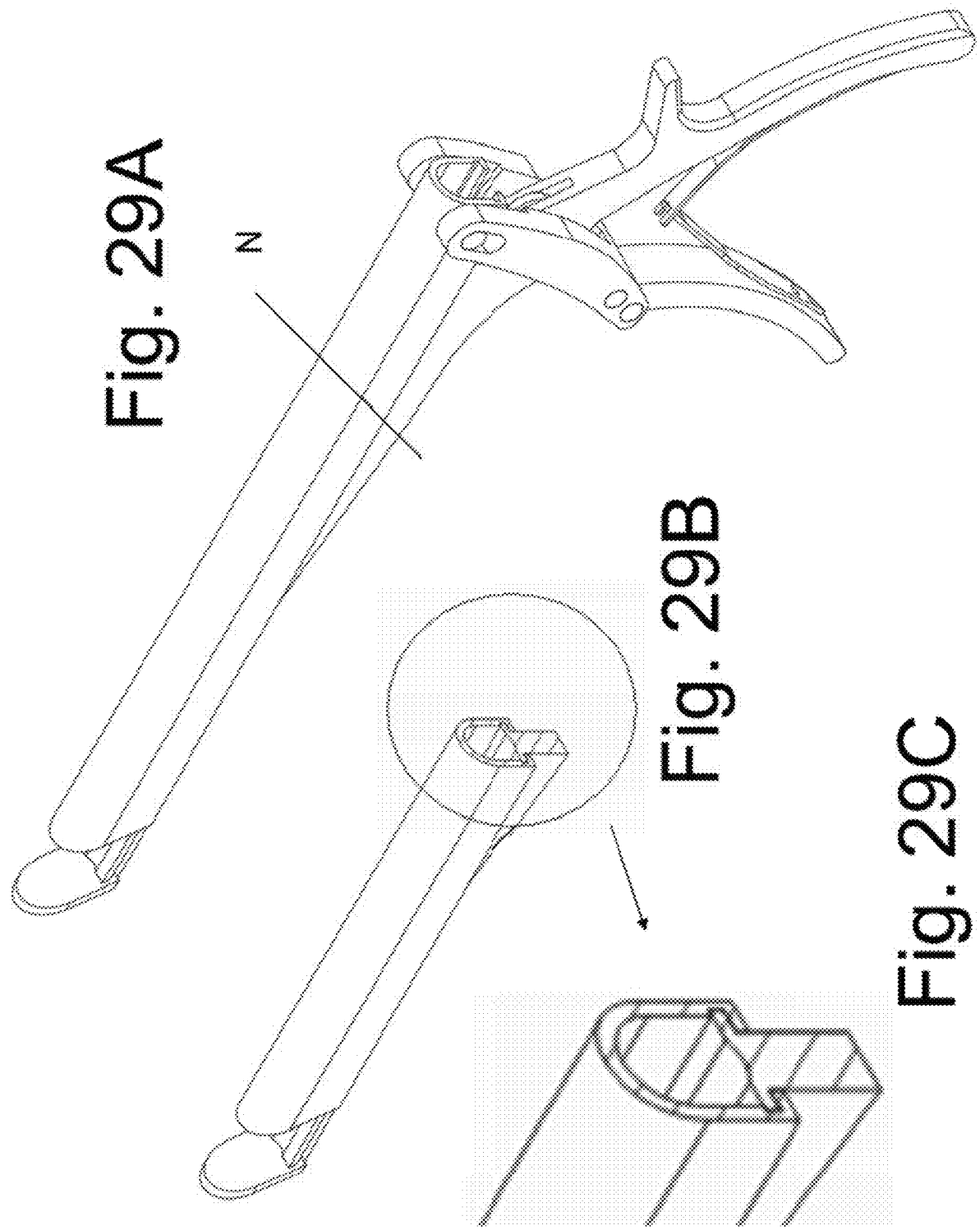
FIGS. 29A-29C show various section views of the instrument.
Figure 30:
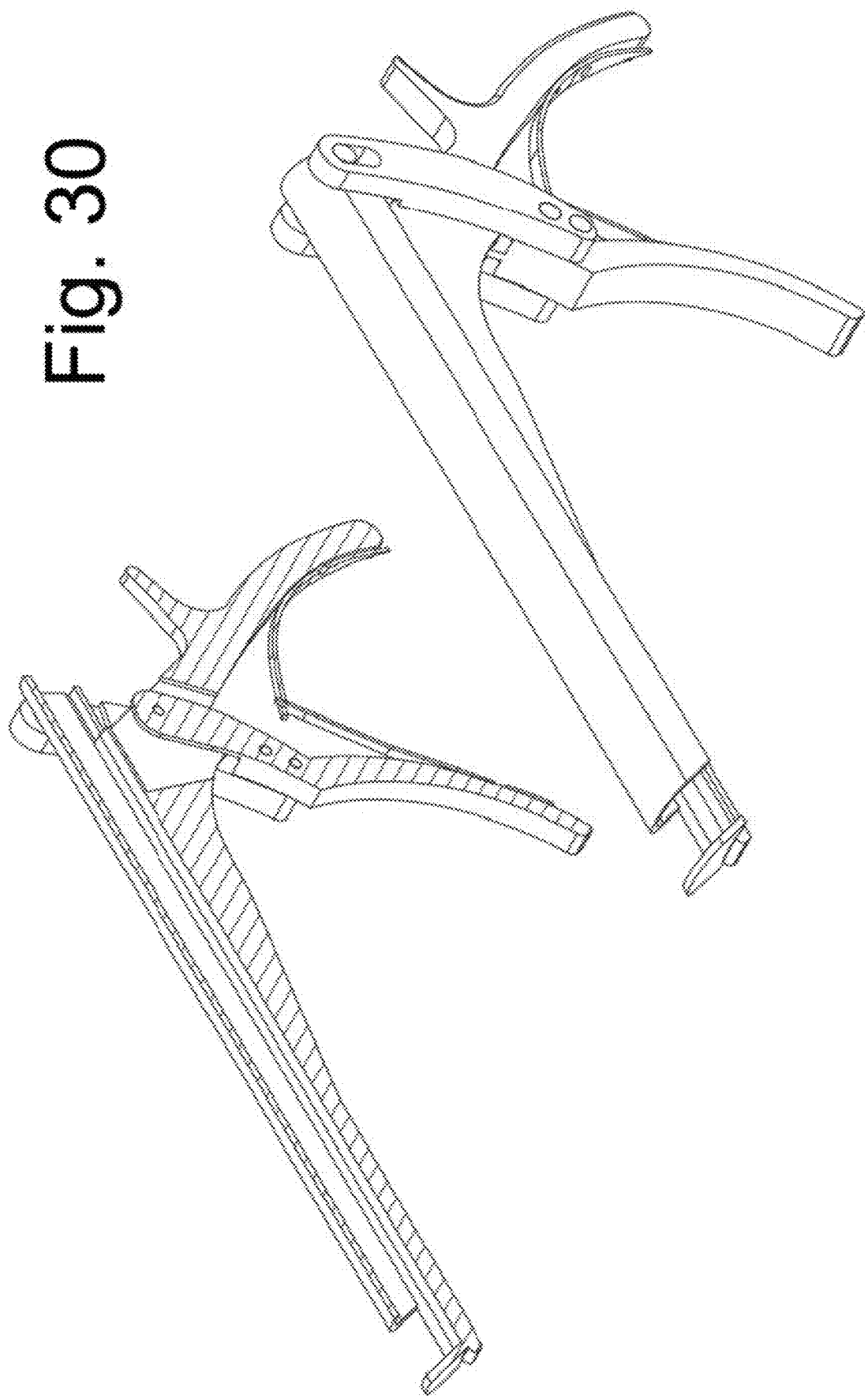
FIG. 30 shows a section view of the instrument.

Instrument 260 is shown in multiple orthogonal views in FIG. 27 and in oblique views in FIG. 26. An exploded view is shown in FIG. 28. Section views are shown in FIGS. 29 and 30. A section view of the device at about plane N is shown in FIG. 29B, wherein a close-up view of the section is shown in FIG. 29C.

A main body 262 has a foot segment 264. While not shown, the foot segment preferably has a sharpened edge about at least a portion of the circumference, wherein the sharpened edge is adapted to cut bone. A movable elongated member 280 has protrusions 282 that are adapted to engage members 296. Member 280 has cut outs 2802 adapted to engage edge 2622 of member 262 so that member 280 can move along the long axis of body member 262. The distal end of member 280 is adapted to forcibly abut the foot segment 264 of body 262, wherein the distal end of member 280 preferably has a sharpened circumferential edge that is adapted to cut bone.

In the assembled device, a central channel 272 is formed between member 262 and 280. A movable handle member 301 is attached to body member 262 using member 296 as shown in the illustrations. Cut out 2962 of member 296 is adapted to engage protrusions 282 of member 280. In use, forcible hand actuation of the handle 301 towards the handle portion 2625 of body 262 produces movement of member 280 relative to body 262 and advances the sharpened distal end of member 280 towards the sharpened foot segment 264. In this way, the intervening bone is cut and instrument 260 functions like a rongeur. Spring members 305 are adapted to return the handle 301 to the pre-actuation position (i.e., the position shown in FIG. 30) after the pressure placed by the surgeon's hand on member 301 has been released.

Figure 31:
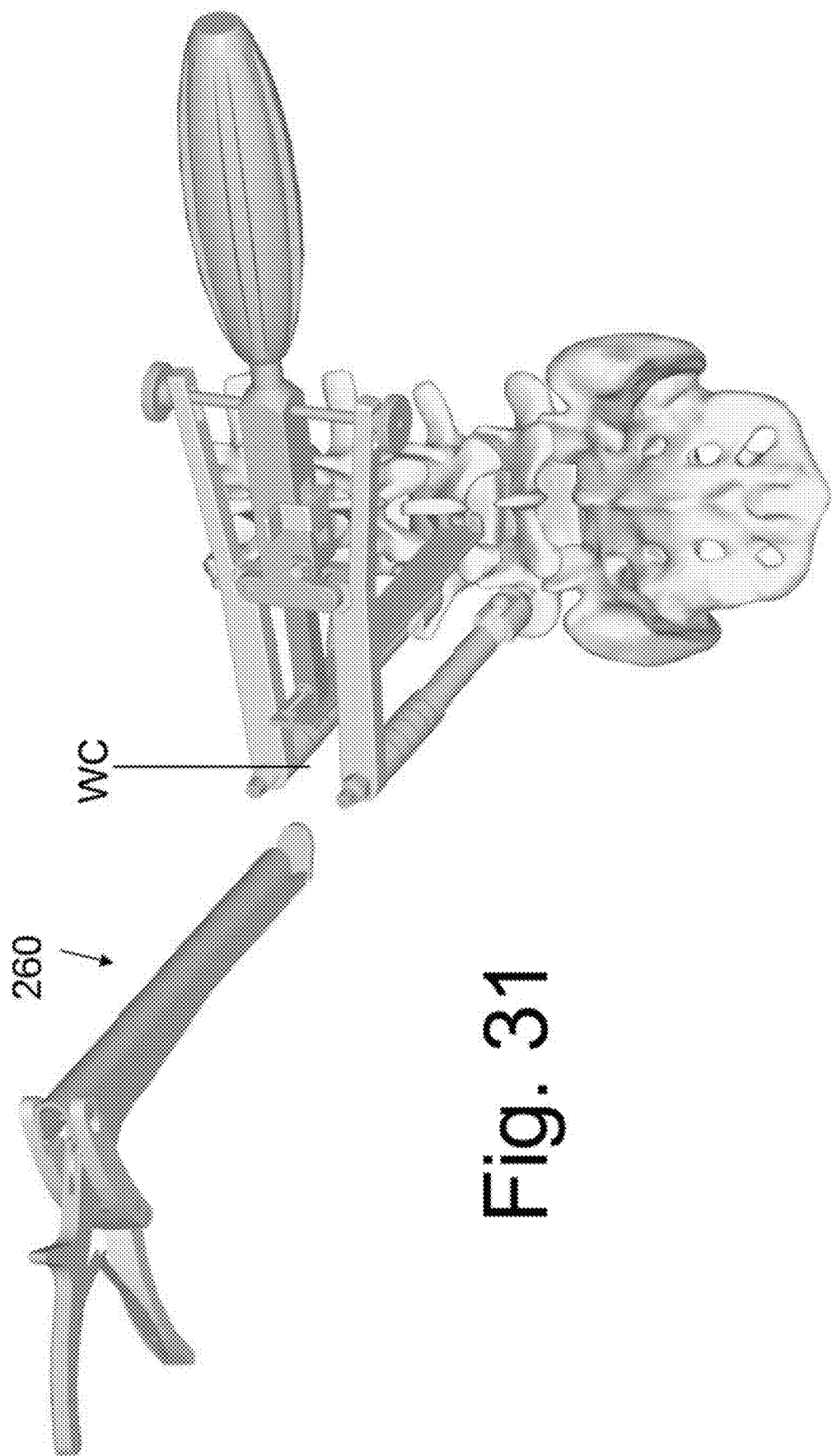
FIG. 31 shows an instrument positioned to be advanced through the working corridor.
Figure 32:
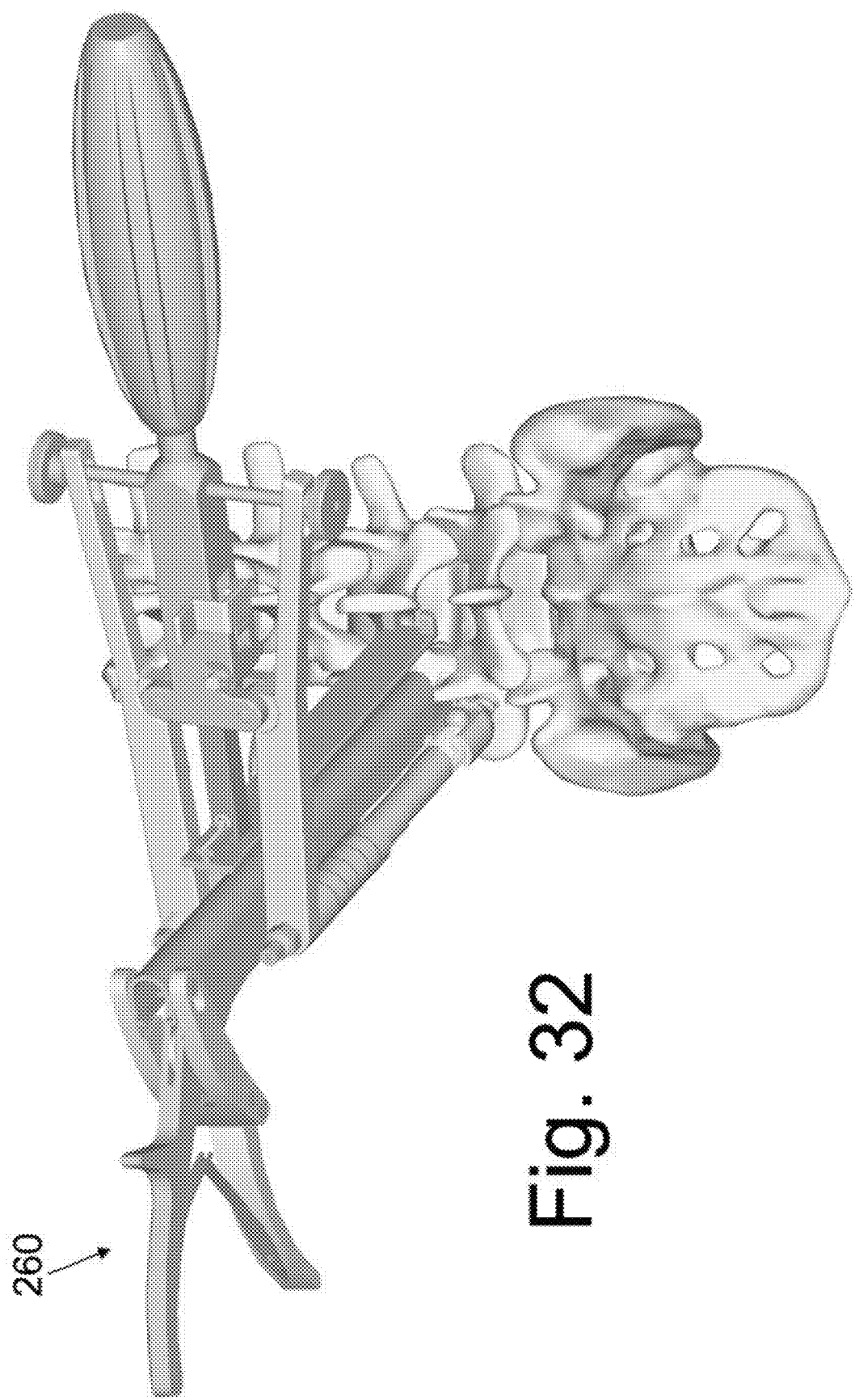
FIG. 32 shows the instrument fully advanced onto the facet joint.
Figure 33:
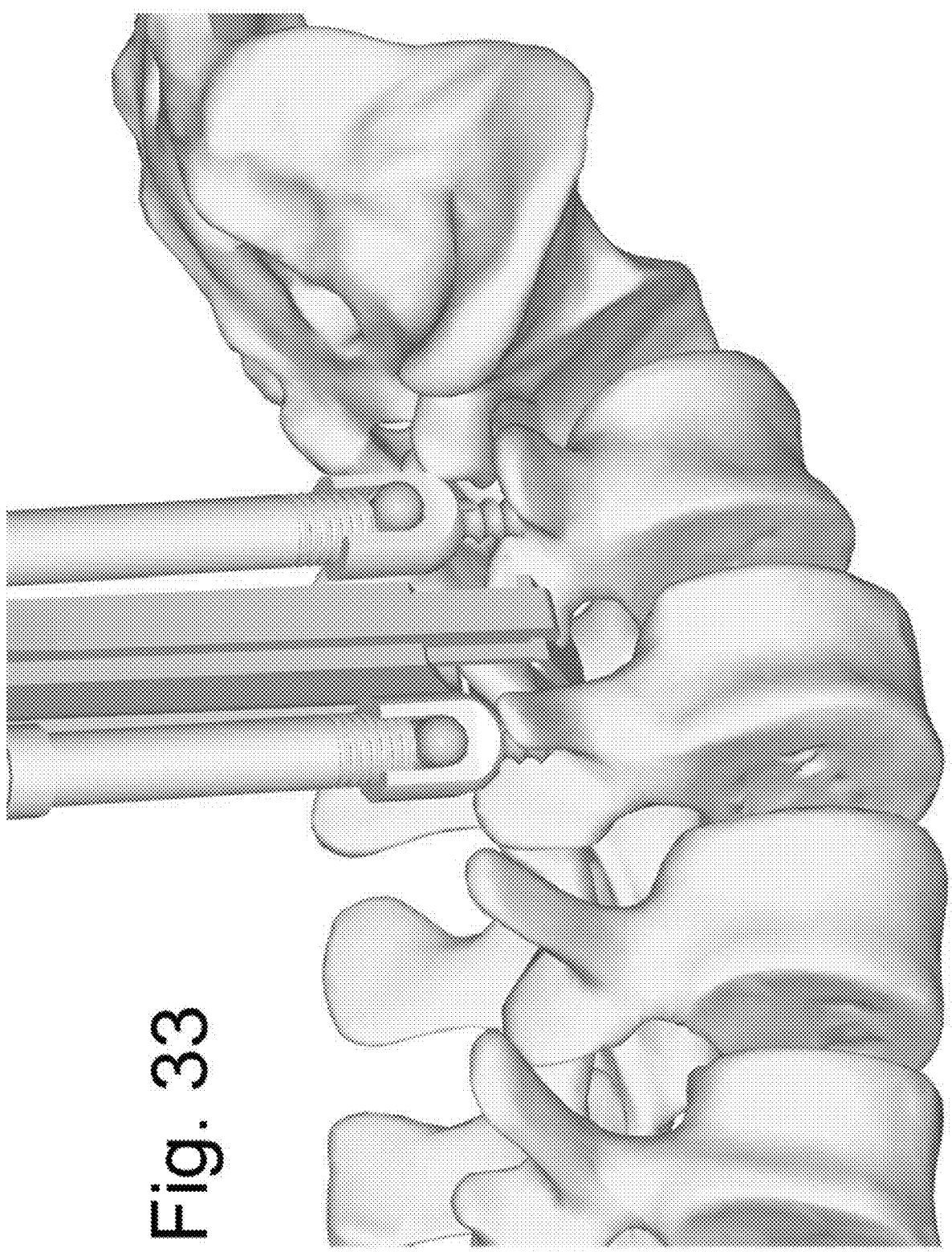
FIG. 33 shows the facet joint positioned between each foot and distal aspect of member of instrument.
Figure 34:
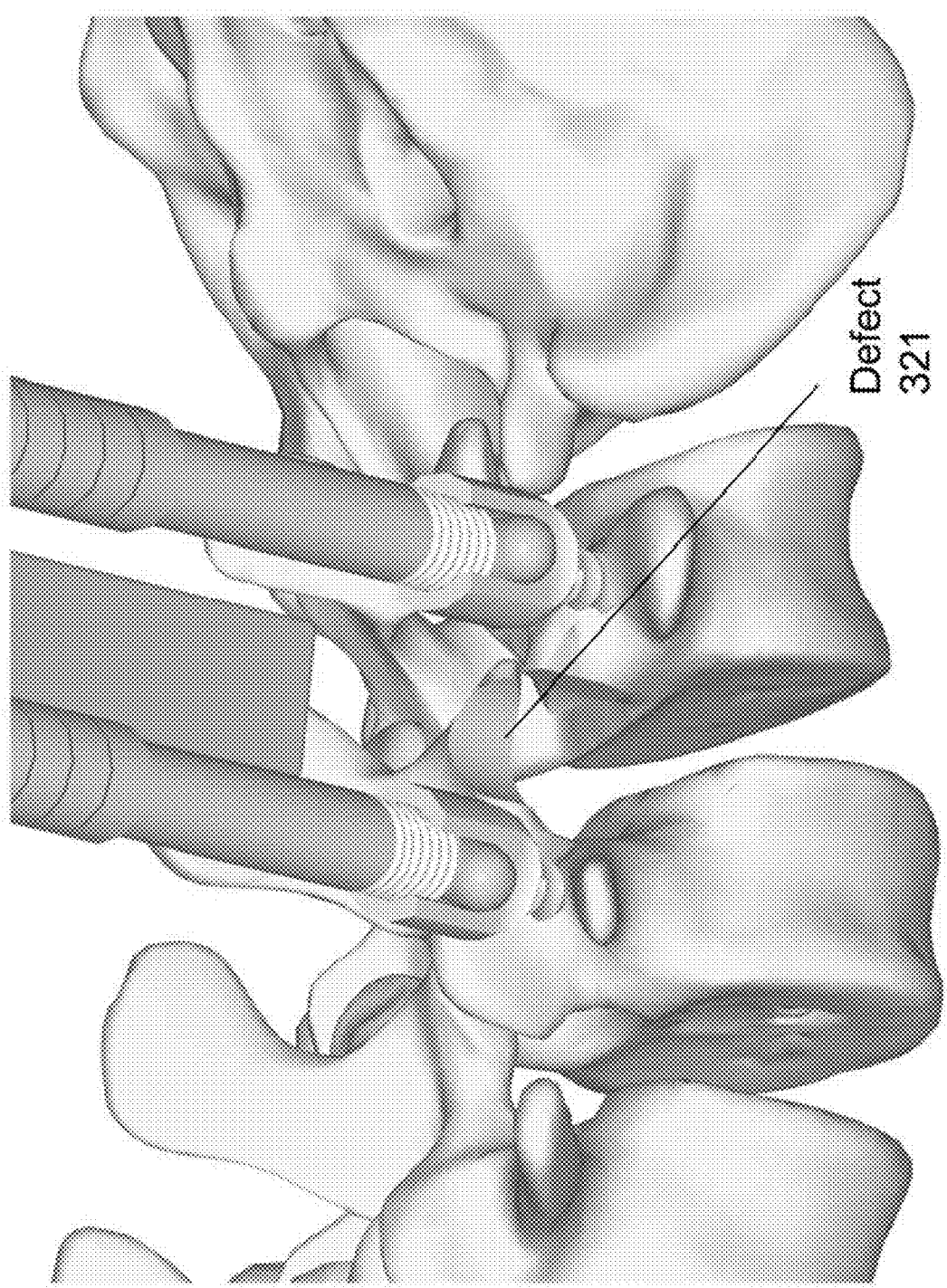
FIG. 34 shows the bone defect formed by instrument with the instrument partially removed.

FIG. 31 shows instrument 260 positioned to be advanced through working corridor WC while FIG. 32 shown the instrument fully advanced onto the facet joint 814. Foot segment 264 of instrument 260 is passed lateral to joint 814 and then moved medially so that the foot segment rests immediately anterior to facet joint 814 (that is, the foot segment 264 resets within the neural foramina of the exiting nerve). The sharpened distal end of member 280 rests posterior to facet joint 814. In this way, the facet joint is positioned between each of foot 264 and distal aspect of member 280 of instrument 260. This is shown in FIG. 33. A drill bit is placed through the central channel 272 of instrument 260 and the facet joint 814 is drilled away until the free end of the drill bit abuts foot member 264. After drilling the facet joint, only a small rim of bone is left between foot 264 and distal aspect of member 280. Hand actuation of handle 301 then cleaves the residual rim of bone. The bone defect 321 formed by instrument 260 is shown in FIG. 34, with the instrument 260 partially removed.

After removal of instrument 260, the surgeon may further remove additional segments of the facet joint with burr, drill, bone rongeur, and the like. If desired, the spinal canal may be also decompressed through the working corridor WC. Removal of at least a portion of the lamina of the superior vertebral bone and at least a portion of the lamina of the inferior vertebral bone permits access to the spinal canal and decompression of both sides of the dural sac and nerve elements. This is schematically shown in FIG. 35, wherein the dural sac (DS) and contained nerve elements are shown decompressed on the posterior and lateral aspects. (For clarity of illustration, the contents of FIG. 35 are represented schematically and those skilled in the art will appreciate that an actual cross section of the human torso may include anatomical details not shown in the illustration.)

After resection of the fact joint, the working corridor WC provides direct access to the posterior aspect of the disc space. The posterior disc space is accessed through a transforaminal corridor that extends, in the superior/inferior direction, between the nerve root that exits the spinal canal beneath the pedicle of the superior vertebral bone (L4 vertebra in the illustration) and the pedicle of the inferior vertebral bone (L5 vertebra in the illustration). If vertebral fusion is desired, then at least partial removal of the disc material is performed and a segment of the bony endplate of each of the inferior surface of the superior vertebral bone (L4) and superior surface of the inferior vertebral bone (L5)

is striped of cartilage material and then decorticated. Preparation of the disc space is well known in the art and will not be described further.

If vertebral fusion is desired, then bone forming material is positioned into the evacuated portion of the disc space. Preferably, but not necessarily, an implant is concurrently implanted into the disc space that can bear at least some of the load transmitted across the disc space and maintain the superior and inferior vertebral bones separated by a desired distance. While embodiments of disc space implants are shown, it is understood that any device adapted for implantation into the disc space (including those adapted to produce vertebral fusion and those intended to preserve vertebral motion, such as, for example, an artificial disc) may be used.

Figure 36B:
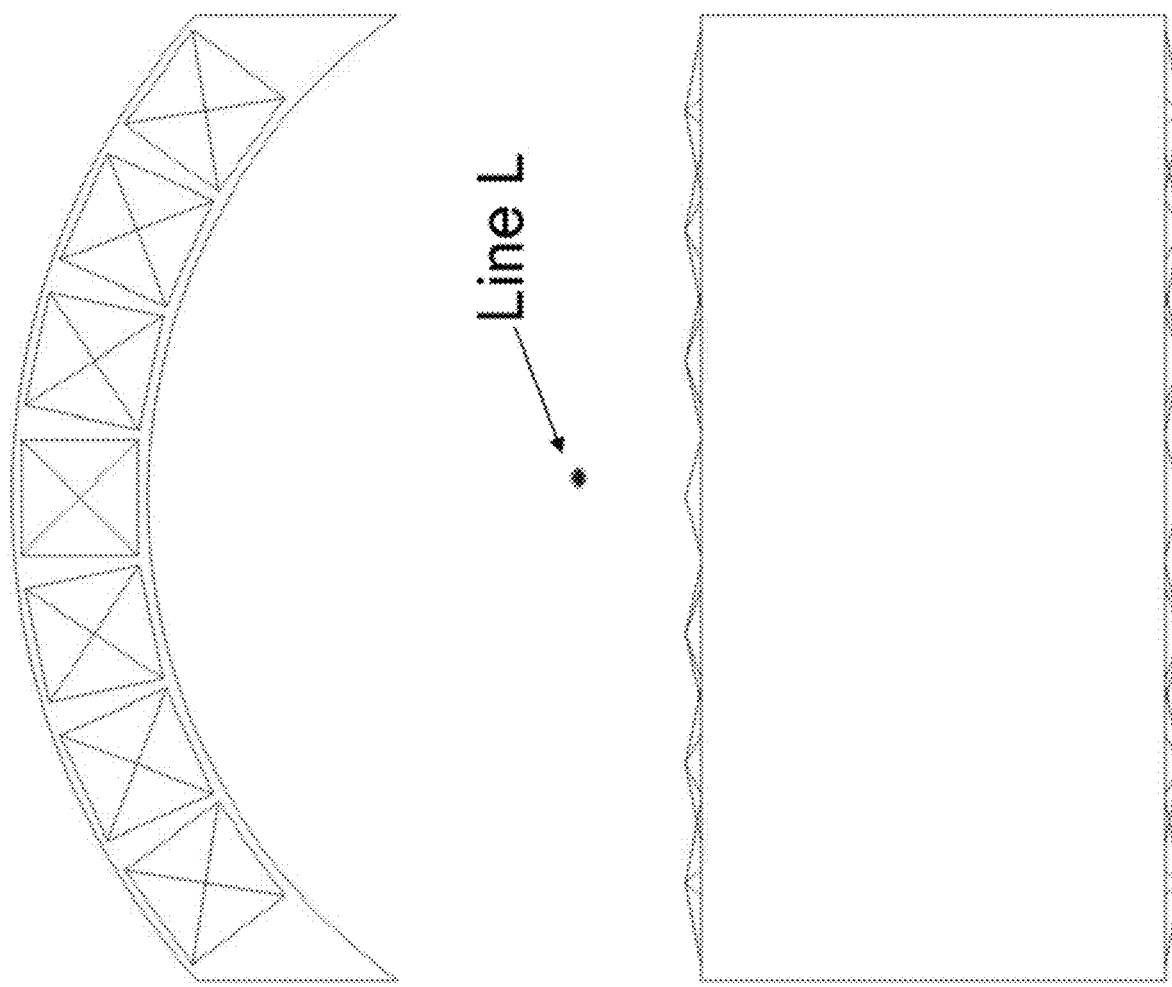
Figure 37:
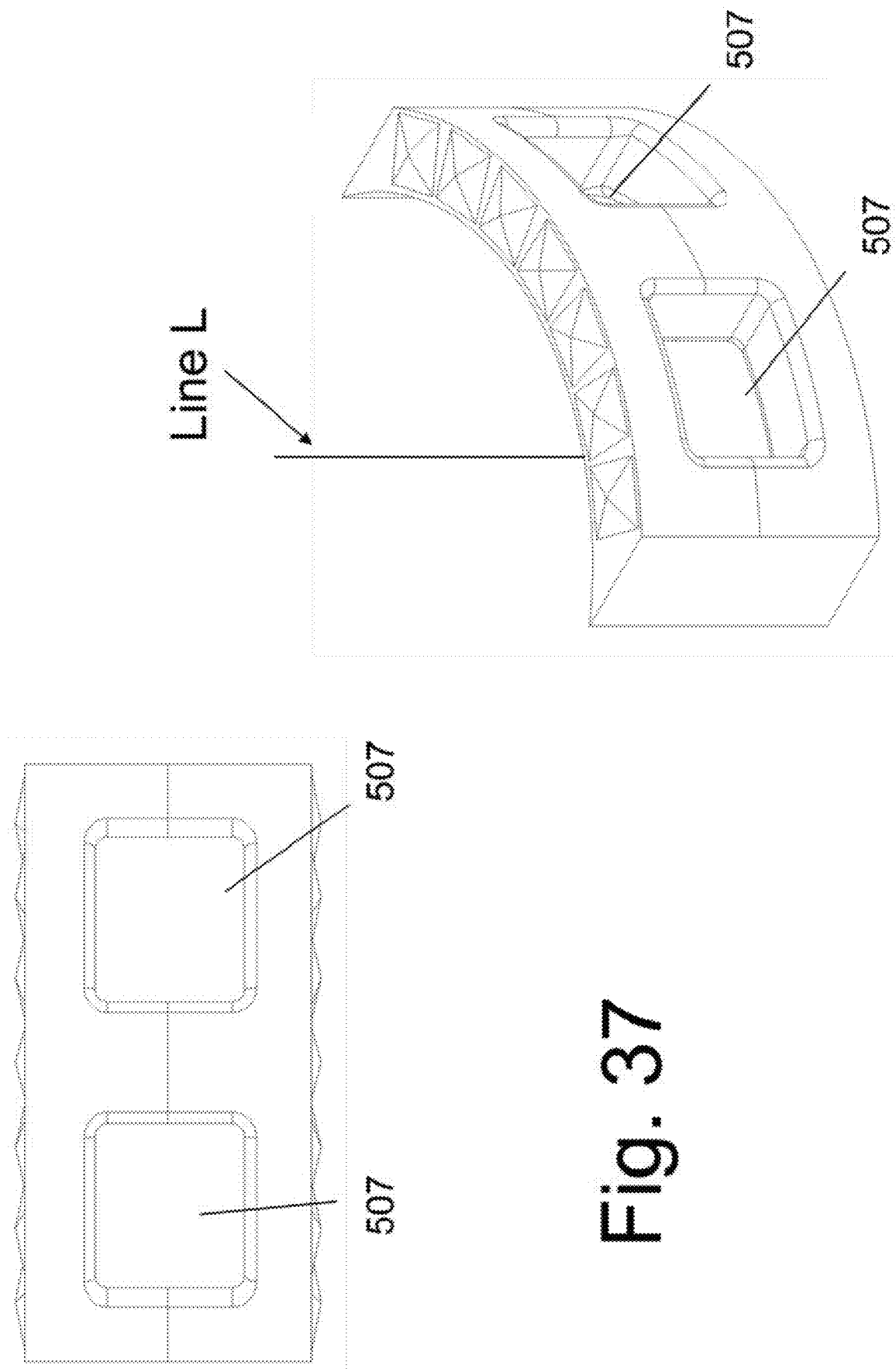
FIG. 37 shows an implant having at least one cavity that permits communication from one side of the implant body to the other.

An embodiment of a disc implant 505 is shown in FIGS. 36A-37. The device is preferably curvilinear. The implant may be solid, as shown in FIGS. 36A-36B, or it may contain a cavity adapted to house bone graft material, wherein the material is adapted to fuse with one or both of the vertebral bones. The implant may be made of allograft bone, PEEK, or any other material that is appropriate for human or animal implantation. Preferably, the implant has a curvature K with center line L. Further, the implant may contain at least one cavity 507 that permits communication from one side of the implant body to the other—as shown in FIG. 37. The cavity permits formation of a bony connection between a fusion mass on one side of the implant body and a fusion mass on the other side of the implant body.

Figure 38B:
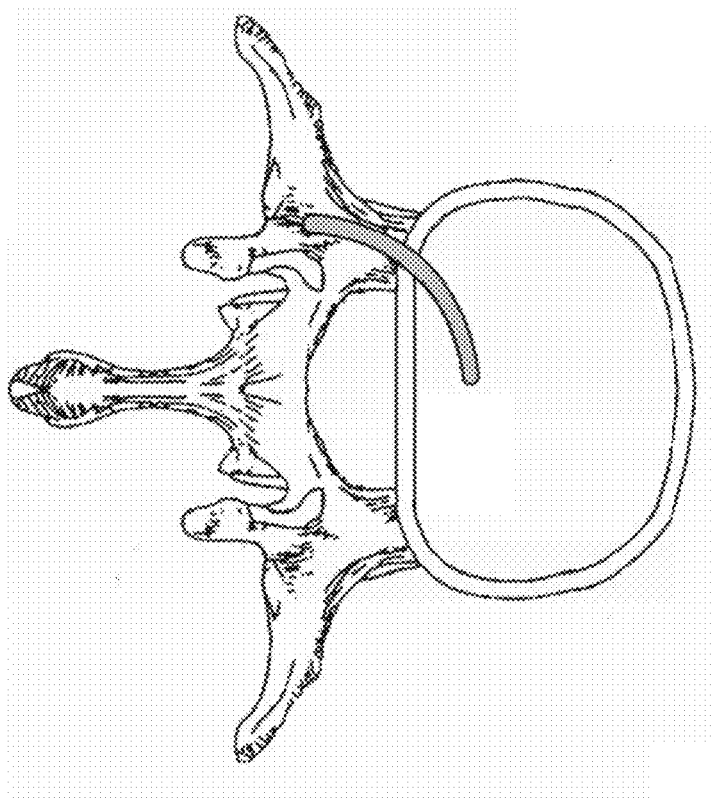
FIGS. 38A-38B show implant positioned at the defect placed in the posterior aspect of the annulus fibrosus of the disc space during disc preparation.
Figure 38A:
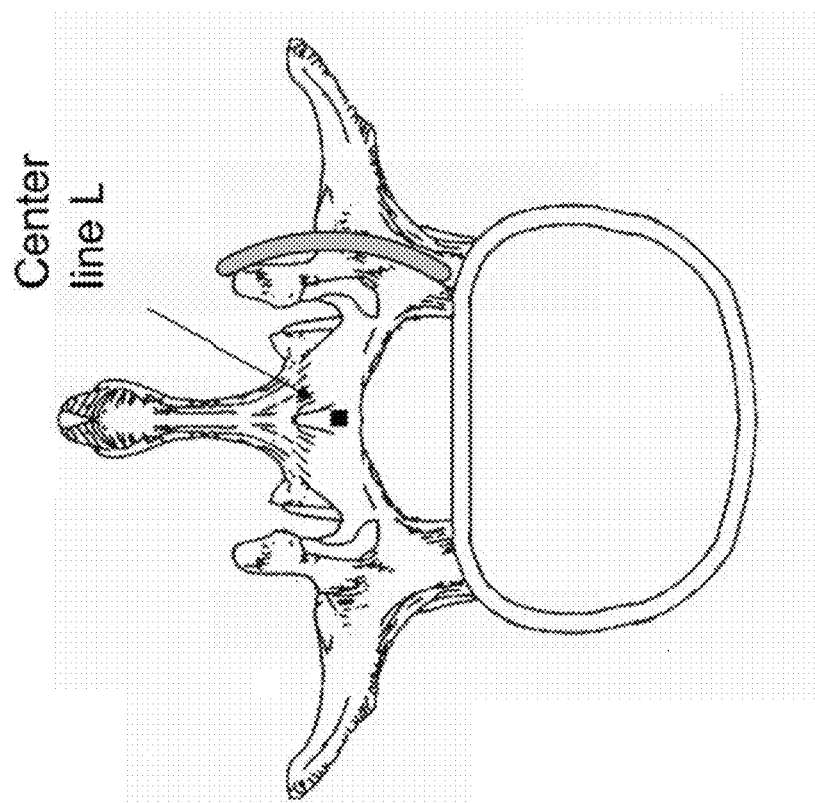
Figure 40B:
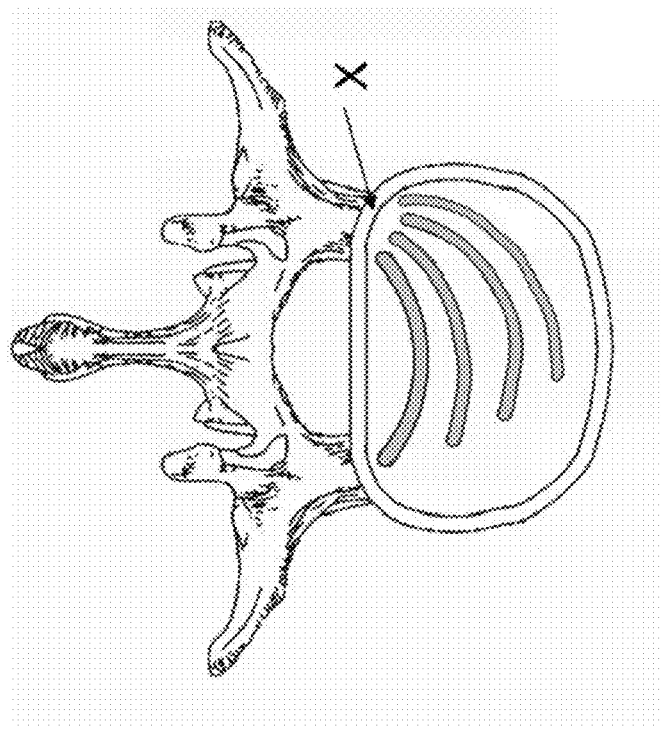
FIGS. 40A-40B show additional embodiments of implant positioning.
Figure 40A:
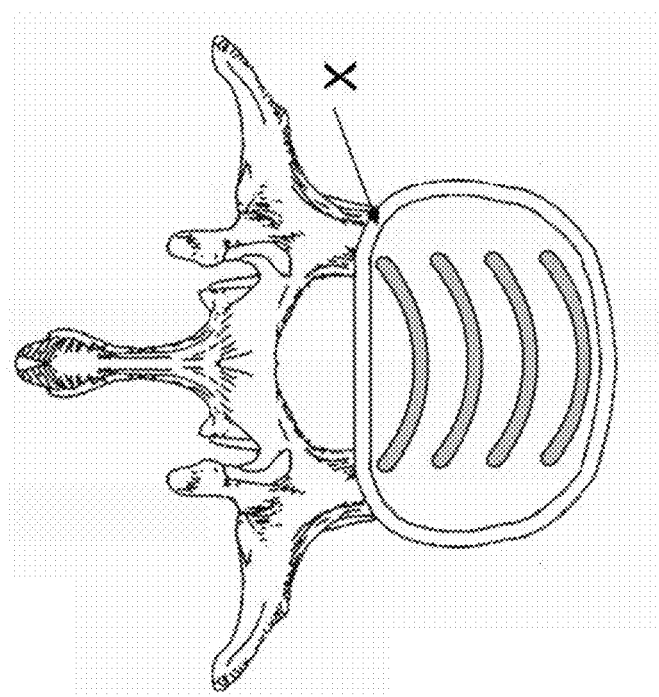

At implantation, the implant 505 is preferably positioned at the defect placed in the posterior aspect of the Annulus Fibrosus of the disc space during disc preparation (see FIG. 38A.) The implant is then rotated along an arc that is centered at the implant's center line L. (Note that center line L goes in and out of the page. Thus, only a point is shown in FIG. 38A indicating an implantation instrument, and the implantation instrument is not shown). The implant is advanced as shown in FIG. 38B until it rests in the position shown in FIG. 39. Bone graft material is then placed into the disc space adjacent to the implant (see FIG. 39). The bone graft material can be placed into the disc space after implant placement (through the space lateral to the implant) or the bone graft material can be placed before implant placement. Further, more than one implant may be advanced into the disc space. FIGS. 40A and 40B illustrate two potential embodiments of implant positioning, wherein the implants are preferably, but not necessarily, placed through a single disc space entry point ("X") within the Annulus Fibrosus.

After implantation of the disc space, the distraction platform is removed. If the surgeon elects to add a fusion mass between the ipsilateral transverse processes of the superior and inferior vertebral bones, then the transverse process of each of the superior and inferior vertebral bones is stripped of the attached muscle and decorticated. A column of bone forming material is then positioned in contact with the transverse process of each of the superior and inferior vertebral bones, wherein the bone forming material also spans the space between the transverse processes. With time, a solid column of mineralized bone should form between the two transverse processes and serve as the fusion mass.

Figure 41A:
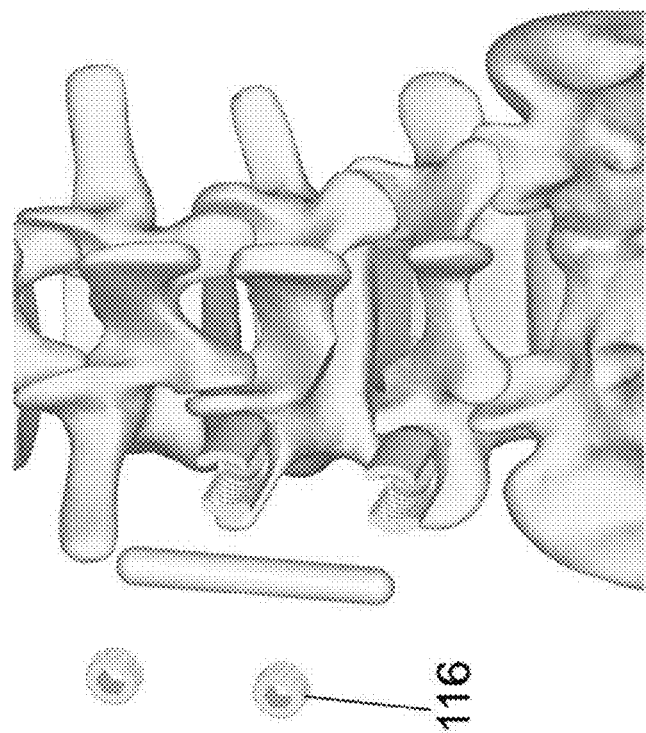
FIGS. 41A-41B show schematic sequence of inter-connecting member used to interconnect fasteners.
Figure 41B:
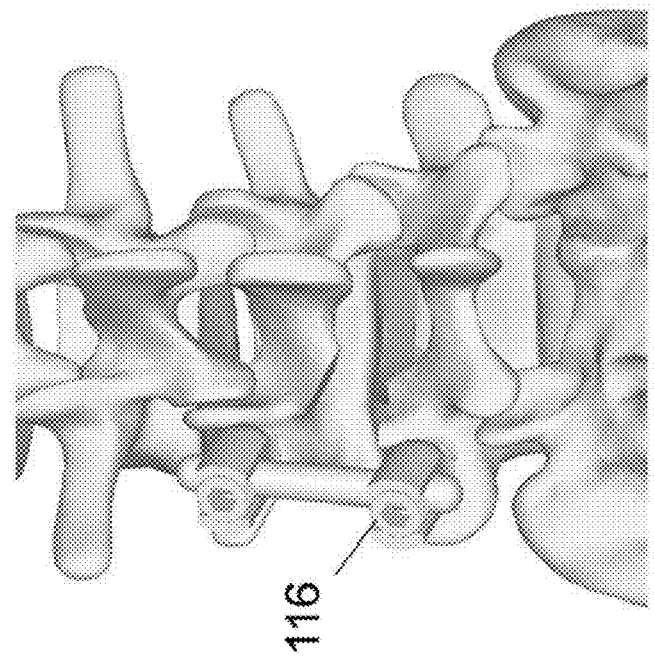

An inter-connecting member (for example, a rod) is used to interconnect each of the superior and inferior bone fasteners 105. A locking element 116 of each bone fastener 105 is then deployed so that each of the bone fasteners is rigidly attached to the interconnecting member. In this way, the fasteners and interconnecting rod member will rigidly interconnect the superior and inferior vertebral bones that abut the implanted disc space and immobilize the FSU containing the target disc space. The sequence is schematically shown in FIGS. 41A-41B.

Additional immobilization may be produced by the implantation of fasteners/interconnecting member into the contra-lateral vertebral pedicles (i.e., on the contra-lateral side of the vertebral midline). A fusion mass may be also positioned, if desired, between the contra-lateral transverse processes of the superior and inferior vertebral bones. Alternatively, or additionally, a spinous process fastener that is adapted to rigidly affix to the spinous process of each of the superior and inferior vertebral bones and rigidly immobilize the FSU may be used as an additional fixation implant. Preferably, the spinous process fastener is placed through the same ipsilateral skin incision used to perform the disc space implantation of the TLIF approach.

Figure 42B:
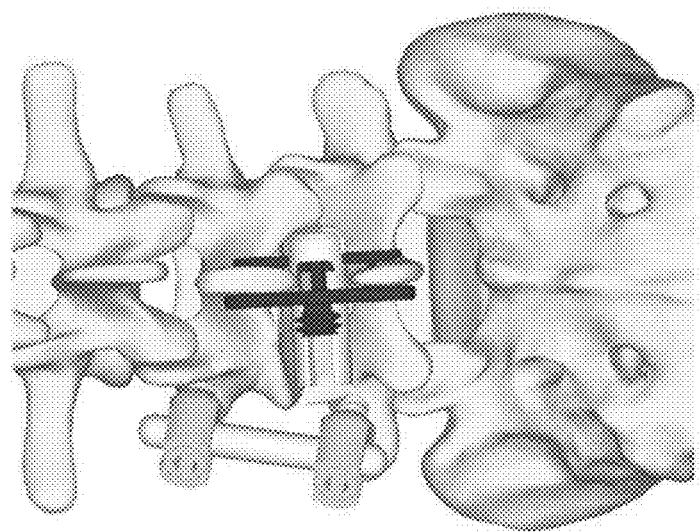
FIGS. 42A-42B show an embodiment of a spinous process device being implanted.
Figure 42A:
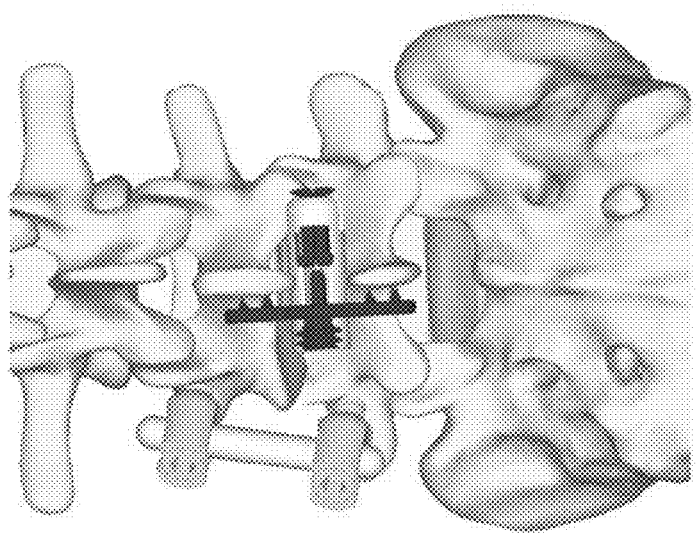

An embodiment of a spinous process device is shown being implanted in FIGS. 42A-42B. The illustrated implant is more fully disclosed in U.S. application Ser. No. 12/940, 960, filed by Abdou, Nov. 5, 2010. The application is hereby incorporated by reference in its entirety.

In some patients, the distance between the pedicles of the superior and inferior vertebral bones of an FSU may be small. Under those circumstances, the positioning of a bone anchor assembly 105 into the pedicles each of the superior and inferior vertebral bones may significantly limit the space of the working corridor WC. Thus, it is contemplated that bone screw 107 may be used alone as a bone attachment for the distractor platform—without being attached to housing 110 or the other members of the bone anchor assembly 105.

For example, a bone screw 107 may be attached to a coupler and then advanced into the ipsilateral pedicle portion of at least one of the superior or inferior vertebral bones. As previously described with bone screw assembly 105, a distractor platform is coupled to each of the two screws 107/coupler and a third retractor blade (preferably, a removable tissue distractor blade) is used to retract the soft tissues medially and expose the facet joint. The facet resection and disc implantation is preferably preformed as previously described—but may be alternatively performed using any specific instruments and techniques that the surgeon desires. After disc space preparation and device implantation (previously described), the distractor platform and couplers are removed. The bone screws 107 are left implanted into the pedicle portions of the vertebral bones. If desired, a bone forming material may be used to interconnect the ipsilateral transverse processes of the vertebral bones that border the implanted disc space—as previously described. With time, a bone fusion mass will develop between the transverse processes.

A housing 610 and other member of the complete bone screw assembly may be attached to the bone screw 107 in order to reconstitute a bone screw assembly that can reversibly accept an interconnecting rod. Bone screw assemblies that permit reversible coupling of the housing member to the bone screw 107 are known in the art. US patents U.S. Pat. Nos. 6,248,105, 6,371,957 and others disclose bone screw assemblies wherein the housing and the bone screw 107 may be reversibly detached by the surgeon at the time of surgery. (Each citation is hereby incorporated by reference in its entirety.) These devices are designed to permit advancement of the bone screw into bone without an attached housing member. After the bone work is done (or at any time the surgeon chooses), the housing member may be attached to the bone screw so that the assembly is reconstituted and ready to accept an interconnecting rod. After attachment of a housing member to each screw 107, an interconnecting rod and a locking feature (may be a locking screw/nut or a feature built into the housing) is used to lock the interconnecting rod within the bone screw assembly.

FIGS. 43A-43C briefly illustrate an example of a device adapted to perform the method. The assembly of coupler member 630 and screw 107 is shown in an exploded view in FIG. 43A and in the assembled view in FIG. 43B. Sectional views are shown in FIG. 43C. Bone screw 107 has a head 1074 and an internal bore 1076, wherein the internal bore has a threaded portion 1078. A hex-shaped receptacle 1079 resides within head 1074. Receptacle 1079 is adapted to accept a screw driver (with, for example, a hex-shaped tip), wherein the driver can deliver a rotational force to screw 107 and drive the threaded shaft into bone.

Coupler member 630 has an elongated body with a proximal threaded segment 6302. Member 630 has a central bore 6304 that extends there through from the top to the bottom surface of member 630. A hex-shaped protrusion 6306 projects distally, wherein hex-shaped protrusion 6306 is adapted to snuggly rest within hex-shaped cut out 1079 of screw 107 such that rotation of member 630 produces rotation of screw 107. An additional hex-shaped protrusion 6308 is located at the top of member 630 (i.e., proximal aspect of member 630).

Member 640 has an elongated body with a proximal head 6402 and distal threads 6404. Head 6402 has an indentation (or protrusion) that is adopted to mate and interact a screw driver (not shown) with complimentary protrusion (or indentation), so that rotation of the driver produces rotation of member 640. An internal bore 6409 extends throughout member 640 so that guide wire 102 (FIG. 10) may be passed freely through member 640, entering at a distal end and exiting at a proximal end of 640. In use, threads 6404 are adapted to cooperatively mate with threaded portion 1078 of screw 107. In this way, the assembly of coupler member 630 and screw 107 is rigidly held in the assembled state by member 640 and the assembly is allowed to function as a unitary device.

At surgery, the assembly of member 630 and screw 107 is passed over guide wire 102 to indentation 811 of the targeted vertebral bone. Screw 107 is advanced into bone by applying a rotational force to segment 6308 of member 630. After advancement into bone, the assembly is attached to the distraction platform as previously described. If desired, nut 1107 mates with threads 6302 of member 130 and permits rigid fixation of the assembly onto the distractor platform. These steps are schematically shown in FIGS. 44A-44B.

Figure 45B:
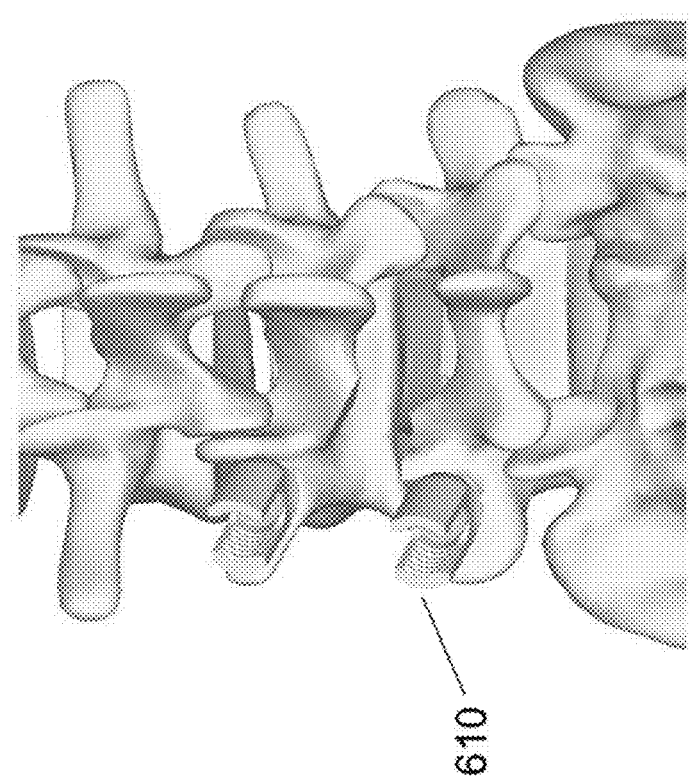
FIGS. 45A-45B show schematically the housing members attached to the bone screws.
Figure 45A:
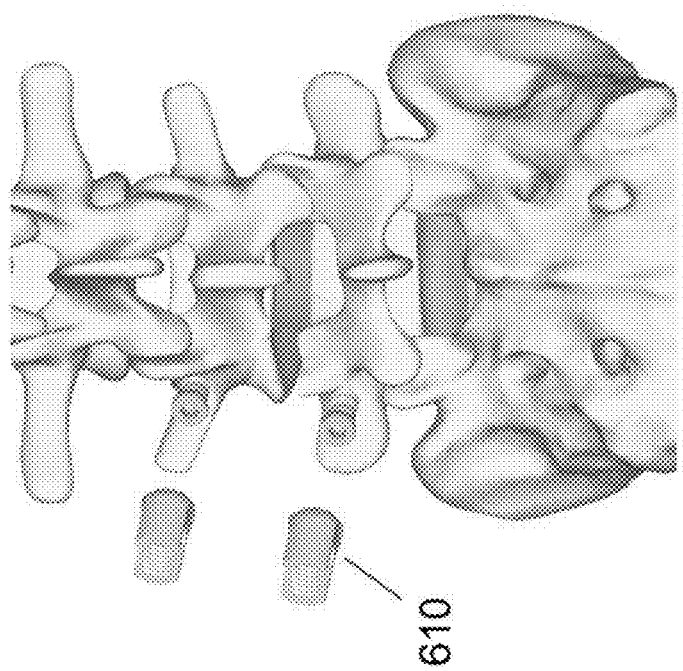

After the bone work is done (or at any point of the surgeon's choosing), member 630 is detached from bone screw 107. Housing members 610 are then attached to the bone screws 107. This is schematically shown in FIGS. 45A-45B. The screw assemblies are then ready to accept an interconnecting rod. The rod/locking screw may be then inserted and used to interconnect the bone screw assemblies as previously described (see FIGS. 41A-41B).

Note that this methods of use differs from the previously illustrated embodiment only in that the screw assembly 105 may be reversibly subdivided at the time of surgery into the bone screw 107 and housing portion. That is, the screw assembly 105 need not be used as a unitary device through out the procedure, but the screw 107 may be used independently for a first portion of the procedure and then coupled to the housing for use as an assembly at a second portion of the operation. Further, it is understood that the preceding method of use may be alternatively employed in any patient group, regardless of the distance between the pedicles of the superior and inferior vertebral bones.

Figure 45C:
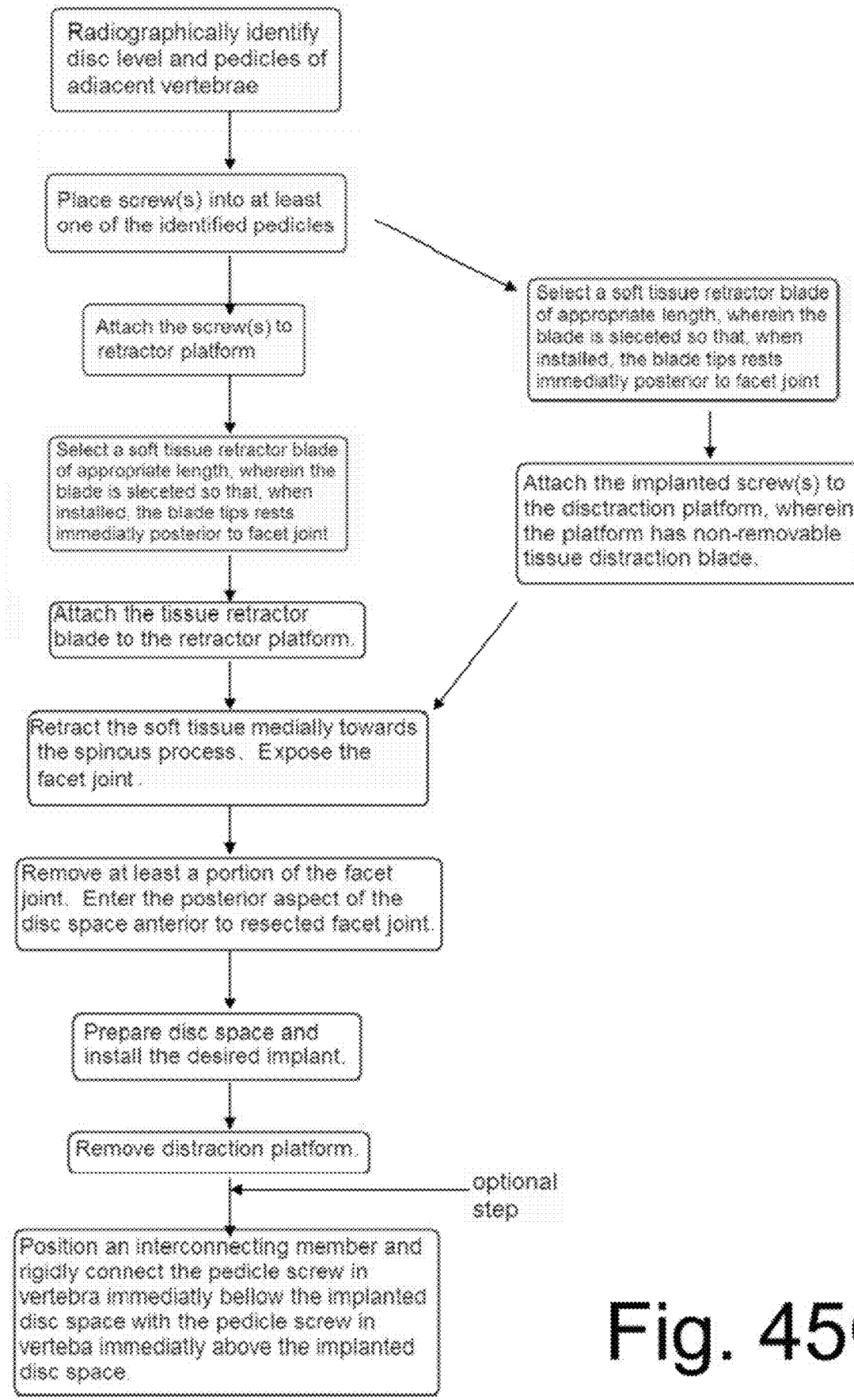
FIG. 45C is a flow diagram summarizing the disclosed methods.

In a modification of the immediately previous method, assembly 630 and screw 107 are left attached after disc space implantation. Instead, the complete 630/107 assembly is removed for the vertebral bone, leaving an evacuated bone screw hole. A separate bone screw assembly 105 (of any applicable design) is then advanced into the pedicles that have been evacuated by the removed coupler member 630/screw 107 assembly. That is, in this method, member 630/screw 107 are used as a temporary distraction screw and coupling platform for distractor 180. After completion of the disc space implantation, the temporary distraction screw (consisting of member 630 and screw 107) is removed and a bone screw assembly 105 is advanced into the evacuated pedicle portion of the vertebral bone. The implanted bone screw assemblies 105 may be then interconnected with a rod—as previously described (see FIGS. 41A-41B). A flow chart summarizing the disclosed methods is shown in FIG. 45C.

Figure 47A:
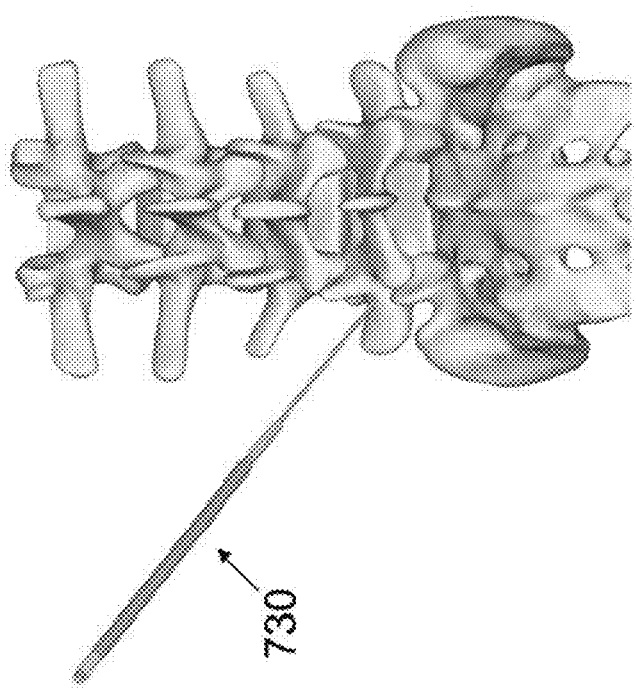
FIGS. 47A-47B show another embodiment of threaded screw member used to anchor distraction platform to pedicle portion of vertebral bone.
Figure 47B:
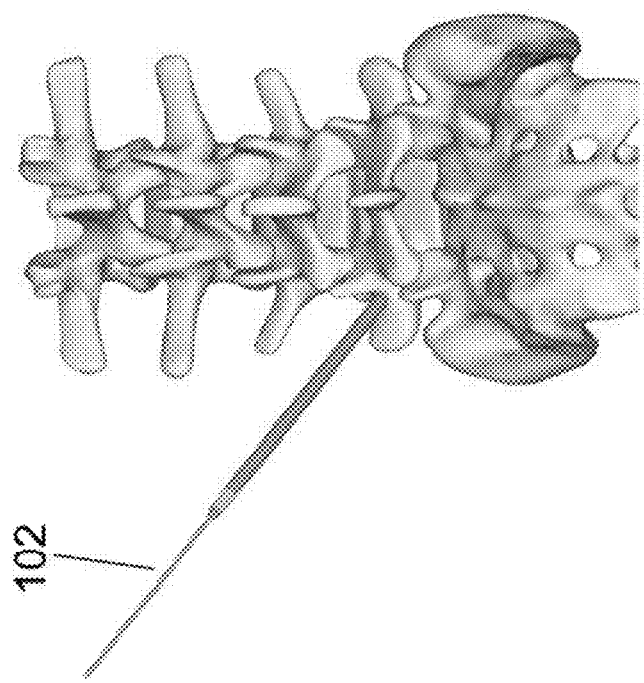

In an additional embodiment, threaded screw member 730 is used to anchor a distraction platform to the pedicle portion of the vertebral bone. Screw 730 has a threaded portion 7310 and elongated body 7300 (FIGS. 47A and 47B). Body 7300 has proximal threaded segment 7302. A hex-shaped protrusion 7308 is located at the top of member 730 (i.e., proximal aspect of member 730). Member 730 has a central bore 7304 that extends there through from the top to the bottom surface so that guide wire 102 (FIG. 10) may be passed freely through member 730.

Figure 48A:
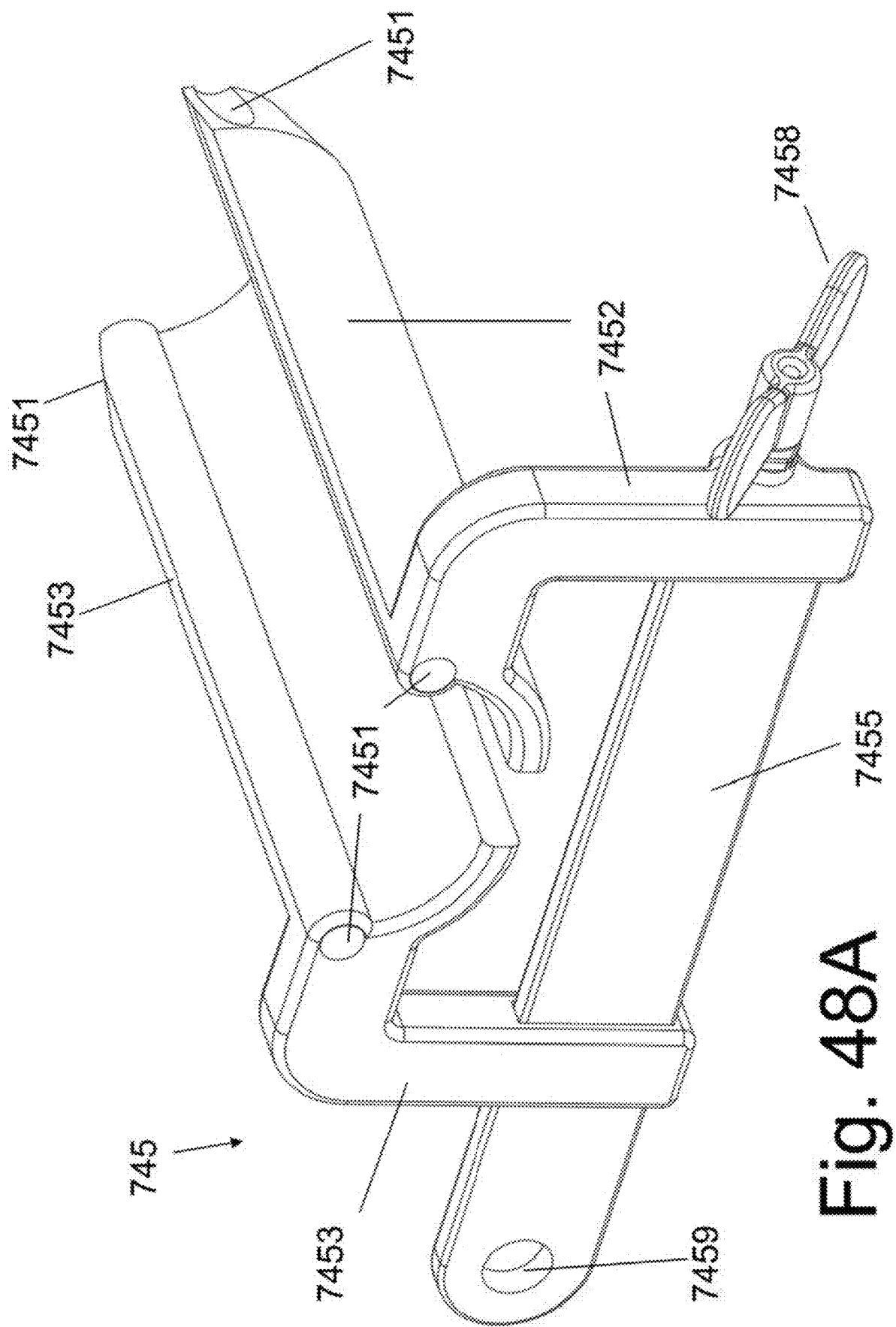

As previously described, at least one guide wire 102 is radiographically guided into the pedicle portion of at least one vertebral bone. Member 730 is passed over guide wire 102 (wire 102 traverses central bore 7304) and threaded portion 7310 is advanced into the pedicle portion of the vertebral—as shown in FIGS. 47A and 47B. Retractor platform 745 is shown in FIGS. 48A-48C. The retractor is known in the art and similar platforms have been disclosed in U.S. Pat. No. 5,795,291, US publications 2005/0021040, 2006/0149278, 2009/0171394 and others. (Each citation is hereby incorporated by reference in its entirety.) Any of these retraction platforms may be alternatively used.

The retractor platform 745 has at least two curvilinear blades 7452 and 7453. Blade 7452 is rigidly connected to bar 7455, while blade 7453 is movable along bar 7455. Thumb wheel 7458 is connected to a screw which threadedly engages threaded bore of blade 7453 (mechanism is not shown). In this way, rotation of thumb wheel 7458 produces translational movement of blade 7453 along bar 7455. Each blade contains at least one bore 7451, wherein the bore 7451 is adapted to accept member 730.

While briefly described above, it is understood that retractor 745 and similar retractor platforms are known in the art and have been disclosed in U.S. Pat. No. 5,795,291, US publications 2005/0021040, 2006/0149278, 2009/0171394 and others. (Each citation is hereby incorporated by reference in its entirety.) Any applicable retractor platforms may be alternatively used to accomplish the illustrated method of exposing the facet joint.

Figure 49:
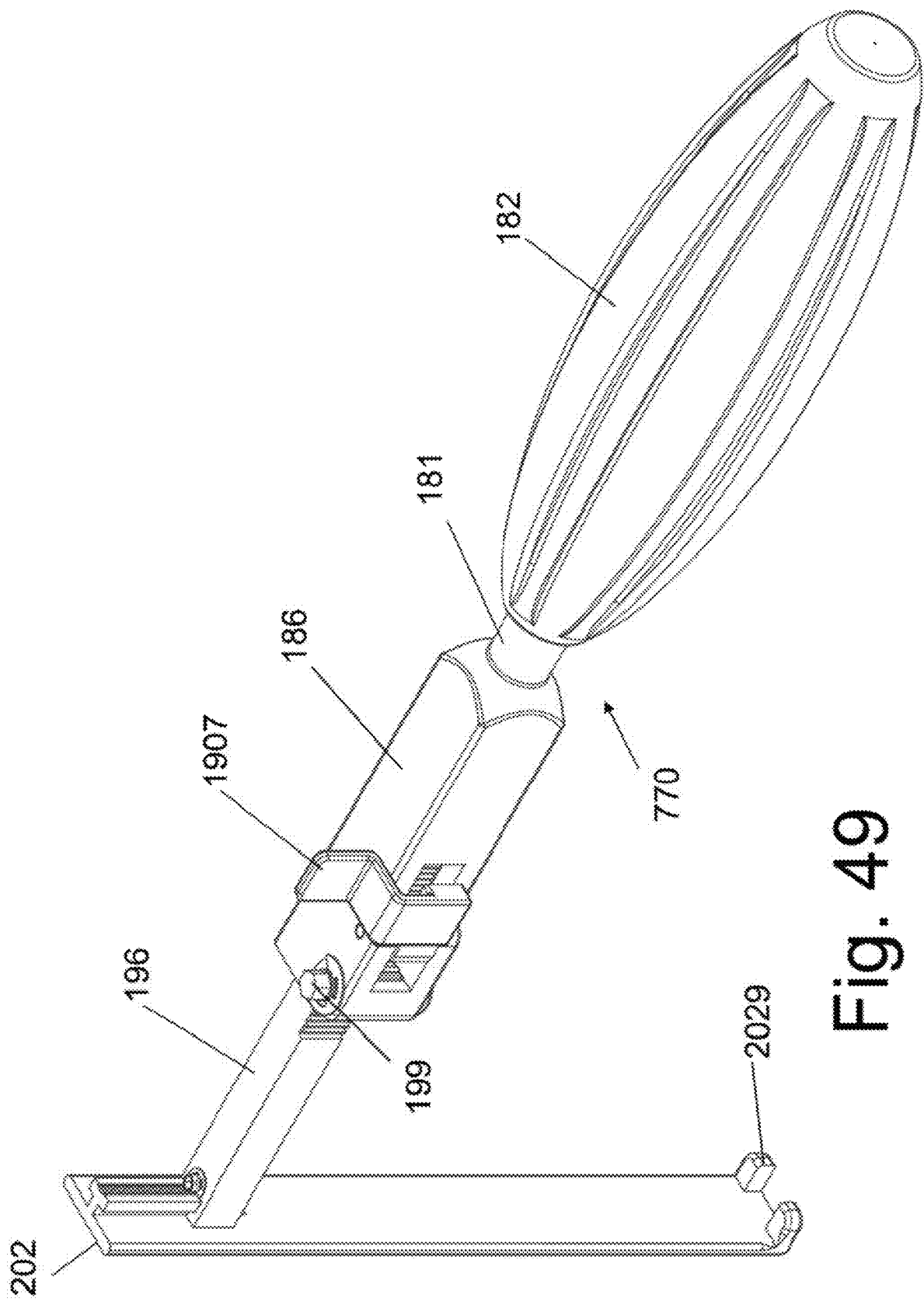
FIG. 49 shows a retractor used to retract the muscle segment medially towards the spinous process.

After advancement of threaded portion 7310 into the pedicle portion of the vertebral bone, the retractor 745 is advanced over member 730 to the correct position and coupled to the underling bone through member 730 (see FIGS. 48B and 48C). A retractor 770 (FIG. 49) is used to retract the muscle segment M1 medially towards the spinous process—as shown in FIG. 48B. Retractor 770 is similar to distractor 180 but lacks side retractor members 190. That is, retractor 770 contains handle 182, central body member 186 and interconnecting cylindrical region 181. Arm 196 rests within a cavity of central body 186 and is movable therein. A spring-loaded (spring not shown) pawl 1907 and member 199 interact with serrations 198 of arm and serve as a mechanism to move arm into and out of bore 1869 of body 186. A removable tissue retractor 202 rests at the distal end of arm 196. Arm 202 has at least one distal extension 2029 that interact with the retracted tissue. A more full description of the distractor is provided above.

Retractors 745 and 770 are preferably connected to a frame device that anchors to the operating table (such as, for example that shown Preferably, the frame device attaches to segment 181 of retractor 770 and to the region of bore 7459 of retractor platform 745. After the frame device is locked and made rigid, the attached retractor platforms 745 and 770 are held in desired positions as shown in FIG. 48C. In this way, a working corridor leading to the facet joint is created wherein two of the retractor blades are connected to a retractor platform which may (or may not) be subsequently connected to a frame device that is attached to the operating table. The third retractor is independently attached to the frame device.

An alternative embodiment is shown in FIG. 50. In this embodiment, both bar 7455 is a member of the frame device that is attached to the operating room table. Each blade member 7453 may be guided to the pedicle by anchored member 730 and then reversibly mountable onto bar 7455. (The blades may be radiographically guided to the pedicle position without prior placement of member 730. In order to illustrate this option, a first blade 7453 is shown attached to screw 730 in FIG. 50 while a second blade 7453 is not) After moving the blade member into the desired position relative to bar 7455, a locking mechanism (set screw 792 here) is actuated to immobilize the blade member relative to bar 7455. As before, retractor platform 770 is also attached to the frame device. In this way, each of the three retractor blades that form and border the working corridor are independently attached to the frame device that attaches to the operating table.

In an alternative embodiment, at least a first vertebral bone of the first and second vertebral bones that must be fused is radiographically identified. A first facet joint is also radiographically identified, wherein the first facet joint forms an articulation between the first and second vertebral bones. A marker is radiographically guided directly into the facet joint and the retractor platform is then advanced over the marker to the facet joint. In the preferred embodiment, a first threaded segment of a first bone fastener is threadedly advanced into the identified first facet joint under radiographic guidance prior to retractor platform placement. The anchored first bone fastener is used to guide and position the retraction platform relative to the first facet joint.

Figure 46B:
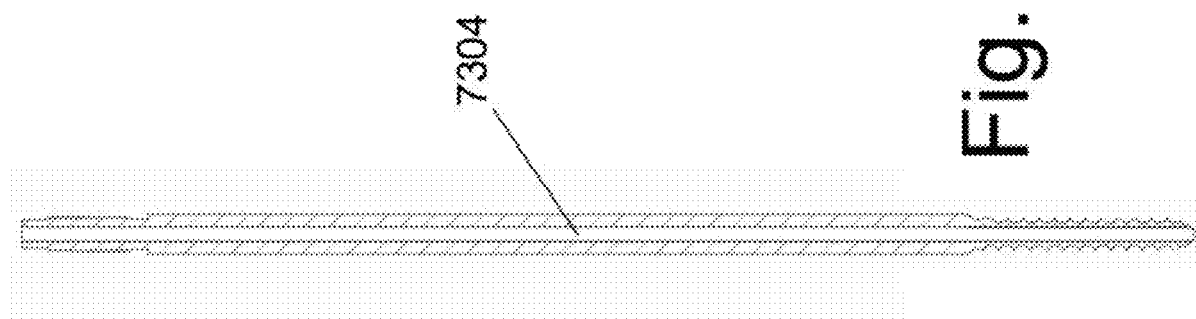
FIGS. 46A-46B show embodiment of a screw member.
Figure 46A:
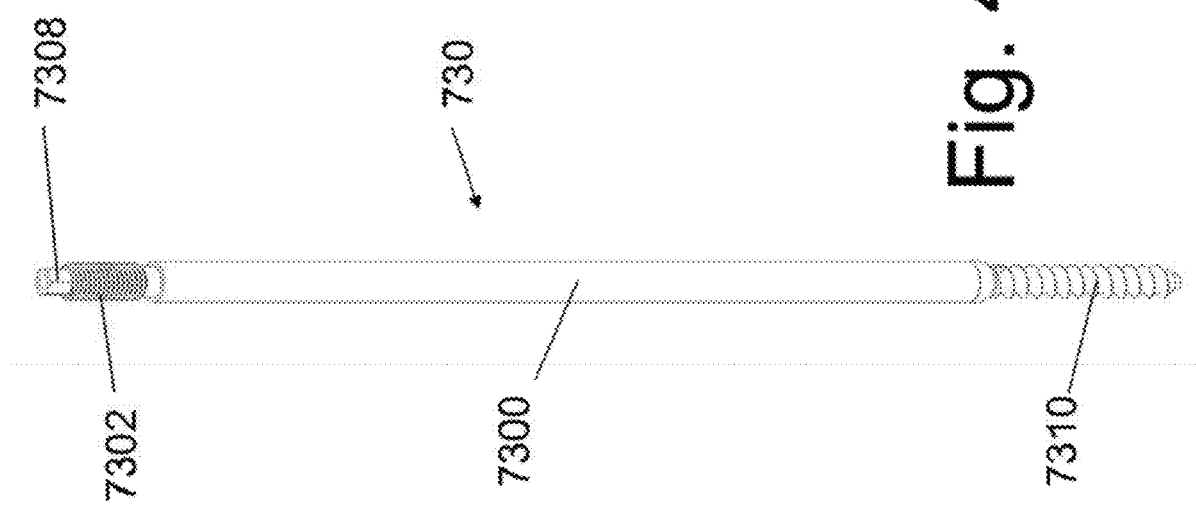
Figure 51B:
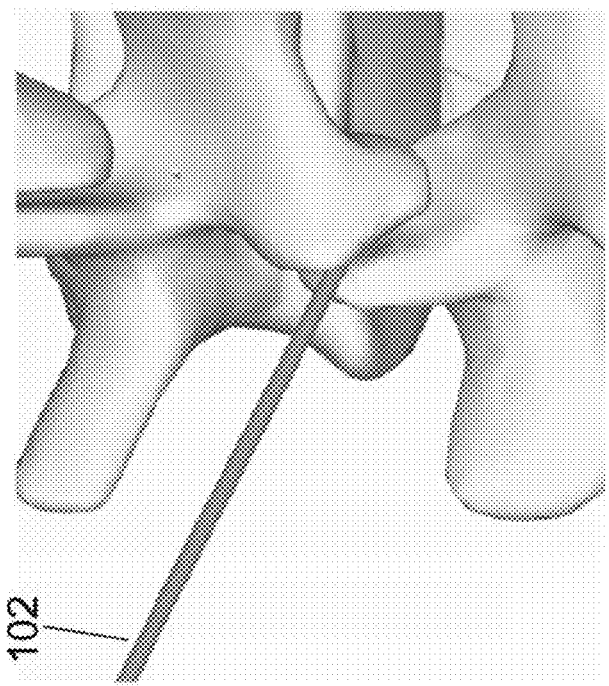
Figure 51A:
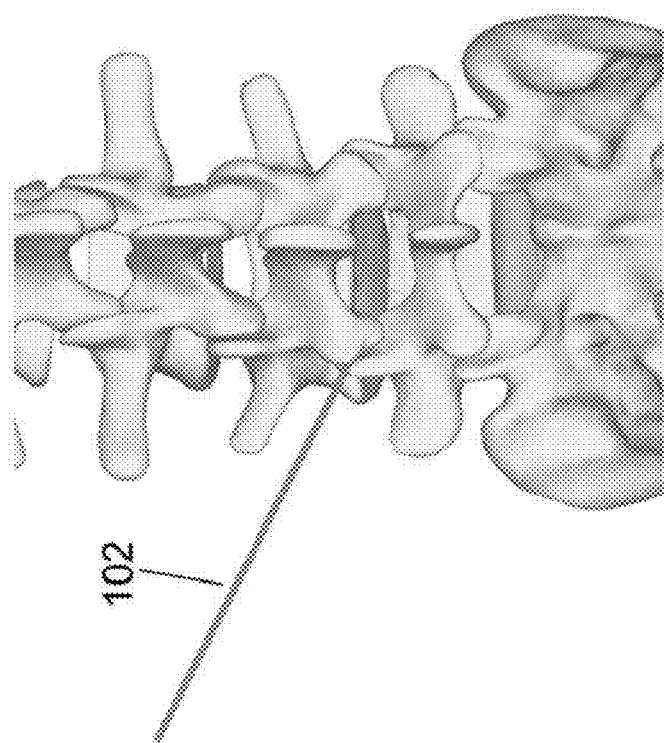

FIGS. 51A and 51B show placement of guide wire 102 directly into the facet joint space between the IAP of the superior vertebral bone and SAP of the interior vertebral bone. (As in prior embodiments, this step is performed under radiographic guidance and prior to direct surgical exposure of the facet joint.) A screw member, such as, for example, member 730 (FIG. 46A-46B) is advanced over the guide wire 102 under radiographic visualization. Threaded segment 7310 is driven into the facet joint so that the threads engage the IAP (superior vertebra) medially and the SAP (inferior vertebra) laterally (FIG. 51C).

Cylindrical tubes of progressively greater diameter are sequentially passed over member 730 in order to dilate the surrounding soft tissue (FIG. 52A). This method of serial advancement of cylindrical tubes is well known to those of ordinary skill in the art. A retractor platform 810 is then advanced over the cylindrical tubes—as shown in FIG. 52B. While the blades are configured differently, the retractor platform 810 is similar to retractor 745 and description of the retractor will not be repeated. The semicircular tissue retraction retractor blades of retractor 810 are preferably, but not necessarily, devoid of bore 7451.

Figure 25D:
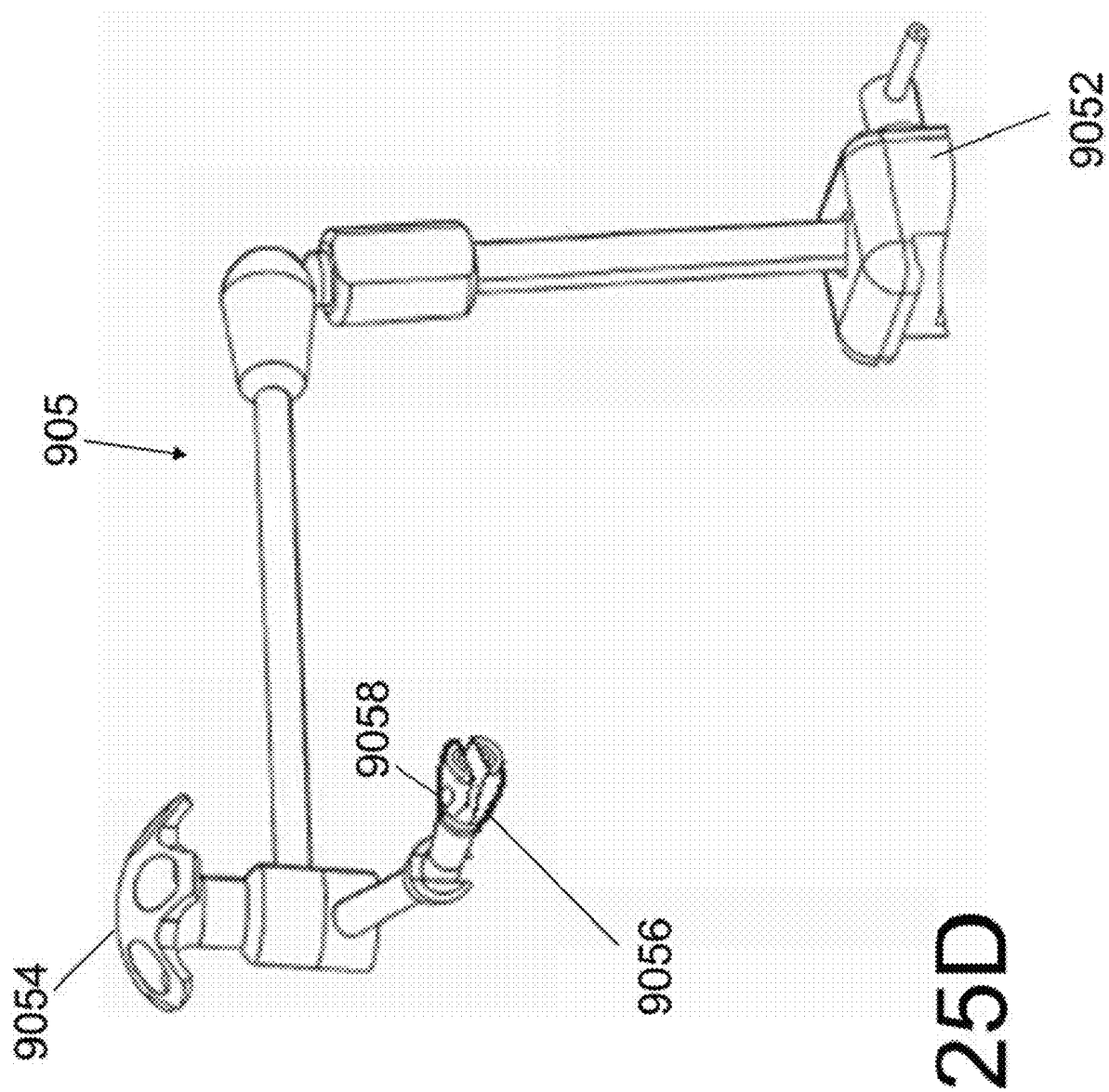
Figure 54:
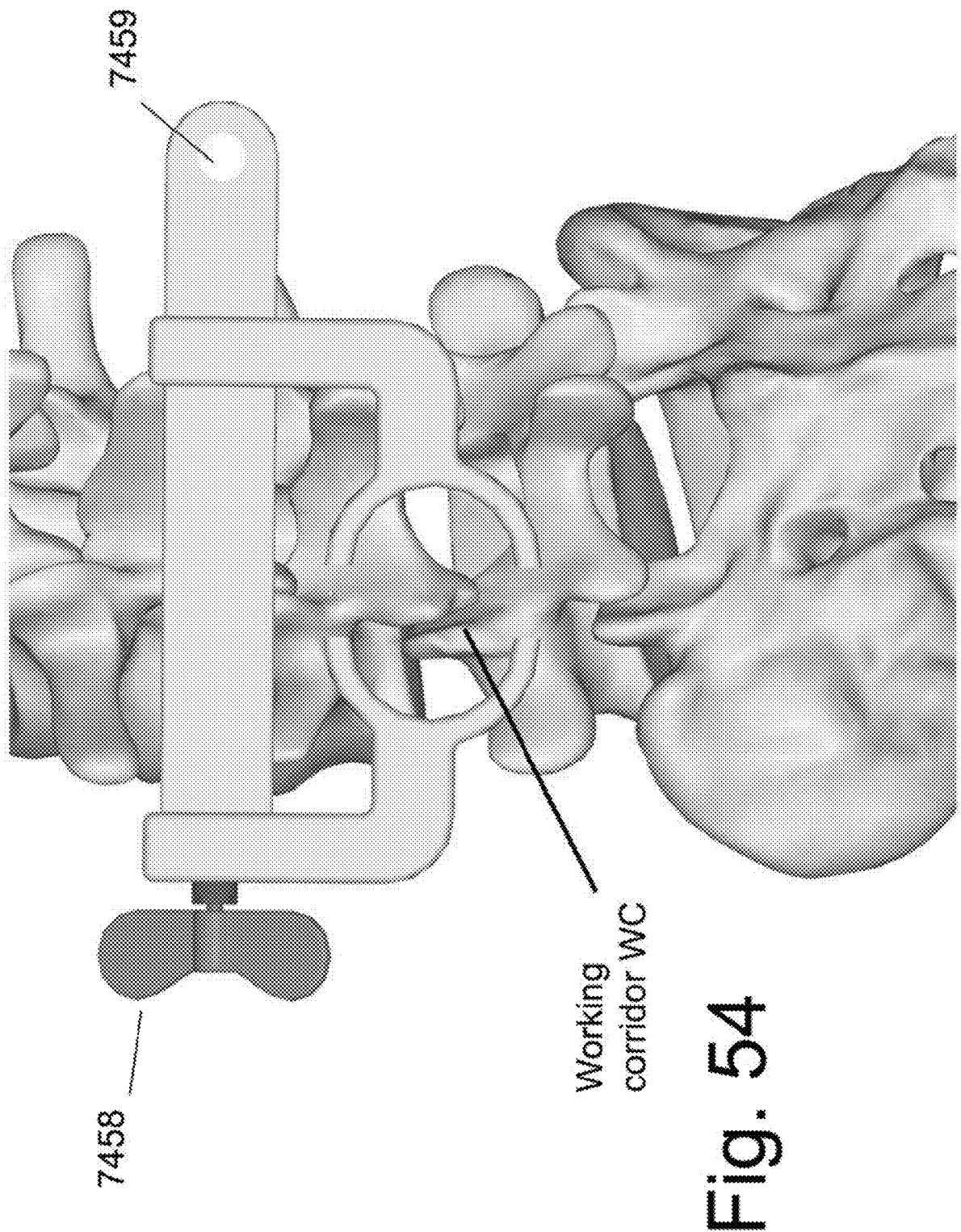
FIG. 54 illustrates a schematic view down the working corridor.

After advancement of retractor platform 810, the cylindrical tubes and member 730 are removed leaving a working corridor within the central aspect of the semi-cylindrical retractor blades (FIG. 53A). The blades may be separated further by actuating thumb wheel 7458 in order to provide a larger working corridor (FIG. 53B). If desired, the platform 810 may be attached to a frame device (similar to FIG. 25D) that is anchored to the operating table. The frame device may attach to the region of bore 7459 of retractor platform 810. FIG. 54 illustrates a schematic view down the working corridor. Note that the facet joint necessarily rests at the bottom of the working corridor since placement of the retractor 810 was guided by member 730. That is, member 730 was anchored to the facet joint as an initial step in the operation and the anchor was then used to define the trajectory of the surgical corridor to the facet joint. The positioned retraction platform 810 may be further coupled to a frame device that anchors to the operating table (FIG. 25D).

After removal of member 730 and the cylindrical tubes, a surgical corridor is left between the tissue retractor blades through which the posterior aspect of the first facet may be accessed. The surgeon visually identifies and verifies that the posterior aspect of the first facet joint is at the distal end of the surgical corridor. Any soft tissue remaining over the posterior aspect of the facet joint is removed. The facet joint is then at least partially removed as described previously in detail. Preferably, at least a portion of the lateral surface of the SAP of inferior vertebral bone is removed with facet joint resection. The posterior aspect of the disc space that is immediately anterior to resected facet joint (and neural foramen) is exposed. The disc space is entered and at least partially evacuated and an orthopedic implant is positioned within the disc space as discussed in detail above.

In specific, the exposed disc entered through a transforaminal corridor, wherein the entry point of the posterior disc is at least partially in between the nerve root that exits the spinal canal beneath the pedicle of the superior vertebral bone and the pedicle of the inferior vertebral bone and lateral to the nerve that exits immediately beneath the pedicle of the inferior vertebral bone. An orthopedic implant is positioned into the disc space, wherein the implant can bear at least some of the load transmitted across the disc space and maintain the superior and inferior vertebral bones separated by a desired distance. Bone forming material is preferably positioned in the disc space if a fusion is desired. The retraction platform is removed.

If desired, prior to retraction platform removal, an additional bone fusion mass may be used to connect the transverse processes adjacent to removed facet joint—as discussed previously. In addition, a first bone screw assembly is anchored into the first pedicle of the superior vertebral bone and a second bone screw assembly is anchored into the ipsilateral pedicle of the inferior vertebral bone. The bone screw assemblies are then rigidly interconnected by a rod member.

Figure 55:
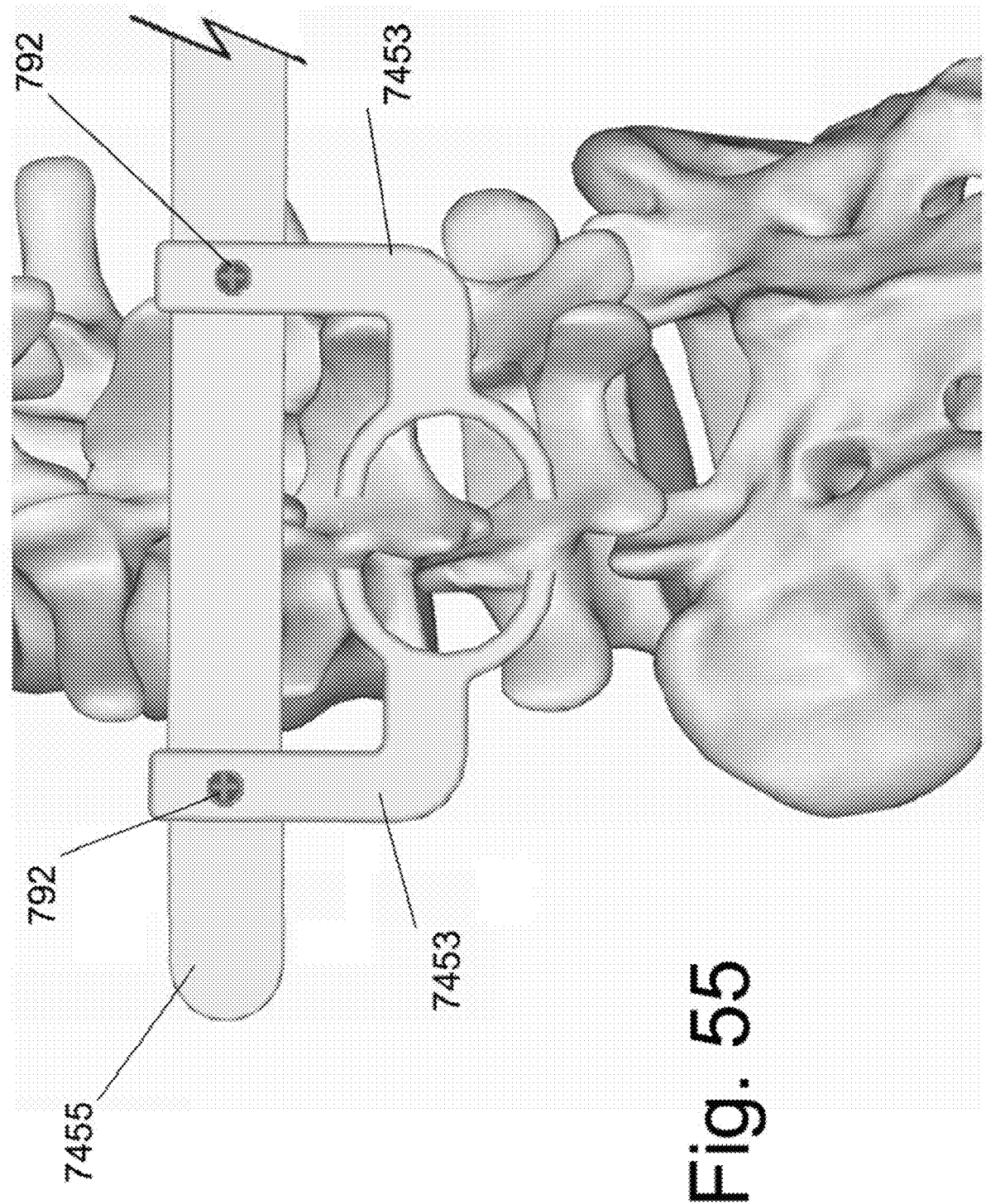
FIG. 55 illustrates an alternative embodiment of the retractor.

A modification of the previous embodiment is shown in FIG. 55. In this embodiment, both bar 7455 is a member of the frame device that is attached to the operating room table. Each blade member 7453 may be guided to the facet joint by anchored member 730 (as shown in the last embodiment)

and then reversibly mounted onto bar 7455. (Further, the blades may be radiographically guided to the facet joint over guide wire 102 and cylindrical tubes without threaded advancement of member 730 into the facet joint. However, use of threaded member 730 provides less movement (and potential error) during retractor advancement). After moving the blade member into the desired position relative to bar 7455, a locking mechanism (set screw 792 here) is actuated to immobilize the blade member relative to bar 7455. As before, retractor platform 770 is also attached to the frame device. In this way, each of the two retractor blades that form and border the working corridor are independently attached to the frame device that anchors to the operating table.

The disclosed devices or any of their components can be made of any biologically adaptable or compatible materials. Materials considered acceptable for biological implantation are well known and include, but are not limited to, stainless steel, titanium, tantalum, combination metallic alloys, various plastics, resins, ceramics, biologically absorbable materials and the like. Any components may be also coated/made with osteo-conductive (such as deminerized bone matrix, hydroxyapatite, and the like) and/or osteo-inductive (such as Transforming Growth Factor "TGF-B," Platelet-Derived Growth Factor "PDGF," Bone-Morphogenic Protein "BMP," and the like) bio-active materials that promote bone formation. Further, any surface may be made with a porous ingrowth surface (such as titanium wire mesh, plasma-sprayed titanium, tantalum, porous CoCr, and the like), provided with a bioactive coating, made using tantalum, and/or helical rosette carbon nanotubes (or other carbon nanotube-based coating) in order to promote bone in-growth or establish a mineralized connection between the bone and the implant, and reduce the likelihood of implant loosening. Lastly, the system or any of its components can also be entirely or partially made of a shape memory material or other deformable material.

While this specification contains many specifics, these should not be construed as limitations on the scope of what is claimed or of what may be claimed, but rather as descriptions of features specific to particular embodiments. Certain features that are described in this specification in the context of separate embodiments can also be implemented in combination in a single embodiment. Conversely, various features that are described in the context of a single embodiment can also be implemented in multiple embodiments separately or in any suitable sub-combination. Moreover, although features may be described above as acting in certain combinations and even initially claimed as such, one or more features from a claimed combination can in some cases be excised from the combination, and the claimed combination may be directed to a sub-combination or a variation of a sub-combination. Similarly, while operations are depicted in the drawings in a particular order, this should not be understood as requiring that such operations be performed in the particular order shown or in sequential order, or that all illustrated operations be performed, to achieve desirable results. Only a few examples and implementations are disclosed. Variations, modifications and enhancements to the described examples and implementations and other implementations may be made based on what is disclosed.

What is claimed is:

1. A surgical system configured to treat a functional spinal unit of a subject, the functional spinal unit comprising a superior vertebral bone, an inferior vertebral bone and the intervertebral disc space positioned there between, the surgical system comprising:

an implantable device comprising at least a top surface, an opposing bottom surface, and interconnecting side surface, the implantable device configured and sized to be at least partially seated within the intervertebral disc space; and a non-implantable device comprising:
   (i) a body member comprising a front side and an opposing back side, a top side, a bottom side opposing the top side, a first side, a second side opposing the first side, and an internal cavity;
   (ii) a first arm movably coupled to the body member, the first arm extending from a proximal first portion to a distal second portion, the proximal first portion comprising a first portion that extends into the first side of the body member;
   (iii) a second arm movably coupled to the body member, the second arm extending from a proximal first portion to a distal second portion, the proximal first portion of the second arm and comprising a portion that at least partially extends into the second side of the body member;
   (iv) a third arm configured to at least partially retract into the internal cavity of the body member, the third arm extending from a proximal end surface to a distal end surface and comprising a proximal first portion and a distal second portion, at least a portion of the proximal first portion disposed within the internal cavity of the body member; and
   (v) a first tissue retention member rotatably coupled with the distal second portion of the first arm; and
   wherein (a) the first arm is configured to rotate about a first rotational axis relative to the body member, the first rotational axis extending from the top side to the bottom side of the body member and through the first portion of the first arm (b) the second arm is configured to rotate about a second rotational axis relative to the body member, the second rotational axis being non-collinear with the first axis, and (c) the proximal end surface of the third arm is positioned within the internal cavity of the body member at least when the third arm is in any retracted position.

2. The surgical system of claim 1, wherein the first tissue retention member is configured to rotate about a third rotational axis relative to the distal second portion of the first arm, the third rotational axis being non-colinear with the first longitudinal axis of the first arm.

3. The surgical system of claim 2, wherein the third rotational axis of the first tissue retention member extends from a top surface to an opposing bottom surface of the distal second portion of the first arm.

4. The surgical system of claim 2, further comprising a second tissue retention member rotatably coupled with the second arm, the second tissue retention member configured to: i) rotate about a fourth rotational axis relative to a distal second portion of the second arm and ii) rotate independent of the rotation of the first tissue retention member about the third rotational axis.

5. The surgical system of claim 4, wherein the fourth rotation axis extends from a top surface to an opposing bottom surface of the distal second portion of the second arm.

6. The surgical system of claim 1, further comprising a second tissue retention member rotatably coupled with the second arm; and
   wherein said rotatable coupling of the first and second tissue retention members to the distal second portion of the first and second arms, respectively, is such that the first tissue retention element and the second tissue retention element can rotate independent of one another.

7. The surgical system of claim 1, further comprising:
(vi) a second tissue retention member rotatably coupled with the distal second portion of the second arm; and
wherein:
at least a portion of distal second portion of each of the first arm and the second arm comprises a substantially planar form factor;
the first tissue retention member is configured to rotate about a third rotational axis, the third rotational axis being at least approximately orthogonal with the a plane defined by the substantially planar form factor of the at least portion of the distal second portion of the first arm; and
the second tissue retention member is configured to rotate about a fourth rotational axis, the fourth rotational axis being at least approximately orthogonal with the a plane defined by the substantially planar form factor of the at least portion of the distal second portion of the second arm.

8. The surgical system of claim 1, further comprising an adjustment mechanism coupled to the third arm, the adjustment mechanism configured to produce, upon actuation, movement of at least a portion of the third arm within the internal cavity of the body.

9. The surgical system of claim 8, wherein the adjustment mechanism comprises at least a first actuator, wherein rotation of the first actuator alters a distance between the proximal end surface of the third arm and the opposing back side of the body member.

10. The surgical system of claim 9, wherein the first actuator is positioned a greater distance from the front side of the body member that at least one of the first rotational axis first arm or the second rotational axis of the second arm.

11. The surgical system of claim 1, wherein the first rotational axis intersects said first arm at a point disposed at least part way between a distal end and a proximal end of the first arm.

12. The surgical system of claim 1, wherein:
the third arm comprises an at least partly planar form factor; and
the non-implantable device further comprises a tissue interface element, the tissue interface element coupled to a distal portion of the third arm and configured to interface with tissue of the subject during at least a portion of said treatment.

13. The surgical system of claim 12, wherein the tissue interface element is configured to operate as a tissue retractor in cooperation with said at least partial retraction of said third arm.

14. The surgical system of claim 13, wherein the tissue interface element, and the first and second tissue retention member collectively form at least a portion of a perimeter of a corridor, the implantable device being sized and shaped to be at least partially advanced through the corridor.

15. A surgical apparatus configured to treat a functional spinal unit of a living being, the functional spinal unit comprising a superior vertebral bone, an inferior vertebral bone and the intervertebral disc space positioned there between, the surgical apparatus comprising:
a non-implantable housing comprising a front side, an opposing back side, a first side, an opposing second side, and an internal cavity;
a non-implantable first arm at least rotatably coupled to the housing, the first arm extending from a proximal first portion to a distal second portion, the proximal first portion at least partially extending into the housing through an opening of the first side, the proximal first portion configured to rotate about a first axis of rotation relative to the housing;
a non-implantable second arm rotatably coupled to the housing, the second arm extending from a proximal first portion to a distal second portion, the proximal first portion of the second arm at least partially extending into the housing through an opening of the second side, the proximal first portion configured to rotate about a second axis of rotation relative to the housing, the first and second axes of rotation being offset from one another;
a non-implantable third arm configured to at least partially retract into the internal cavity of the housing, the third arm extending from a proximal first portion to a distal second portion thereof;
a first non-implantable tissue interface extension coupled with the distal second portion of the first arm;
a second non-implantable tissue interface extension coupled with the distal second portion of the second arm;
a third non-implantable tissue interface extension coupled with the distal second portion of the third arm;
a non-implantable adjustment mechanism at least partially contained within the housing, the adjustment mechanism configured to produce, upon actuation, a retraction of the third arm into the internal cavity, the proximal end surface of the third arm being retained within the internal cavity when the adjustment mechanism is any position; and
an implantable member comprising at least a first top surface, an opposing first bottom surface, and a side connecting the first top and the first bottom surfaces, the implantable member sized to be at least partially received within the intervertebral disc space; and
wherein:
i) the first, second and third non-implantable tissue interface extensions are configured to cooperatively form a perimeter of a channel, the channel sized to permit passage of at least a portion of the implantable member therethrough; and
ii) the adjustment mechanism comprising at least a first actuator that is positioned a greater distance from front side of the housing than at least one of the first rotational axis first arm or the second rotational axis of the second arm.

16. The surgical apparatus of claim 15, wherein the adjustment mechanism comprises a multi-toothed mechanism which permits incremental amounts of said retraction of said third arm when actuated.

17. The surgical apparatus of claim 15, wherein at least the first and second tissue interface extensions each comprise at least one curvilinear portion having an outer convex edge, the outer convex edge configured to engage tissue during said delivery of said implantable device.

18. The surgical apparatus of claim 15, wherein:
the first non-implantable tissue interface extension is rotatably coupled with the distal second portion of the first arm such that the first non-implantable tissue interface extension can rotate about an axis passing through the distal second portion of the first arm.

19. The surgical apparatus of claim 15, wherein the first, second and third non-implantable tissue interface extensions each comprise elongate members having a longitudinal axis, and each of the first, second and third non-implantable tissue interface extensions are disposed such that their longitudinal axes are capable of being positioned parallel with one another.

20. The surgical apparatus of claim 15, further comprising at least one mechanism configured to exert a lateral force on at least a portion of the non-implantable first arm so as to cause said non-implantable first arm to rotate about said first axis.

21. The surgical apparatus of claim 20, wherein said rotation about said first axis caused by said at least one mechanism causes said first non-implantable tissue interface extension to engage and retract tissue during said delivery.

22. The surgical apparatus of claim 15, wherein the first proximal portion and the second distal portion of the non-implantable first arm are joined at a central portion which causes a longitudinal axis of the first proximal portion to be at a non-zero angle with respect to a longitudinal axis of the second distal portion.

23. A surgical apparatus configured to treat a functional spinal unit, the functional spinal unit comprising a superior vertebral bone, an inferior vertebral bone and an intervertebral disc space positioned in between, the surgical apparatus comprising a non-implantable tissue retraction assembly and an implantable device configured to alter movement between the superior vertebral bone and the inferior vertebral bone, wherein:

the implantable device comprises a first member configured to engage the first vertebral bone, a second member configured to engage the second vertebral bone, and a connecting member configured to couple the first member and the second member; and the non-implantable tissue retraction assembly comprises:

a housing member comprising an external casing and an internal cavity, the casing comprising a front portion, an opposing back portion, and first and second sides;

an elongated handle configured to couple with the opposing back portion of the casing, at least a portion of the elongated handle extending, along a longitudinal axis, from a distal end to a proximal end of the elongated handle;

a first arm extending from a distal end surface to a proximal end surface, the first arm configured to movably retract through at least a part of the front portion of the casing and, upon actuation, to translate within the internal cavity;

a second arm extending from a proximal first portion to a distal second portion, the proximal first position forming a rotational coupling with the first side of the casing, the second arm configured to rotate about a rotational axis that extends from a top surface to a bottom surface of the casing;

a third arm extending from a proximal first portion to a distal second portion, the proximal first portion comprising a rotatable coupling with the second side of the casing, the third arm configured to rotate about a rotational axis that extends from the top surface to the bottom surface of the casing and is non-colinear with the rotational axis of the second arm; and an adjustment mechanism comprising a first actuator that is disposed external to the casing, the first actuator configured to, upon actuation, movably translate at least a portion of the first arm within the internal cavity; and wherein:

the first actuator is positioned a greater distance from the front portion of the casing than at least one of the rotational axis of the second arm or the rotational axis of the third arm, and the proximal end surface of the first arm is retained within the internal cavity when the adjustment mechanism is any position.

24. The surgical apparatus of claim 23, wherein the first arm is disposed with the internal cavity with its first longitudinal axis parallel with the longitudinal axis of the elongated handle.

25. The surgical apparatus of claim 23, wherein the first arm is disposed with the internal cavity with its first longitudinal axis substantially colinear with the longitudinal axis of the elongated handle.

* * * * *